United States Patent
Radin

(10) Patent No.: US 12,168,784 B2
(45) Date of Patent: Dec. 17, 2024

(54) METHOD OF CO-EXPRESSING A SULFATASE AND A SULFATASE MODIFYING FACTOR IN A PLANT OR PLANT CELL

(71) Applicant: BIOSTRATEGIES LC, State University, AR (US)

(72) Inventor: David N. Radin, Jonesboro, AR (US)

(73) Assignee: BioStrategies LC, State University, AR (US)

( * ) Notice: Subject to any disclaimer, the term of this patent is extended or adjusted under 35 U.S.C. 154(b) by 0 days.

(21) Appl. No.: 17/651,106

(22) Filed: Feb. 15, 2022

(65) Prior Publication Data

US 2022/0251522 A1     Aug. 11, 2022

Related U.S. Application Data

(63) Continuation of application No. 15/325,661, filed as application No. PCT/US2015/040030 on Jul. 10, 2015, now abandoned.

(60) Provisional application No. 62/023,571, filed on Jul. 11, 2014.

(51) Int. Cl.
| | |
|---|---|
| C12N 15/82 | (2006.01) |
| A61K 38/16 | (2006.01) |
| A61K 38/17 | (2006.01) |
| A61K 38/44 | (2006.01) |
| C07K 14/42 | (2006.01) |
| C12N 9/00 | (2006.01) |
| C12N 9/02 | (2006.01) |
| C12N 9/16 | (2006.01) |

(52) U.S. Cl.
CPC .......... *C12N 9/0051* (2013.01); *A61K 38/168* (2013.01); *A61K 38/17* (2013.01); *A61K 38/44* (2013.01); *C07K 14/42* (2013.01); *C12N 9/16* (2013.01); *C12N 15/8257* (2013.01); *C12Y 108/99* (2013.01); *C12Y 301/06* (2013.01); *C07K 2319/00* (2013.01); *C07K 2319/02* (2013.01); *C07K 2319/04* (2013.01)

(58) Field of Classification Search
None
See application file for complete search history.

(56) References Cited

U.S. PATENT DOCUMENTS

| | | | |
|---|---|---|---|
| 4,938,949 A | 7/1990 | Borch et al. | |
| 4,956,282 A * | 9/1990 | Goodman | C12N 15/8257 435/69.51 |
| 5,034,322 A | 7/1991 | Rogers et al. | |
| 5,106,739 A | 4/1992 | Comai et al. | |
| 5,433,946 A | 7/1995 | Allen, Jr. et al. | |
| 5,589,610 A | 12/1996 | De Beuckeleer et al. | |
| 5,625,136 A | 4/1997 | Koziel et al. | |
| 5,639,948 A | 6/1997 | Michiels et al. | |
| 5,661,017 A | 8/1997 | Dunahay et al. | |
| 5,929,304 A * | 7/1999 | Radin | C12Y 302/01049 435/320.1 |
| 6,455,760 B1 | 9/2002 | Zhao et al. | |
| 6,462,185 B1 | 10/2002 | Takakura et al. | |
| 6,696,623 B1 | 2/2004 | Doerner et al. | |
| 6,740,526 B1 | 5/2004 | Curtis | |
| 7,722,865 B2 | 5/2010 | Vellard et al. | |
| 8,765,437 B2 | 7/2014 | Koppaka et al. | |
| 9,061,059 B2 | 6/2015 | Chakraborty et al. | |
| 2002/0120953 A1 | 8/2002 | McDonald et al. | |
| 2003/0084486 A1 | 5/2003 | Bruce et al. | |
| 2003/0177536 A1 | 9/2003 | Grundler et al. | |
| 2004/0019934 A1 | 1/2004 | Ekramoddoullah et al. | |
| 2004/0067506 A1 | 4/2004 | Scheres et al. | |

(Continued)

FOREIGN PATENT DOCUMENTS

| | | |
|---|---|---|
| EP | 1528104 | 5/2005 |
| EP | 2330204 | 6/2011 |

(Continued)

OTHER PUBLICATIONS

Medrano et al. Rapid system for evaluating bioproduction capacity of complex pharmaceutical proteins in plants. (2009) Methods Mol. Biol.; vol. 483; pp. 51-67 (Year: 2009).*

(Continued)

*Primary Examiner* — Cathy Kingdon Worley

(74) *Attorney, Agent, or Firm* — SALIWANCHIK, LLOYD & EISENSCHENK

(57) ABSTRACT

The subject invention concerns materials and methods for treating or preventing disease and conditions associated with various sulfatase enzymes that are defective or that are not properly expressed in a person or animal. In one embodiment, the disease is Sanfilippo A (MPS-IIIA) disease. The subject invention also concerns materials and methods for treating or preventing multiple sulfatase deficiency (MSD) in a person or animal. Compounds of the invention include a fusion protein comprising i) a mammalian sulfatase, or an enzymatically active fragment or variant thereof, and ii) a plant lectin or a binding subunit thereof. In a specific embodiment, the mammalian sulfatase is a human sulfatase, or an enzymatically active fragment or variant thereof. Polynucleotides encoding the fusion proteins are also contemplated for the subject invention. The subject invention also concerns materials and methods for producing proteins of the invention. The subject invention further provides a method of co-expressing sulfatase and sulfatase modifying factor in a plant or plant cell.

7 Claims, 3 Drawing Sheets

Figure 1:
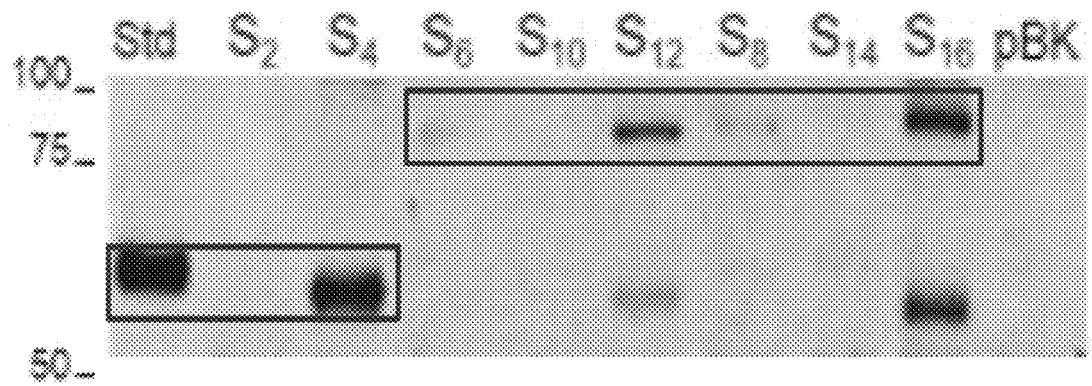

Specification includes a Sequence Listing.

(56) References Cited

U.S. PATENT DOCUMENTS

| | | | |
|---|---|---|---|
| 2004/0078841 | A1 | 4/2004 | Atkinson et al. |
| 2004/0123349 | A1 | 6/2004 | Xie et al. |
| 2004/0229250 | A1 | 11/2004 | Figura et al. |
| 2006/0204487 | A1 | 9/2006 | Shaaltiel et al. |
| 2010/0240597 | A1* | 9/2010 | Cramer ............... C07K 14/415 530/370 |
| 2013/0172403 | A1 | 7/2013 | von Figura et al. |
| 2013/0323221 | A1 | 12/2013 | Radin |
| 2019/0040368 | A1* | 2/2019 | Vervecken ............ C12N 15/815 |
| 2023/0140157 | A1* | 5/2023 | Radin ................ C07K 14/5434 435/200 |

FOREIGN PATENT DOCUMENTS

| | | | | |
|---|---|---|---|---|
| EP | | 2325302 | 1/2016 | |
| WO | WO 2009/134418 | | 11/2009 | |
| WO | WO 2012/012718 | | 1/2012 | |
| WO | WO-2012012718 A2 * | | 1/2012 | ............ A61K 38/46 |
| WO | WO 2012/085622 | | 6/2012 | |
| WO | WO 2013/181454 | | 12/2013 | |

OTHER PUBLICATIONS

Aviezer et al. A plant-derived recombinant human glucocerebrosidase enzyme-a preclinical and phase I investigation. (2009) PLoS One; vol. 4; e4792 (Year: 2009).*

Chargelegue et al. a murine monoclonal antibody produced in transgenic plants with plant-specific glycans is not immunogenic in mice. (2009) Transgenic Research; vol. 9; pp. 187-194 (Year: 2009).*

D'Aoust et al. The production of hemagglutinin-based virus-like particles in plants: a rapid, efficient and safe response to pandemic influenza. (2010) Plant Biotechnol J.; vol. 8; pp. 607-619 (Year: 2010).*

Du et al. Wolman disease/cholesteryl ester storage disease: efficacy of plant-produced human lysosomal acid lipase in mice. (2008) J. Lipid Res.; vol. 49; pp. 1646-1657 (Year: 2008).*

Furtado et al. Tools for use in the genetic engineering of barley. (2002) Proceedings of the 10th Australian Barley Technical Symposium, Canberra, ACT, Australia (Year: 2002).*

Angulo et al. High-resolution structural insights on the sugar-recognition and fusion tag properties of a versatile B-trefoil lectin domain from the mushroom *Laetiporus sulphureus* (Glycobiology (2011); vol. 21; pp. 1349-1361) (Year: 2011).*

Beck, M. Therapy for Lysosomal Storage Disorders. *IUBMB Life*, Jan. 2010, pp. 33-40, vol. 62, No. 1.

Database NCBI [Online] Accession No. XM_002534603, "*Ricinus communis* Ricin precursor, mRNA" Aug. 6, 2009, pp. 1-2.

Acosta-Gamboa, W. "Development of plant lectin RTB for delivery of therapeutic proteins" Jonesboro, AR: PhD dissertation. Arkansas State University; 2012.

Altschul, S. F. et al. Basic Local Alignment Search Tool. *J. Mol. Biol.* 1990, 215:402-410.

Altschul, S. F. et al. Gapped BLAST and PSI-BLAST: A New Generation of Protein Database Search Programs. *Nucl. Acids Res.* 1997, 25:3389-3402.

Annunziata, I. et al. Multiple sulfatase deficiency is due to hypomorphic mutations of the SUMF1 gene. *Hum Mutat* 2007, 28(9):928.

Audi, J. et al. Ricin poisoning: a comprehensive review. *JAMA* 2005, 294(18):2342-2351.

Aviezer, D. et al. A plant-derived recombinant human glucocerebrosidase enzyme-a preclinical and phase I investigation. *PLoS One* 2009, 4(3):e4792.

Bachmeier, C.J. et al. Comparison of drug efflux transport kinetics in various blood-brain barrier models. *Drug Metab Dispos* 2006, 34(6):998-1003.

Battelli, M.G. et al. Toxicity and cytotoxicity of nigrin b, a two-chain ribosome-inactivating protein from *Sambucus nigra*: comparison with ricin. *Arch Toxicol* 1997, 71(6):360-364.

Begley, D.J. et al. Lysosomal storage diseases and the blood-brain barrier. *Curr Pharm Design* 2008, 14(16):1566-1580.

Bell, C.L. et al. Identification of the galactose binding domain of the adeno-associated virus serotype 9 capsid. *J Virol* 2012, 86(13):7326-7333.

Bevan et al. The structure and transcription start site of a major potato tuber protein gene. *Nucleic Acid Res.* 14 (11), 4625-4638 (1986).

Blanz, J. et al. Reversal of peripheral and central neural storage and ataxia after recombinant enzyme replacement therapy in alpha-mannosidosis mice. *Hum Mol Genet* 2008, 17(22):3437-3445.

Boado, R.J. et al. Reversal of lysosomal storage in brain of adult MPS-I mice with intravenous Trojan horse-iduronidase fusion protein. *Mol Pharm* 2011, 8(4):1342-1350.

Broadwell, R.D. et al. Transcytotic pathway for blood-borne protein through the blood-brain barrier. *Proc Natl Acad Sci USA* 1988, 85(2):632-636.

Chargelegue, D. et al. A murine monoclonal antibody produced in transgenic plants with plant-specific glycans is not immunogenic in mice. *Transgenic Res* 2000, 9(3):187-194.

Chen, X. et al. Design of an in vivo cleavable disulfide linker in recombinant fusion proteins *BioTechniques*, 2010, 49:513-518.

Choi, N. et al. Mucosal immunization with a ricin toxin B subunit-rotavirus NSP4 fusion protein stimulates a Th1 lymphocyte response. *J Biotechnol* 2006, 121(2):272-283.

Citores, L. et al. Evidence for distinct cellular internalization pathways of ricin and nigrin b. *Cell Mol Biol* 2003, 49 Online Pub:OL461-465.

Clancy, M. and Hannah, L.C. Splicing of the maize Sh1 first intron is essential for enhancement of gene expression, and a T-rich motif increases expression without affecting splicing *Plant Physiol.* 2002, 130(2):918-29.

Cosma, M.P. et al. The multiple sulfatase deficiency gene encodes an essential and limiting factor for the activity of sulfatases. *Cell* 2003, 113(4):445-456.

Cosma, M.P. et al. Molecular and functional analysis of SUMF1 mutations in multiple sulfatase deficiency. *Hum Mutat* 2004, 23(6):576-581.

Crawley, A.C. et al. Characterization of a C57BL/6 congenic mouse strain of mucopolysaccharidosis type IIIA. *Brain Res*, 2006, 1104(1):1-17.

D'Aoust, M.A. et al. The production of hemagglutinin-based virus-like particles in plants: a rapid, efficient and safe response to pandemic influenza. *Plant Biotechnol J* 2010, 8(5):607-619.

Diez-Roux, G. and Ballabio, A. Sulfatases and human disease. *Annu Rev Genom Hum Genet* 2005, 6:355-379.

Donayre-Torres, A. et al. Production and purification of immunologically active core protein p24 from HIV-1 fused to ricin toxin B subunit in *E. coli*. *Virol J* 2009, 6:17.

Du, H. et al. Wolman disease/cholesteryl ester storage disease: efficacy of plant-produced human lysosomal acid lipase in mice. *J Lipid Res* 2008, 49(8):1646-1657.

Ferreras, J. et al. Use of Ribosome-Inactivating Proteins from Sambucus for the Construction of Immunotoxins and Conjugates for Cancer Therapy *Toxins* 2011, 3:420-441.

Fraldi, A, et al. Functional correction of CNS lesions in an MPS-IIIA mouse model by intracerebral AAV-mediated delivery of sulfamidase and SUMF1 genes. *Hum Mol Genet* 2007, 16(22):2693-2702.

Frankel, A. et al. Lectin-deficient ricin toxin intoxicates cells bearing the D-mannose receptor. *Carbohyd Res* 1997, 300(3):251-258.

Furtado, A. et al. "Tools for Use in the Genetic Engineering of Barley" *Proceedings of the 10th Australian Barley Technical Symposium, Canberra, ACT*, Australia, 2002.

Gliddon, B.L. and Hopwood, J.J. Enzyme-replacement therapy from birth delays the development of behavior and learning problems in mucopolysaccharidosis type IIIA mice. *Pediatr Res* 2004, 56(1):65-72.

Good, X. et al. Reduced ethylene synthesis by transgenic tomatoes expressing S-adenosylmethionine hydrolase *Plant Molec. Biol.* 1994, 26:781-790.

(56) References Cited

OTHER PUBLICATIONS

Grabowski, G.A. Treatment perspectives for the lysosomal storage diseases. *Expert Opin Emerg Drugs* 2008, 13(1):197-211.
Grubb, J.H. et al. Infused Fc-tagged beta-glucuronidase crosses the placenta and produces clearance of storage in utero in mucopolysaccharidosis VII mice. *Proc Natl Acad Sci USA* 2008, 105(24):8375-8380.
Hemsley, K.M. et al. Effect of high dose, repeated intracerebrospinal fluid injection of sulphamidase on neuropathology in MPS IIIA mice. *Genes Brain Behav* 2008, 7:740-753.
Hemsley, K.M. et al. Injection of recombinant human sulfamidase into the CSF via the cerebellomedullary cistern in MPS IIIA mice. *Mol Genet Metab* 2007, 90(3):313-328.
Hemsley, K.M. et al. Examination of intravenous and intra-CSF protein delivery for treatment of neurological disease. *Eur J Neurosci* 2009, 29(6):1197-1214.
Hemsley, K.M. et al. Effect of cisternal sulfamidase delivery in MPS IIIA Huntaway dogs—a proof of principle study. *Mol Genet Metab* 2009, 98(4):383-392.
Hollak, C.E. et al. Limitations of drug registries to evaluate orphan medicinal products for the treatment of lysosomal storage disorders. *Orphanet J Rare Dis* 2011, 6:16.
Huang, Z. et al. A DNA replicon system for rapid high-level production of virus-like particle in plants. Biotechnol Bioeng, 2009, 103(4): 706-714.
Huang, Z. et al. High-level rapid production of full-size monoclonal antibodies in plants by a single-vector DNA replicon system. *Biotechnol Bioeng* 2010, 106(1):9-17.
Huynh, H.T. et al. Biochemical evidence for superior correction of neuronal storage by chemically modified enzyme in murine mucopolysaccharidosis VII. *Proc Natl Acad Sci USA* 2012, 109(42):17022-17027.
Hwang, Y-S. et al. Analysis of the Rice Endosperm-Specific Globulin Promoter in Transformed Rice Cells *Plant Cell Rep.* 2002, 20:842-847.
Jackman, M.R. et al. Inhibition of apical but not basolateral endocytosis of ricin and folate in Caco-2 cells by cytochalasin D. *J Cell Sci* 1994, 107 (Pt 9):2547-2556.
Karlin, S. and Altschul, S.F. Methods for Assessing the Statistical Significance of Molecular Sequence Features by Using General Scoring Schemes *Proc. Natl. Acad. Sci. USA* 1990, 87:2264-2268.
Karlin, S. and Altschul, S.F. Applications and Statistics for Multiple High-Scoring Segments in Molecular Sequences *Proc. Natl. Acad. Sci. USA* 1993, 90:5873-5877.
Karpova, E.A. et al. A fluorimetric enzyme assay for the diagnosis of Sanfilippo disease type A (MPS IIIA). *J Inherit Metab Dis* 1996, 19(3):278-285.
Komarova, T.V. et al. Transient expression systems for plant-derived biopharmaceuticals. *Expert Rev Vaccines* 2010, 9(8):859-876.
Lai, H. and Chen, Q. Bioprocessing of plant-derived virus-like particles of Norwalk virus capsid protein under current Good Manufacture Practice regulations. *Plant Cell Rep* 2012, 31(3):573-584.
Landgrebe, J. et al. The human SUMF1 gene, required for post-translational sulfatase modification, defines a new gene family which is conserved from pro- to eukaryotes. *Gene* 2003, 316:47-56.
Landis, S.C. et al. A call for transparent reporting to optimize the predictive value of preclinical research. *Nature* 2012, 490(7419):187-191.
Landry, N. et al. Preclinical and clinical development of plant-made virus-like particle vaccine against avian H5N1 influenza. *PLoS One* 2010, 5(12):e15559.
Lavín De Juan, L. et al. Pharmaceutical applications of lectins *J. Drug Del. Sci. Tech.*, 2017, 42:126-133.
Liu, J. Plant-derived murine IL-12 and ricin b-murine IL-12 fusions. Blacksburg, VA: PhD Dissertation, Virginia Polytechnic Institute and Arkansas State University; 2006.
Lovrinovic, M. and Niemeyer, C. Rapid synthesis of DNA-cysteine conjugates for expressed protein ligation *Biochem. Biophy. Res. Comm.* 2005, 335:943-948.
Mariappan, M. et al. The non-catalytic N-terminal extension of formylglycine-generating enzyme is required for its biological activity and retention in the endoplasmic reticulum. *J Biol Chem* 2008, 283(17):11556-11564.
Matzner, U. et al. Enzyme replacement improves ataxic gait and central nervous system histopathology in a mouse model of metachromatic leukodystrophy. *Mol Ther* 2009, 17(4):600-606.
Maveyraud, L. et al. Structural basis for sugar recognition, including the tn carcinoma antigen, by the lectin sna-ii from sambucus nigra *Proteins* 2009, 75:89-103.
McCullen, C.A. and Binns, A.N. *Agrobacterium tumefaciens* and plant cell interactions and activities required for interkingdom macromolecular transfer. *Annu Rev Cell Dev Biol* 2006, 22:101-127.
Medina-Bolivar, F. et al. A non-toxic lectin for antigen delivery of plant-based mucosal vaccines. *Vaccine* 2003, 21(9-10):997-1005.
Medrano, G. et al. Rapid system for evaluating bioproduction capacity of complex pharmaceutical proteins in plants. *Methods Mol Biol* 2009, 483:51-67.
Meikle, P.J. et al. Prevalence of lysosomal storage disorders. *JAMA* 1999, 281(3):249-254.
Montfort, W. et al. The three-dimensional structure of ricin at 2.8Å *J. Biol. Chem.* 1987, 262(11):5398-5403.
Morlon-Guyot, J. et al. Identification of the ricin lipase site and implication in cytotoxicity. *J Biol Chem* 2003, 278(19):17006-17011.
Pastores, G. et al. Plant cell-expressed recombinant glucocerebrosidase: Taliglucerase alfa as therapy for Gaucher disease in adults patients previously treated with imiglucerase: 24-month results. *Mol Genet Metab* 2013, 108(2):S73-S74.
Polito, V.A. et al. Correction of CNS defects in the MPSII mouse model via systemic enzyme replacement therapy. *Hum Mol Genet* 2010, 19(24):4871-4885.
Rayon, C. et al. The protein N-glycosylation in plants. *J Exp Bot* 1998, 49(326):1463-1472.
Reidy, M.J. Engineering of the RTB lectin as a carrier platform for proteins and antigens. Blacksburg, VA: PhD Dissertation, Virginia Polytechnic Institute and Arkansas State University; 2007.
Rozaklis, T. et al. Impact of high-dose, chemically modified sulfamidase on pathology in a murine model of MPS IIIA. *Exp Neurol* 2011, 230(1):123-130.
Sandvig, K. and Van Deurs, B. Endocytosis and intracellular transport of ricin: recent discoveries. *FEBS Lett* 1999, 452(1-2):67-70.
Sardiello, M. et al. Sulfatases and sulfatase modifying factors: an exclusive and promiscuous relationship. *Hum Mol Genet* 2005, 14(21):3203-3217.
Settembre, C. et al. Sytemic inflammation and neurodegeneration of a mouse model of multiple sulfatase deficiency. *Proc. Natl. Acad. Sci USA*, 2007, 104:4506-11.
Shen, S. et al. Terminal N-linked galactose is the primary receptor for adeno-associated virus 9. *J Biol Chem* 2011, 286(15):13532-13540.
Simmons, B.M. et al. Mannose receptor-mediated uptake of ricin toxin and ricin A chain by macrophages. Multiple intracellular pathways for a chain translocation. *J Biol Chem* 1986, 261(17):7912-7920.
Smallshaw, J.E. and Vitetta, E.S. Ricin vaccine development. *Curr Top Microbiol Immunol* 2012, 357:259-272.
Sorrentino, N.C. et al. A highly secreted sulphamidase engineered to cross the blood-brain barrier corrects brain lesions of mice with mucopolysaccharidoses type IIIA. *EMBO Mol Med* 2013, 5(5):675-690.
Stechmann, B. et al. Inhibition of retrograde transport protects mice from lethal ricin challenge. *Cell* 2010, 141(2):231-242.
Tessitore, A. et al. GM1-ganglioside-mediated activation of the unfolded protein response causes neuronal death in a neurodegenerative gangliosidosis. *Mol Cell* 2004, 15(5):753-766.
Thorne, R.G. et al. Quantitative analysis of the olfactory pathway for drug delivery to the brain. *Brain Res* 1995, 692(1-2):278-282.

(56) References Cited

OTHER PUBLICATIONS

Trickler, W.J. et al. Silver nanoparticle induced blood-brain barrier inflammation and increased permeability in primary rat brain microvessel endothelial cells. *Toxicol Sci* 2010, 118(1):160-170.
Trim, P.J. et al. A simple method for early age phenotype confirmation using toe tissue from a mouse model of MPS IIIA. *Rapid Commun Mass Spectrom* 2014, 28(8):933-938.
Van Damme, E. et al. Characterization and molecular cloning of *Sambucus nigra* agglutinin V (nigrin b), a GalNAc-specific type-2 ribosome-inactivating protein from the bark of elderberry (*Sambucus nigra*). *Eur. J. Biochem.* 1996, 237(2):505-513.
Van Damme, E. et al. Plant Lectins: A Composite of Several Distinct Families of Structurally and Evolutionary Related Proteins with Diverse Biological Roles. *Crit. Rev. Plant Sci.* 1998, 17:575-692.
Van De Kamp, J.J.P. et al. Genetic heterogeneity and clinical variability in the Sanfilippo syndrome (type A, B, and C). *Clin. Genet.* 1981, 20(2):152-160.
Vogler, C. et al. Overcoming the blood-brain barrier with high-dose enzyme replacement therapy in murine mucopolysaccharidosis VII. *Proc Natl Acad Sci USA* 2005, 102(41):14777-14782.
Whaley, K.J. et al. Emerging antibody products and *Nicotiana* manufacturing. *Hum Vaccines* 2011, 7(3):349-356.
Whitfield, P.D. et al. Correlation among genotype, phenotype, and biochemical markers in Gaucher disease: implications for the prediction of disease severity. *Mol Genet Metab* 2002, 75(1):46-55.
Wu, C-L. et al. Promoters of Rice Seed Storage Protein Genes Direct Endosperm-Specific Gene Expression in Transgenic Rice. *Plant and Cell Physiology* 1998, 39(8):885-889.
Xu, D. et al. Systemic induction of a potato pin2 promoter by wounding, methyl jasmonate, and abscisic acid in transgenic rice plants. *Plant Molecular Biology* 1993, 22:573-588.
Yermakova, A. and Mantis, N.J. Protective immunity to ricin toxin conferred by antibodies against the toxin's binding subunit (RTB). *Vaccine* 2011, 29(45):7925-7935.
Zhang, Y. and Pardridge, W.M. Delivery of beta-galactosidase to mouse brain via the blood-brain barrier transferrin receptor. *J Pharmacol Exp Ther* 2005, 313(3):1075-1081.
Zimran, A. et al. Pivotal trial with plant cell-expressed recombinant glucocerebrosidase, taliglucerase alfa, a novel enzyme replacement therapy for Gaucher disease. *Blood* 2011, 118(22):5767-5773.
Zito, E. et al. Sulfatase modifying factor 1 trafficking through the cells: from endoplasmic reticulum to the endoplasmic reticulum. *EMBO J* 2007, 26(10):2443-2453.
Dickson, P. et al. "Immune tolerance improves the efficacy of enzyme replacement therapy in canine mucopolysaccharidosis I" *J. Clin. Invest.*, 2008, 118(8):2868-2876.
Willis, R. "Good things in small packages. Nanotech advances are producing mega-results in drug delivery" *Modern Drug Discover*, 2004, pp. 30-36.
Zambidis, E. and Scott, D. "Epitope-specific tolerance induction with an engineered immunoglobulin" *Proc. Natl. Acad. Sci. USA*, 1996, 93:5019-5024.

* cited by examiner

SEQUENCE LISTING

```
<160> NUMBER OF SEQ ID NOS: 82

<210> SEQ ID NO 1
<211> LENGTH: 2380
<212> TYPE: DNA
<213> ORGANISM: Homo sapiens

<400> SEQUENCE: 1
aggccccgcc   ccgcagccca   gccggaaggg   ccggcggacg   ctcgctaggt   cggctcgctg        60
```

| | |
|---|---:|
| gccgggctc cgcggctccc gtggttgcca tggcggcggt tgtcgcggcg acgaggtggt | 120 |
| ggcagctgtt gctggtgctc agcgccgcgg ggatgggggc ctcgggcgcc ccgcagcccc | 180 |
| ccaacatcct gctcctgctc atggacgaca tgggatgggg tgacctcggg gtgtatggag | 240 |
| agccctccag agagacccccg aatttggacc ggatggctgc agaagggctg cttttcccaa | 300 |
| acttctattc tgccaaccct ctgtgctcgc catcgagggc ggcactgctc acaggacggc | 360 |
| tacccatccg caatggcttc tacaccacca cgcccatgc cagaaacgcc tacacaccgc | 420 |
| aggagattgt gggcggcatc ccagactcgg agcagctcct gccggagctt ctgaagaagg | 480 |
| ccggctacgt cagcaagatt gtcggcaagt ggcatctggg tcacaggccc cagttccacc | 540 |
| ccctgaagca cggatttgat gagtggtttg atcccccaa ctgccacttt ggaccttatg | 600 |
| acaacaaggc caggcccaac atccctgtgt cagggactg ggagatggtt ggcagatatt | 660 |
| atgaagaatt tcctattaat ctgaagacgg gggaagccaa cctcacccag atctacctgc | 720 |
| aggaagccct ggacttcatt aagagacagg cacggcacca cccctttttc ctctactggg | 780 |
| ctgtcgacgc cacgcacgca cccgtctatg cctccaaacc cttcttgggc accagtcagc | 840 |
| gagggcggta tggagacgcc gtccgggaga ttgatgacag cattgggaag atactggagc | 900 |
| tcctccaaga cctgcacgtc gcggacaaca ccttcgtctt cttcacgtcg acaacggcg | 960 |
| ctgccctcat ttccgccccc gaacaaggtg gcagcaacgg ccccttctg tgtgggaagc | 1020 |
| agaccacgtt tgaaggaggg atgagggagc ctgccctcgc atggtggcca gggcacgtca | 1080 |
| ctgcaggcca ggtgagccac cagctgggca gcatcatgga cctcttcacc accagcctgg | 1140 |
| cccttgcggg cctgacgccg cccagcgaca gggccattga tggcctcaac ctcctcccca | 1200 |
| ccctcctgca gggccggctg atggacaggc ctatcttcta ttaccgtggc gacacgctga | 1260 |
| tggcggccac cctcgggcag cacaaggctc acttctggac ctggaccaac tcctgggaga | 1320 |
| acttcagaca gggcattgat ttctgccctg gcagaacgt tcaggggtc acaactcaca | 1380 |
| atctggaaga ccacacgaag ctgccccctga tcttccacct gggacgggac caggggagaa | 1440 |
| ggttcccccct cagctttgcc agcgccgagt accaggaggc cctcagcagg atcacctcgg | 1500 |
| tcgtccagca gcaccaggag gccttggtcc ccgcgcagcc ccagctcaac gtgtgcaact | 1560 |
| gggcggtcat gaactgggca cctccgggct gtgaaaagtt agggaagtgt ctgacacctc | 1620 |
| cagaatccat tcccaagaag tgcctctggt cccactagca cctgcgcaga ctcaggccag | 1680 |
| gcctagaatc tccggttggc cctgcaagtg cctggaggaa ggatggctct ggcctcggtc | 1740 |
| ctccccccaac cctgcccaag ccagacagac agcacctgca gacgcagggg gactgcacaa | 1800 |
| ttccacctgc ccaggacctg accctggcgt gtgcttggcc ctcctcctcg cccacggcgc | 1860 |
| ctcagatttc aggaccctcc tcctcgccca cggcgcctca gacctcagga ccctgccgtc | 1920 |
| tcacgccttt gtgaacccca aatatctgag accagtctca gtttattttg ccaaggttaa | 1980 |
| ggatgcacct gtgacagcct caggaggtcc tgacaacagg tgcctgaggt ggctggggat | 2040 |
| acagtttgcc tttatacatc ttagggagac acaagatcag tatgtgtatg cgtacattg | 2100 |
| gttcagtcag ccttccactg aatacacgat tgagtctggc ccagtgaatc cgcatttta | 2160 |
| tgtaaacagt aagggaacgg ggcaatcata taagcgtttg tctcagggga gccccagagg | 2220 |
| gatgacttcc agttccgtct gtcctttgtc cacaaggaat ttccctggac gctaattatg | 2280 |
| agggaggcgt gtagcttctt atcattgtaa ctatgttatt tagaaataaa acgggaggca | 2340 |
| ggtttgccta attcccagct tgaaaaaaaa aaaaaaaaa | 2380 |

-continued

```
<210> SEQ ID NO 2
<211> LENGTH: 522
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Ala | Ala | Val | Val | Ala | Ala | Thr | Arg | Trp | Trp | Gln | Leu | Leu | Leu | Val |
| 1 | | | | 5 | | | | | 10 | | | | | 15 | |
| Leu | Ser | Ala | Ala | Gly | Met | Gly | Ala | Ser | Gly | Ala | Pro | Gln | Pro | Pro | Asn |
| | | | 20 | | | | | 25 | | | | | 30 | | |
| Ile | Leu | Leu | Leu | Leu | Met | Asp | Asp | Met | Gly | Trp | Gly | Asp | Leu | Gly | Val |
| | | | 35 | | | | | 40 | | | | | 45 | | |
| Tyr | Gly | Glu | Pro | Ser | Arg | Glu | Thr | Pro | Asn | Leu | Asp | Arg | Met | Ala | Ala |
| | 50 | | | | | 55 | | | | | 60 | | | | |
| Glu | Gly | Leu | Leu | Phe | Pro | Asn | Phe | Tyr | Ser | Ala | Asn | Pro | Leu | Cys | Ser |
| 65 | | | | | 70 | | | | | 75 | | | | | 80 |
| Pro | Ser | Arg | Ala | Ala | Leu | Leu | Thr | Gly | Arg | Leu | Pro | Ile | Arg | Asn | Gly |
| | | | | 85 | | | | | 90 | | | | | 95 | |
| Phe | Tyr | Thr | Thr | Asn | Ala | His | Ala | Arg | Asn | Ala | Tyr | Thr | Pro | Gln | Glu |
| | | | | 100 | | | | | 105 | | | | | 110 | |
| Ile | Val | Gly | Gly | Ile | Pro | Asp | Ser | Glu | Gln | Leu | Leu | Pro | Glu | Leu | Leu |
| | | | | 115 | | | | | 120 | | | | | 125 | |
| Lys | Lys | Ala | Gly | Tyr | Val | Ser | Lys | Ile | Val | Gly | Lys | Trp | His | Leu | Gly |
| | 130 | | | | | 135 | | | | | 140 | | | | |
| His | Arg | Pro | Gln | Phe | His | Pro | Leu | Lys | His | Gly | Phe | Asp | Glu | Trp | Phe |
| 145 | | | | | 150 | | | | | 155 | | | | | 160 |
| Gly | Ser | Pro | Asn | Cys | His | Phe | Gly | Pro | Tyr | Asp | Asn | Lys | Ala | Arg | Pro |
| | | | | 165 | | | | | 170 | | | | | 175 | |
| Asn | Ile | Pro | Val | Tyr | Arg | Asp | Trp | Glu | Met | Val | Gly | Arg | Tyr | Tyr | Glu |
| | | | | 180 | | | | | 185 | | | | | 190 | |
| Glu | Phe | Pro | Ile | Asn | Leu | Lys | Thr | Gly | Glu | Ala | Asn | Leu | Thr | Gln | Ile |
| | | | | 195 | | | | | 200 | | | | | 205 | |
| Tyr | Leu | Gln | Glu | Ala | Leu | Asp | Phe | Ile | Lys | Arg | Gln | Ala | Arg | His | His |
| | 210 | | | | | 215 | | | | | 220 | | | | |
| Pro | Phe | Phe | Leu | Tyr | Trp | Ala | Val | Asp | Ala | Thr | His | Ala | Pro | Val | Tyr |
| 225 | | | | | 230 | | | | | 235 | | | | | 240 |
| Ala | Ser | Lys | Pro | Phe | Leu | Gly | Thr | Ser | Gln | Arg | Gly | Arg | Tyr | Gly | Asp |
| | | | | 245 | | | | | 250 | | | | | 255 | |
| Ala | Val | Arg | Glu | Ile | Asp | Asp | Ser | Ile | Gly | Lys | Ile | Leu | Glu | Leu | Leu |
| | | | | 260 | | | | | 265 | | | | | 270 | |
| Gln | Asp | Leu | His | Val | Ala | Asp | Asn | Thr | Phe | Val | Phe | Thr | Ser | Asp | |
| | | | 275 | | | | | 280 | | | | | 285 | | |
| Asn | Gly | Ala | Ala | Leu | Ile | Ser | Ala | Pro | Glu | Gln | Gly | Gly | Ser | Asn | Gly |
| | 290 | | | | | 295 | | | | | 300 | | | | |
| Pro | Phe | Leu | Cys | Gly | Lys | Gln | Thr | Thr | Phe | Glu | Gly | Gly | Met | Arg | Glu |
| 305 | | | | | 310 | | | | | 315 | | | | | 320 |
| Pro | Ala | Leu | Ala | Trp | Trp | Pro | Gly | His | Val | Thr | Ala | Gly | Gln | Val | Ser |
| | | | | 325 | | | | | 330 | | | | | 335 | |
| His | Gln | Leu | Gly | Ser | Ile | Met | Asp | Leu | Phe | Thr | Thr | Ser | Leu | Ala | Leu |
| | | | | 340 | | | | | 345 | | | | | 350 | |
| Ala | Gly | Leu | Thr | Pro | Pro | Ser | Asp | Arg | Ala | Ile | Asp | Gly | Leu | Asn | Leu |
| | | | | 355 | | | | | 360 | | | | | 365 | |
| Leu | Pro | Thr | Leu | Leu | Gln | Gly | Arg | Leu | Met | Asp | Arg | Pro | Ile | Phe | Tyr |
| | 370 | | | | | 375 | | | | | 380 | | | | |

```
Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
            405                 410                 415

Asp Phe Cys Pro Gly Gln Asn Val Ser Gly Val Thr Thr His Asn Leu
        420                 425                 430

Glu Asp His Thr Lys Leu Pro Leu Ile Phe His Leu Gly Arg Asp Pro
    435                 440                 445

Gly Glu Arg Phe Pro Leu Ser Phe Ala Ser Ala Glu Tyr Gln Glu Ala
    450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
            500                 505                 510

Ser Ile Pro Lys Lys Cys Leu Trp Ser His
            515                 520
```

<210> SEQ ID NO 3
<211> LENGTH: 5144
<212> TYPE: DNA
<213> ORGANISM: Homo sapiens

<400> SEQUENCE: 3

```
ccctgtccct ggctcacgtg atcgcgccta gggagaaaac gtctgactcc agccaccggc     60
cttcaaggca cggcttttta ttccttcggc tggtcggcct ctcgcccttc agctacctgt    120
gcgtccctcc gtcccgtccc gtccggggt caccccggag cctgtccgct atgcggctcc     180
tgcctctagc cccaggtcgg ctccggcggg gcagcccccg ccacctgccc tcctgcagcc    240
cagcgctgct actgctggtg ctgggcggct gcctgggggt cttcggggtg ctgcgggaa     300
cccggaggcc aacgtggtg ctgctcctca cggacgacca ggacgaagtg ctcggcggca     360
tgacaccgct aaagaaaacc aaagctctca tcggagagat ggggatgact ttttccagtg    420
cttatgtgcc aagtgctctc tgctgcccca gcagagccag tatcctgaca ggaaagtacc    480
cacataatca tcacgttgtg aacaacactc tggagggaa ctgcagtagt aagtcctggc     540
agaagatcca agaaccaaat actttcccag caattctcag atcaatgtgt ggttatcaga    600
cctttttgc agggaaatat ttaaatgagt acggagcccc agatgcaggt ggactagaac     660
acgttcctct gggttggagt tactggtatg ccttggaaaa gaattctaag tattataatt    720
acaccctgtc tatcaatggg aaggcacgga gcatggtga aaactatagt gtggactacc    780
tgacagatgt tttggctaat gtctccttgg actttctgga ctacaagtcc aactttgagc    840
ccttcttcat gatgatcgcc actccagcgc ctcattcgcc ttggacagct gcacctcagt    900
accagaaggc tttccagaat gtctttgcac caagaaacaa gaacttcaac atccatggaa    960
cgaacaagca ctggttaatt aggcaagcca agactccaat gactaattct tcaatacagt   1020
ttttagataa tgcatttagg aaaggtggc aaactctcct ctcagttgat gaccttgtgg    1080
agaaactggt caagaggctg gagttcactg gggagctcaa caacacttac atcttctata   1140
cctcagacaa tggctatcac acaggacagt tttccttgcc aatagacaag agacagctgt   1200
atgagtttga tatcaaagtt ccactgttgg ttcgaggacc tgggatcaaa ccaaatcaga    1260
caagcaagat gctggttgcc aacattgact tgggtcctac tattttggac attgctggct   1320
```

-continued

| | | | | | |
|---|---|---|---|---|---|
| acgacctaaa | taagacacag | atggatggga | tgtccttatt | gcccattttg | agaggtgcca | 1380 |
| gtaacttgac | ctggcgatca | gatgtcctgg | tggaatacca | aggagaaggc | cgtaacgtca | 1440 |
| ctgacccaac | atgcccttcc | ctgagtcctg | gcgtatctca | atgcttccca | gactgtgtat | 1500 |
| gtgaagatgc | ttataacaat | acctatgcct | gtgtgaggac | aatgtcagca | ttgtggaatt | 1560 |
| tgcagtattg | cgagtttgat | gaccaggagg | tgtttgtaga | agtctataat | ctgactgcag | 1620 |
| acccagacca | gatcactaac | attgctaaaa | ccatagaccc | agagcttta | ggaaagatga | 1680 |
| actatcggtt | aatgatgtta | cagtcctgtt | ctgggccaac | ctgtcgcact | ccaggggttt | 1740 |
| ttgaccccgg | atacaggttt | gaccccgtc | tcatgttcag | caatcgcggc | agtgtcagga | 1800 |
| ctcgaagatt | ttccaaacat | cttctgtagc | gacctcacac | agcctctgca | gatggatccc | 1860 |
| tgcacgcctc | tttctgatga | agtgattgta | gtaggtgtct | gtagctagtc | ttcaagacca | 1920 |
| cacctggaag | agtttctggg | ctggctttaa | gtcctgtttg | aaaaagcaac | ccagtcagct | 1980 |
| gacttcctcg | tgcaatgtgt | taaactgtga | actctgccca | tgtgtcagga | gtggctgtct | 2040 |
| ctggtctctt | cctttagctg | acaaggacac | tcctgaggtc | tttgttctca | ctgtattctt | 2100 |
| tttatcctgg | ggccacagtt | cttgattatt | cctcttgtgg | ttaaagactg | aatttgtaaa | 2160 |
| cccattcaga | taaatggcag | tactttagga | cacacacaaa | cacacagaca | cacctttga | 2220 |
| tatgtaagct | tgacctaaag | tcaaaggacc | tgtgtagcat | ttcagattga | gcacttcact | 2280 |
| atcaaaaata | ctaacatcac | atggcttgaa | gagtaaccat | cagagctgaa | tcatccaagt | 2340 |
| aagaacaagt | accattgttg | attgataagt | agagatacat | tttttatgat | gttcatcaca | 2400 |
| gtgtggtaag | gttgcaaatt | caaaacatgt | cacccaagct | ctgttcatgt | ttttgtgaat | 2460 |
| tctaggctgg | tgctgcactg | aaatagagca | gtaagcttgt | gataaaggcc | aattccaggt | 2520 |
| agctcttgaa | ggtgatagcc | atctactttc | cagtggctgc | caaccacagg | gagtgccagt | 2580 |
| taacactgga | aggattaagg | caaggtccct | tctcttgaga | ctcccctctg | agatctgaaa | 2640 |
| aatgaagtgg | cttaggaaca | tcagcagtga | agaactgcca | agagttggtg | aaggttgtct | 2700 |
| cttccgaggg | ccttctgaag | acagggctct | tgaacagaca | agtggaaggg | ctgtaccagg | 2760 |
| gataaaggaa | agaagtgcct | gtccagcagg | gagcttgaat | ttaagttcca | tgtatgaagt | 2820 |
| cattggctct | atctgcattt | ttctgtcatt | ctcttcattt | gttttaaggt | ggaaaatttt | 2880 |
| cttacagttg | atgcaaagta | tcaactactt | taccctacct | tctccccttt | tagatgggtt | 2940 |
| cttcctgagt | tttggagtct | tgtatgatta | tcagtattcc | cctgtcaaaa | tcaaatctat | 3000 |
| tcaggtttct | tcactgttga | gaacacctaa | atgtttttat | ttttgagaag | tggggacaga | 3060 |
| gtctcactat | gtcacccagg | ctggagtgca | atggcatgat | ctcagctcac | tgcaaccttc | 3120 |
| gcctcctggg | ttcaagcgat | tctcctgcct | ccgcctcctg | agtagctggg | attataggca | 3180 |
| cgcaccacca | cgcccagcta | attttttgta | tttttagtag | agacagagtt | tcaccatgtt | 3240 |
| ggccaggctg | gtcttgaact | cctgaccttg | tgatccaccc | acctcggcct | cccagagtgc | 3300 |
| tgggattaca | ggcatgagcc | accacgcttg | gctaagaaca | cctaaatttt | tatgtttctt | 3360 |
| ggctcaaaaa | ccagttccat | ttctaatgtt | gtcctcacaa | gaaggctaat | tggtggtgag | 3420 |
| acagcagggg | aggaggaaga | gctgtggttt | gtaacttgtt | caactcaggc | aataagcgat | 3480 |
| tttagctttta | tttaaagtct | tctgtccagc | tttaagcact | ttgtaagaca | tggctgaaag | 3540 |
| tagcttttct | atcagaattg | cagatagtca | tgttgggcta | acagtcaatt | ggatatattc | 3600 |
| ctttacctca | catgacccca | gcaactgtgg | tggtatctag | aggtgaaaca | ggcaagtgaa | 3660 |
| atggacacct | ctgctgtgaa | tgttttagag | aaggaaattc | aaaaaatgtt | gtaactgaaa | 3720 |

```
gcactgttga atatgggtat cggctttctt tttcactttg actcttaaca ttatcagtca    3780
acttccacat taatgaaagt tgaccatagt tatttccaaa taaaaagaaa ccaactctta    3840
ccaggtcttg gactgtgatg tcatattatt cagttttatg cttgttcctg agcagaactc    3900
ataagagtga catagtcagc tgctgacggc acctcagcca cgccactctt actcagttca    3960
gtgggtgtgc ttcgtggta ggatgtggtg cagccctctc tacgctcttc tattttggt     4020 atatttccta tctaaccttc aaatagcttc caattctttt tttcttggac tggcttcatt    4080
ctgaatttgt gctaaaataa tctttcataa agagacctca gtttatagcg taacagacta    4140
cacaatgcac tgatgttttc ataatgttta agggacccac tgcaagaagc ttgctgcctc    4200
cttttaattg tattcattta gattttgatt ttccatgtta agaaggtgag gtccatgttg    4260
gtgcccttca gagtagagaa ccatgtaaac attaggaatg aacagaggcc ttaggaatga    4320
atagagagtt tgccttatac aatttcctgt tacaaagctc tccctctcat gcaaagtagg    4380
gaacaccttt tgagcatctt tgaatttgac aaatggtgct gttgcaaaca cttttttttt    4440
gagatgaagt ctcgcggttg tcacccgggc tggagtgcag tggcgtgatc tcggctcact    4500
gcaacttcca cctcctgggt tcagcagtt ctcctgcctc agcctcccaa gtagctgaga    4560
ttacaggcgc ctgccacccc acctggctga ttttgtaat tttagtagag acggggtttc    4620
accatgttgg ccaggctgat taactcctga cctcaggtga tccacctttc tcggcctccc    4680
aaagtgctgg gattacgggt gtgagccacc gtgcccggcc tgcaaacaca ttttaattga    4740
caacactagg gctgttgtac aaaatagtaa tgatagccat ggaagtttta ccttattctg    4800
tgagaagtgt tcttaaactt attaagtgtc taaactaagg tttagtgctt ttttaaagga    4860
aagttgtccc aggattcatc ctaaagaaag caaaagttaa ttcaactgat ccaccaatgg    4920
aattagatgg gtagagttgg gttcttgagt tttaccacca cttagttccc actgaatttt    4980
gtaacttcct gtgtttgcat cctctgttcc tattctgccc ttgctctgtg tcatctcagt    5040
catttgactt agaaagtgcc cttcaaaagg accctgttca ctgctgcact tttcaatgaa    5100
ttaaaattta tttctgttct agtgggaaaa aaaaaaaaa aaaa                     5144
```

<210> SEQ ID NO 4
<211> LENGTH: 552
<212> TYPE: PRT
<213> ORGANISM: Homo sapiens

<400> SEQUENCE: 4

```
Met Arg Leu Leu Pro Leu Ala Pro Gly Arg Leu Arg Arg Gly Ser Pro
1               5                   10                  15

Arg His Leu Pro Ser Cys Ser Pro Ala Leu Leu Leu Val Leu Gly
            20                  25                  30

Gly Cys Leu Gly Val Phe Gly Val Ala Ala Gly Thr Arg Arg Pro Asn
        35                  40                  45

Val Val Leu Leu Leu Thr Asp Asp Gln Asp Glu Val Leu Gly Gly Met
    50                  55                  60

Thr Pro Leu Lys Lys Thr Lys Ala Leu Ile Gly Glu Met Gly Met Thr
65                  70                  75                  80

Phe Ser Ser Ala Tyr Val Pro Ser Ala Leu Cys Cys Pro Ser Arg Ala
                85                  90                  95

Ser Ile Leu Thr Gly Lys Tyr Pro His Asn His His Val Val Asn Asn
            100                 105                 110

Thr Leu Glu Gly Asn Cys Ser Ser Lys Ser Trp Gln Lys Ile Gln Glu
```

```
            115                 120                 125
Pro Asn Thr Phe Pro Ala Ile Leu Arg Ser Met Cys Gly Tyr Gln Thr
130                 135                 140

Phe Phe Ala Gly Lys Tyr Leu Asn Glu Tyr Gly Ala Pro Asp Ala Gly
145                 150                 155                 160

Gly Leu Glu His Val Pro Leu Gly Trp Ser Tyr Trp Tyr Ala Leu Glu
                165                 170                 175

Lys Asn Ser Lys Tyr Tyr Asn Tyr Thr Leu Ser Ile Asn Gly Lys Ala
                180                 185                 190

Arg Lys His Gly Glu Asn Tyr Ser Val Asp Tyr Leu Thr Asp Val Leu
                195                 200                 205

Ala Asn Val Ser Leu Asp Phe Leu Asp Tyr Lys Ser Asn Phe Glu Pro
210                 215                 220

Phe Phe Met Met Ile Ala Thr Pro Ala Pro His Ser Pro Trp Thr Ala
225                 230                 235                 240

Ala Pro Gln Tyr Gln Lys Ala Phe Gln Asn Val Phe Ala Pro Arg Asn
                245                 250                 255

Lys Asn Phe Asn Ile His Gly Thr Asn Lys His Trp Leu Ile Arg Gln
                260                 265                 270

Ala Lys Thr Pro Met Thr Asn Ser Ser Ile Gln Phe Leu Asp Asn Ala
                275                 280                 285

Phe Arg Lys Arg Trp Gln Thr Leu Leu Ser Val Asp Asp Leu Val Glu
290                 295                 300

Lys Leu Val Lys Arg Leu Glu Phe Thr Gly Glu Leu Asn Asn Thr Tyr
305                 310                 315                 320

Ile Phe Tyr Thr Ser Asp Asn Gly Tyr His Thr Gly Gln Phe Ser Leu
                325                 330                 335

Pro Ile Asp Lys Arg Gln Leu Tyr Glu Phe Asp Ile Lys Val Pro Leu
                340                 345                 350

Leu Val Arg Gly Pro Gly Ile Lys Pro Asn Gln Thr Ser Lys Met Leu
                355                 360                 365

Val Ala Asn Ile Asp Leu Gly Pro Thr Ile Leu Asp Ile Ala Gly Tyr
370                 375                 380

Asp Leu Asn Lys Thr Gln Met Asp Gly Met Ser Leu Leu Pro Ile Leu
385                 390                 395                 400

Arg Gly Ala Ser Asn Leu Thr Trp Arg Ser Asp Val Leu Val Glu Tyr
                405                 410                 415

Gln Gly Glu Gly Arg Asn Val Thr Asp Pro Thr Cys Pro Ser Leu Ser
                420                 425                 430

Pro Gly Val Ser Gln Cys Phe Pro Asp Cys Val Cys Glu Asp Ala Tyr
                435                 440                 445

Asn Asn Thr Tyr Ala Cys Val Arg Thr Met Ser Ala Leu Trp Asn Leu
                450                 455                 460

Gln Tyr Cys Glu Phe Asp Asp Gln Glu Val Phe Val Glu Val Tyr Asn
465                 470                 475                 480

Leu Thr Ala Asp Pro Asp Gln Ile Thr Asn Ile Ala Lys Thr Ile Asp
                485                 490                 495

Pro Glu Leu Leu Gly Lys Met Asn Tyr Arg Leu Met Met Leu Gln Ser
                500                 505                 510

Cys Ser Gly Pro Thr Cys Arg Thr Pro Gly Val Phe Asp Pro Gly Tyr
                515                 520                 525

Arg Phe Asp Pro Arg Leu Met Phe Ser Asn Arg Gly Ser Val Arg Thr
530                 535                 540
```

Arg Arg Phe Ser Lys His Leu Leu
545                 550

<210> SEQ ID NO 5
<211> LENGTH: 2770
<212> TYPE: DNA
<213> ORGANISM: Homo sapiens

<400> SEQUENCE: 5

| | | | | | |
|---|---|---|---|---|---|
| gaccggggtc | ggggcagggg | gcggggccga | gcgggagacc | agagagccgg | agccggatcc | 60 |
| cgatcccgag | tccgaccgc | cgccgccatg | agctgccccg | tgcccgcctg | ctgcgcgctg | 120 |
| ctgctagtcc | tggggctctg | ccgggcgcgt | ccccggaacg | cactgctgct | cctcgcggat | 180 |
| gacggaggct | ttgagagtgg | cgcgtacaac | aacagcgcca | tcgccacccc | gcacctggac | 240 |
| gccttggccc | gccgcagcct | cctctttcgc | aatgccttca | cctcggtcag | cagctgctct | 300 |
| cccagccgcg | ccagcctcct | cactggcctg | ccccagcatc | agaatgggat | gtacgggctg | 360 |
| caccaggacg | tgcaccactt | caactccttc | gacaaggtgc | ggagcctgcc | gctgctgctc | 420 |
| agccaagctg | gtgtgcgcac | aggcatcatc | gggaagaagc | acgtggggcc | ggagaccgtg | 480 |
| tacccgtttg | actttgcgta | cacggaggag | aatggctccg | tcctccaggt | ggggcggaac | 540 |
| atcactagaa | ttaagctgct | cgtccggaaa | ttcctgcaga | ctcaggatga | ccggcctttc | 600 |
| ttcctctacg | tcgccttcca | cgaccccac | cgctgtgggc | actcccagcc | ccagtacgga | 660 |
| accttctgtg | agaagtttgg | caacggagag | agcggcatgg | gtcgtatccc | agactggacc | 720 |
| ccccaggcct | acgacccact | ggacgtgctg | gtgccttact | cgtcccaa | caccccggca | 780 |
| gcccgagccg | acctggccgc | tcagtacacc | accgtcggcc | gcatggacca | aggagttgga | 840 |
| ctggtgctcc | aggagctgcg | tgacgccggt | gtcctgaacg | acacactggt | gatcttcacg | 900 |
| tccgacaacg | ggatccccctt | ccccagcggc | aggaccaacc | tgtactggcc | gggcactgct | 960 |
| gaacccttac | tggtgtcatc | cccggagcac | ccaaaacgct | ggggccaagt | cagcgaggcc | 1020 |
| tacgtgagcc | tcctagacct | cacgcccacc | atcttggatt | ggttctcgat | cccgtaccc | 1080 |
| agctacgcca | tctttggctc | gaagaccatc | cacctcactg | gccggtccct | cctgccggcg | 1140 |
| ctggaggccg | agcccctctg | ggccaccgtc | tttggcagcc | agagccacca | cgaggtcacc | 1200 |
| atgtcctacc | ccatgcgctc | cgtgcagcac | cggcacttcc | gctcgtgca | caacctcaac | 1260 |
| ttcaagatgc | ccttttccat | cgaccaggac | ttctacgtct | cacccacctt | ccaggacctc | 1320 |
| ctgaaccgca | ccacagctgg | tcagcccacg | ggctggtaca | aggacctccg | tcattactac | 1380 |
| taccggggcg | gctgggagct | ctacgaccgg | agccgggacc | ccacgagac | ccagaacctg | 1440 |
| gccaccgacc | cgcgctttgc | tcagcttctg | gagatgcttc | gggaccagct | ggccaagtgg | 1500 |
| cagtgggaga | cccacgaccc | ctgggtgtgc | gcccccgacg | gcgtcctgga | ggagaagctc | 1560 |
| tctcccagt | gccagcccct | ccacaatgag | ctgtgaccat | cccaggaggc | ctgtgcacac | 1620 |
| atcccaggca | tgtcccagac | acatcccaca | cgtgtccgtg | tggccggcca | gcctggggag | 1680 |
| tagtggcaac | agcccttccg | tccacactcc | catccaagga | gggttcttcc | ttcctgtggg | 1740 |
| gtcactcttg | ccattgcctg | gaggggggacc | agagcatgtg | accagagcat | gtgcccagcc | 1800 |
| cctccaccac | caggggcact | gccgtcatgg | caggggacac | agttgtcctt | gtgtctgaac | 1860 |
| catgtcccag | cacgggaatt | ctagacatac | gtggtctgcg | gacagggcag | cgcccccagc | 1920 |
| ccatgacaag | ggagtcttgt | tttctggctt | ggtttgggga | cctgcaaatg | ggaggcctga | 1980 |
| ggccctcttc | aggctttggc | agccacagat | acttctgaac | ccttcacaga | gagcaggcag | 2040 |

```
gggcttcggt gccgcgtggg cagtacgcag gtcccaccga cactcacctg ggagcacggc   2100
gcctggctct taccagcgtc tggcctagag gaagcctttg agcgaccttt gggcaggttt   2160
ctgcttcttc tgttttgccc catggtcaag tccctgttcc ccaggcaggt ttcagctgat   2220
tggcagcagg ctccctgagt gatgagcttg aacctgtggt gtttctgggc agaagcttat   2280 ctttttgag agtgtccgaa gatgaaggca tggcgatgcc cgtcctctgg cttgggttaa   2340
ttcttcggtg acactggcat tgctgggtgg tgatgcccgt cctctggctt gggttaattc   2400
ttcggtgaca ctggcgttgc tgggtggcaa tgcccatcct ctgccttggg ttaattcttc   2460
ggtgacactg gcgttgctgg gtggcgatgc ccgtcctctg gcttgggtta attcttggat   2520
gacgtcggcg ttgctgggag aatgtgccgt tcctgccctg cctccaccca cctcgggagc   2580
agaagcccgg cctggacacc cctcggcctg acaccccctc gaaggagagg gcgcttcctt   2640
gagtaggtgg gctccccttg cccttccctc cctatcactc catactgggg tgggctggag   2700
gaggccacag gccagctatt gtaaaagctt tttattttag taaaatatac agaagttctt   2760
tttctgaaaa                                                          2770
```

<210> SEQ ID NO 6
<211> LENGTH: 502
<212> TYPE: PRT
<213> ORGANISM: Homo sapiens

<400> SEQUENCE: 6

```
Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240
```

```
Thr Thr Val Gly Arg Met Asp Gln Gly Val Gly Leu Val Leu Gln Glu
            245                 250                 255

Leu Arg Asp Ala Gly Val Leu Asn Asp Thr Leu Val Ile Phe Thr Ser
                260                 265                 270

Asp Asn Gly Ile Pro Phe Pro Ser Gly Arg Thr Asn Leu Tyr Trp Pro
            275                 280                 285

Gly Thr Ala Glu Pro Leu Leu Val Ser Ser Pro Glu His Pro Lys Arg
        290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 7
<211> LENGTH: 5710
<212> TYPE: DNA
<213> ORGANISM: Homo sapiens

<400> SEQUENCE: 7
aggttacttg actgggagtt ctcagacctc cagtttcagc cctgccctca gcctccaatc      60
cgtaagagac acccagcccc agcaattgga ttgggcagcc cgtcttgaca caccactgtg     120
ctgagtgctt gaggacgtgt ttcaacagat ggttggggtt agtgtgtgtc atcacattcg     180 agtgggatt aagagaagga aggctgcctt gctggagctg tgtggtcttc tccaagtgag     240
agtcgcaggc aatagaacta ctttgctttt ggaggaaaag gaggaattca ttttcagcag     300
acacaagaaa agcagttttt ttttcaggga ttcttcactt ctcttgaaca aggaactcac     360
tcagagacta acacaaagga agtaatttct tacctggtca ttatttagtc tacaataagt     420
tcatccttct tcagtgtgac cagtaaaatt ttcccatact cttgaagaga gcataattgg     480
aatggagagg tgctgacggc cacccaccat catctaaaga agataaaactt ggcaaatgac     540 atgcaggttc ttcaaggcag aataattgca gaaaatcttc aaaggaccct atctgcagat     600
```

-continued

| | |
|---|---|
| gttctgaata cctctgagaa tagagattga ttattcaacc aggataccta attcaagaac | 660 |
| tccagaaatc aggagacgga gacattttgt cagttttgca acattggacc aaatacaatg | 720 |
| aagtattctt gctgtgctct ggttttggct gtcctgggca cagaattgct gggaagcctc | 780 |
| tgttcgactg tcagatcccc gaggttcaga ggacggatac agcaggaacg aaaaaacatc | 840 |
| cgacccaaca ttattcttgt gcttaccgat gatcaagatg tggagctggg gtccctgcaa | 900 |
| gtcatgaaca aaacgagaaa gattatggaa catggggggg ccaccttcat caatgccttt | 960 |
| gtgactacac ccatgtgctg cccgtcacgg tcctccatgc tcaccgggaa gtatgtgcac | 1020 |
| aatcacaatg tctacaccaa caacgagaac tgctcttccc cctcgtggca ggccatgcat | 1080 |
| gagcctcgga cttttgctgt atatcttaac aacactggct acagaacagc cttttttgga | 1140 |
| aaatacctca atgaatataa tggcagctac atcccccctg ggtggcgaga atggcttgga | 1200 |
| ttaatcaaga attctcgctt ctataattac actgtttgtc gcaatggcat caaagaaaag | 1260 |
| catggatttg attatgcaaa ggactacttc acagacttaa tcactaacga gagcattaat | 1320 |
| tacttcaaaa tgtctaagag aatgtatccc cataggcccg ttatgatggt gatcagccac | 1380 |
| gctgcgcccc acggcccgga ggactcagcc ccacagtttt ctaaactgta ccccaatgct | 1440 |
| tcccaacaca taactcctag ttataactat gcaccaaata tggataaaca ctggattatg | 1500 |
| cagtacacag gaccaatgct gcccatccac atggaattta caaacattct acagcgcaaa | 1560 |
| aggctccaga ctttgatgtc agtggatgat tctgtggaga ggctgtataa catgctcgtg | 1620 |
| gagacggggg agctggagaa tacttacatc atttacaccg ccgaccatgg ttaccatatt | 1680 |
| gggcagtttg gactggtcaa ggggaaatcc atgccatatg actttgatat tcgtgtgcct | 1740 |
| ttttttattc gtggtccaag tgtagaacca ggatcaatag tcccacagat cgttctcaac | 1800 |
| attgacttgg cccccacgat cctggatatt gctgggctcg acacacctcc tgatgtggac | 1860 |
| ggcaagtctg tcctcaaact tctggaccca gaaaagccag taacaggtt tcgaacaaac | 1920 |
| aagaaggcca aaatttggcg tgatacattc ctagtggaaa gaggcaaatt tctacgtaag | 1980 |
| aaggaagaat ccagcaagaa tatccaacag tcaaatcact tgcccaaata tgaacgggtc | 2040 |
| aaagaactat gccagcaggc caggtaccag acagcctgtg aacaaccggg gcagaagtgg | 2100 |
| caatgcattg aggatacatc tggcaagctt cgaattcaca agtgtaaagg acccagtgac | 2160 |
| ctgctcacag tccggcagag cacgcggaac ctctacgctc gcggcttcca tgacaaagac | 2220 |
| aaagagtgca gttgtaggga gtctggttac cgtgccagca aagccaaag aaagagtcaa | 2280 |
| cggcaattct tgagaaacca ggggactcca aagtacaagc ccagatttgt ccatactcgg | 2340 |
| cagacacgtt ccttgtccgt cgaatttgaa ggtgaaatat atgacataaa tctggaagaa | 2400 |
| gaagaagaat tgcaagtgtt gcaaccaaga acattgcta agcgtcatga tgaaggccac | 2460 |
| aaggggccaa gagatctcca ggcttccagt ggtggcaaca ggggcaggat gctggcagat | 2520 |
| agcagcaacg ccgtgggccc acctaccact gtccgagtga cacacaagtg ttttattctt | 2580 |
| cccaatgact ctatccattg tgagagagaa ctgtaccaat cggccagagc gtggaaggac | 2640 |
| cataaggcat acattgacaa agagattgaa gctctgcaag ataaaattaa gaatttaaga | 2700 |
| gaagtgagag gacatctgaa gagaaggaag cctgaggaat gtagctgcag taaacaaagc | 2760 |
| tattacaata agagaaagg tgtaaaaaag caagagaaat aaagagcca tcttcaccca | 2820 |
| ttcaaggagg ctgctcagga agtagatagc aaactgcaac ttttcaagga gaacaaccgt | 2880 |
| aggaggaaga aggagaggaa ggagaagaga cggcagagga aggggaaga gtgcagcctg | 2940 |

```
cctggcctca cttgcttcac gcatgacaac aaccactggc agacagcccc gttctggaac    3000
ctgggatctt tctgtgcttg cacgagttct aacaataaca cctactgtg tttgcgtaca    3060 gttaatgaga cgcataattt tcttttctgt gagtttgcta ctggcttttt ggagtatttt    3120
gatatgaata cagatcctta tcagctcaca aatacagtgc acacggtaga acgaggcatt    3180
ttgaatcagc tacacgtaca actaatggag ctcagaagct gtcaaggata taagcagtgc    3240
aacccaagac ctaagaatct tgatgttgga aataaagatg gaggaagcta tgacctacac    3300
agaggacagt tatgggatgg atgggaaggt taatcagccc cgtctcactg cagacatcaa    3360
ctggcaaggc ctagaggagc tacacagtgt gaatgaaaac atctatgagt acagacaaaa    3420
ctacagactt agtctggtgg actggactaa ttacttgaag gatttagata gagtatttgc    3480
actgctgaag agtcactatg agcaaaataa aacaataaag actcaaactg ctcaaagtga    3540
cgggttcttg gttgtctctg ctgagcacgc tgtgtcaatg gagatggcct ctgctgactc    3600
agatgaagac ccaaggcata aggttgggaa aacacctcat ttgaccttgc cagctgacct    3660
tcaaaccctg catttgaacc gaccaacatt aagtccagag agtaaacttg aatgaataa    3720 cgacattcca gaagttaatc atttgaattc tgaacactgg agaaaaaccg aaaaatggac    3780
ggggcatgaa gagactaatc atctggaaac cgatttcagt ggcgatggca tgacagagct    3840
agagctcggg cccagcccca ggctgcagcc cattcgcagg cacccgaaag aacttcccca    3900
gtatggtggt cctggaaagg acattttga agatcaacta tatcttcctg tgcattccga    3960
tggaatttca gttcatcaga tgttcaccat ggccaccgca gaacaccgaa gtaattccag    4020
catagcgggg aagatgttga ccaaggtgga gaagaatcac gaaaaggaga agtcacagca    4080
cctagaaggc agcgcctcct cttcactctc ctctgattag atgaaactgt taccttaccc    4140
taaacacagt atttcttttt aactttttta tttgtaaact aataaaggta atcacagcca    4200
ccaacattcc aagctaccct gggtaccttt gtgcagtaga agctagtgag catgtgagca    4260
agcggtgtgc acacggagac tcatcgttat aatttactat ctgccaagag tagaaagaaa    4320 ggctgggat atttggttg gcttggtttt gattttttgc ttgtttgttt gttttgtact    4380
aaaacagtat tatcttttga atatcgtagg gacataagta tatacatgtt atccaatcaa    4440
gatggctaga atggtgcctt tctgagtgtc taaaacttga caccctggt aaatctttca    4500 acacacttcc actgcctgcg taatgaagtt ttgattcatt tttaaccact ggaattttc    4560 aatgccgtca ttttcagtta gatgattttg cactttgaga ttaaaatgcc atgtctattt    4620
gattagtctt atttttttat ttttacaggc ttatcagtct cactgttggc tgtcattgtg    4680
acaaagtcaa ataaccccc aaggacgaca cacagtatgg atcacatatt gtttgacatt    4740
aagcttttgc cagaaaatgt tgcatgtgtt ttacctcgac ttgctaaaat cgattagcag    4800
aaaggcatgg ctaataatgt tggtggtgaa aataaataaa taagtaaaca aaatgaagat    4860
tgcctgctct ctctgtgcct agcctcaaag cgttcatcat acatcatacc tttaagattg    4920
ctatattttg ggttatttc ttgacaggag aaaaagatct aaagatcttt tattttcatc    4980 tttttggtt ttcttggcat gactaagaag cttaaatgtt gataaaatat gactagtttt    5040
gaatttacac caagaacttc tcaataaaag aaaatcatga atgctccaca atttcaacat    5100
accacaagag aagttaattt cttaacattg tgttctatga ttatttgtaa gaccttcacc    5160
aagttctgat atctttttaaa gacatagttc aaaattgctt ttgaaaatct gtattcttga    5220
aaatatcctt gttgtgtatt aggttttaa ataccagcta aaggattacc tcactgagtc    5280
atcagtaccc tcctattcag ctcccaaga tgatgtgttt ttgcttaccc taagagaggt    5340
```

-continued

```
tttcttctta tttttagata attcaagtgc ttagataaat tatgttttct ttaagtgttt      5400
atggtaaact cttttaaaga aaatttaata tgttatagct gaatcttttt ggtaacttta      5460
aatctttatc atagactctg tacatatgtt caaattagct gcttgcctga tgtgtgtatc      5520
atcggtggga tgacagaaca aacatattta tgatcatgaa tatgtgctt tgtaaaaaga      5580

tttcaagtta ttaggaagca tactctgтттт tttaatcatg tataatattc catgatactt      5640

ttatagaaca attctggctt caggaaagtc tagaagcaat atttcttcaa ataaaggtg      5700

tttaaactttt                                                          5710
```

<210> SEQ ID NO 8
<211> LENGTH: 871
<212> TYPE: PRT
<213> ORGANISM: Homo sapiens

<400> SEQUENCE: 8

```
Met Lys Tyr Ser Cys Cys Ala Leu Val Leu Ala Val Leu Gly Thr Glu
1               5                   10                  15

Leu Leu Gly Ser Leu Cys Ser Thr Val Arg Ser Pro Arg Phe Arg Gly
            20                  25                  30

Arg Ile Gln Gln Glu Arg Lys Asn Ile Arg Pro Asn Ile Ile Leu Val
        35                  40                  45

Leu Thr Asp Asp Gln Asp Val Glu Leu Gly Ser Leu Gln Val Met Asn
    50                  55                  60

Lys Thr Arg Lys Ile Met Glu His Gly Gly Ala Thr Phe Ile Asn Ala
65                  70                  75                  80

Phe Val Thr Thr Pro Met Cys Cys Pro Ser Arg Ser Ser Met Leu Thr
                85                  90                  95

Gly Lys Tyr Val His Asn His Asn Val Tyr Thr Asn Asn Glu Asn Cys
            100                 105                 110

Ser Ser Pro Ser Trp Gln Ala Met His Glu Pro Arg Thr Phe Ala Val
        115                 120                 125

Tyr Leu Asn Asn Thr Gly Tyr Arg Thr Ala Phe Phe Gly Lys Tyr Leu
    130                 135                 140

Asn Glu Tyr Asn Gly Ser Tyr Ile Pro Pro Gly Trp Arg Glu Trp Leu
145                 150                 155                 160

Gly Leu Ile Lys Asn Ser Arg Phe Tyr Asn Tyr Thr Val Cys Arg Asn
                165                 170                 175

Gly Ile Lys Glu Lys His Gly Phe Asp Tyr Ala Lys Asp Tyr Phe Thr
            180                 185                 190

Asp Leu Ile Thr Asn Glu Ser Ile Asn Tyr Phe Lys Met Ser Lys Arg
        195                 200                 205

Met Tyr Pro His Arg Pro Val Met Met Val Ile Ser His Ala Ala Pro
    210                 215                 220

His Gly Pro Glu Asp Ser Ala Pro Gln Phe Ser Lys Leu Tyr Pro Asn
225                 230                 235                 240

Ala Ser Gln His Ile Thr Pro Ser Tyr Asn Tyr Ala Pro Asn Met Asp
                245                 250                 255

Lys His Trp Ile Met Gln Tyr Thr Gly Pro Met Leu Pro Ile His Met
            260                 265                 270

Glu Phe Thr Asn Ile Leu Gln Arg Lys Arg Leu Gln Thr Leu Met Ser
        275                 280                 285

Val Asp Asp Ser Val Glu Arg Leu Tyr Asn Met Leu Val Glu Thr Gly
    290                 295                 300
```

```
Glu Leu Glu Asn Thr Tyr Ile Ile Tyr Thr Ala Asp His Gly Tyr His
305                 310                 315                 320

Ile Gly Gln Phe Gly Leu Val Lys Gly Lys Ser Met Pro Tyr Asp Phe
                325                 330                 335

Asp Ile Arg Val Pro Phe Phe Ile Arg Gly Pro Ser Val Glu Pro Gly
            340                 345                 350

Ser Ile Val Pro Gln Ile Val Leu Asn Ile Asp Leu Ala Pro Thr Ile
        355                 360                 365

Leu Asp Ile Ala Gly Leu Asp Thr Pro Pro Asp Val Asp Gly Lys Ser
370                 375                 380

Val Leu Lys Leu Leu Asp Pro Glu Lys Pro Gly Asn Arg Phe Arg Thr
385                 390                 395                 400

Asn Lys Lys Ala Lys Ile Trp Arg Asp Thr Phe Leu Val Glu Arg Gly
                405                 410                 415

Lys Phe Leu Arg Lys Lys Glu Glu Ser Ser Lys Asn Ile Gln Gln Ser
            420                 425                 430

Asn His Leu Pro Lys Tyr Glu Arg Val Lys Glu Leu Cys Gln Gln Ala
        435                 440                 445

Arg Tyr Gln Thr Ala Cys Glu Gln Pro Gly Gln Lys Trp Gln Cys Ile
450                 455                 460

Glu Asp Thr Ser Gly Lys Leu Arg Ile His Lys Cys Lys Gly Pro Ser
465                 470                 475                 480

Asp Leu Leu Thr Val Arg Gln Ser Thr Arg Asn Leu Tyr Ala Arg Gly
                485                 490                 495

Phe His Asp Lys Asp Lys Glu Cys Ser Cys Arg Glu Ser Gly Tyr Arg
            500                 505                 510

Ala Ser Arg Ser Gln Arg Lys Ser Gln Arg Gln Phe Leu Arg Asn Gln
        515                 520                 525

Gly Thr Pro Lys Tyr Lys Pro Arg Phe Val His Thr Arg Gln Thr Arg
530                 535                 540

Ser Leu Ser Val Glu Phe Glu Gly Glu Ile Tyr Asp Ile Asn Leu Glu
545                 550                 555                 560

Glu Glu Glu Glu Leu Gln Val Leu Gln Pro Arg Asn Ile Ala Lys Arg
                565                 570                 575

His Asp Glu Gly His Lys Gly Pro Arg Asp Leu Gln Ala Ser Ser Gly
            580                 585                 590

Gly Asn Arg Gly Arg Met Leu Ala Asp Ser Ser Asn Ala Val Gly Pro
        595                 600                 605

Pro Thr Thr Val Arg Val Thr His Lys Cys Phe Ile Leu Pro Asn Asp
610                 615                 620

Ser Ile His Cys Glu Arg Glu Leu Tyr Gln Ser Ala Arg Ala Trp Lys
625                 630                 635                 640

Asp His Lys Ala Tyr Ile Asp Lys Glu Ile Glu Ala Leu Gln Asp Lys
                645                 650                 655

Ile Lys Asn Leu Arg Glu Val Arg Gly His Leu Lys Arg Arg Lys Pro
            660                 665                 670

Glu Glu Cys Ser Cys Ser Lys Gln Ser Tyr Tyr Asn Lys Glu Lys Gly
        675                 680                 685

Val Lys Lys Gln Glu Lys Leu Lys Ser His Leu His Pro Phe Lys Glu
690                 695                 700

Ala Ala Gln Glu Val Asp Ser Lys Leu Gln Leu Phe Lys Glu Asn Asn
705                 710                 715                 720
```

```
Arg Arg Arg Lys Lys Glu Arg Lys Glu Lys Arg Gln Arg Lys Gly
            725                 730                 735

Glu Glu Cys Ser Leu Pro Gly Leu Thr Cys Phe Thr His Asp Asn Asn
        740                 745                 750

His Trp Gln Thr Ala Pro Phe Trp Asn Leu Gly Ser Phe Cys Ala Cys
        755                 760                 765

Thr Ser Ser Asn Asn Asn Thr Tyr Trp Cys Leu Arg Thr Val Asn Glu
770                 775                 780

Thr His Asn Phe Leu Phe Cys Glu Phe Ala Thr Gly Phe Leu Glu Tyr
785                 790                 795                 800

Phe Asp Met Asn Thr Asp Pro Tyr Gln Leu Thr Asn Thr Val His Thr
                805                 810                 815

Val Glu Arg Gly Ile Leu Asn Gln Leu His Val Gln Leu Met Glu Leu
            820                 825                 830

Arg Ser Cys Gln Gly Tyr Lys Gln Cys Asn Pro Arg Pro Lys Asn Leu
835                 840                 845

Asp Val Gly Asn Lys Asp Gly Ser Tyr Asp Leu His Arg Gly Gln
        850                 855                 860

Leu Trp Asp Gly Trp Glu Gly
865                 870

<210> SEQ ID NO 9
<211> LENGTH: 3909
<212> TYPE: DNA
<213> ORGANISM: Homo sapiens

<400> SEQUENCE: 9
gagcgagagt gtgtcgagtg agtgtgcgtc tgtgtgtccc ggcgagggtg cgcgctcggc        60
gccgggagcg cggccagccg agtccggagg catcgggagg tcgagagccg ccgggacccc       120
agctctgcgt tcactgcccc gtccggagct ggacttcggg gccggggccg ggccgtgcg        180 ccggggacag gcaggccgg gtcgcgggcc gcgcgtcccc caggccggag atctgcgagt       240
gaagagggac gagggaaaag aaacaaagcc acagacgcaa cttgagactc ccgcatccca       300
aaagaagcac cagatcagca aaaaagaag atgggccccc cgagcctcgt gctgtgcttg       360
ctgtccgcaa ctgtgttctc cctgctgggt ggaagctcgg ccttcctgtc gcaccaccgc       420
ctgaaaggca ggtttcagag ggaccgcagg aacatccgcc caacatcat cctggtgctg       480 acggacgacc aggatgtgga gctgggttcc atgcaggtga tgaacaagac ccggcgcatc       540
atggagcagg gcggggcgca cttcatcaac gccttcgtga ccacacccat gtgctgcccc       600
tcacgctcct ccatcctcac tggcaagtac gtccacaacc acaacaccta caccaacaat       660
gagaactgct cctcgccctc ctggcaggca cagcacgaga ccgcaccctt tgccgtgtac       720
ctcaatagca ctggctaccg gacagctttc ttcgggaagt atcttaatga atacaacggc       780
tcctacgtgc cacccggctg aaggagtgg gtcggactcc ttaaaaactc ccgctttat       840 aactacacgc tgtgtcggaa cggggtgaaa gagaagcacg gctccgacta ctccaaggat       900
tacctcacag acctcatcac caatgacagc gtgagcttct ccgcacgtc caagaagatg       960 tacccgcaca ggccagtcct catggtcatc agccatgcag ccccccacgg ccctgaggat      1020
tcagccccac aatattcacg cctcttccca aacgcatctc agcacatcac gccgagctac      1080
aactacgcgc caaccccgga caaacactgg atcatgcgct acacggggcc catgaagccc      1140
atccacatgg aattcaccaa catgctccag cggaagcgct gcagaccct catgtcggtg      1200 gacgactcca tggagacgat ttacaacatg ctggttgaga cgggcgagct ggacaacacg      1260
```

```
tacatcgtat acaccgccga ccacggttac cacatcggcc agtttggcct ggtgaaaggg    1320
aaatccatgc catatgagtt tgacatcagg gtcccgttct acgtgagggg ccccaacgtg    1380
gaagccggct gtctgaatcc ccacatcgtc ctcaacattg acctggcccc caccatcctg    1440
gacattgcag gcctggacat acctgcggat atggacggga atccatcct caagctgctg     1500 gacacggagc ggccggtgaa tcggtttcac ttgaaaaaga agatgagggt ctggcgggac    1560
tccttcttgg tggagagagg caagctgcta cacaagagac acaatgacaa ggtggacgcc    1620
caggaggaga actttctgcc caagtaccag cgtgtgaagg acctgtgtca gcgtgctgag    1680
taccagacgc gtgtgagca gctgggacag aagtggcagt gtgtggagga cgccacgggg     1740
aagctgaagc tgcataagtg caagggcccc atgcggctgg gcggcagcag agccctctcc    1800
aacctcgtgc ccaagtacta cgggcagggc agcgaggcct gcacctgtga cagcggggac    1860
tacaagctca gcctggccgg acgccggaaa aaactcttca agaagaagta caaggccagc    1920
tatgtccgca gtcgctccat ccgctcagtg gccatcgagg tggacggcag ggtgtaccac    1980
gtaggcctgg gtgatgccgc ccagccccga aacctcacca gcggcactg gccaggggcc      2040 cctgaggacc aagatgacaa ggatggtggg gacttcagtg gcactggagg ccttcccgac    2100
tactcagccg ccaaccccat taaagtgaca catcggtgct acatcctaga gaacgacaca    2160
gtccagtgtg acctggacct gtacaagtcc ctgcaggcct ggaaagacca caagctgcac    2220
atcgaccacg agattgaaac cctgcagaac aaaattaaga acctgaggga agtccgaggt    2280
cacctgaaga aaaagcggcc agaagaatgt gactgtcaca aaatcagcta ccacacccag    2340
cacaaaggcc gcctcaagca cagaggctcc agtctgcatc ctttcaggaa gggcctgcaa    2400
gagaaggaca aggtgtggct gttgcgggag cagaagcgca agaagaaact ccgcaagctg    2460
ctcaagcgcc tgcagaacaa cgacacgtgc agcatgccag gcctcacgtg cttcacccac    2520
gacaaccagc actggcagac ggcgcctttc tggacactgg ggccttcctg tgcctgcacc    2580
agcgccaaca ataacacgta ctggtgcatg aggaccatca atgagactca caatttcctc    2640
ttctgtgaat ttgcaactgg cttcctagag tactttgatc tcaacacaga ccccctaccag    2700 ctgatgaatg cagtgaacac actggacagg gatgtcctca accagctaca cgtacagctc    2760
atggagctga ggagctgcaa gggttacaag cagtgtaacc cccggactcg aaacatggac    2820
ctgggactta agatggagg aagctatgag caatacaggc agtttcagcg tcgaaagtgg    2880
ccagaaatga agagaccttc ttccaaatca ctgggacaac tgtgggaagg ctgggaaggt    2940
taagaaacaa cagaggtgga cctccaaaaa catagaggca tcacctgact gcacaggcaa    3000
tgaaaaacca tgtgggtgat ttccagcaga cctgtggtat tggccaggag gcctgagaaa    3060
gcaagcacgc actctcagtc aacatgacag attctggagg ataaccagca ggagcagaga    3120
taacttcagg aagtccattt ttgccctgc tttgctttg gattatacct caccagctgc      3180
acaaaatgca ttttttcgta tcaaaaagtc accactaacc ctcccccaga agctcacaaa    3240 ggaaacgga gagagcgagc gagagagatt tccttggaaa tttctcccaa gggcgaaagt     3300
cattggaatt tttaaatcat aggggaaaag cagtcctgtt ctaaatcctc ttattctttt    3360
ggtttgtcac aaagaaggaa ctaagaagca ggacagaggc aacgtggaga ggctgaaaac    3420
agtgcagaga cgtttgacaa tgagtcagta gcacaaaaga gatgacattt acctagcact    3480
ataaaccctg gttgcctctg aagaaactgc cttcattgta tatatgtgac tatttacatg    3540
taatcaacat gggaactttt aggggaacct aataagaaat cccaattttc aggagtggtg    3600
```

```
gtgtcaataa acgctctgtg gccagtgtaa aagaaaatcc ctcgcagttg tggacatttc    3660
tgttcctgtc cagataccat ttctcctagt atttctttgt tatgtcccag aactgatgtt    3720 tttttttaa ggtactgaaa agaaatgaag ttgatgtatg tcccaagttt tgatgaaact      3780
gtatttgtaa aaaaatttt gtagtttaag tattgtcata cagtgttcaa accccagcc       3840 aatgaccagc agttggtatg aagaaccttt gacattttgt aaaaggccat ttcttgggaa    3900
aaaaaaaaa                                                            3909
```

<210> SEQ ID NO 10
<211> LENGTH: 870
<212> TYPE: PRT
<213> ORGANISM: Homo sapiens

<400> SEQUENCE: 10

```
Met Gly Pro Pro Ser Leu Val Leu Cys Leu Leu Ser Ala Thr Val Phe
1               5                   10                  15

Ser Leu Leu Gly Gly Ser Ser Ala Phe Leu Ser His His Arg Leu Lys
            20                  25                  30

Gly Arg Phe Gln Arg Asp Arg Arg Asn Ile Arg Pro Asn Ile Ile Leu
        35                  40                  45

Val Leu Thr Asp Asp Gln Asp Val Glu Leu Gly Ser Met Gln Val Met
    50                  55                  60

Asn Lys Thr Arg Arg Ile Met Glu Gln Gly Gly Ala His Phe Ile Asn
65                  70                  75                  80

Ala Phe Val Thr Thr Pro Met Cys Cys Pro Ser Arg Ser Ser Ile Leu
                85                  90                  95

Thr Gly Lys Tyr Val His Asn His Asn Thr Tyr Thr Asn Asn Glu Asn
            100                 105                 110

Cys Ser Ser Pro Ser Trp Gln Ala Gln His Glu Ser Arg Thr Phe Ala
        115                 120                 125

Val Tyr Leu Asn Ser Thr Gly Tyr Arg Thr Ala Phe Phe Gly Lys Tyr
    130                 135                 140

Leu Asn Glu Tyr Asn Gly Ser Tyr Val Pro Pro Gly Trp Lys Glu Trp
145                 150                 155                 160

Val Gly Leu Leu Lys Asn Ser Arg Phe Tyr Asn Tyr Thr Leu Cys Arg
                165                 170                 175

Asn Gly Val Lys Glu Lys His Gly Ser Asp Tyr Ser Lys Asp Tyr Leu
            180                 185                 190

Thr Asp Leu Ile Thr Asn Asp Ser Val Ser Phe Phe Arg Thr Ser Lys
        195                 200                 205

Lys Met Tyr Pro His Arg Pro Val Leu Met Val Ile Ser His Ala Ala
    210                 215                 220

Pro His Gly Pro Glu Asp Ser Ala Pro Gln Tyr Ser Arg Leu Phe Pro
225                 230                 235                 240

Asn Ala Ser Gln His Ile Thr Pro Ser Tyr Asn Tyr Ala Pro Asn Pro
                245                 250                 255

Asp Lys His Trp Ile Met Arg Tyr Thr Gly Pro Met Lys Pro Ile His
            260                 265                 270

Met Glu Phe Thr Asn Met Leu Gln Arg Lys Arg Leu Gln Thr Leu Met
        275                 280                 285

Ser Val Asp Asp Ser Met Glu Thr Ile Tyr Asn Met Leu Val Glu Thr
    290                 295                 300

Gly Glu Leu Asp Asn Thr Tyr Ile Val Tyr Thr Ala Asp His Gly Tyr
305                 310                 315                 320
```

-continued

His Ile Gly Gln Phe Gly Leu Val Lys Gly Lys Ser Met Pro Tyr Glu
            325                 330                 335

Phe Asp Ile Arg Val Pro Phe Tyr Val Arg Gly Pro Asn Val Glu Ala
            340                 345                 350

Gly Cys Leu Asn Pro His Ile Val Leu Asn Ile Asp Leu Ala Pro Thr
            355                 360                 365

Ile Leu Asp Ile Ala Gly Leu Asp Ile Pro Ala Asp Met Asp Gly Lys
370                 375                 380

Ser Ile Leu Lys Leu Leu Asp Thr Glu Arg Pro Val Asn Arg Phe His
385                 390                 395                 400

Leu Lys Lys Lys Met Arg Val Trp Arg Asp Ser Phe Leu Val Glu Arg
                405                 410                 415

Gly Lys Leu Leu His Lys Arg Asp Asn Asp Lys Val Asp Ala Gln Glu
                420                 425                 430

Glu Asn Phe Leu Pro Lys Tyr Gln Arg Val Lys Asp Leu Cys Gln Arg
                435                 440                 445

Ala Glu Tyr Gln Thr Ala Cys Glu Gln Leu Gly Gln Lys Trp Gln Cys
                450                 455                 460

Val Glu Asp Ala Thr Gly Lys Leu Lys Leu His Lys Cys Lys Gly Pro
465                 470                 475                 480

Met Arg Leu Gly Gly Ser Arg Ala Leu Ser Asn Leu Val Pro Lys Tyr
                485                 490                 495

Tyr Gly Gln Gly Ser Glu Ala Cys Thr Cys Asp Ser Gly Asp Tyr Lys
                500                 505                 510

Leu Ser Leu Ala Gly Arg Arg Lys Lys Leu Phe Lys Lys Tyr Lys
                515                 520                 525

Ala Ser Tyr Val Arg Ser Arg Ser Ile Arg Ser Val Ala Ile Glu Val
                530                 535                 540

Asp Gly Arg Val Tyr His Val Gly Leu Gly Asp Ala Ala Gln Pro Arg
545                 550                 555                 560

Asn Leu Thr Lys Arg His Trp Pro Gly Ala Pro Glu Asp Gln Asp Asp
                565                 570                 575

Lys Asp Gly Gly Asp Phe Ser Gly Thr Gly Leu Pro Asp Tyr Ser
            580                 585                 590

Ala Ala Asn Pro Ile Lys Val Thr His Arg Cys Tyr Ile Leu Glu Asn
            595                 600                 605

Asp Thr Val Gln Cys Asp Leu Asp Leu Tyr Lys Ser Leu Gln Ala Trp
            610                 615                 620

Lys Asp His Lys Leu His Ile Asp His Glu Ile Glu Thr Leu Gln Asn
625                 630                 635                 640

Lys Ile Lys Asn Leu Arg Glu Val Arg Gly His Leu Lys Lys Lys Arg
                645                 650                 655

Pro Glu Glu Cys Asp Cys His Lys Ile Ser Tyr His Thr Gln His Lys
            660                 665                 670

Gly Arg Leu Lys His Arg Gly Ser Ser Leu His Pro Phe Arg Lys Gly
                675                 680                 685

Leu Gln Glu Lys Asp Lys Val Trp Leu Leu Arg Glu Gln Lys Arg Lys
            690                 695                 700

Lys Lys Leu Arg Lys Leu Leu Lys Arg Leu Gln Asn Asn Asp Thr Cys
705                 710                 715                 720

Ser Met Pro Gly Leu Thr Cys Phe Thr His Asp Asn Gln His Trp Gln
                725                 730                 735

```
Thr Ala Pro Phe Trp Thr Leu Gly Pro Phe Cys Ala Cys Thr Ser Ala
            740                 745                 750

Asn Asn Asn Thr Tyr Trp Cys Met Arg Thr Ile Asn Glu Thr His Asn
        755                 760                 765

Phe Leu Phe Cys Glu Phe Ala Thr Gly Phe Leu Glu Tyr Phe Asp Leu
    770                 775                 780

Asn Thr Asp Pro Tyr Gln Leu Met Asn Ala Val Asn Thr Leu Asp Arg
785                 790                 795                 800

Asp Val Leu Asn Gln Leu His Val Gln Leu Met Glu Leu Arg Ser Cys
                805                 810                 815

Lys Gly Tyr Lys Gln Cys Asn Pro Arg Thr Arg Asn Met Asp Leu Gly
            820                 825                 830

Leu Lys Asp Gly Gly Ser Tyr Glu Gln Tyr Arg Gln Phe Gln Arg Arg
        835                 840                 845

Lys Trp Pro Glu Met Lys Arg Pro Ser Ser Lys Ser Leu Gly Gln Leu
    850                 855                 860

Trp Glu Gly Trp Glu Gly
865                 870

<210> SEQ ID NO 11
<211> LENGTH: 5876
<212> TYPE: DNA
<213> ORGANISM: Homo sapiens

<400> SEQUENCE: 11
```

| | | | | | |
|---|---|---|---|---|---|
| agaacccgcc | ccggagggga | gggacgcagg | gaagagtcgc | acggacgcac | tcgcgctgcg | 60 |
| gccagcgccc | gggcctgcgg | gcccgggcgg | cggctgtgtt | gcgcagtctt | catgggttcc | 120 |
| cgacgaggag | gtctctgtgg | ctgcggcggc | ggctgctaac | tgcgccacct | gctgcagcct | 180 |
| gtccccgccg | ctctgaagcg | gccgcgtcga | agccgaaatg | ccgccacccc | ggaccggccg | 240 |
| aggccttctc | tggctgggtc | tggttctgag | ctccgtctgc | gtcgcccctcg | gatccgaaac | 300 |
| gcaggccaac | tcgaccacag | atgctctgaa | cgttcttctc | atcatcgtgg | atgacctgcg | 360 |
| cccctccctg | ggctgttatg | gggataagct | ggtgaggtcc | ccaaatattg | accaactggc | 420 |
| atcccacagc | ctcctcttcc | agaatgcctt | tgcgcagcaa | gcagtgtgcg | ccccgagccg | 480 |
| cgtttctttc | ctcactggca | ggagacctga | caccacccgc | ctgtacgact | tcaactccta | 540 |
| ctggagggtg | cacgctggaa | acttctccac | catcccccag | tacttcaagg | agaatggcta | 600 |
| tgtgaccatg | tcggtgggaa | aagtctttca | ccctgggata | tcttctaacc | ataccgatga | 660 |
| ttctccgtat | agctggtctt | ttccaccttca | tcatccttcc | tctgagaagt | atgaaaacac | 720 |
| taagacatgt | cgagggccag | atggagaact | ccatgccaac | ctgctttgcc | ctgtggatgt | 780 |
| gctggatgtt | cccgagggca | ccttgcctga | caaacagagc | actgagcaag | ccatacagtt | 840 |
| gttggaaaag | atgaaaacgt | cagccagtcc | tttcttcctg | gccgttgggt | atcataagcc | 900 |
| acacatcccc | ttcagatacc | ccaaggaatt | tcagaagttg | tatccttgg | agaacatcac | 960 |
| cctggccccc | gatcccgagg | tccctgatgg | cctaccccct | gtggcctaca | accctggat | 1020 |
| ggacatcagg | caacgggaag | acgtccaagc | cttaaacatc | agtgtgccgt | atggtccaat | 1080 |
| tcctgtggac | tttcagcgga | aaatccgcca | gagctacttt | gcctctgtgt | catatttgga | 1140 |
| tacacaggtc | ggccgcctct | tgagtgcttt | ggacgatctt | cagctggcca | acagcaccat | 1200 |
| cattgcattt | acctcggatc | atgggtgggc | tctaggtgaa | catggagaat | gggccaaata | 1260 |
| cagcaatttt | gatgttgcta | cccatgttcc | cctgatattc | tatgttcctg | gaaggacggc | 1320 |

```
ttcacttccg gaggcaggcg agaagctttt cccttacctc gacccttttg attccgcctc    1380
acagttgatg gagccaggca ggcaatccat ggaccttgtg gaacttgtgt ctcttttcc    1440
cacgctggct ggacttgcag gactgcaggt tccacctcgc tgcccgttc cttcattca    1500
cgttgagctg tgcagagaag gcaagaacct tctgaagcat tttcgattcc gtgacttgga    1560
agaggatccg tacctccctg gtaatcccg tgaactgatt gcctatagcc agtatccccg    1620
gccttcagac atccctcagt ggaattctga caagccgagt ttaaaagata taaagatcat    1680
gggctattcc atacgcacca tagactatag gtatactgtg tgggttggct tcaatcctga    1740
tgaatttcta gctaactttt ctgacatcca tgcaggggaa ctgtattttg tggattctga    1800
cccattgcag gatcacaata tgtataatga ttcccaaggt ggagatcttt tccagttgtt    1860
gatgccttga gttttgccaa ccatggatgg caaatgtgat gtgctccctt ccagctggtg    1920
agaggaggag ttagagctgg tcgttttgtg attacccata atattggaag cagcctgagg    1980
gctagttaat ccaaacatgc atcaacaatt tggcctgaga atatgtaaca gccaaacctt    2040
ttcgtttagt ctttattaaa atttataatt ggtaattgga ccagttttt ttttaatttc    2100
cctctttta aaacagttac ggcttattta ctgaataaat acaaagcaaa caaactcaag    2160
ttatgtcata ccttttggata cgaagaccat acataataac caaacataac attatacaca    2220
aagaatactt tcattatttg tggaatttag tgcatttcaa aaagtaatca tatatcaaac    2280
taggcaccac actaagttcc tgattatttt gtttataatt taataatata tcttatgagc    2340
cctatatatt caaaatatta tgttaacatg taatccatgt ttcttttca aatctaaagt    2400
taaaaaaaa tagcagaagc cagtgtctta aagtctatct tttgtttcta agaccatggg    2460
atttcataat ctcaagataa aatatgtatg aagtaattaa tgtagaattt ttacaccaaa    2520
taataaataa tgcttaataa actagagata tgagatgtgt aggaaatttg gttaaacttt    2580
tttcagatac tttctggccc aaataataat ttgttagcaa ataatatgac ccttgaactc    2640
aatggccatc tattaaaaga ctgttgttca cactggaaaa catttaaaga tgtgactata    2700
tccatgggtg gattgaatca ctcaaaatat attagtatcc ttctttaggg atggttggtt    2760
acagacatgt atttattcag gaggcagaaa atattccatt ttaattgctt attaaagaaa    2820
acattaaatt ctaaattatt ttgaggactg tgaagacttt tcattagtgt aatattaggt    2880
cattgtcaat ctcccagaat gtagttctat attctctaaa tatgaaagta tccagaaagg    2940
ccagtggtag taaaaagctt agtgtatata atctcaaaag ggatggaata tttacaactc    3000
atatttataa catgttgaat cttctcagtt atcagtagtc atcagaagtg tcaatagctt    3060
tctaaataaa tattaaatat ctactgtcct gtagtgaagg agtaattttt agtaattttc    3120
tctttacaaa gtctccagtg tttccaggta aatatttgtg aaacaaaata cagcaaacta    3180
cattgttact tcagtgtatt gttgccaaaa atgacaagat attatattaa aatcagtaaa    3240
ttttagacag atttttaaaaa ttaattagcc tacaatagag gttatatggt aacacggtga    3300
tcttctaagc agttaagtga ctgactgttc tggcaacaac gacttctccg tgactgaagg    3360
gccctgttca tttcctgatc ctgaagctcg tctctctttt gagcctccgc ttgctttggt    3420
cgatggtttc cctcagcttt ttctttgctg ttcttcatcc tcgttgttgc tgtcatcatg    3480
ttcactgtgg cttttacaat acagcctgta aattccttat gacatagttc agtgcatttg    3540
gctttattgc ctgctccaca gttctttacc tttacttggc ttagagaaac tgtatctttg    3600
ttgcttcata taacctttcc ccaaccccac taagctggac ataacttatt agtggtcctc    3660
ccgtcacttt atttgtagaa atctctcttt cacatgagca ggggttcttt catgtggttt    3720
```

```
agctgacagc agaactagtg attctagaca ttttgcatgg ccctcattca gtggctcaca   3780
aacatgaggg agcatcagaa ctacttgagg ggcttgttaa acccagtgc gttagaagtc    3840
ggatgcggtg gctcacacct gtaatcccag cactttggga ggcccaggca ggcggatcac   3900
ttgaggttag gagttcaaga ccagcctggc caacatggtg aaaccccgtc tctactaaaa   3960
atacaaaagt tagccgggtg tggtggtgca tgcctgtaat cccagcttct gggaggcca    4020
aggcacaaga atcgcttgaa ccaggagacg gaggtttcag tgaatgaaga tcgtgccatt   4080
gtattccagc ctcggcaaca cagcaggact gtgattttct ttggagactc ctagattttc   4140
tgtggttttg aactgaattt gttggatgtt ggcaagtgcc tcttatgagc tgtttcttta   4200
tcctgcattt gccccacaaa gacttatctg gaggtgagca agtatgtttt ggtagtgagg   4260
tcacaaaggc aatcagcccc ttcctcccca ctcccattgc catcttctca gtccttctcc   4320
ctttctttcc aagtagttta cccacccctc ctctttcctc ccctgtccct aaaataatcc   4380
acgtgtcttc ctaaaatctc tctttgatcc tgtcctttga taacaccgtc agtgcctact   4440
actgggtcta gacagacctc tgttgagcag tcagagtctt ccctgactcc acaatgcccc   4500
ttccttggc tgaccagtat gactactggt ccccaccttt ccttgccta tcctacctc    4560
cctcctacta ggttgtccca tccctctctt cacccattca ttcatgacca ttttcacta   4620
ccaagctccc cccctcccga aggaggctga ggttttgtg actctctaga ctctattgtg   4680
ggatggaatg aacattgcta aagaatcttg tgttcgcttt actttaaaaa ggtatttttt   4740
tcctaattat aaaactgatg tgtcagttac ggaaaaatta gaaatgcagc acaaatacat   4800
gaatattta ccacaaaatt gccatataat atcttgtctt ttttgggggt gtgaattttt   4860
tgcattgttc tggtcatatt ctttatcatg taatttatgt tctttttac taagtattat   4920
gtgtggttat tatagatttt cacaaagata tattgctggt aatatatttt attgtgtagt   4980
cttataattt acttaaccctt ctttcaattg ttagaaatttt aggctatttc cagattttca  5040
gtattgtaaa taatgctgtg atgaccaatt ttgtgaataa aatgttttta tgtatttcag   5100
attattccct taggatagtc tctcagtgcc aagttgtcaa aaacatctct attttgctta   5160
tcttcctgct ctcttgctgc cttaggggt agtaaactga aacataaagt aaacatgcat    5220
acaaataaaa aacataaaac aaaaataagc aacctgatgg taataggtga agtggtaac    5280
ctgttttaac tttgaattct tgccgggcgc ggtggctcac gcctgtaatc ccagcacttt   5340
gggaggctga ggcgggtgga tcacgaggtc aggagttcaa aaccagcctg gccaagatgg   5400
tgaaatcccg tctctactaa aaatacaaaa attagccggg cgtggtggcg ggcgcctgta   5460
atcccagcta cttgggaggc tgaggcagag aattgcttga acccaggagg cggaggttgc   5520
agtgagccaa gatcgcgcca ctgcactcca gcctgggtga cagagcgaga ctccgtctca   5580
aataaaaaac aacaaaaac aaaaaaaact taaaattctt tgcttgttag tgaccttgat   5640
catggttctc tttgtacgat agtttgggcat ctgtatttcc acttgtgtga atttgccttt   5700
aaattttggt tatgggtttc accttttaaa ataatcaaac atatttatct tttcctgtgt   5760
gataggtttt tttctgtatc ttttcctgtt aaacacacag acccctcccc aatctggaca   5820
ttgaataaat attcattttc ctttgcattg ttaaaaaaaa aaaaaaaaaa aaaaaa       5876
```

<210> SEQ ID NO 12
<211> LENGTH: 550
<212> TYPE: PRT
<213> ORGANISM: Homo sapiens

<400> SEQUENCE: 12

```
Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415
```

```
Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Leu Ile Ala Tyr Ser
450                     455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
                515                 520                 525

Pro Leu Gln Asp His Asn Met Tyr Asn Asp Ser Gln Gly Gly Asp Leu
            530                 535                 540

Phe Gln Leu Leu Met Pro
545                 550

<210> SEQ ID NO 13
<211> LENGTH: 4325
<212> TYPE: DNA
<213> ORGANISM: Homo sapiens

<400> SEQUENCE: 13
cacaggtcac ggggcggggc cgaggcggaa gcgcccgcag cccggtaccg gctcctcctg      60
ggctccctct agcgccttcc ccccggcccg actccgctgg tcagcgccaa gtgacttacg     120
cccccgaccc tgagcccgga ccgctaggcg aggaggatca gatctccgct cgagaatctg     180
aaggtgccct ggtcctggag gagttccgtc ccagcccgcg gtctcccggt actgtcgggc     240
cccggccctc tggagcttca ggaggcgccc gtcagggtcg gggagtattt gggtccgggg     300
tctcagggaa gggcggcgcc tgggtctgcg gtatcggaaa gagcctgctg gagccaagta     360 gccctcccte tcttgggaca gacccctcgg tcccatgtcc atgggggcac gcggtccct      420 cctcctggcc ctggctgctg gctggccgt tgcccgtccg cccaacatcg tgctgatctt     480
tgccgacgac ctcggctatg ggacctgggc tgctatggg cacccagct ctaccactcc      540 caacctggac cagctggcgg cgggagggct gcggttcaca gacttctacg tgcctgtgtc     600
tctgtgcaca ccctctaggg ccgccctcct gaccggccgg ctcccggttc ggatgggcat     660
gtaccctggc gtcctggtgc ccagctcccg ggggggcctg ccctggagg aggtgaccgt      720 ggccgaagtc ctggctgccc gaggctacct cacaggaatg gccggcaagt ggcaccttgg     780
ggtggggcct gaggggggcct tcctgccccc ccatcagggc ttccatcgat ttctaggcat     840
cccgtactcc cacgaccagg gccctgcca gaacctgacc tgcttcccgc cggccactcc      900
ttgcgacggt ggctgtgacc agggcctggt ccccatccca ctgttggcca acctgtccgt      960
ggaggcgcag ccccctggc tgccggact agaggcccgc tacatggctt cgcccatga     1020 cctcatggcc gacgcccagc gccaggatcg ccccttcttc ctgtactatg cctctcacca     1080
cacccactac cctcagttca gtgggcagag ctttgcagag cgttcaggcc gcgggccatt     1140 tgggactcc ctgatggagc tggatgcagc tgtgggacc ctgatgacag ccatagggga     1200
cctggggctg cttgaagaga cgctggtcat cttcactgca gacaatggac ctgagaccat     1260
gcgtatgtcc cgaggcggct gctccggtct cttgcggtgt ggaaagggaa cgacctacga     1320
```

-continued

```
gggcggtgtc cgagagcctg ccttggcctt ctggccaggt catatcgctc ccggcgtgac    1380
ccacgagctg gccagctccc tggacctgct gcctaccctg gcagcccggg ctggggcccc    1440
actgcccaat gtcaccttgg atggctttga cctcagcccc ctgctgctgg cacaggcaa    1500
gagccctcgg cagtctctct tcttctaccc gtcctaccca gacgaggtcc gtggggtttt    1560
tgctgtgcgg actggaaagt acaaggctca cttcttcacc cagggctctg cccacagtga    1620
taccactgca gaccctgcct gccacgcctc cagctctctg actgctcatg agcccccgct    1680
gctctatgac ctgtccaagg accctggtga aactacaaac ctgctggggg gtgtggccgg    1740
ggccacccca gaggtgctgc aagccctgaa acagcttcag ctgctcaagg cccagttaga    1800
cgcagctgtg accttcggcc ccagccaggt ggcccggggc gaggaccccg ccctgcagat    1860
ctgctgtcat cctggctgca ccccccgccc agcttgctgc cattgcccag atccccatgc    1920
ctgagggccc ctcggctggc ctgggcatgt gatggctcct cactgggagc ctgtggggga    1980
ggctcaggtg tctggagggg gtttgtgcct gataacgtaa taacaccagt ggagacttgc    2040
agatgtgaca attcgtccaa tcctggggta atgctgtgtg ctggtgccgg tccctgtgg    2100
tacgaatgag gaaactgagg tgcagagagg ttcaggactt gtacaagatc acccagccag    2160
aaagaggttg ggctgggatt tgaaccctgg tgtcgtggct ctggaagctg ccctggcgcc    2220
ttggtgatct gcgtgggtca gtgcacacag gcacacgtca gcctcaagga catgggcaca    2280
tctgttcaca ggagcagcgc cacgtgcctt tgagtgccag gaacggggtg ggagggtggg    2340
agggtgtgag ggccagaaga ctcagaagat gcaaagtgcc tgagagagac gggatattcc    2400
cccagaagaa gcattcttag agacacaggc actggacctc cttggttctt ataagaaacc    2460
tgtctgaagc tgggtgatga gttgcacact ccaggtgggg ctaagggccc tggagcccct    2520
gctggctcct aggaaggcac agcagcaggc cctgagacgg ctcctctggg gcccctccac    2580
cctcccaggc ctctgcattt cacctgtgcc cacacttctg tctcctgcct tcaccttttg    2640
acccactact aacgattctc cacccagcag acaaagtgat ctcttaaaaa tatctgttgg    2700
ctgggcacgg tggctcacgc ctgtaatccc agcactttag gaagccgagg cgggtggatc    2760
acctgaggtc gggagttcga gaccagcctg accaacatgg agaaacccca tctctactaa    2820
aaatacaaaa ttagccaggt gtagtggtgc atccctgtaa tcccagctac ttgggagtct    2880
gaggctggag aatcacttga acctgggagg cggtggttgc agtgagccga gatcgcacca    2940
ttgcactcca gcctgggcaa caagagaaaa actctgtctc aaaaaacaaa aaatctgtta    3000
ggctgcacac ggcgattcac tcctgtattc ccagtgcttt gggaggctga ggtgagagga    3060
tgcctgaggc caggaattca gaccagcctg ggcaacatag tgagacccca gctctaaaga    3120
tttgttttg tttttttttt tttttttttt tttttttttt ttttttttt gagacggagt    3180
ctcgctctgt cgcccaggct agagtgcagt ggtaccatct ccgctcactg caacctccgc    3240
ctcccgggtt ccaggattc tcctgcctca gcctccctag tagctggaac tacaggtgtg    3300
tgctgccatg cccagctaat ttttttttat ttaatagaga caagatttca ccatgttggc    3360
caggctggtc tcaaactcct gacctcaggt gatccaccg cctcagcctc ccaaagtgct    3420
gggattacag gtgtgaacca ccacacctgg ccaacaatat ttgttttaat tagccaggcg    3480
tggtagcatt tgtcctagca atttgggagg ttgaggtggg agaatcactt cagcccacta    3540
ggtcgaggct gtagtgagct ataattgtac cactgcactc cagcctcggg acagagtga    3600
gaccctgtct gcaaataaac aaataaaaca tcaggctggg cttgagcatc tattcctgct    3660
```

-continued

```
caaaatttcg caggcttctc agaagaaaat ccaaacccct tacagtgacc cagtttgccc    3720
ttgaggcctc cacccacacc ccctttcccc cagtcttagg gggtggcctg gctgttccct    3780
tcaacggcaa cgctctgcct ccattgttgg cctcctctgc agggagggac tgtctgagca    3840
cctgcccgtg tctgtgcagc atggcacact gacgtcaggc ccacgtgcat gcccaggtgg    3900
ccagtcacac gccaggtgct ccctcagtgt tggccaagtg agaggagcac accttccggg    3960
cgttcagaca cctccccgtg gcagacaccg ttcgttgcta ccaaacagcc acctccttcc    4020
taatgggctc ccattttttca gtgctgggca aaggtcccctt gatcttggag ttgcagcctc    4080
tttctctcca aggagggcgg tgaccagcct gagccagtca atccagtgat tggttcagga    4140
gtagcctgtg accaggagtc ctggtagtga acgactgggg cagccctggg ggtgaggacc    4200
ttgcgcagcc gtcacaggcc ctgattggac actgggcagc tgctaaccca gtgtctccag    4260
ctgcctacct ggagagctcc aagcgtaaga aaataaaccc tgcctgttga agccaaaaaa    4320
aaaaa                                                                4325
```

<210> SEQ ID NO 14
<211> LENGTH: 509
<212> TYPE: PRT
<213> ORGANISM: Homo sapiens

<400> SEQUENCE: 14

```
Met Ser Met Gly Ala Pro Arg Ser Leu Leu Ala Leu Ala Ala Gly
1               5                   10                  15

Leu Ala Val Ala Arg Pro Pro Asn Ile Val Leu Ile Phe Ala Asp Asp
                20                  25                  30

Leu Gly Tyr Gly Asp Leu Gly Cys Tyr Gly His Pro Ser Ser Thr Thr
            35                  40                  45

Pro Asn Leu Asp Gln Leu Ala Ala Gly Gly Leu Arg Phe Thr Asp Phe
        50                  55                  60

Tyr Val Pro Val Ser Leu Cys Thr Pro Ser Arg Ala Ala Leu Leu Thr
65                  70                  75                  80

Gly Arg Leu Pro Val Arg Met Gly Met Tyr Pro Gly Val Leu Val Pro
                85                  90                  95

Ser Ser Arg Gly Gly Leu Pro Leu Glu Glu Val Thr Val Ala Glu Val
                100                 105                 110

Leu Ala Ala Arg Gly Tyr Leu Thr Gly Met Ala Gly Lys Trp His Leu
            115                 120                 125

Gly Val Gly Pro Glu Gly Ala Phe Leu Pro Pro His Gln Gly Phe His
        130                 135                 140

Arg Phe Leu Gly Ile Pro Tyr Ser His Asp Gln Gly Pro Cys Gln Asn
145                 150                 155                 160

Leu Thr Cys Phe Pro Pro Ala Thr Pro Cys Asp Gly Gly Cys Asp Gln
                165                 170                 175

Gly Leu Val Pro Ile Pro Leu Leu Ala Asn Leu Ser Val Glu Ala Gln
            180                 185                 190

Pro Pro Trp Leu Pro Gly Leu Glu Ala Arg Tyr Met Ala Phe Ala His
        195                 200                 205

Asp Leu Met Ala Asp Ala Gln Arg Gln Asp Arg Pro Phe Phe Leu Tyr
    210                 215                 220

Tyr Ala Ser His His Thr His Tyr Pro Gln Phe Ser Gly Gln Ser Phe
225                 230                 235                 240

Ala Glu Arg Ser Gly Arg Gly Pro Phe Gly Asp Ser Leu Met Glu Leu
                245                 250                 255
```

Asp Ala Ala Val Gly Thr Leu Met Thr Ala Ile Gly Asp Leu Gly Leu
                260                 265                 270

Leu Glu Glu Thr Leu Val Ile Phe Thr Ala Asp Asn Gly Pro Glu Thr
        275                 280                 285

Met Arg Met Ser Arg Gly Gly Cys Ser Gly Leu Leu Arg Cys Gly Lys
290                 295                 300

Gly Thr Thr Tyr Glu Gly Gly Val Arg Glu Pro Ala Leu Ala Phe Trp
305                 310                 315                 320

Pro Gly His Ile Ala Pro Gly Val Thr His Glu Leu Ala Ser Ser Leu
                325                 330                 335

Asp Leu Leu Pro Thr Leu Ala Ala Leu Ala Gly Ala Pro Leu Pro Asn
                340                 345                 350

Val Thr Leu Asp Gly Phe Asp Leu Ser Pro Leu Leu Leu Gly Thr Gly
            355                 360                 365

Lys Ser Pro Arg Gln Ser Leu Phe Phe Tyr Pro Ser Tyr Pro Asp Glu
        370                 375                 380

Val Arg Gly Val Phe Ala Val Arg Thr Gly Lys Tyr Lys Ala His Phe
385                 390                 395                 400

Phe Thr Gln Gly Ser Ala His Ser Asp Thr Thr Ala Asp Pro Ala Cys
                405                 410                 415

His Ala Ser Ser Ser Leu Thr Ala His Glu Pro Pro Leu Leu Tyr Asp
                420                 425                 430

Leu Ser Lys Asp Pro Gly Glu Asn Tyr Asn Leu Leu Gly Gly Val Ala
        435                 440                 445

Gly Ala Thr Pro Glu Val Leu Gln Ala Leu Lys Leu Gln Leu Leu
450                 455                 460

Lys Ala Gln Leu Asp Ala Ala Val Thr Phe Gly Pro Ser Gln Val Ala
465                 470                 475                 480

Arg Gly Glu Asp Pro Ala Leu Gln Ile Cys Cys His Pro Gly Cys Thr
                485                 490                 495

Pro Arg Pro Ala Cys Cys His Cys Pro Asp Pro His Ala
                500                 505

<210> SEQ ID NO 15
<211> LENGTH: 6076
<212> TYPE: DNA
<213> ORGANISM: Homo sapiens

<400> SEQUENCE: 15
aaaagtgaat acatgatttt atttaactca ttaataagga aattggtaag gtgttaaaac      60
caattcaaag gacaatccaa agaacagatc aggaatacta aaataaatat gcaagcggag     120
gtgaaactgt tttccttggt agtggtggag gggaaggatt gctactccgc tggataaagt     180
tcatttgtgt atatataaat aagaattatt ttccattgtt atttatctat aacttataaa     240
gttgtaaaca acttccacgg aatcagactc aacctggaag ggtatggtct ctaggcaatg     300 caaaatttt cccctacacc tgttaacaac tataatatct ccagacagag tagacagaaa     360
gtctggatgg caacgggaat ctactggtca tacggctaac ttcctaattc aataagcacg     420
tgactaaagg atttttttcct tccactcaga tatttcaggc taactagata ctgtgtgctt     480
cttagtgtca ctgcttagtg ggggagccag ctctgagtgg ggtcatatcc ggacaagcga     540
atgagctatt tattcaatga ccacgcaaca ctccaaatcc tcccagggca acttgaaagt     600
aaccgcacct tccaaagggc accgtgcaat cagactgtgt gtttggcctc ctgtttgcta     660

| | | | | |
|---|---|---|---|---|
| gtggggagga | agcggcttca | tgggtgtaca | ctacgcataa | atgaatgtga | aaggctattt | 720 |
| agacctctgc | cttttcaccg | tcctcccacc | tgccacaggc | tgggctcttg | tgctagaaat | 780 |
| gacttgctag | ctagacatca | tggttcagga | tctgagtcag | aggtttaacc | atttataagc | 840 |
| ttttttctta | tgaaaaattg | gcactaatta | taatgtctaa | ctgtcagagt | tgttgcaggc | 900 |
| tttacaggag | acgcgggctg | tgaagatgct | ttgtaaattg | tgaagcgtta | ttaaagaaca | 960 |
| catcttttt | ttttaggaaa | ccacagtgca | aatttaattg | ccggggaaga | taacgggcct | 1020 |
| tggtgccctc | caagcgtcag | ctgagtttcc | aagaagccgg | gcagcgggcg | cccgcgggtt | 1080 |
| cgtctctggc | tcctcctccg | ccacagcagc | cgggggcccg | ggtcggaggc | ggcggggggcc | 1140 |
| gagcgcccgg | cctcgcaagc | ccacggcccg | ctggggtgc | cgtcccgcgc | cggggcggag | 1200 |
| caggcccccgg | cagcccagtt | cctcattcta | tcagcggtac | aaggggctgg | tggcgccaca | 1260 |
| ggcgctggga | ccgcgggcgg | acaaggatgg | gtccgcgcgg | cgcggcgagc | ttgccccgag | 1320 |
| gccccggacc | tcggcggctg | ctcctccccg | tcgtcctccc | gctgctgctg | ctgctgttgt | 1380 |
| tggcgccgcc | gggctcgggc | gccggggcca | gccggccgcc | ccacctggtc | ttcttgctgg | 1440 |
| cagacgacct | aggctggaac | gacgtcggct | tccacggctc | ccgcatccgc | acgccgcacc | 1500 |
| tggacgcgct | ggcggccggc | ggggtgctcc | tggacaacta | ctacacgcag | ccgctgtgca | 1560 |
| cgccgtcgcg | gagccagctg | ctcactgggc | gctaccagat | ccgtacaggt | ttacagcacc | 1620 |
| aaataatctg | gccctgtcag | cccagctgtg | ttcctctgga | tgaaaactc | ctgccccagc | 1680 |
| tcctaaaaga | agcaggttat | actacccata | tggtcggaaa | atggcacctg | ggaatgtacc | 1740 |
| ggaagaatg | ccttccaacc | cgccgaggat | ttgataccta | ctttggatat | ctcctgggta | 1800 |
| gtgaagatta | ttattcccat | gaacgctgta | cattaattga | cgctctgaat | gtcacacgat | 1860 |
| gtgctcttga | ttttcgagat | ggcgaagaag | ttgcaacagg | atataaaaat | atgtattcaa | 1920 |
| caaacatatt | caccaaaagg | gctatagccc | tcataactaa | ccatccacca | gagaagcctc | 1980 |
| tgttttctcta | ccttgctctc | cagtctgtgc | atgagcccct | tcaggtccct | gaggaatact | 2040 |
| tgaagccata | tgactttatc | caagacaaga | acaggcatca | ctatgcagga | atggtgtccc | 2100 |
| ttatggatga | agcagtagga | aatgtcactg | cagctttaaa | aagcagtggg | ctctggaaca | 2160 |
| acacggtgtt | catcttttct | acagataacg | gagggcagac | tttggcaggg | ggtaataact | 2220 |
| ggccccttcg | aggaagaaaa | tggagcctgt | gggaaggagg | cgtccgaggg | gtgggctttg | 2280 |
| tggcaagccc | cttgctgaag | cagaagggcg | tgaagaaccg | ggagctcatc | cacatctctg | 2340 |
| actggctgcc | aacactcgtg | aagctggcca | ggggacacac | caatggcaca | aagcctctgg | 2400 |
| atggcttcga | cgtgtggaaa | accatcagtg | aaggaagccc | atcccccaga | attgagctgc | 2460 |
| tgcataatat | tgacccgaac | ttcgtggact | cttcaccgtg | tcccaggaac | agcatggctc | 2520 |
| cagcaaagga | tgactcttct | cttccagaat | attcagcctt | taacacatct | gtccatgctg | 2580 |
| caattagaca | tggaaattgg | aaactcctca | cgggctaccc | aggctgtggt | tactggttcc | 2640 |
| ctccaccgtc | tcaatacaat | gtttctgaga | taccctcatc | agacccacca | accaagaccc | 2700 |
| tctggctctt | tgatattgat | cgggaccctg | aagaagaca | tgacctgtcc | agagaatatc | 2760 |
| ctcacatcgt | cacaaagctc | ctgtcccgcc | tacagttcta | ccataaacac | tcagtccccg | 2820 |
| tgtacttccc | tgcacaggac | ccccgctgtg | atcccaaggc | cactggggtg | tggggccctt | 2880 |
| ggatgtagga | tttcagggag | gctagaaaac | cttttcaattg | gaagttggac | ctcaggcctt | 2940 |
| ttctcacgac | tcttgtctca | tttgttatcc | caacctgggt | tcacttggcc | cttctcttgc | 3000 |
| tcttaaacca | caccgaggtg | tctaatttca | accccctaatg | catttaagaa | gctgataaaa | 3060 |

```
tctgcaacac tcctgctgtt ggctggagca tgtgtctaga ggtgggggtg gctgggttta    3120
tccccctttc ctaagccttg ggacagctgg gaacttaact tgaaatagga agttctcact    3180
gaatcctgga ggctggaaca gctggctctt ttagactcac aagtcagacg ttcgattccc    3240
ctctgccaat agccagtttt attggagtga atcacatttc ttacgcaaat gaagggagca    3300
gacagtgatt aatggttctg ttggccaagg cttctccctg tcggtgaagg atcatgttca    3360
ggcactccaa gtgaaccacc cctcttggtt caccccttac tcacttatct catcacagag    3420
cataaggccc attttgttgt tcaggtcaac agcaaaatgc ctgcaccatg actgtggctt    3480
ttaaaataaa gaaatgtgtt tttatcgtaa tttatttccc cccagccatt gctcactctg    3540
tctagacttc ctgccacttc caattcttct gtggcttttc ctgccttttc ttttgacctc    3600
agtagtccta tccctgggaa ggccactttg cttctctacc tgagcacccc tgatttctgg    3660
aacgctgctg agccctgcct tacttttgcc cctagggctg aagctagagg cctccccgta    3720
ataggcggtg gagttgctct gtgaggatgt tcatggtaga cactaagagg gctgggtggg    3780
agatgcttgg ctctgtggca tctgttcagc gaggcttttc ctatattgca tggagttagt    3840
cattgtgatt gtagctttat ttcataatat attaagactt gcactgctat ttactagcag    3900
tgagaagaaa cctcaggaaa ggatatgaaa aagcaagtgg ccagtgtctg ggatactggg    3960
ccttggtaaa gcagaggagg gcacacccac agtcctctta ttctctgttt tactgcttgt    4020
tttgaggttc tggggtctgg caaagaggat gcagtttgac acctgcagcc ctttctcaat    4080
cccactaatg tcttactaat gtggaacagt ccatattagc tccagagagt gtcaaaccca    4140
gagaaatgtg tgcaaaaatg atactctttt ctgcattagc cccaccattg tgttcaccaa    4200
tgcttggaac actgcctgaa ggcactcatt ttttaatttt tattttattt ttaattttt     4260
atatctttat gagacgatct cactctgtca ccaggttgga gtacagtggt acaatcacaa    4320
ctcaccgtag cctcaaactc ctgggctcaa gtgattctcc cacctcaggc acccaaatag    4380
ctggaactac aggcatatac cgccacaccc agctaatttt atttttttgaa aagacaaggt   4440
tccctatgtt gcccagctgg tcttaaactc ctgggctcca gcaattatcc cagcttgggc    4500
tccaaaagtg ctgggattac aggcatgagt caccatgcct ggcctcattt tttaaaacaa    4560
atgaataaat ggacaaatga gtaaatgaga aagtctcaca ccatgaaaga tgctagtcca    4620
atgagctgaa tacagaggta atataaatgt cttccagctg ttgcttttct gttctcaagc    4680
tgcccctcct ggggtaggag cataatctac atcactgggc agtcacagga cactctatag    4740
caaggttgta gcgtcctctc cagtgggggg agaaaaggaa ctgtgcctac caaaggtact    4800
ctcttgtcag caatttccat ttctatactt tatgggacac tagaaactaa aagcaacaaa    4860
taatctgata taagtccttg tatagtcatc cttcaattca gtagcaatat tttctggtca    4920
ctactaacct gtattgtatt aaaatgagac tattggaagg aaatggtgct aaaactaata    4980
acatctctta ccaaccttta cccaactcct gggttggcaa acagctgacc aaaactgccat   5040
cacctcccac ttggaagtgt atggccgaca gcatgaaata gctgagccca gatgttcctt    5100
ctgcatcctc cgaatcccag ggctgggtgt aggtagccgt tggaggccat cgctacaggg    5160
cacctatctg ttatcgctgc tgtcctccca acagctgtct ccagtctag ttccttggtt     5220
ttcaggcaca gtggggatg ttctgcaccc agtggacttc aaaagagttt tgaagactta     5280
atttttgta aaacaagtac ttgagatttt ggtttatcca taatagaatg tatttcatta     5340
gattctctga ttctatataa gaatgtgaaa agattgatat attgttgtta gaaataatgt    5400
```

-continued

```
tatttcttc  caattttttt  ttttttttt   tttgagatgg  agtctcgctc  tgtcacccag   5460
gctggagtgc  agtggtgtga  tctcggctca  ctgcagcctc  taactcccag  gttcaagcta   5520
ttctcctgcc  tcagcctccc  aagtagctgg  attacaggca  tacaccacca  cgcctggcta   5580
tgttttgtat  ttttcgtaga  gatagggttt  caccatgttg  gccaggctgg  tctcaaactc   5640
ctgacctcaa  gtgatccacc  cacttcagct  tcccaaagca  ctgggattac  aggtgtgagc   5700
cactgtgccc  ggcaaatttt  tttacccttta cagaaggttt  tgcttattta  attgtgagct   5760
catttttctt  tgttactttt  gtccccccag  atttggggga  caaataaaa   ttaatctttt   5820
aaaatgtgtc  agccatatgt  atggggcttc  catttgggt   gaggagaaag  ttctggaact   5880
agatagtggt  catggttata  caacatcata  aatgcaatta  ctgccactga  attgtatgtt   5940
ttaaagtggt  taaatgtta   agttttatgt  tttattacaa  tttttaaatg  tgtcaaccaa   6000
ctttatagta  cataaattat  atctcagtaa  agctgttaaa  taaataaata  tagtaaaaat   6060
tttagaacta  aaaaaa                                                      6076
```

<210> SEQ ID NO 16
<211> LENGTH: 533
<212> TYPE: PRT
<213> ORGANISM: Homo sapiens

<400> SEQUENCE: 16

```
Met Gly Pro Arg Gly Ala Ala Ser Leu Pro Arg Gly Pro Gly Pro Arg
1               5                   10                  15

Arg Leu Leu Leu Pro Val Val Leu Pro Leu Leu Leu Leu Leu Leu Leu
            20                  25                  30

Ala Pro Pro Gly Ser Gly Ala Gly Ala Ser Arg Pro Pro His Leu Val
        35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
                85                  90                  95

Gln Leu Leu Thr Gly Arg Tyr Gln Ile Arg Thr Gly Leu Gln His Gln
            100                 105                 110

Ile Ile Trp Pro Cys Gln Pro Ser Cys Val Pro Leu Asp Glu Lys Leu
        115                 120                 125

Leu Pro Gln Leu Leu Lys Glu Ala Gly Tyr Thr Thr His Met Val Gly
    130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
                165                 170                 175

Ser His Glu Arg Cys Thr Leu Ile Asp Ala Leu Asn Val Thr Arg Cys
            180                 185                 190

Ala Leu Asp Phe Arg Asp Gly Glu Glu Val Ala Thr Gly Tyr Lys Asn
        195                 200                 205

Met Tyr Ser Thr Asn Ile Phe Thr Lys Arg Ala Ile Ala Leu Ile Thr
    210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Glu Tyr Leu Lys Pro Tyr Asp
                245                 250                 255
```

```
Phe Ile Gln Asp Lys Asn Arg His His Tyr Ala Gly Met Val Ser Leu
                260                 265                 270
Met Asp Glu Ala Val Gly Asn Val Thr Ala Ala Leu Lys Ser Ser Gly
            275                 280                 285
Leu Trp Asn Asn Thr Val Phe Ile Phe Ser Thr Asp Asn Gly Gly Gln
        290                 295                 300
Thr Leu Ala Gly Gly Asn Asn Trp Pro Leu Arg Gly Arg Lys Trp Ser
305                 310                 315                 320
Leu Trp Glu Gly Gly Val Arg Gly Val Gly Phe Val Ala Ser Pro Leu
                325                 330                 335
Leu Lys Gln Lys Gly Val Lys Asn Arg Glu Leu Ile His Ile Ser Asp
            340                 345                 350
Trp Leu Pro Thr Leu Val Lys Leu Ala Arg Gly His Thr Asn Gly Thr
        355                 360                 365
Lys Pro Leu Asp Gly Phe Asp Val Trp Lys Thr Ile Ser Glu Gly Ser
            370                 375                 380
Pro Ser Pro Arg Ile Glu Leu Leu His Asn Ile Asp Pro Asn Phe Val
385                 390                 395                 400
Asp Ser Ser Pro Cys Pro Arg Asn Ser Met Ala Pro Ala Lys Asp Asp
                405                 410                 415
Ser Ser Leu Pro Glu Tyr Ser Ala Phe Asn Thr Ser Val His Ala Ala
            420                 425                 430
Ile Arg His Gly Asn Trp Lys Leu Leu Thr Gly Tyr Pro Gly Cys Gly
        435                 440                 445
Tyr Trp Phe Pro Pro Ser Gln Tyr Asn Val Ser Glu Ile Pro Ser
            450                 455                 460
Ser Asp Pro Pro Thr Lys Thr Leu Trp Leu Phe Asp Ile Asp Arg Asp
465                 470                 475                 480
Pro Glu Glu Arg His Asp Leu Ser Arg Glu Tyr Pro His Ile Val Thr
                485                 490                 495
Lys Leu Leu Ser Arg Leu Gln Phe Tyr His Lys His Ser Val Pro Val
            500                 505                 510
Tyr Phe Pro Ala Gln Asp Pro Arg Cys Asp Pro Lys Ala Thr Gly Val
        515                 520                 525
Trp Gly Pro Trp Met
    530

<210> SEQ ID NO 17
<211> LENGTH: 6377
<212> TYPE: DNA
<213> ORGANISM: Homo sapiens

<400> SEQUENCE: 17
tccgcctcac attatctgcc caagcacagt gctgttggcc aagcctccag cagctgacgg      60
gacccagctg tagtgaggtt gcagtgattg agtaggattg cctgcttca aagcagaggt     120 ttctcatggg aatatgctta ttaaactccc actggtgcag aaaccatgaa cagaggatga     180
acaagtgaag ttgcaatctc ctccatcaca gctcagttcc ccaacaacag gatcacaagc     240
tggagatgcc tttaaggaag atgaagatcc ctttcctcct actgttcttt ctgtgggaag     300
ccgagagcca cgcagcatca aggccgaaca tcatcctggt gatggctgac gacctcggca     360
ttggagatcc tgggtgctat gggaacaaaa ctatcaggac tcccaatatc gaccggttgg     420
ccagtggggg agtgaaactc actcagcacc tggcagcatc accgctgtgc acaccaagca     480
```

```
gggcagcctt catgactggc cggtaccctg tccgatcagg aatggcatct tggtcccgca    540
ctggagtttt cctcttcaca gcctcttcgg gaggacttcc caccgatgag attacctttg    600
ctaagcttct gaaggatcaa ggttattcaa cagcactgat agggaaatgg caccttggga    660
tgagctgtca cagcaagact gacttctgtc accacccttt acatcacggc ttcaattatt    720
tctatgggat ctctttgacc aatctgagag actgcaagcc cggagagggc agtgtcttca    780
ccacgggctt caagaggctg gtcttcctcc ccctgcagat cgtcgggtc accctcctta     840 cccttgctgc actcaattgt ctggggctac tccacgtgcc tctaggcgtt ttttcagcc     900 ttctcttcct agcagcccta atcctgaccc ttttcttggg cttccttcat tacttccggc    960
ccctgaactg cttcatgatg aggaactacg agatcattca gcagcccatg tcctatgaca   1020
atctcaccca gaggctaacg gtggaggcgg cccagttcat acagcggaac actgagactc   1080
cgttcctgct tgtcttgtcc tacctccacg tgcacacagc cctgttctcc agcaaagact   1140
ttgctggcaa aagtcaacac ggagtctacg gggatgctgt tgaggaaatg gactggagtg   1200
tggggcagat cttgaacctt ctggatgagc tgagattggc taatgatacc ctcatctact   1260
tcacatcgga ccaggagca catgtagaag aagtgtcttc caaggagaa attcatggcg     1320 gaagtaatgg gatctataaa ggaggaaaag caaacaactg gaaggaggt atccgggttc    1380 caggcatcct tcgttggccc agggtgatac aggctggcca agagattgat gagcccacta   1440
gcaacatgga catatttcct acagtagcca agctggctgg agctcccttg cctgaggaca   1500
ggatcattga tggacgtgat ctgatgcccc tgcttgaagg aaaaagccaa cgctccgatc   1560
atgagtttct cttccattac tgcaacgcct acttaaatgc tgtgcgctgg caccctcaga   1620
acagcacatc catctggaag gccttttct tcaccccca cttcaacccc gtgggttcca    1680
acggatgctt tgccacacac gtgtgcttct gtttcgggag ttatgtcacc catcacgacc   1740 caccttact ctttgatatt ccaaagatc cagagagag aaacccacta actccagcat     1800
ccgagccccg gttttatgaa atcctcaaag tcatgcagga agctgcggac agacacaccc   1860
agaccctgcc agaggtgccc gatcagtttt catggaacaa cttttctttgg aagccctggc  1920 ttcagctgtg ctgtccttcc accggcctgt cttgccagtg tgatagagaa aaacaggata   1980
agagactgag ccgctagcag cgcctgggga ccagacagac gcatgtggca aagctcacca   2040
tcttcactac aaaacgcct gagagtggca ctggggaaac ataactccat ctacaccttg    2100
gatttggact gattctccat tttatcacct gaaggcttgg gccagagctc aacagctact   2160
caactggagg ggtgagggg ataaggtctg tagtatacag acaggaagat ggtaggttta    2220
tgccttctgt ggccagagtc ttggactcat ggaaatagaa tgaatagagg ggcattcaca   2280
aggcacacca gtgcaagcag atgacaaaaa ggtgcagaag gcaatcttaa aacagaaagg   2340
tgcaggaggt accttaactc acccctcagc aaatacctat gtcaacagta taagttacca   2400
tttactctat aatctgcagt gatgcaataa ccagcataat aaaaaggcaa tcacataaaa   2460
aagagtttag tcgtctaaac ataagtaact ttaaggtgaa tgaaagatct tctttaggaa   2520
taatagatga tggtaagttc cactttggtt attggaaggc aagtcattat tactggtatt   2580
agttaaaaca catatcaaat gcttgctctt catcatatat atagttatgc atacatacac   2640
acacacacat acagtatatt cttcctcaa aagggttaag atgtctaaaa tagggaccta    2700
gaagcttaac actatttaag taaatacagt agaagctcac aaatagattt ctttgcacaa   2760
tgattttttg caaaattta cagtaataat aatcccaagg caaatctctc ctgaactgct    2820
ttccattcca taatttgtag tataattctt ggattccact gttttctttg gggaatggaa   2880
```

```
gttctgaatt aaaagcccac tgtggagatg ctgtggttca tggaatctct tccagtgtaa    2940
ttcagaatca ttggcctaga aagtctctga tatttggagg ggaacaaaaa tcactcacaa    3000
gcaatccatg atctatacac ataagcataa tttcctttag ttctagttag tcatcagaga    3060
acagtcatgt atgcaagttt tgtgactgag aaatttctgt gcttccaatc cacaatgaga    3120
tgcatgattt tgttttcatc ccatttcccc caagcccctg taaatcaggg aaaatgcgca    3180
actgatcgcc taggagaggg cctcgtagtg gcacagctgg agatagtttc aaagtctaaa    3240
ccaccagccc atcctgagga aagcctccta tggaatgtaa agtgcaatca tttcttcaga    3300
tataagactt tccccaacaa tgtgattgga ttcctttatg gcaaaatcga gagaagctgc    3360
catccacctg cttatgcatt tatctctttt gtggacttgt ctgaccacct tctatttgcc    3420
cagagtttgc tcaattccaa gacagtgccc atgaatggga cacctgtaat gtaacccaca    3480
cagcggtttg cagagaatgt tagccatgac ttgggctttc tgaaagttgg ctataatttc    3540
tctatcccta cccacaaccc tgggaagttg gagcaagagg ggcatactat tgggctggga    3600
ggatttgaca gcatttcccc agttgccctt taagttcttc tatttcaaac gttaattttg    3660
cttctctttc taaaaaaaaa aaaaaaaaag aagagaagaa aagaagtgat tcctaccccc    3720
tacctccaga gttgttgaaa gctgaaaagc atacaagatt cttccttta acttggattt    3780 ctcgttccag aaattgtggg ataatctgta ttcttgcttt agaaaacatt cttagagagg    3840
gtactagctt actgatgatg tgttaggatt gctactgatg ctgtcatgtg gaaactattt    3900
aaaggcacta ttataaattt atcctataag atgacaatgt ttactcaaag tctaacatat    3960
tcaatgcaag taagactttc tgaaaacact tgatgatgtg gaaatgctgc aggattaaat    4020
aacttgaaga gccctttatag attatatgaa tgcctatttg tgtctagaac cagttattta    4080
acctgtaaaa tgtcaatagc aaatgaagga tgaagtatat ctctagatgc aaatacattg    4140
agtttaaaag tgcctcaaaa taattgagat cacatttcag gacatttgga aatcaggtcg    4200
atttgtggta actgtagtca tcttaaattt caaaccattt accatctgaa agttttgatt    4260
tgaatgtaaa acaggaaatt ggaattcctt tgtccaggag aaacctcaca aaccttcttt    4320
aaggcatagt tttgttgttt gtttgcttgt ttgttgcagg ctgtaaggca tggctgcttg    4380
tttacaaagc atctcattca tattacctgt ggagttgcat atccaaacct tagtgagttt    4440
tgaagcttta agcaaattct tttaaaaaat tcttgtattt ctagcattac tagatattaa    4500
aagttaagca aatagattaa tgacgtatac ataggcatca tttcacaagg tcagtaatgc    4560
tgcaggaaaa gcaaaattgc aatctacgta tctatggtac taaggaagtc ctgtttttca    4620
aaaatggaag cccacttctc agatttttct gaagggcata caatgaaaag tgaaggggaa    4680
acacacacac acaaaaaaac aagtatttgg cttgtcacag gaatctgatt gcattaagtg    4740
aaaggattat ttagaatatg ttaatgcaaa gctaaaataa aattttcctt ggcaattaaa    4800
aatgctgtgc gctaataccc tgcttttctat cgtgactcaa ttcaacaatg tggggaatgt    4860
ttactacatt tccaacttga tgtcaagcaa tggggaatac aagttccagt tctgcaaaga    4920
ttcgtcaact ttcttagctc aagagagagg ctgagaaatg cagagaagaa taagacataa    4980
aatagctccg acctccatga tccgagagtg ggaaaaggcc cgattattac ccataaggca    5040
cactctctaa ggccttttaa ggggcctaca aaatgttttt attttataat cagaagaaaa    5100
ggaaatgaac attggggatt gaaaatcata ttggtatttg caccaacata gtcataaaat    5160
agtatgttaa tatgtttta ctttatatat ttatatatta aaatatattt aatatgtttt    5220
```

-continued

```
gcctttgtgg cccatgaaag tcttactggg ccctggggaa ggtatcctac cctggtgaag    5280
cagctgcttt gctctacaaa tacctggggc agaaatttga tttgaaaagt attattctct    5340
cttctctttg tttcaactgg attcctttgg aaaaccaaac tagtatcaga acaaaccccg    5400
aaacagtaag aaattggagt gagaagggca tggtattggg actaggatcg gctctcattc    5460
gatcgagcta ttctcttaaa atgacaaaaa gtgtccataa agaggctgct ggagagtgcg    5520
tggccatagg gagccgacat gcccgggagg aaaggtgttg attacatgga tacttctaaa    5580
agctaaagcc ttgttgcctt ctctttaatg cctagagaat gggatgtgtg atgcaaatgc    5640
tcaaaacctc ttaaatcata gctgtctgac ctctacggac ctcacatcca tctgaggctt    5700
catggacaaa gattctccac ttggccaaac tttagccaag ctcctcaacc ttctcccagg    5760
cccaatctgg gcacttcctt gtaaaatcta gttttggcaa gaagtctatt aggtcagttt    5820
agcaagaaca cctaaccccc ccatatctgt tcaacctcag tatctgatca ggctcctcag    5880
cctccaccat cccccaggtg atgtctggtc aactggcctg ccttcagcta gaatcctgtt    5940
aggtcggttt agatgaatgc tccctgatat ttcctcttgg taatcttcca tccactgccc    6000
ctgaccctgt tccctgtcta taaatcccca gttttccatg gtgtattcag agctgagtcc    6060
agtctctctc ccctactaca agtccccatt gctgtggtcc ccgtacctgt catgatggtc    6120
ctaaataaag tcttactgtg ctttaatagg tagcattgaa aaatttttt ctttgacatc    6180
attcatgaca acatgaaacc tattgggaca gcatgactgt gcagggtctt tagagctcag    6240
ctttctgagg ccctgagcat tcttggtttt ccgacatcgt gaacctgttc tgtgttgcaa    6300
gatatcactc aagccagtgt tgcttaatac catctctttg tgtaatagat ctgaataaag    6360
taattgtaat acaccaa                                                   6377
```

<210> SEQ ID NO 18
<211> LENGTH: 583
<212> TYPE: PRT
<213> ORGANISM: Homo sapiens

<400> SEQUENCE: 18

```
Met Pro Leu Arg Lys Met Lys Ile Pro Phe Leu Leu Leu Phe Phe Leu
1               5                   10                  15

Trp Glu Ala Glu Ser His Ala Ala Ser Arg Pro Asn Ile Ile Leu Val
                20                  25                  30

Met Ala Asp Asp Leu Gly Ile Gly Asp Pro Gly Cys Tyr Gly Asn Lys
            35                  40                  45

Thr Ile Arg Thr Pro Asn Ile Asp Arg Leu Ala Ser Gly Gly Val Lys
        50                  55                  60

Leu Thr Gln His Leu Ala Ala Ser Pro Leu Cys Thr Pro Ser Arg Ala
65                  70                  75                  80

Ala Phe Met Thr Gly Arg Tyr Pro Val Arg Ser Gly Met Ala Ser Trp
                85                  90                  95

Ser Arg Thr Gly Val Phe Leu Phe Thr Ala Ser Ser Gly Gly Leu Pro
            100                 105                 110

Thr Asp Glu Ile Thr Phe Ala Lys Leu Leu Lys Asp Gln Gly Tyr Ser
        115                 120                 125

Thr Ala Leu Ile Gly Lys Trp His Leu Gly Met Ser Cys His Ser Lys
    130                 135                 140

Thr Asp Phe Cys His His Pro Leu His His Gly Phe Asn Tyr Phe Tyr
145                 150                 155                 160

Gly Ile Ser Leu Thr Asn Leu Arg Asp Cys Lys Pro Gly Glu Gly Ser
```

```
                165                 170                 175
Val Phe Thr Thr Gly Phe Lys Arg Leu Val Phe Leu Pro Leu Gln Ile
            180                 185                 190
Val Gly Val Thr Leu Leu Thr Leu Ala Ala Leu Asn Cys Leu Gly Leu
            195                 200                 205
Leu His Val Pro Leu Gly Val Phe Phe Ser Leu Leu Phe Leu Ala Ala
            210                 215                 220
Leu Ile Leu Thr Leu Phe Leu Gly Phe Leu His Tyr Phe Arg Pro Leu
225                 230                 235                 240
Asn Cys Phe Met Met Arg Asn Tyr Glu Ile Ile Gln Gln Pro Met Ser
                245                 250                 255
Tyr Asp Asn Leu Thr Gln Arg Leu Thr Val Glu Ala Ala Gln Phe Ile
            260                 265                 270
Gln Arg Asn Thr Glu Thr Pro Phe Leu Leu Val Leu Ser Tyr Leu His
            275                 280                 285
Val His Thr Ala Leu Phe Ser Ser Lys Asp Phe Ala Gly Lys Ser Gln
            290                 295                 300
His Gly Val Tyr Gly Asp Ala Val Glu Glu Met Asp Trp Ser Val Gly
305                 310                 315                 320
Gln Ile Leu Asn Leu Leu Asp Glu Leu Arg Leu Ala Asn Asp Thr Leu
                325                 330                 335
Ile Tyr Phe Thr Ser Asp Gln Gly Ala His Val Glu Glu Val Ser Ser
            340                 345                 350
Lys Gly Glu Ile His Gly Gly Ser Asn Gly Ile Tyr Lys Gly Gly Lys
            355                 360                 365
Ala Asn Asn Trp Glu Gly Gly Ile Arg Val Pro Gly Ile Leu Arg Trp
            370                 375                 380
Pro Arg Val Ile Gln Ala Gly Gln Lys Ile Asp Glu Pro Thr Ser Asn
385                 390                 395                 400
Met Asp Ile Phe Pro Thr Val Ala Lys Leu Ala Gly Ala Pro Leu Pro
                405                 410                 415
Glu Asp Arg Ile Ile Asp Gly Arg Asp Leu Met Pro Leu Leu Glu Gly
            420                 425                 430
Lys Ser Gln Arg Ser Asp His Glu Phe Leu Phe His Tyr Cys Asn Ala
            435                 440                 445
Tyr Leu Asn Ala Val Arg Trp His Pro Gln Asn Ser Thr Ser Ile Trp
            450                 455                 460
Lys Ala Phe Phe Phe Thr Pro Asn Phe Asn Pro Val Gly Ser Asn Gly
465                 470                 475                 480
Cys Phe Ala Thr His Val Cys Phe Cys Phe Gly Ser Tyr Val Thr His
                485                 490                 495
His Asp Pro Pro Leu Leu Phe Asp Ile Ser Lys Asp Pro Arg Glu Arg
            500                 505                 510
Asn Pro Leu Thr Pro Ala Ser Glu Pro Arg Phe Tyr Glu Ile Leu Lys
            515                 520                 525
Val Met Gln Glu Ala Ala Asp Arg His Thr Gln Thr Leu Pro Glu Val
            530                 535                 540
Pro Asp Gln Phe Ser Trp Asn Asn Phe Leu Trp Lys Pro Trp Leu Gln
545                 550                 555                 560
Leu Cys Cys Pro Ser Thr Gly Leu Ser Cys Gln Cys Asp Arg Glu Lys
                565                 570                 575
Gln Asp Lys Arg Leu Ser Arg
            580
```

<210> SEQ ID NO 19
<211> LENGTH: 5199
<212> TYPE: DNA
<213> ORGANISM: Homo sapiens

<400> SEQUENCE: 19

| | | | | | |
|---|---|---|---|---|---|
| cccagatccc | gcagctgaga | gggcggaagc | cttggcacta | gcggcgcccg | ggcgcggagt | 60 |
| gcgcagggca | aggtcctgcg | ctctgggcca | gcgctcggcc | atgcgatccc | ccgcgcggag | 120 |
| gggacgcgcc | gcgcccgccg | ccagggactc | tttgccggtg | ctactgtttt | tatgcttgct | 180 |
| tctgaagacg | tgtgaaccta | aaactgcaaa | tgcctttaaa | ccaaatatcc | tactgatcat | 240 |
| ggcggatgat | ctaggcactg | ggatctcgg | ttgctacggg | aacaatacac | tgagaacgcc | 300 |
| gaatattgac | cagcttgcag | aggaaggtgt | gaggctcact | cagcacctgg | cggccgcccc | 360 |
| gctctgcacc | ccaagccgag | ctgcattcct | cacagggaga | cattccttca | gatcaggcat | 420 |
| ggacgccagc | aatggatacc | gggcccttca | gtggaacgca | ggctcaggtg | gactccctga | 480 |
| gaacgaaacc | acttttgcaa | gatcttgca | gcagcatggc | tatgcaaccg | gcctcatagg | 540 |
| aaaatggcac | cagggtgtga | attgtgcatc | ccgcggggat | cactgccacc | acccctgaa | 600 |
| ccacggattt | gactatttct | acggcatgcc | cttcacgctc | acaaacgact | gtgacccagg | 660 |
| caggccccc | gaagtggacg | ccgccctgag | ggcgcagctc | tggggttaca | cccagttcct | 720 |
| ggcgctgggg | attctcaccc | tggctgccgg | ccagacctgc | ggtttcttct | ctgtctccgc | 780 |
| gagagcagtc | accggcatgg | ccggcgtggg | ctgcctgttt | ttcatctctt | ggtactcctc | 840 |
| cttcgggttt | gtgcgacgct | ggaactgtat | cctgatgaga | aaccatgacg | tcacggagca | 900 |
| acccatggtt | ctggagaaaa | cagcgagtct | tatgctaaag | gaagctgttt | cctatattga | 960 |
| aagacacaag | catgggccat | ttctcctctt | cctttctttg | ctgcatgtgc | acattcccct | 1020 |
| tgtgaccacg | agtgcattcc | tggggaaaag | tcagcatggc | ttatatggtg | ataatgtgga | 1080 |
| ggagatggac | tggctcatag | gtaaggttct | taatgccatc | gaagacaatg | gtttaaagaa | 1140 |
| ctcaacattc | acgtatttca | cctctgacca | tggaggacat | ttagaggcaa | gagatggaca | 1200 |
| cagccagtta | gggggatgga | acggaattta | caaaggtggg | aagggcatgg | aggatgggaa | 1260 |
| aggtgggatc | cgcgtgcccg | ggatcttcca | ctggccgggg | gtgctcccgg | ccggccgagt | 1320 |
| gattggagag | cccacgagcc | tgatgacgt | gttccctact | gtggtccagc | tggtgggtgg | 1380 |
| cgaggtgccc | caggacaggg | tgattgatgg | ccacagcctg | gtaccttgc | tgcagggagc | 1440 |
| tgaggcacgc | tcggcacatg | agttcctgtt | tcattactgt | gggcagcatc | ttcacgcagc | 1500 |
| acgctggcac | cagaaggaca | gtggaagcgt | ctggaaggtt | cattacacga | ccccgcagtt | 1560 |
| ccaccccgag | ggagcggggg | cctgctacgg | ccgaggcgtc | tgcccatgct | ccggggaggg | 1620 |
| cgtgacccat | cacagacccc | ctttgctctt | tgacctctcc | agggacccct | ccgaggcacg | 1680 |
| gccctgacc | cccgactccg | agccctgta | ccacgccgtg | atagcaaggg | taggtgccgc | 1740 |
| ggtgtcggag | catcggcaga | ccctgagtcc | tgtgcccag | cagttttcca | tgagcaacat | 1800 |
| cctgtggaag | ccgtggctgc | agccgtgctg | cggacatttc | ccgttctgtt | catgccacga | 1860 |
| ggatggggat | ggcacccct | gaatgccagg | actgtgagag | aggatccagg | agagcctgac | 1920 |
| tgcgttgcaa | acaaaattct | ccaagcttgg | ttctatcttc | agcttccctt | tttgcaagga | 1980 |
| acatgccctg | gactgagagt | gggtccccac | tttctttctt | tctttctttc | tttttgaga | 2040 |
| cagagtgtcg | ctctgtccct | caggctggaa | tgcaatggca | cgatctctgc | tcactgcaac | 2100 |

```
ctccgcctcc cgggttcaag cgatttcct gcctcagcct cctgagtacc caggattaca    2160
ggcaccaggc acctgccacc atgcctagct aatttttgta gttttagtag agacagggtt    2220
tcaccatgtt gcccaggctg gtctcgcact cctgacctca agtcatccac ctgcctcagc    2280
ctcccaaagt gctgggatta caggcacgag ccactgcgcc catgtagggt ttccctttcc    2340
tgatttgtga ataagactg tcccagtagg cacccactga tgcctcctct tcctcttcta    2400
aatctcaggg ttcgtcattg tgccaatgcc cgatgttttc accctccgt cttaaagcat    2460
tgttgcaatt tcatcaccta gatgacataa cagccttaca aaggacagg gaggagtgtc    2520
tgttcctact ctcacatagc ggaggaaagt tagagcctct cagtctctgt ttatgaggac    2580
tcattaatct caaataattg atgcatttt catacattag ggtctctgtc catgtgtctt    2640
cctgatattg ttatagaaat ggcttcaggc tgctggtaac agatgctgcg gaaaagaat     2700
gccttaaaca aagccaggca cggtgactca cacctgtaat cccagcactt tgggaggcta    2760
aggtgggagg atcacttgag cctaggagtt agacacctac ccagcctgag caacacagtg    2820
agacctcatc tctacaaaaa acaaataatt agctagatgt cgtggcgcac agctgtagtc    2880
tcagctactt aggaggctga ggcgggagga ttatttgagc ctgggaggtc aaaactgcaa    2940
tgagctaaga ttgcactact gcactccggg ctggagaca gagtaagacc ctgccttaaa     3000
aaaaaaaaa aaaaatgcc ttaaagaaaa taataagaga agggtgtgtt ctcttccaag      3060
taatgagccg atcaagggga agcaacccaa ggctagcagg ctctttcaa ttcccagctc     3120
tgccactctt agcatggcag agagttggcc tcattatgcc agtatggctg ccacagtgtc    3180
agacatcaca ttccaggcag tggaaggag aaagaaccaa agggcatccc ttctcttga     3240
agcagtccct gtgagggggg attatctgga agccccaacc caatttctgc ttccaaccat    3300
tatccataga aacaactgga agttgagaag tgcagtcttt taggtgggca cctggctgcc    3360
ctgtatgaaa ccagaattag gttggtcagc aggaaaacaa gaaaacactt actgtgttga    3420
ctgaggtttt tgacgcatcg ctttattgtc aaattaaaca actctatctc attctgcact    3480
gaaacacgta ctaccattgc ctataattgg aaaatgatcc tcagaggcac agaagatgcc    3540
ctgatggaaa gtttgcccct tgggcaaaga gacagccatg gaaccttca gacatagaga    3600
gagaaggtgg cttttctccc tacattcctc aaatagctaa gattggcca gtgtgttttc    3660
taagtcaatt ctagtgtgtt tcatcctcac ctcttccctc tgtggctttg atgatggaag    3720
tgtagtccta acctactgca cagctgggac cccctgcccc tagatcccaa tactggggat    3780
gggaggacct tgcactattc ccctcagtcc atctatcgag gtcttgcag gaagcatact    3840
gggaattgaa acgagagcct aaatgacatc taagaaaggc agtgttcaat accaggtatt    3900
aggtgaggat gggattctaa ggacatcagt gggaggcagg gagccacctt cagacctcag    3960
catggaagct tccaagatcc agaggaagag gcaacagcac tgagagtcat aggtagaaga    4020
atcatcacag ccctgctaac caggcagctg atgcccctct ccctggctc cctgtgtcca    4080
aatcctacag gggcatctgt tggctgaact caacctgaag ccaaagagaa gatgagtgga    4140
gagaggcaac atttatagag ctcaggtttc tagggctgga gagggatctg gagggacaca    4200
caggagacac ctggcataac caaaaaatga ttaaaaaaaa aaaaaaaaag aaacatctat    4260
ggagcatggg acacggggag tggaggcagc taaaagccat ctcatctttc accgtattca    4320
acaagcccat tataacaagt ctttcacgct caaccattca aacaatccca acaatcccag    4380
cctaagaatt tcctggcatt tgatgaaaat ggctgtgggt tttgctatct ttaagctccc    4440
tgggaagcag gatataagcc cagggctggc aggctctttc tagctacctg ctcttgcaca    4500
```

-continued

```
tagagtttgc ctcatggttg caagaaggct gccatagctc cagatggcac atagacattc    4560
caggcagcag gaaaaaggaa ggagcactta accgaaggag gtcagggagt tggttagtct    4620
ccacctgaag aagagagcca tgaaccagct tcagttgact aacgggctcc tgtgagtgca    4680
tctttggact tttctggagg ttgaaatcta gatgtggtat gtgtcttaaa gcagccacca    4740
actcctccca ttaccttcca agtgagccca actacacgat ggagcctctt ccctgccctt    4800
ggatctgggc tgagcctctg acttgcgttg accaacagaa tgcagtgaaa gtgatgccga    4860
tactaccctc cctgccctag acttgggata cctggcagct atattcttcc attcctcagg    4920
acttgcaaaa acgggtctca gcatgccttc ccagagccat gaggtgtttc tttgcccatt    4980
cattgatctg agaagtgagt gtaaggagtt taaatcaacc tctgttctgt gctagttaag    5040
gtaataaagt tgctgcagtc caggggtag gtacctgtgg acggctctgc gaataggaca    5100
gttgcatttc ttgggaatca agtgcatccc taggctggca gtgcagcaga aatactgaat    5160
aaaatgtgac aaatctccct ggaaaaaaaa aaaaaaaa                            5199
```

<210> SEQ ID NO 20
<211> LENGTH: 593
<212> TYPE: PRT
<213> ORGANISM: Homo sapiens

<400> SEQUENCE: 20

```
Met Arg Ser Ala Ala Arg Arg Gly Arg Ala Pro Ala Ala Arg Asp
1               5                   10                  15

Ser Leu Pro Val Leu Leu Phe Leu Cys Leu Leu Lys Thr Cys Glu
            20                  25                  30

Pro Lys Thr Ala Asn Ala Phe Lys Pro Asn Ile Leu Leu Ile Met Ala
        35                  40                  45

Asp Asp Leu Gly Thr Gly Asp Leu Gly Cys Tyr Gly Asn Asn Thr Leu
    50                  55                  60

Arg Thr Pro Asn Ile Asp Gln Leu Ala Glu Gly Val Arg Leu Thr
65                  70                  75                  80

Gln His Leu Ala Ala Ala Pro Leu Cys Thr Pro Ser Arg Ala Ala Phe
                85                  90                  95

Leu Thr Gly Arg His Ser Phe Arg Ser Gly Met Asp Ala Ser Asn Gly
                100                 105                 110

Tyr Arg Ala Leu Gln Trp Asn Ala Gly Ser Gly Gly Leu Pro Glu Asn
            115                 120                 125

Glu Thr Thr Phe Ala Arg Ile Leu Gln Gln His Gly Tyr Ala Thr Gly
        130                 135                 140

Leu Ile Gly Lys Trp His Gln Gly Val Asn Cys Ala Ser Arg Gly Asp
145                 150                 155                 160

His Cys His His Pro Leu Asn His Gly Phe Asp Tyr Phe Tyr Gly Met
                165                 170                 175

Pro Phe Thr Leu Thr Asn Asp Cys Asp Pro Gly Arg Pro Pro Glu Val
                180                 185                 190

Asp Ala Ala Leu Arg Ala Gln Leu Trp Gly Tyr Thr Gln Phe Leu Ala
            195                 200                 205

Leu Gly Ile Leu Thr Leu Ala Ala Gly Gln Thr Cys Gly Phe Phe Ser
        210                 215                 220

Val Ser Ala Arg Ala Val Thr Gly Met Ala Gly Val Gly Cys Leu Phe
225                 230                 235                 240

Phe Ile Ser Trp Tyr Ser Ser Phe Gly Phe Val Arg Arg Trp Asn Cys
```

```
                    245                 250                 255
Ile Leu Met Arg Asn His Asp Val Thr Glu Gln Pro Met Val Leu Glu
                260                 265                 270
Lys Thr Ala Ser Leu Met Leu Lys Glu Ala Val Ser Tyr Ile Glu Arg
            275                 280                 285
His Lys His Gly Pro Phe Leu Phe Leu Ser Leu Leu His Val His
        290                 295                 300
Ile Pro Leu Val Thr Thr Ser Ala Phe Leu Gly Lys Ser Gln His Gly
305                 310                 315                 320
Leu Tyr Gly Asp Asn Val Glu Glu Met Asp Trp Leu Ile Gly Lys Val
                325                 330                 335
Leu Asn Ala Ile Glu Asp Asn Gly Leu Lys Asn Ser Thr Phe Thr Tyr
            340                 345                 350
Phe Thr Ser Asp His Gly Gly His Leu Glu Ala Arg Asp Gly His Ser
        355                 360                 365
Gln Leu Gly Gly Trp Asn Gly Ile Tyr Lys Gly Gly Lys Gly Met Gly
    370                 375                 380
Gly Trp Glu Gly Gly Ile Arg Val Pro Gly Ile Phe His Trp Pro Gly
385                 390                 395                 400
Val Leu Pro Ala Gly Arg Val Ile Gly Glu Pro Thr Ser Leu Met Asp
                405                 410                 415
Val Phe Pro Thr Val Gln Leu Val Gly Gly Glu Val Pro Gln Asp
            420                 425                 430
Arg Val Ile Asp Gly His Ser Leu Val Pro Leu Leu Gln Gly Ala Glu
        435                 440                 445
Ala Arg Ser Ala His Glu Phe Leu Phe His Tyr Cys Gly Gln His Leu
    450                 455                 460
His Ala Ala Arg Trp His Gln Lys Asp Ser Gly Ser Val Trp Lys Val
465                 470                 475                 480
His Tyr Thr Thr Pro Gln Phe His Pro Glu Gly Ala Gly Ala Cys Tyr
                485                 490                 495
Gly Arg Gly Val Cys Pro Cys Ser Gly Glu Gly Val Thr His His Arg
            500                 505                 510
Pro Pro Leu Leu Phe Asp Leu Ser Arg Asp Pro Ser Glu Ala Arg Pro
        515                 520                 525
Leu Thr Pro Asp Ser Glu Pro Leu Tyr His Ala Val Ile Ala Arg Val
    530                 535                 540
Gly Ala Ala Val Ser Glu His Arg Gln Thr Leu Ser Pro Val Pro Gln
545                 550                 555                 560
Gln Phe Ser Met Ser Asn Ile Leu Trp Lys Pro Trp Leu Gln Pro Cys
                565                 570                 575
Cys Gly His Phe Pro Phe Cys Ser Cys His Glu Asp Gly Asp Gly Thr
            580                 585                 590
Pro

<210> SEQ ID NO 21
<211> LENGTH: 2220
<212> TYPE: DNA
<213> ORGANISM: Homo sapiens

<400> SEQUENCE: 21
ttggtagacg tgggcgtggc tttgagattc ccccatgctg cgatgtgggg ggagtctgct    60
ctgtctgtcc taactctctc tgatcttctg acttgggaaa acaaactcg aagttaatca    120
```

| | |
|---|---|
| ttcccagctc aaagccttgt gcaagtgctc tctgccttca cgcttgcttc ctttgggaga | 180 |
| gaaccttcct cttcttgatc ggggattcag gaaggagccc aggagcagag gaagtagaga | 240 |
| gagagacaac atgttacatc tgcaccattc ttgtttgtgt ttcaggagct ggctgccagc | 300 |
| gatgctcgct gtactgctaa gtttggcacc atcagcttcc agcgacattt ccgcctcccg | 360 |
| accgaacatc cttcttctga tggcggacga ccttggcatt ggggacattg gctgctatgg | 420 |
| caacaacacc atgaggactc cgaatattga ccgccttgca gaggacggcg tgaagctgac | 480 |
| ccaacacatc tctgccgcat ctttgtgcac cccaagcaga gccgccttcc tcacgggcag | 540 |
| atacccctgtg cgatcaggga tggtttccag cattggttac cgtgttcttc agtggaccgg | 600 |
| agcatctgga ggtcttccaa caaatgagac aacttttgca aaaatactga aagagaaagg | 660 |
| ctatgccact ggactcattg gaaaatggca tctgggtctc aactgtgagt cagccagtga | 720 |
| tcattgccac caccctctcc atcatggctt tgaccatttc tacggaatgc ctttctcctt | 780 |
| gatgggtgat tgcgcccgct gggaactctc agagaagcgt gtcaacctgg aacaaaaact | 840 |
| caacttcctc ttccaagtcc tggccttggt tgccctcaca ctggtagcag gaagctcac | 900 |
| acacctgata cccgtctcgt ggatgccggt catctggtca gcccttcgg ccgtcctcct | 960 |
| cctcgcaagc tcctattttg tgggtgctct gattgtccat gccgattgct ttctgatgag | 1020 |
| aaaccacacc atcacggagc agcccatgtg cttccaaaga cgacacccc ttattctgca | 1080 |
| ggaggttgcg tcctttctca aaggaataa gcatgggcct ttcctcctct ttgtttcctt | 1140 |
| tctacacgtt cacatccctc ttatcactat ggagaacttc ctcgggaaga gtctccacgg | 1200 |
| gctgtatggg gacaacgtag aggagatgga ctggatggta ggacggatcc ttgacacttt | 1260 |
| ggacgtggag ggtttgagca acagcaccct catttatttt acgtcggatc acggcggttc | 1320 |
| cctagagaat caacttggaa acacccagta tggtggctgg aatggaattt ataaaggtgg | 1380 |
| gaagggcatg ggaggatggg aaggtgggat ccgcgtgccc gggatcttcc gctggcccgg | 1440 |
| ggtgctcccg gccggccgag tgattggcga gcccacgagt ctgatggacg tgttccccac | 1500 |
| cgtggtccgg ctggcgggcg cgaggtgcc ccaggacaga gtgattgacg ccaagacct | 1560 |
| tctgcccttg ctcctgggga cagcccaaca ctcagaccac gagttcctga tgcattattg | 1620 |
| tgagaggttt ctgcacgcag ccaggtggca tcaacgggac agaggaacaa tgtggaaagt | 1680 |
| ccactttgtg acgcctgtgt tccagccaga gggagccggt gcctgctatg aagaaaaggt | 1740 |
| ctgcccgtgc tttggggaaa aagtagtcca ccacgatcca ccttgctct ttgacctctc | 1800 |
| aagagaccct tctgagaccc acatcctcac accagcctca gagcccgtgt tctatcaggt | 1860 |
| gatggaacga gtccagcagg cggtgtggga acaccagcgg acactcagcc cagttcctct | 1920 |
| gcagctggac aggctgggca acatctggag accgtggctg cagccctgct gtggcccgtt | 1980 |
| ccccctctgc tggtgcctta gggaagatga cccacaataa atgtctgcag tgaaaagctg | 2040 |
| gagccccgat tcctaaattt tgtcactcaa attgaaacaa accagctggc catggtggtt | 2100 |
| gtcatcccag cactttagga ggccaccaca ggaggatcac tcccgtgatc aaaaccaacc | 2160 |
| tgggcaacat gatgaaactc tagctctaca aaacaaaaat aaaaaaaaaa ttagcctgca | 2220 |

<210> SEQ ID NO 22
<211> LENGTH: 589
<212> TYPE: PRT
<213> ORGANISM: Homo sapiens

<400> SEQUENCE: 22

Met Leu His Leu His His Ser Cys Leu Cys Phe Arg Ser Trp Leu Pro

-continued

```
1               5                   10                  15
Ala Met Leu Ala Val Leu Leu Ser Leu Ala Pro Ser Ala Ser Ser Asp
            20                  25                  30

Ile Ser Ala Ser Arg Pro Asn Ile Leu Leu Met Ala Asp Asp Leu
            35                  40                  45

Gly Ile Gly Asp Ile Gly Cys Tyr Gly Asn Asn Thr Met Arg Thr Pro
            50                  55                  60

Asn Ile Asp Arg Leu Ala Glu Asp Gly Val Lys Leu Thr Gln His Ile
65                  70                  75                  80

Ser Ala Ala Ser Leu Cys Thr Pro Ser Arg Ala Ala Phe Leu Thr Gly
                85                  90                  95

Arg Tyr Pro Val Arg Ser Gly Met Val Ser Ser Ile Gly Tyr Arg Val
                100                 105                 110

Leu Gln Trp Thr Gly Ala Ser Gly Gly Leu Pro Thr Asn Glu Thr Thr
                115                 120                 125

Phe Ala Lys Ile Leu Lys Glu Lys Gly Tyr Ala Thr Gly Leu Ile Gly
            130                 135                 140

Lys Trp His Leu Gly Leu Asn Cys Glu Ser Ala Ser Asp His Cys His
145                 150                 155                 160

His Pro Leu His His Gly Phe Asp His Phe Tyr Gly Met Pro Phe Ser
                165                 170                 175

Leu Met Gly Asp Cys Ala Arg Trp Glu Leu Ser Glu Lys Arg Val Asn
                180                 185                 190

Leu Glu Gln Lys Leu Asn Phe Leu Phe Gln Val Leu Ala Leu Val Ala
                195                 200                 205

Leu Thr Leu Val Ala Gly Lys Leu Thr His Leu Ile Pro Val Ser Trp
210                 215                 220

Met Pro Val Ile Trp Ser Ala Leu Ser Ala Val Leu Leu Leu Ala Ser
225                 230                 235                 240

Ser Tyr Phe Val Gly Ala Leu Ile Val His Ala Asp Cys Phe Leu Met
                245                 250                 255

Arg Asn His Thr Ile Thr Glu Gln Pro Met Cys Phe Gln Arg Thr Thr
                260                 265                 270

Pro Leu Ile Leu Gln Glu Val Ala Ser Phe Leu Lys Arg Asn Lys His
            275                 280                 285

Gly Pro Phe Leu Leu Phe Val Ser Phe Leu His Val His Ile Pro Leu
            290                 295                 300

Ile Thr Met Glu Asn Phe Leu Gly Lys Ser Leu His Gly Leu Tyr Gly
305                 310                 315                 320

Asp Asn Val Glu Glu Met Asp Trp Met Val Gly Arg Ile Leu Asp Thr
                325                 330                 335

Leu Asp Val Glu Gly Leu Ser Asn Ser Thr Leu Ile Tyr Phe Thr Ser
                340                 345                 350

Asp His Gly Gly Ser Leu Glu Asn Gln Leu Gly Asn Thr Gln Tyr Gly
            355                 360                 365

Gly Trp Asn Gly Ile Tyr Lys Gly Gly Lys Gly Met Gly Gly Trp Glu
            370                 375                 380

Gly Gly Ile Arg Val Pro Gly Ile Phe Arg Trp Pro Gly Val Leu Pro
385                 390                 395                 400

Ala Gly Arg Val Ile Gly Glu Pro Thr Ser Leu Met Asp Val Phe Pro
                405                 410                 415

Thr Val Val Arg Leu Ala Gly Gly Glu Val Pro Gln Asp Arg Val Ile
                420                 425                 430
```

```
Asp Gly Gln Asp Leu Leu Pro Leu Leu Leu Gly Thr Ala Gln His Ser
        435                 440                 445

Asp His Glu Phe Leu Met His Tyr Cys Glu Arg Phe Leu His Ala Ala
    450                 455                 460

Arg Trp His Gln Arg Asp Arg Gly Thr Met Trp Lys Val His Phe Val
465                 470                 475                 480

Thr Pro Val Phe Gln Pro Glu Gly Ala Gly Ala Cys Tyr Gly Arg Lys
                485                 490                 495

Val Cys Pro Cys Phe Gly Glu Lys Val Val His Asp Pro Pro Leu
                500                 505                 510

Leu Phe Asp Leu Ser Arg Asp Pro Ser Glu Thr His Ile Leu Thr Pro
            515                 520                 525

Ala Ser Glu Pro Val Phe Tyr Gln Val Met Glu Arg Val Gln Ala
        530                 535                 540

Val Trp Glu His Gln Arg Thr Leu Ser Pro Val Pro Leu Gln Leu Asp
545                 550                 555                 560

Arg Leu Gly Asn Ile Trp Arg Pro Trp Leu Gln Pro Cys Cys Gly Pro
                565                 570                 575

Phe Pro Leu Cys Trp Cys Leu Arg Glu Asp Asp Pro Gln
        580                 585

<210> SEQ ID NO 23
<211> LENGTH: 2048
<212> TYPE: DNA
<213> ORGANISM: Homo sapiens

<400> SEQUENCE: 23
aaaagaggca gagcctttgc agaacagcct gtctgttctg ctcctagaca ttagagagat      60
aatacggctg atagacaaca agaaggtatt ccaagctgca caatgaggcc caggagaccc     120
ttggtcttca tgtctttggt gtgtgcactc ttgaacacat gccaggcaca cagggtgcat     180
gacgacaagc ctaatattgt cctaatcatg gttgatgacc tgggtattgg agatctgggc     240
tgctacggca tgacaccat gaggacgcct cacatcgacc gccttgccag ggaaggcgtg      300
cgactgactc agcacatctc tgccgcctcc ctctgcagcc caagccggtc cgcgttcttg     360
acgggaagat accccatccg atcaggtatg gtttctagtg gtaatagacg tgtcatccaa     420
aatcttgcag tccccgcagg cctccctctt aatgagacaa cacttgcagc cttgctaaag     480
aagcaaggat acagcacggg gcttataggc aaatggcacc aaggcttgaa ctgcgactcc     540
cgaagtgacc agtgccacca tccatataat tatgggtttg actactacta tggcatgccg     600
ttcactctcg ttgacagctg ctggccggac ccctctcgta acacggaatt agcctttgag     660
agtcagctct ggctctgtgt gcagctagtt gccattgcca tcctcaccct aacctttggg     720
aagctgagcg gctgggtctc tgttccctgg ctcctgatct tctccatgat tctgtttatt     780
ttcctcttgg gctatgcttg gttctccagc cacacgtccc cttttatactg ggactgcctc     840
ctcatgcggg ggcacgagat cacggagcag cccatgaagg ctgaacgagc tggatccatt     900
atggtgaagg aagcgatttc cttttttagaa aggcacagta aggaaacttt ccttctcttt     960
ttctcctttc ttcacgtgca cacctctc cccaccacgg acgatttcac tggcaccagc      1020
aagcatggct tgtatgggga taatgtggaa gagatggact ccatggtggg caagattctt     1080
gatgctatcg atgattttgg cctaaggaac aacacccttg tctactttac atcagatcac     1140
ggagggcatt tggaagctag gcgagggcat gcccaacttg gtggatggaa tggaatatac     1200
```

```
aaaggtggaa aaggcatggg gggctgggaa ggtggaatcc gcgtcccagg aattgtccga   1260
tggcctggaa aggtaccagc tggacggttg attaaggaac ctacaagttt aatggatatt   1320
ttaccaactg tcgcatcagt gtcaggagga agtctccctc aggacagggt cattgacggc   1380
cgagacctca tgcccttgct gcagggcaac gtcaggcact cggagcatga atttcttttc   1440
cactactgtg gctcctacct gcacgccgtg cggtggatcc ccaaggacga cagtgggtca   1500
gtttggaagg ctcactatgt gaccccggta ttccagccac cagcttctgg tggctgctat   1560
gtcacctcat tatgcagatg tttcggagaa caggttacct accacaaccc ccctctgctc   1620
ttcgatctct ccagggaccc ctcagagtcc acacccctga cacctgccac agagcccctc   1680
catgattttg tgattaaaaa ggtggccaac gccctgaagg aacaccagga aaccatcgtg   1740
cctgtgacct accaactctc agaactgaat cagggcagga cgtggctgaa gccttgctgt   1800
ggggtgttcc cattttgtct gtgtgacaag gaagaggaag tctctcagcc tcgggggtcct   1860 aacgagaaga gataattaca atcaggctac cagaggaagc ctttggtcct aacgagaaga   1920
gataattaca atcaggctac caaaggaagc actaactttg gtgctttcaa gttggcaagg   1980
agtgcattta atagtcaata aattcatcta ccattccaga ttattaaagg cccactggtt   2040
gttccact                                                            2048
```

<210> SEQ ID NO 24
<211> LENGTH: 590
<212> TYPE: PRT
<213> ORGANISM: Homo sapiens

<400> SEQUENCE: 24

```
Met Arg Pro Arg Pro Leu Val Phe Met Ser Leu Val Cys Ala Leu
1               5                   10                  15

Leu Asn Thr Cys Gln Ala His Arg Val His Asp Asp Lys Pro Asn Ile
            20                  25                  30

Val Leu Ile Met Val Asp Asp Leu Gly Ile Gly Asp Leu Gly Cys Tyr
        35                  40                  45

Gly Asn Asp Thr Met Arg Thr Pro His Ile Asp Arg Leu Ala Arg Glu
    50                  55                  60

Gly Val Arg Leu Thr Gln His Ile Ser Ala Ala Ser Leu Cys Ser Pro
65                  70                  75                  80

Ser Arg Ser Ala Phe Leu Thr Gly Arg Tyr Pro Ile Arg Ser Gly Met
                85                  90                  95

Val Ser Ser Gly Asn Arg Arg Val Ile Gln Asn Leu Ala Val Pro Ala
            100                 105                 110

Gly Leu Pro Leu Asn Glu Thr Thr Leu Ala Ala Leu Leu Lys Lys Gln
        115                 120                 125

Gly Tyr Ser Thr Gly Leu Ile Gly Lys Trp His Gln Gly Leu Asn Cys
    130                 135                 140

Asp Ser Arg Ser Asp Gln Cys His His Pro Tyr Asn Tyr Gly Phe Asp
145                 150                 155                 160

Tyr Tyr Tyr Gly Met Pro Phe Thr Leu Val Asp Ser Cys Trp Pro Asp
                165                 170                 175

Pro Ser Arg Asn Thr Glu Leu Ala Phe Glu Ser Gln Leu Trp Leu Cys
            180                 185                 190

Val Gln Leu Val Ala Ile Ala Ile Leu Thr Leu Thr Phe Gly Lys Leu
        195                 200                 205

Ser Gly Trp Val Ser Val Pro Trp Leu Leu Ile Phe Ser Met Ile Leu
    210                 215                 220
```

```
Phe Ile Phe Leu Leu Gly Tyr Ala Trp Phe Ser Ser His Thr Ser Pro
225                 230                 235                 240

Leu Tyr Trp Asp Cys Leu Leu Met Arg Gly His Glu Ile Thr Glu Gln
                245                 250                 255

Pro Met Lys Ala Glu Arg Ala Gly Ser Ile Met Val Lys Glu Ala Ile
            260                 265                 270

Ser Phe Leu Glu Arg His Ser Lys Glu Thr Phe Leu Leu Phe Phe Ser
        275                 280                 285

Phe Leu His Val His Thr Pro Leu Pro Thr Thr Asp Asp Phe Thr Gly
290                 295                 300

Thr Ser Lys His Gly Leu Tyr Gly Asp Asn Val Glu Glu Met Asp Ser
305                 310                 315                 320

Met Val Gly Lys Ile Leu Asp Ala Ile Asp Asp Phe Gly Leu Arg Asn
                325                 330                 335

Asn Thr Leu Val Tyr Phe Thr Ser Asp His Gly Gly His Leu Glu Ala
            340                 345                 350

Arg Arg Gly His Ala Gln Leu Gly Gly Trp Asn Gly Ile Tyr Lys Gly
        355                 360                 365

Gly Lys Gly Met Gly Gly Trp Glu Gly Gly Ile Arg Val Pro Gly Ile
370                 375                 380

Val Arg Trp Pro Gly Lys Val Pro Ala Gly Arg Leu Ile Lys Glu Pro
385                 390                 395                 400

Thr Ser Leu Met Asp Ile Leu Pro Thr Val Ala Ser Val Ser Gly Gly
                405                 410                 415

Ser Leu Pro Gln Asp Arg Val Ile Asp Gly Arg Asp Leu Met Pro Leu
            420                 425                 430

Leu Gln Gly Asn Val Arg His Ser Glu His Glu Phe Leu Phe His Tyr
        435                 440                 445

Cys Gly Ser Tyr Leu His Ala Val Arg Trp Ile Pro Lys Asp Asp Ser
450                 455                 460

Gly Ser Val Trp Lys Ala His Tyr Val Thr Pro Val Phe Gln Pro Pro
465                 470                 475                 480

Ala Ser Gly Gly Cys Tyr Val Thr Ser Leu Cys Arg Cys Phe Gly Glu
                485                 490                 495

Gln Val Thr Tyr His Asn Pro Pro Leu Leu Phe Asp Leu Ser Arg Asp
            500                 505                 510

Pro Ser Glu Ser Thr Pro Leu Thr Pro Ala Thr Glu Pro Leu His Asp
        515                 520                 525

Phe Val Ile Lys Lys Val Ala Asn Ala Leu Lys Glu His Gln Glu Thr
530                 535                 540

Ile Val Pro Val Thr Tyr Gln Leu Ser Glu Leu Asn Gln Gly Arg Thr
545                 550                 555                 560

Trp Leu Lys Pro Cys Cys Gly Val Phe Pro Phe Cys Leu Cys Asp Lys
                565                 570                 575

Glu Glu Glu Val Ser Gln Pro Arg Gly Pro Asn Glu Lys Arg
            580                 585                 590

<210> SEQ ID NO 25
<211> LENGTH: 2785
<212> TYPE: DNA
<213> ORGANISM: Homo sapiens

<400> SEQUENCE: 25
ggctgcgccc aggccggcgg gcccagcagc tgcgaaccgc cggcgcacca cctgtttccg    60
```

-continued

```
cgcccgggga cttccccggc ggggctcaga agtgtgggat cggtcgcttg gcttccctg      120
gcgtcagcga cccagggtaa cctcctccac tgctgcgtgc cgtgcaggcc tgcctgtgtg    180
agagccacgt gtgccgcgct ctgggcacag ccttggaaag tcaggaccgc gacggcagca    240
gagcagaaac cttacagaaa catgaagccc tcaaccatct gctactcagt tattcggggc    300
tgacggcggc ttctagaaca tccaggtgtt ctgcagatgc gagaactcat cctgtagtca    360
ccagatggag tcccaaacag ccaagcagat gtaaggcctg tgctgtggct ctgaggccct    420
gaatacagaa gggtcacttt cttagtggcc aaagagcagt tgttgacatt gatgtctaat    480
tattgaacac gaccagtcat tttactgagc tgcggtgagg aaacactgac catagaagat    540
caagccaaat gagggattgc aaatttcctg attcttttga attaggattc cagatggggg    600
cctcatttct acagccccca acattcctat agccgttatc actgccatca ccactgccac    660
cagcatcttc ttgcagattc caccctgct ccccagagac ttcctgcttt gaaagtgagc     720
agaaaggaag ctctcagaaa aatctctagt ggtggctgcc gtcgctccag acaatcggaa    780
tcctgccttc accaccatgg gctggctttt tctaaaggtt ttgttggcgg gagtgagttt    840
ctcaggattt ctttatcctc ttgtggattt ttgcatcagt gggaaaacaa gaggacagaa    900
gccaaacttt gtgattattt tggccgatga catggggtgg ggtgacctgg gagcaaactg    960
ggcagaaaca aaggacactg ccaaccttga taagatggct tcggagggaa tgaggtttgt   1020
ggatttccat gcagctgcct ccacctgctc accctcccgg gcttccttgc tcaccggccg   1080
gcttggcctt cgcaatggag tcacacgcaa ctttgcagtc acttctgtgg gaggccttcc   1140
gctcaacgag accaccttgg cagaggtgct gcagcaggcg ggttacgtca ctgggataat   1200
aggcaaatgg catcttggac accacggctc ttatcacccc aacttccgtg gttttgatta   1260
ctactttgga atcccatata gccatgatat gggctgtact gatactccag gctacaacca   1320
ccctccttgt ccagcgtgtc cacagggtga tggaccatca aggaaccttc aaagagactg   1380
ttacactgac gtggccctcc ctctttatga aaacctcaac attgtggagc agccggtgaa   1440
cttgagcagc cttgcccaga agtatgctga aaagcaacc cagttcatcc agcgtgcaag    1500
caccagcggg aggcccttcc tgctctatgt ggctctggcc cacatgcacg tgcccttacc   1560
tgtgactcag ctaccagcag cgccacgggg cagaagcctg tatggtgcag ggctctggga   1620
gatggacagt ctggtgggcc agatcaagga caaagttgac cacacagtga aggaaaacac   1680
attcctctgg tttacaggag acaatggccc gtgggctcag aagtgtgagc tagcgggcag   1740
tgtgggtccc ttcactggat tttggcaaac tcgtcaaggg ggaagtccag ccaagcagac   1800
gacctgggaa ggagggcacc gggtcccagc actggcttac tggcctggca gagttccagt   1860
taatgtcacc agcactgcct tgttaagcgt gctggacatt tttccaactg tggtagccct   1920
ggcccaggcc agcttacctc aaggacggcg ctttgatggt gtggacgtct ccgaggtgct   1980
ctttggccgg tcacagcctg gcacagggt gctgttccac cccaacgcg gggcagctgg    2040
agagtttgga gccctgcaga ctgtccgcct ggagcgttac aaggccttct acattaccgg   2100
tggagccagg gcgtgtgatg ggagcacggg gcctgagctg cagcataagt ttcctctgat   2160
tttcaacctg gaagacgata ccgcagaagc tgtgcccct gaaagaggtg gtgcggagta    2220
ccaggctgtg ctgcccgagg tcagaaaggt tcttgcagac gtcctccaag acattgccaa   2280
cgacaacatc tccagcgcag attacactca ggacccttca gtaactccct gctgtaatcc   2340
ctaccaaatt gcctgccgct gtcaagccgc ataacagacc aatttttatt ccacgaggag   2400
```

-continued

```
gagtacctgg aaattaggca agtttgcttc caaatttcat ttttaccctc tttacaaaca    2460
cacgctttag tttagtcttg gagtttagtt ttggagttag ccttgcatat cccttctgta    2520
tcctgtccct cctccacgcc gacccgagag cagctgagct gcgctggctc tgggcaggga    2580
gtgtgcctta atgggaagca cacgggcttt ggagtcaggc acaggtgcca gctccagctt    2640
ttgaacttgg gcaattgttt aacctaacct gcaagttgat tttgagggtt aaataaaggc    2700
atacatgaaa atgcctggca aattacctga cacagagcag acattcaata cattttagtt    2760
tccttgtttc aaaaaaaaaa aaaaa                                          2785
```

<210> SEQ ID NO 26
<211> LENGTH: 525
<212> TYPE: PRT
<213> ORGANISM: Homo sapiens

<400> SEQUENCE: 26

```
Met Gly Trp Leu Phe Leu Lys Val Leu Leu Ala Gly Val Ser Phe Ser
1               5                   10                  15

Gly Phe Leu Tyr Pro Leu Val Asp Phe Cys Ile Ser Gly Lys Thr Arg
            20                  25                  30

Gly Gln Lys Pro Asn Phe Val Ile Ile Leu Ala Asp Asp Met Gly Trp
        35                  40                  45

Gly Asp Leu Gly Ala Asn Trp Ala Glu Thr Lys Asp Thr Ala Asn Leu
    50                  55                  60

Asp Lys Met Ala Ser Glu Gly Met Arg Phe Val Asp Phe His Ala Ala
65                  70                  75                  80

Ala Ser Thr Cys Ser Pro Ser Arg Ala Ser Leu Leu Thr Gly Arg Leu
                85                  90                  95

Gly Leu Arg Asn Gly Val Thr Arg Asn Phe Ala Val Thr Ser Val Gly
            100                 105                 110

Gly Leu Pro Leu Asn Glu Thr Thr Leu Ala Glu Val Leu Gln Gln Ala
        115                 120                 125

Gly Tyr Val Thr Gly Ile Ile Gly Lys Trp His Leu Gly His His Gly
    130                 135                 140

Ser Tyr His Pro Asn Phe Arg Gly Phe Asp Tyr Tyr Phe Gly Ile Pro
145                 150                 155                 160

Tyr Ser His Asp Met Gly Cys Thr Asp Thr Pro Gly Tyr Asn His Pro
                165                 170                 175

Pro Cys Pro Ala Cys Pro Gln Gly Asp Gly Pro Ser Arg Asn Leu Gln
            180                 185                 190

Arg Asp Cys Tyr Thr Asp Val Ala Leu Pro Leu Tyr Glu Asn Leu Asn
        195                 200                 205

Ile Val Glu Gln Pro Val Asn Leu Ser Ser Leu Ala Gln Lys Tyr Ala
    210                 215                 220

Glu Lys Ala Thr Gln Phe Ile Gln Arg Ala Ser Thr Ser Gly Arg Pro
225                 230                 235                 240

Phe Leu Leu Tyr Val Ala Leu Ala His Met His Val Pro Leu Pro Val
                245                 250                 255

Thr Gln Leu Pro Ala Ala Pro Arg Gly Arg Ser Leu Tyr Gly Ala Gly
            260                 265                 270

Leu Trp Glu Met Asp Ser Leu Val Gly Gln Ile Lys Asp Lys Val Asp
        275                 280                 285

His Thr Val Lys Glu Asn Thr Phe Leu Trp Phe Thr Gly Asp Asn Gly
    290                 295                 300
```

```
Pro Trp Ala Gln Lys Cys Glu Leu Ala Gly Ser Val Gly Pro Phe Thr
305                 310                 315                 320

Gly Phe Trp Gln Thr Arg Gln Gly Gly Ser Pro Ala Lys Gln Thr Thr
                325                 330                 335

Trp Glu Gly Gly His Arg Val Pro Ala Leu Ala Tyr Trp Pro Gly Arg
            340                 345                 350

Val Pro Val Asn Val Thr Ser Thr Ala Leu Leu Ser Val Leu Asp Ile
        355                 360                 365

Phe Pro Thr Val Val Ala Leu Ala Gln Ala Ser Leu Pro Gln Gly Arg
    370                 375                 380

Arg Phe Asp Gly Val Asp Val Ser Glu Val Leu Phe Gly Arg Ser Gln
385                 390                 395                 400

Pro Gly His Arg Val Leu Phe His Pro Asn Ser Gly Ala Ala Gly Glu
                405                 410                 415

Phe Gly Ala Leu Gln Thr Val Arg Leu Glu Arg Tyr Lys Ala Phe Tyr
            420                 425                 430

Ile Thr Gly Gly Ala Arg Ala Cys Asp Gly Ser Thr Gly Pro Glu Leu
        435                 440                 445

Gln His Lys Phe Pro Leu Ile Phe Asn Leu Glu Asp Asp Thr Ala Glu
    450                 455                 460

Ala Val Pro Leu Glu Arg Gly Gly Ala Glu Tyr Gln Ala Val Leu Pro
465                 470                 475                 480

Glu Val Arg Lys Val Leu Ala Asp Val Leu Gln Asp Ile Ala Asn Asp
                485                 490                 495

Asn Ile Ser Ser Ala Asp Tyr Thr Gln Asp Pro Ser Val Thr Pro Cys
            500                 505                 510

Cys Asn Pro Tyr Gln Ile Ala Cys Arg Cys Gln Ala Ala
        515                 520                 525

<210> SEQ ID NO 27
<211> LENGTH: 1689
<212> TYPE: DNA
<213> ORGANISM: Homo sapiens

<400> SEQUENCE: 27
atgacaagaa acgccagacc caacattgtc ctgctgatgg cagatgacct tggagtgggg     60
gatttgtgct gctacggtaa taactcagtg agcacaccta atattgaccg cctggcaagt    120
gaaggagtga ggcttaccca gcatctcgca gctgcttcca tgtgcacccc aagtcgggct    180
gccttcctga ccggccggta ccccatcaga tcagggatgg tgtctgccta caacctgaac    240
cgtgccttca gtggcttggt gggtcaggt ggtcttccca ccaatgaaac gactttgcc    300 aagctgctgc agcaccgtgg ctaccgcacg ggactcatag caaatggca cctgggtttg    360 agctgcgcct ctcggaatga tcactgttac cacccgctca accatggttt tcactacttt    420
tacggggtgc ctttggact tttaagcgac tgccaggcat ccaagacacc agaactgcac    480
cgctggctca ggatcaaact gtggatctcc acgtagccc ttgccctggt tccttttctg    540
cttctcattc ccaagttcgc ccgctggttc tcagtgccat ggaaggtcat ctttgtcttt    600
gctctcctcg cctttctgtt tttcacttcc tggtactcta gttatggatt tactcgacgt    660
tggaattgca tccttatgag gaaccatgaa attatccagc agccaatgaa agaggagaaa    720
gtagcttccc tcatgctgaa ggaggcactt gctttcattg aaaggtacaa aagggaacct    780
tttctcctct ttttttcctt cctgcacgta catactccac tcatctccaa aaagaagttt    840
gttgggcgca gtaaatatgg caggtatggg acaatgtag aagaaatgga ttggatggtg    900
```

```
ggtaaaatcc tggatgccct ggaccaggag cgcctggcca accacacctt ggtgtacttc    960
acctctgaca acgggggcca cctggagccc ctggacgggg ctgttcagct gggtggctgg   1020
aacgggatct acaaaggtgg caaaggaatg ggaggatggg aaggaggtat ccgtgtgcca   1080
gggatattcc ggtggccgtc agtcttggag gctgggagag tgatcaatga gcccaccagc   1140
ttaatggaca tctatccgac gctgtcttat ataggcggag ggatcttgtc ccaggacaga   1200
gtgattgacg ccagaacct aatgcccctg ctggaaggaa gggcgtccca ctccgaccac   1260
gagttcctct tccactactg tggggtctat ctgcacacgg tcaggtggca tcagaaggac   1320
tgtgcaactg tgtggaaagc tcattatgtg actcctaaat tctaccctga aggaacaggt   1380
gcctgctatg ggagtggaat atgttcatgt tcggggatgt aacctacca cgacccacca   1440
ctcctctttg acatctcaag agaccttca gaagccttc cactgaaccc tgacaatgag   1500
ccattatttg actccgtgat caaaaagatg gaggcagcca agagagca tcgtaggaca   1560
ctaacacctg tcccacagca gttctctgtg ttcaacacaa tttggaaacc atggctgcag   1620
ccttgctgtg ggaccttccc cttctgtggg tgtgacaagg aagatgacat ccttcccatg   1680
gctccctga                                                           1689

<210> SEQ ID NO 28
<211> LENGTH: 562
<212> TYPE: PRT
<213> ORGANISM: Homo sapiens

<400> SEQUENCE: 28

Met Thr Arg Asn Ala Arg Pro Asn Ile Val Leu Leu Met Ala Asp Asp
1               5                   10                  15

Leu Gly Val Gly Asp Leu Cys Cys Tyr Gly Asn Asn Ser Val Ser Thr
            20                  25                  30

Pro Asn Ile Asp Arg Leu Ala Ser Glu Gly Val Arg Leu Thr Gln His
        35                  40                  45

Leu Ala Ala Ala Ser Met Cys Thr Pro Ser Arg Ala Ala Phe Leu Thr
    50                  55                  60

Gly Arg Tyr Pro Ile Arg Ser Gly Met Val Ser Ala Tyr Asn Leu Asn
65                  70                  75                  80

Arg Ala Phe Thr Trp Leu Gly Ser Gly Gly Leu Pro Thr Asn Glu
            85                  90                  95

Thr Thr Phe Ala Lys Leu Leu Gln His Arg Gly Tyr Arg Thr Gly Leu
            100                 105                 110

Ile Gly Lys Trp His Leu Gly Leu Ser Cys Ala Ser Arg Asn Asp His
            115                 120                 125

Cys Tyr His Pro Leu Asn His Gly Phe His Tyr Phe Tyr Gly Val Pro
130                 135                 140

Phe Gly Leu Leu Ser Asp Cys Gln Ala Ser Lys Thr Pro Glu Leu His
145                 150                 155                 160

Arg Trp Leu Arg Ile Lys Leu Trp Ile Ser Thr Val Ala Leu Ala Leu
            165                 170                 175

Val Pro Phe Leu Leu Leu Ile Pro Lys Phe Ala Arg Trp Phe Ser Val
            180                 185                 190

Pro Trp Lys Val Ile Phe Val Phe Ala Leu Leu Ala Phe Leu Phe Phe
            195                 200                 205

Thr Ser Trp Tyr Ser Ser Tyr Gly Phe Thr Arg Arg Trp Asn Cys Ile
    210                 215                 220
```

```
Leu Met Arg Asn His Glu Ile Ile Gln Gln Pro Met Lys Glu Glu Lys
225                 230                 235                 240

Val Ala Ser Leu Met Leu Lys Glu Ala Leu Ala Phe Ile Glu Arg Tyr
            245                 250                 255

Lys Arg Glu Pro Phe Leu Leu Phe Phe Ser Phe Leu His Val His Thr
                260                 265                 270

Pro Leu Ile Ser Lys Lys Lys Phe Val Gly Arg Ser Lys Tyr Gly Arg
            275                 280                 285

Tyr Gly Asp Asn Val Glu Glu Met Asp Trp Met Val Gly Lys Ile Leu
        290                 295                 300

Asp Ala Leu Asp Gln Glu Arg Leu Ala Asn His Thr Leu Val Tyr Phe
305                 310                 315                 320

Thr Ser Asp Asn Gly Gly His Leu Glu Pro Leu Asp Gly Ala Val Gln
                325                 330                 335

Leu Gly Gly Trp Asn Gly Ile Tyr Lys Gly Lys Gly Met Gly Gly
                340                 345                 350

Trp Glu Gly Gly Ile Arg Val Pro Gly Ile Phe Arg Trp Pro Ser Val
            355                 360                 365

Leu Glu Ala Gly Arg Val Ile Asn Glu Pro Thr Ser Leu Met Asp Ile
370                 375                 380

Tyr Pro Thr Leu Ser Tyr Ile Gly Gly Gly Ile Leu Ser Gln Asp Arg
385                 390                 395                 400

Val Ile Asp Gly Gln Asn Leu Met Pro Leu Leu Glu Gly Arg Ala Ser
                405                 410                 415

His Ser Asp His Glu Phe Leu Phe His Tyr Cys Gly Val Tyr Leu His
            420                 425                 430

Thr Val Arg Trp His Gln Lys Asp Cys Ala Thr Val Trp Lys Ala His
            435                 440                 445

Tyr Val Thr Pro Lys Phe Tyr Pro Glu Gly Thr Gly Ala Cys Tyr Gly
        450                 455                 460

Ser Gly Ile Cys Ser Cys Ser Gly Asp Val Thr Tyr His Asp Pro Pro
465                 470                 475                 480

Leu Leu Phe Asp Ile Ser Arg Asp Pro Ser Glu Ala Leu Pro Leu Asn
                485                 490                 495

Pro Asp Asn Glu Pro Leu Phe Asp Ser Val Ile Lys Lys Met Glu Ala
            500                 505                 510

Ala Ile Arg Glu His Arg Arg Thr Leu Thr Pro Val Pro Gln Gln Phe
        515                 520                 525

Ser Val Phe Asn Thr Ile Trp Lys Pro Trp Leu Gln Pro Cys Cys Gly
    530                 535                 540

Thr Phe Pro Phe Cys Gly Cys Asp Lys Glu Asp Asp Ile Leu Pro Met
545                 550                 555                 560

Ala Pro

<210> SEQ ID NO 29
<211> LENGTH: 3225
<212> TYPE: DNA
<213> ORGANISM: Homo sapiens

<400> SEQUENCE: 29
gcgtcccgcc cctccacctg gggctcggcc cggcccggca gatgttacaa ctttttcgaa    60
ttctctcccg ccgtgtcccc tcgacccgcc caacttgtgc ctcccctccc ttccctctg    120 gggtcctgcc cacctccctg cagggagctg gctgttttta aggactccgg gtggggcgag   180
```

|   |   |
|---|---|
| aggccgggaa agcagaggag agagaaatta ggaggcggga gaaatccagg gcaagaagga | 240 |
| agaggggagt cagaggatgg tagagagcac ttttttggaag ctgccacgcc gcgtctcagg | 300 |
| ctggccgggc tgagctgggg aagagggagc aaaggcggcg cagggcctgc gcttaggcag | 360 |
| cgggaggcag ctcggcgcgg gcctgacctc cccagagcgc cccgctgcgg ccgagcagat | 420 |
| ccggcccagc cgtccggcag ccagtcccgg accagacact ggaccgtccc cgggggggcgc | 480 |
| tgaactccct cgcagcatcc gagccggcgg gccggtggtg cgcctgggc gcgcgaggtg | 540 |
| gtgaggcccc aggagcccgg cgcgccggga cgcgcgggcc ggcttggcga tgcacaccct | 600 |
| cactggcttc tccctggtca gcctgctcag cttcggctac ctgtcctggg actgggccaa | 660 |
| gccgagcttc gtggccgacg ggcccgggga ggctggcgag cagccctcgg ccgctccgcc | 720 |
| ccagcctccc cacatcatct tcatcctcac ggacgaccaa ggctaccacg acgtgggcta | 780 |
| ccatggttca gatatcgaga cccctacgct ggacaggctg gcggccaagg gggtcaagtt | 840 |
| ggagaattat tacatccagc ccatctgcac gccttcgcgg agccagctcc tcactgcag | 900 |
| gtaccagatc cacacaggac tccagcattc catcatccgc ccacagcagc caactgcct | 960 |
| gccccctggac caggtgacac tgccacagaa gctgcaggag gcaggttatt ccacccatat | 1020 |
| ggtgggcaag tggcacctgg gcttctaccg gaaggagtgt ctgcccaccc gtcgggcttt | 1080 |
| cgacaccttc ctgggctcgc tcacgggcaa tgtggactat tacacctatg acaactgtga | 1140 |
| tggcccaggc gtgtgcggct tcgacctgca cgagggtgag aatgtggcct gggggctcag | 1200 |
| cggccagtac tccactatgc tttatgccca gcgcgccagc catatcctgg ccagccacag | 1260 |
| ccctcagcgt cccctcttcc tctatgtggc cttccaggca gtacacacac ccctgcagtc | 1320 |
| ccctcgtgag tacctgtacc gctaccgcac catgggcaat gtggcccggc ggaagtacgc | 1380 |
| ggccatggtg acctgcatgg atgaggctgt gcgcaacatc acctgggccc tcaagcgcta | 1440 |
| cggtttctac aacaacagtg tcatcatctt ctccagtgac aatggtggcc agactttctc | 1500 |
| gggggggcagc aactggccgc tccgaggacg caagggcact tattgggaag gtggcgtgcg | 1560 |
| gggcctaggc tttgtccaca gtccctgct caagcgaaag caacggacaa gccgggcact | 1620 |
| gatgcacatc actgactggt acccgaccct ggtgggtctg gcaggtggta ccacctcagc | 1680 |
| agccgatggg ctagatggct acgacgtgtg gccggccatc agcgagggcc gggcctcacc | 1740 |
| acgcacggag atcctgcaca acattgaccc actctacaac catgcccagc atggctccct | 1800 |
| ggagggcggc tttggcatct ggaacaccgc cgtgcaggct gccatccgcg tgggtgagtg | 1860 |
| gaagctgctg acaggagacc ccggctatgg cgattggatc ccaccgcaga cactggccac | 1920 |
| cttcccgggt agctggtgga acctggaacg aatggccagt gtccgccagg ccgtgtggct | 1980 |
| cttcaacatc agtgctgacc cttatgaacg ggaggacctg gctggccagc ggcctgatgt | 2040 |
| ggtccgcacc ctgctggctc gcctggccga atataaccgc acagccatcc cggtacgcta | 2100 |
| cccagctgag aacccccggg ctcatcctga ctttaatggg ggtgcttggg ggccctgggc | 2160 |
| cagtgatgag gaagaggagg aagaggaagg gagggctcga agcttctccc ggggtcgtcg | 2220 |
| caagaaaaaa tgcaagattt gcaagcttcg atccttttc cgtaaactca acaccaggct | 2280 |
| aatgtcccaa cggatctgat ggtgggggagg gagaaaactg tcctttagag gatcttcccc | 2340 |
| actccggctt ggccctgctg tttctcaggg agaagcctgt cacatctcca tctacaggga | 2400 |
| gttggagggt gtagagtccc ttggttgaac agggtaggga gcctggatag gagtgggtgg | 2460 |
| gaataaacca gactgggatg cctgtgtctc agtcctgcct cctcacgac ttgctctgtg | 2520 |
| acctcaggtg acccacatga gctttagcc tcagtttcct catctgtaaa atgagctcta | 2580 |

-continued

```
atgactttgt gactctttgg tgtggccctg gagcctgggg ccacggtgga gttcctggcc    2640
ggccttgcca cttgacaact cctttaaggc ttcccccta  acacgggatc cctgtggtgg    2700
tgtttgggag ttgcctggag gcaactccaa gcctggcccc cagctgaagc atggcaatct    2760
ggctgctctc tacagggacc cccaagcgct gtgggtggag ggcaggggtc ggggggttg     2820
accttcttgg gtcttcacat ggcctaggcc agtcctccgg tcagactggt gtcaggcacc    2880
gtggtgcaaa attcctcttc tggccctcc  agtacccaga gaaactggct gggccattaa    2940
ctgctgcagc accaagggtg gtagaaagag ctgtgaagag cccccaaacc agtaccagga    3000
cacctgggtt ctcctgtgac ctggggcaca gttcttgccc tctaggcctt gatttcccca    3060
cctgcaagtg gggatgccag ccctggctct gcctccttca tgaggctctg gaagactggc    3120
caaggttgtg gaggagcttg tgaacttgat taaagtgtcg taacatgaaa aaaaaaaaa     3180
aaaaaaaaa  aaaaaaaaaa aaaaaaaaa  aaaaaaaaa  aaaaa                    3225
```

<210> SEQ ID NO 30
<211> LENGTH: 569
<212> TYPE: PRT
<213> ORGANISM: Homo sapiens

<400> SEQUENCE: 30

Met His Thr Leu Thr Gly Phe Ser Leu Val Ser Leu Leu Ser Phe Gly
1               5                   10                  15

Tyr Leu Ser Trp Asp Trp Ala Lys Pro Ser Phe Val Ala Asp Gly Pro
            20                  25                  30

Gly Glu Ala Gly Glu Gln Pro Ser Ala Ala Pro Gln Pro Pro His
        35                  40                  45

Ile Ile Phe Ile Leu Thr Asp Asp Gln Gly Tyr His Asp Val Gly Tyr
    50                  55                  60

His Gly Ser Asp Ile Glu Thr Pro Thr Leu Asp Arg Leu Ala Ala Lys
65                  70                  75                  80

Gly Val Lys Leu Glu Asn Tyr Tyr Ile Gln Pro Ile Cys Thr Pro Ser
                85                  90                  95

Arg Ser Gln Leu Leu Thr Gly Arg Tyr Gln Ile His Thr Gly Leu Gln
            100                 105                 110

His Ser Ile Ile Arg Pro Gln Gln Pro Asn Cys Leu Pro Leu Asp Gln
        115                 120                 125

Val Thr Leu Pro Gln Lys Leu Gln Glu Ala Gly Tyr Ser Thr His Met
    130                 135                 140

Val Gly Lys Trp His Leu Gly Phe Tyr Arg Lys Glu Cys Leu Pro Thr
145                 150                 155                 160

Arg Arg Gly Phe Asp Thr Phe Leu Gly Ser Leu Thr Gly Asn Val Asp
                165                 170                 175

Tyr Tyr Thr Tyr Asp Asn Cys Asp Gly Pro Gly Val Cys Gly Phe Asp
            180                 185                 190

Leu His Glu Gly Glu Asn Val Ala Trp Gly Leu Ser Gly Gln Tyr Ser
        195                 200                 205

Thr Met Leu Tyr Ala Gln Arg Ala Ser His Ile Leu Ala Ser His Ser
    210                 215                 220

Pro Gln Arg Pro Leu Phe Leu Tyr Val Ala Phe Gln Ala Val His Thr
225                 230                 235                 240

Pro Leu Gln Ser Pro Arg Glu Tyr Leu Tyr Arg Tyr Arg Thr Met Gly
                245                 250                 255

```
Asn Val Ala Arg Arg Lys Tyr Ala Ala Met Val Thr Cys Met Asp Glu
            260                 265                 270
Ala Val Arg Asn Ile Thr Trp Ala Leu Lys Arg Tyr Gly Phe Tyr Asn
        275                 280                 285
Asn Ser Val Ile Ile Phe Ser Ser Asp Asn Gly Gly Gln Thr Phe Ser
    290                 295                 300
Gly Gly Ser Asn Trp Pro Leu Arg Gly Arg Lys Gly Thr Tyr Trp Glu
305                 310                 315                 320
Gly Gly Val Arg Gly Leu Gly Phe Val His Ser Pro Leu Leu Lys Arg
                325                 330                 335
Lys Gln Arg Thr Ser Arg Ala Leu Met His Ile Thr Asp Trp Tyr Pro
            340                 345                 350
Thr Leu Val Gly Leu Ala Gly Gly Thr Thr Ser Ala Ala Asp Gly Leu
        355                 360                 365
Asp Gly Tyr Asp Val Trp Pro Ala Ile Ser Glu Gly Arg Ala Ser Pro
    370                 375                 380
Arg Thr Glu Ile Leu His Asn Ile Asp Pro Leu Tyr Asn His Ala Gln
385                 390                 395                 400
His Gly Ser Leu Glu Gly Gly Phe Gly Ile Trp Asn Thr Ala Val Gln
                405                 410                 415
Ala Ala Ile Arg Val Gly Glu Trp Lys Leu Leu Thr Gly Asp Pro Gly
            420                 425                 430
Tyr Gly Asp Trp Ile Pro Pro Gln Thr Leu Ala Thr Phe Pro Gly Ser
        435                 440                 445
Trp Trp Asn Leu Glu Arg Met Ala Ser Val Arg Gln Ala Val Trp Leu
    450                 455                 460
Phe Asn Ile Ser Ala Asp Pro Tyr Glu Arg Glu Asp Leu Ala Gly Gln
465                 470                 475                 480
Arg Pro Asp Val Val Arg Thr Leu Leu Ala Arg Leu Ala Glu Tyr Asn
                485                 490                 495
Arg Thr Ala Ile Pro Val Arg Tyr Pro Ala Glu Asn Pro Arg Ala His
            500                 505                 510
Pro Asp Phe Asn Gly Gly Ala Trp Gly Pro Trp Ala Ser Asp Glu Glu
        515                 520                 525
Glu Glu Glu Glu Glu Gly Arg Ala Arg Ser Phe Ser Arg Gly Arg Arg
    530                 535                 540
Lys Lys Lys Cys Lys Ile Cys Lys Leu Arg Ser Phe Phe Arg Lys Leu
545                 550                 555                 560
Asn Thr Arg Leu Met Ser Gln Arg Ile
                565

<210> SEQ ID NO 31
<211> LENGTH: 4689
<212> TYPE: DNA
<213> ORGANISM: Homo sapiens

<400> SEQUENCE: 31
ctggagagaa aagagggagg aggcaaaaga actcggagtg ccaaagctaa ataagttagc      60
tgagaaaacg cacgcagttt gcagcgcctg cgccgggtgc gccaactacg caaagaccaa     120
gcgggctccg cgcggaccgg ccgcggggct agggacccgg ctttggcctt caggctccct     180
agcagcgggg aaaaggaatt gctgcccgga gtttctgcgg aggtggaggg agatcaggaa     240
acggcttctt cctcacttcg ccgcctggtg agtgtcgggg agattggcaa acgcctagga     300
aaggactggg gaaaatagcc ctgggaaagt ggagaaggtg atcaggaggc cggtccacta     360
```

```
cggcagttta tctgtctgat cagagccaga cgcgacgcgt ccacttcgca gttctttcca    420
ggtgtgggga ccgcaggaca gacggccgat cccgccgccc tccgtaccag cactcccagg    480
agagtcagcc tcgctcccca acgtcgaggg cgctctggcc acgaaaagtt cctgtccact    540
gtgattctca attccttgct tggttttttt ctccagagaa cttttgggtg agatattaa     600 cttttttctt tttttttcc ttggtggaag ctgctctagg gagggggag gaggaggaga      660 aagtgaaatg tgctggagaa gagcgagccc tccttgttct tccggagtcc catccattaa    720
gccatcactt ctggaagatt aaagttgtcg gacatggtga cagctgagag gagaggagga    780
tttcttgcca ggtggagagt cttcaccgtc tgttgggtgc atgtgtgcgc ccgcagcggc    840
gcggggcgcg tggttctccg cgtggagtct cacctgggac ctgagtgaat ggctcccagg    900
ggctgtgcgg ggcatccgcc tccgccttct ccacaggcct gtgtctgtcc tggaaagatg    960
ctagcaatgg gggcgctggc aggattctgg atcctctgcc tcctcactta tggttacctg   1020
tcctggggcc aggccttaga agaggaggaa gaaggggcct tactagctca agctggagag   1080
aaactagagc ccagcacaac ttccacctcc cagccccatc tcattttcat cctagcggat   1140 gatcaggat ttagagatgt gggttaccac ggatctgaga ttaaaacacc tactcttgac    1200
aagctcgctg ccgaaggagt taaactggag aactactatg tccagcctat ttgcacacca   1260
tccaggagtc agtttattac tggaaagtat cagatacaca ccggacttca acattctatc   1320
ataagaccta cccaacccaa ctgtttacct ctggacaatg ccaccctacc tcagaaactg   1380
aaggaggttg gatattcaac gcatatggtc ggaaaatggc acttgggttt ttacagaaaa   1440
gaatgcatgc ccaccagaag aggatttgat acctttttg gttccctttt gggaagtggg    1500
gattactata cacactacaa atgtgacagt cctgggatgt gtggctatga cttgtatgaa   1560
aacgacaatg ctgcctggga ctatgacaat ggcatatact ccacacagat gtacactcag   1620
agagtacagc aaatcttagc ttcccataac cccacaaagc ctatattttt atatattgcc   1680
tatcaagctg ttcattcacc actgcaagct cctggcaggt atttcgaaca ctaccgatcc   1740
attatcaaca taaacaggag gagatatgct gccatgcttt cctgcttaga tgaagcaatc   1800
aacaacgtga cattggctct aaagacttat ggtttctata caacagcat tatcatttac    1860 tcttcagata atggtggcca gcctacggca ggagggagta actggcctct cagaggtagc   1920
aaaggaacat attgggaagg agggatccgg gctgtaggct tgtgcatag cccacttctg    1980 aaaaacaagg gaacagtgtg taaggaactt gtgcacatca ctgactggta ccccactctc   2040
atttcactgg ctgaaggaca gattgatgag gacattcaac tagatggcta tgatatctgg   2100
gagaccataa gtgagggtct tcgctcaccc cgagtagata ttttgcataa cattgacccc   2160
atatacacca aggcaaaaaa tggctcctgg gcagcaggct atgggatctg gaacactgca   2220
atccagtcag ccatcagagt gcagcactgg aaattgctta caggaaatcc tggctacagc   2280
gactgggtcc cccctcagtc tttcagcaac ctggaccga accggtggca caatgaacgg    2340
atcaccttgt caactggcaa agtgtatggc tttttcaaca tcacagccga cccatatgag   2400
agggtggacc tatctaacag gtatccagga atcgtgaaga agctcctacg gaggctctca   2460
cagttcaaca aaactgcagt gccggtcagg tatcccccca agacccagt aagtaaccct    2520 aggctcaatg gaggggtctg gggaccatgg tataagagg aaccaagaa aaagaagcca    2580 agcaaaaatc aggctgagaa aaagcaaaag aaaagcaaaa aaagaagaa gaaacagcag   2640 aaagcagtct caggttcaac ttgccattca ggtgttactt gtggataagc acaaatattt   2700
```

-continued

```
cctgtttggt taaactttaa tcagttctta tctttcatct gtttcctagg taaaccagca    2760
aatttggctc gataatatcg ctggcctaag cgtcaggctt gttttcatgc tgtgccactc    2820
cagagacttc tgccacctgg ccgccacact gaaaactgtc ctgctcagtg ccaaggtgct    2880
actcttgcaa gccacactta gagagagtgg agatgtttat ttctcttgct cctttagaaa    2940
acgtggtgag tcctgagttc cactgctgtg cttcagtcaa ctgaccaaac actgctttga    3000
attataggag gagaacaata acctaccatc cgcaagcatg ctaatttgat ggaagttaca    3060
gggtatacca tccgcaagca tgctaatttg atggaagtta cagggtagca tgattaaaac    3120
tacctttgat aaattacagt caaagattgt gtcacctcaa aggccttgaa gaatatattt    3180
tcttggtgaa ttttgtatg tctgtcatat gacacttggg ttttttaatt aattctattt     3240
tatatatata tatatgtttc ttttcctgtg aaaagctgtt tttctcacat gtgaacagct    3300
tgcacctcat tttaccatgc gtgagggaat ggcaaataag aatgtttgag cacactgccc    3360
acaatgaatg taactatttt ctaaacactt tactagaaga acatttcagt ataaaaaacc    3420
taatttattt ttacagaaaa atattttgtt gttttttataa aaagttatgc aaatgacttt   3480
attttatttt tatttcctgc ataccattag aataatttta tttcatttct tcaaattacc    3540
aagcactgta atactataaa ttaatgtaat actgtgtgaa ttcagactat aaaaaacatc    3600
attcagaaaa ctttataatc gtcattgttc aaccaagatt ttgaatgtaa taagatgaat    3660
atattcctta caaattactt ggaaattcaa tgtttgtgca gagttgagac aactttattg    3720
tttctatcat aaactattta tgtatcttaa ttattaaaat gatttacttt atggcactag    3780
aaaatttact gtggcttttc tgatctaact tctagctaaa attgtatcat tggtcctaaa    3840
aaataaaaat ctttactaat aggcaattga aggaatggtt tgctaacaac cacagtaata    3900
taatatgatt ttacagatag atgcttcccc ttggctatga catggagaaa gattttccca    3960
taataataac taacatttat attaggttgg tgcaaaacta gttgcggttt ttcccattaa    4020
aagtaataaa cttactctta tacaaagtgg cactgtggg gagatacaga gaaatggaag     4080
atacggatcc tgcctggagt aggtaacctt gcttggaaac cccacatgca aacgtcatga    4140
ggagaattaa aggagtatta tcagtaatga agtttatcat gggtcatcaa tgagcataga    4200
ttggtgtgga tcctgtagac cctggtgttt tctttgaagt gccctctcct aatgcagagg    4260
ccttgaagct tacagtatac acttgaaaag tcacagatag ctagaattat gatctttgaa    4320
gttataactg tgatctgaaa atgtgtgtgg tggtatgaca gcataccatt aaatacattt    4380
acatcacagc tcaaaggact gtgatataat ccatttatat cacaactcaa aggactgtga    4440
tataatccat ttatatcaca gctcacagtt tctgaaaatg tataaaagaa tctataatct    4500
agtactgaaa ttactaaatt gggtaagatg atttaaatga ttttaatttt aacattttat    4560
ttctagaata tatggctcca tttttattta tagtgtaaag ttgtatttcc taaagtttgt    4620
gttttgtcga cagtatcttt taaatgagtc ttaaaaataa aggcatattg ttcatgttaa    4680
aaaaaaaaa                                                             4689
```

<210> SEQ ID NO 32
<211> LENGTH: 599
<212> TYPE: PRT
<213> ORGANISM: Homo sapiens

<400> SEQUENCE: 32

```
Met Ala Pro Arg Gly Cys Ala Gly His Pro Pro Pro Ser Pro Gln
1               5                   10                  15
```

```
Ala Cys Val Cys Pro Gly Lys Met Leu Ala Met Gly Ala Leu Ala Gly
                20                  25                  30

Phe Trp Ile Leu Cys Leu Leu Thr Tyr Gly Tyr Leu Ser Trp Gly Gln
        35                  40                  45

Ala Leu Glu Glu Glu Glu Gly Ala Leu Leu Ala Gln Ala Gly Glu
    50                  55                  60

Lys Leu Glu Pro Ser Thr Thr Ser Thr Ser Gln Pro His Leu Ile Phe
65                  70                  75                  80

Ile Leu Ala Asp Asp Gln Gly Phe Arg Asp Val Gly Tyr His Gly Ser
                85                  90                  95

Glu Ile Lys Thr Pro Thr Leu Asp Lys Leu Ala Ala Glu Gly Val Lys
                100                 105                 110

Leu Glu Asn Tyr Tyr Val Gln Pro Ile Cys Thr Pro Ser Arg Ser Gln
            115                 120                 125

Phe Ile Thr Gly Lys Tyr Gln Ile His Thr Gly Leu Gln His Ser Ile
        130                 135                 140

Ile Arg Pro Thr Gln Pro Asn Cys Leu Pro Leu Asp Asn Ala Thr Leu
145                 150                 155                 160

Pro Gln Lys Leu Lys Glu Val Gly Tyr Ser Thr His Met Val Gly Lys
                165                 170                 175

Trp His Leu Gly Phe Tyr Arg Lys Glu Cys Met Pro Thr Arg Arg Gly
            180                 185                 190

Phe Asp Thr Phe Phe Gly Ser Leu Leu Gly Ser Gly Asp Tyr Tyr Thr
        195                 200                 205

His Tyr Lys Cys Asp Ser Pro Gly Met Cys Gly Tyr Asp Leu Tyr Glu
    210                 215                 220

Asn Asp Asn Ala Ala Trp Asp Tyr Asp Asn Gly Ile Tyr Ser Thr Gln
225                 230                 235                 240

Met Tyr Thr Gln Arg Val Gln Gln Ile Leu Ala Ser His Asn Pro Thr
                245                 250                 255

Lys Pro Ile Phe Leu Tyr Ile Ala Tyr Gln Ala Val His Ser Pro Leu
            260                 265                 270

Gln Ala Pro Gly Arg Tyr Phe Glu His Tyr Arg Ser Ile Ile Asn Ile
        275                 280                 285

Asn Arg Arg Arg Tyr Ala Ala Met Leu Ser Cys Leu Asp Glu Ala Ile
290                 295                 300

Asn Asn Val Thr Leu Ala Leu Lys Thr Tyr Gly Phe Tyr Asn Asn Ser
305                 310                 315                 320

Ile Ile Ile Tyr Ser Ser Asp Asn Gly Gly Gln Pro Thr Ala Gly Gly
                325                 330                 335

Ser Asn Trp Pro Leu Arg Gly Ser Lys Gly Thr Tyr Trp Glu Gly Gly
                340                 345                 350

Ile Arg Ala Val Gly Phe Val His Ser Pro Leu Leu Lys Asn Lys Gly
        355                 360                 365

Thr Val Cys Lys Glu Leu Val His Ile Thr Asp Trp Tyr Pro Thr Leu
    370                 375                 380

Ile Ser Leu Ala Glu Gly Gln Ile Asp Glu Asp Ile Gln Leu Asp Gly
385                 390                 395                 400

Tyr Asp Ile Trp Glu Thr Ile Ser Glu Gly Leu Arg Ser Pro Arg Val
                405                 410                 415

Asp Ile Leu His Asn Ile Asp Pro Ile Tyr Thr Lys Ala Lys Asn Gly
            420                 425                 430

Ser Trp Ala Ala Gly Tyr Gly Ile Trp Asn Thr Ala Ile Gln Ser Ala
```

```
         435                 440                 445
Ile Arg Val Gln His Trp Lys Leu Leu Thr Gly Asn Pro Gly Tyr Ser
    450                 455                 460

Asp Trp Val Pro Pro Gln Ser Phe Ser Asn Leu Gly Pro Asn Arg Trp
465                 470                 475                 480

His Asn Glu Arg Ile Thr Leu Ser Thr Gly Lys Ser Val Trp Leu Phe
                485                 490                 495

Asn Ile Thr Ala Asp Pro Tyr Glu Arg Val Asp Leu Ser Asn Arg Tyr
            500                 505                 510

Pro Gly Ile Val Lys Lys Leu Leu Arg Arg Leu Ser Gln Phe Asn Lys
        515                 520                 525

Thr Ala Val Pro Val Arg Tyr Pro Pro Lys Asp Pro Arg Ser Asn Pro
    530                 535                 540

Arg Leu Asn Gly Gly Val Trp Gly Pro Trp Tyr Lys Glu Glu Thr Lys
545                 550                 555                 560

Lys Lys Lys Pro Ser Lys Asn Gln Ala Glu Lys Gln Lys Lys Ser
                565                 570                 575

Lys Lys Lys Lys Lys Lys Gln Gln Lys Ala Val Ser Gly Ser Thr Cys
            580                 585                 590

His Ser Gly Val Thr Cys Gly
        595

<210> SEQ ID NO 33
<211> LENGTH: 3345
<212> TYPE: DNA
<213> ORGANISM: Homo sapiens

<400> SEQUENCE: 33
aggagttgta gttctgcggg tgaagctcgg cgttactatc aagcaaccaa actgcaagct    60
ttgggagttg ttcgctgtcc ctgccctgct ctgctaggga gagaacgcca gagggaggcg   120
gctggcccgg cggcaggctc tcagaaccgc taccggcgat gctactgctg tgggtgtcgg   180
tggtcgcagc cttggcgctg gcggtactgg cccccggagc aggggagcag aggcggagag   240
cagccaaagc gcccaatgtg gtgctggtcg tgagcgactc cttcgatgga aggttaacat   300 tcatccagg aagtcaggta gtgaaacttc cttttatcaa ctttatgaag acacgtggga   360
cttcctttct gaatgcctac acaaactctc aatttgttg cccatcacgc gcagcaatgt   420
ggagtggcct cttcactcac ttaacagaat cttggaataa ttttaagggt ctagatccaa   480
attatacaac atggatggat gtcatggaga ggcatggcta ccgaacacag aaatttggga   540
aactggacta tacttcagga catcactcca ttagtaatcg tgtggaagcg tggacaagag   600
atgttgcttt cttactcaga caagaaggca ggcccatggt taatcttatc cgtaacagga   660
ctaaagtcag agtgatggaa agggattggc agaatacaga caaagcagta aactggttaa   720
gaaaggaagc aattaattac actgaaccat ttgttattta cttgggatta aatttaccac   780 accccttaccc ttcaccatct tctggagaaa attttggatc ttcaacattt cacacatctc   840
tttattggct tgaaaaagtg tctcatgatg ccatcaaaat cccaaagtgg tcacctttgt   900
cagaaatgca ccctgtagat tattactctt cttatacaaa aaactgcact ggaagattta   960
caaaaaaaga aattaagaat attagagcat tttattatgc tatgtgtgct gagacagatg  1020
ccatgcttgg tgaaattatt ttggcccttc atcaattaga tcttcttcag aaaactattg  1080
tcatatactc ctcagaccat ggagagctgg ccatggaaca tcgacagttt tataaaatga  1140
gcatgtacga ggctagtgca catgttccgc ttttgatgat gggaccagga attaaagccg  1200
```

```
gcctacaagt atcaaatgtg gtttctcttg tggatattta ccctaccatg cttgatattg    1260
ctggaattcc tctgcctcag aacctgagtg gatactcttt gttgccgtta tcatcagaaa    1320
catttaagaa tgaacataaa gtcaaaaacc tgcatccacc ctggattctg agtgaattcc    1380
atggatgtaa tgtgaatgcc tccacctaca tgcttcgaac taaccactgg aaatatatag    1440
cctattcgga tggtgcatca atattgcctc aactctttga tctttcctcg gatccagatg    1500
aattaacaaa tgttgctgta aaatttccag aaattactta ttctttggat cagaagcttc    1560
attccattat aaactaccct aaagtttctg cttctgtcca ccagtataat aaagagcagt    1620
ttatcaagtg gaaacaaagt ataggacaga attattcaaa cgttatagca aatcttaggt    1680
ggcaccaaga ctggcagaag gaaccaagga agtatgaaaa tgcaattgat cagtggctta    1740
aaacccatat gaatccaaga gcagtttgaa caaaaagttt aaaaatagtg ttctagagat    1800
acatataaat atattacaag atcataatta tgtattttaa atgaaacagt tttaataatt    1860
accaagtttt ggccgggcac agtggctcac acctgtaatc ccaggacttt gggaggctga    1920
ggaaagcaga tcacaaggtc aagagattga gaccatcctg gccaacatgg tgaaaccctg    1980
tctctactaa aaatacaaaa attagctggg cgcggtggtg cacacctata gtctcagcta    2040
ctcagaggct gaggcaggag gatcgcttga acccgggagg cagcagttgc agtgagctga    2100
gattgcgcca ctgtactcca gcctggcaac agagtgagac tgtgtcgcaa aaaaataaaa    2160
ataaaataat aataattacc aatttttcat tattttgtaa gaatgtagtg tattttaaga    2220
taaaatgcca atgattataa aatcacatat tttcaaaaat ggttattatt taggcctttg    2280
tacaatttct aacaatttag tggaagtatc aaaagaattg aagcaaatac tgtaacagtt    2340
atgttccttt aaataataga gaatataaaa tattgtaata atatgtatca taaaatagtt    2400
gtatgtgagc atttgatggt gctcgatgag ttacttgtat ttgatgggat tgtttggatg    2460
tatttaatgg gagtatttgg agtatttaac gggatgtaaa ccctggatgt acctgatttt    2520
gttactgttt tattttaata ggtaatatat atacagggta aaagcttcaa atggtacaaa    2580
agggttaaca gtgatcgtga agtctctgtc ctttccctct tccctgccat ccagttcccc    2640
ctccaagaag caagtaccga aaccacctgc ttacgcattt ttagagattg gccacaaatt    2700
tataaacaaa tgtatatatt cctttccccc tacacaaacg gtaacatact gcacacattg    2760

ttctgcatgt tgcttctttt tccтттттттт tttcacttaa cagtagatat ctagaggtga    2820
aattactgag tcaagactat atttagcaaa attacactag atactacaaa ttacctctaa    2880
agaaggtata ctaactgata atctcaccat caatgcatgt cttcttatcc tttgccaacc    2940
taacagataa aaatgttcta tttttatttt tctttttatg agtaacgtag agcatatttt    3000
catgtattta acagccactg gaatctgctt taccatggcc tttcctattt ctattctttg    3060
cctatttttc tgttggttgt tggtctttgt tttgtattac aggtgtgctt tagatattag    3120
ctttttgtaa gagatcctgc aaatatcttc tttccagttt gtcattgtca tttgtctttt    3180
gactttgttc tggtattttt tgatatgtag aaatttttat tttcatgtaa gcaaatttat    3240
gaatctttgt acaccataag tatatacaat tatgatttgt caattaaaaa tattagtaca    3300
aaatttacag atctttgctt ttgtggcttt tgggattttg tatca                    3345
```

<210> SEQ ID NO 34
<211> LENGTH: 536
<212> TYPE: PRT
<213> ORGANISM: Homo sapiens -continued

```
<400> SEQUENCE: 34

Met Leu Leu Leu Trp Val Ser Val Val Ala Leu Ala Leu Ala Val
1               5                   10                  15

Leu Ala Pro Gly Ala Gly Glu Gln Arg Arg Ala Ala Lys Ala Pro
                20                  25                  30

Asn Val Leu Val Val Ser Asp Ser Phe Asp Gly Arg Leu Thr Phe
            35                  40                  45

His Pro Gly Ser Gln Val Val Lys Leu Pro Phe Ile Asn Phe Met Lys
50                  55                  60

Thr Arg Gly Thr Ser Phe Leu Asn Ala Tyr Thr Asn Ser Pro Ile Cys
65                  70                  75                  80

Cys Pro Ser Arg Ala Ala Met Trp Ser Gly Leu Phe Thr His Leu Thr
                85                  90                  95

Glu Ser Trp Asn Asn Phe Lys Gly Leu Asp Pro Asn Tyr Thr Thr Trp
                100                 105                 110

Met Asp Val Met Glu Arg His Gly Tyr Arg Thr Gln Lys Phe Gly Lys
            115                 120                 125

Leu Asp Tyr Thr Ser Gly His His Ser Ile Ser Asn Arg Val Glu Ala
    130                 135                 140

Trp Thr Arg Asp Val Ala Phe Leu Leu Arg Gln Glu Gly Arg Pro Met
145                 150                 155                 160

Val Asn Leu Ile Arg Asn Arg Thr Lys Val Arg Val Met Glu Arg Asp
                165                 170                 175

Trp Gln Asn Thr Asp Lys Ala Val Asn Trp Leu Arg Lys Glu Ala Ile
                180                 185                 190

Asn Tyr Thr Glu Pro Phe Val Ile Tyr Leu Gly Leu Asn Leu Pro His
            195                 200                 205

Pro Tyr Pro Ser Pro Ser Ser Gly Glu Asn Phe Gly Ser Ser Thr Phe
    210                 215                 220

His Thr Ser Leu Tyr Trp Leu Glu Lys Val Ser His Asp Ala Ile Lys
225                 230                 235                 240

Ile Pro Lys Trp Ser Pro Leu Ser Glu Met His Pro Val Asp Tyr Tyr
                245                 250                 255

Ser Ser Tyr Thr Lys Asn Cys Thr Gly Arg Phe Thr Lys Lys Glu Ile
                260                 265                 270

Lys Asn Ile Arg Ala Phe Tyr Tyr Ala Met Cys Ala Glu Thr Asp Ala
        275                 280                 285

Met Leu Gly Glu Ile Ile Leu Ala Leu His Gln Leu Asp Leu Leu Gln
    290                 295                 300

Lys Thr Ile Val Ile Tyr Ser Ser Asp His Gly Glu Leu Ala Met Glu
305                 310                 315                 320

His Arg Gln Phe Tyr Lys Met Ser Met Tyr Glu Ala Ser Ala His Val
                325                 330                 335

Pro Leu Leu Met Met Gly Pro Gly Ile Lys Ala Gly Leu Gln Val Ser
            340                 345                 350

Asn Val Val Ser Leu Val Asp Ile Tyr Pro Thr Met Leu Asp Ile Ala
        355                 360                 365

Gly Ile Pro Leu Pro Gln Asn Leu Ser Gly Tyr Ser Leu Leu Pro Leu
    370                 375                 380

Ser Ser Glu Thr Phe Lys Asn Glu His Lys Val Lys Asn Leu His Pro
385                 390                 395                 400

Pro Trp Ile Leu Ser Glu Phe His Gly Cys Asn Val Asn Ala Ser Thr
                405                 410                 415
```

Tyr Met Leu Arg Thr Asn His Trp Lys Tyr Ile Ala Tyr Ser Asp Gly
            420                 425                 430

Ala Ser Ile Leu Pro Gln Leu Phe Asp Leu Ser Ser Asp Pro Asp Glu
            435                 440                 445

Leu Thr Asn Val Ala Val Lys Phe Pro Glu Ile Thr Tyr Ser Leu Asp
450                 455                 460

Gln Lys Leu His Ser Ile Ile Asn Tyr Pro Lys Val Ser Ala Ser Val
465                 470                 475                 480

His Gln Tyr Asn Lys Glu Gln Phe Ile Lys Trp Lys Ser Ile Gly
            485                 490                 495

Gln Asn Tyr Ser Asn Val Ile Ala Asn Leu Arg Trp His Gln Asp Trp
            500                 505                 510

Gln Lys Glu Pro Arg Lys Tyr Glu Asn Ala Ile Asp Gln Trp Leu Lys
            515                 520                 525

Thr His Met Asn Pro Arg Ala Val
            530                 535

<210> SEQ ID NO 35
<211> LENGTH: 2179
<212> TYPE: DNA
<213> ORGANISM: Homo sapiens

<400> SEQUENCE: 35

| | | | | |
|---|---|---|---|---|
| cacgtgacca | accgggtcac | atggcccgcg | ggacaacatg gctgcgcccg | cactagggct | 60 |
| ggtgtgtgga | cgttgccctg | agctgggtct | cgtcctcttg ctgctgctgc | tctcgctgct | 120 |
| gtgtggagcg | gcagggagcc | aggaggccgg | gaccggtgcg ggcgcggggt | cccttgcggg | 180 |
| ttcttgcggc | tgcggcacgc | cccagcggcc | tggcgcccat ggcagttcgg | cagccgctca | 240 |
| ccgatactcg | cgggaggcta | acgctccggg | ccccgtaccc ggagagcggc | aactcgcgca | 300 |
| ctcaaagatg | gtccccatcc | ctgctggagt | atttacaatg gcacagatg | atcctcagat | 360 |
| aaagcaggat | ggggaagcac | ctgcgaggag | agttactatt gatgcctttt | acatggatgc | 420 |
| ctatgaagtc | agtaatactg | aatttgagaa | gtttgtgaac tcaactggct | atttgacaga | 480 |
| ggctgagaag | tttggcgact | cctttgtctt | tgaaggcatg ttgagtgagc | aagtgaagac | 540 |
| caatattcaa | caggcagttg | cagctgctcc | ctggtggtta cctgtgaaag | cgctaactg | 600 |
| gagacaccca | gaagggcctg | actctactat | tctgcacagg ccggatcatc | cagttctcca | 660 |
| tgtgtcctgg | aatgatgcgg | ttgcctactg | cacttgggca gggaagcggc | tgcccacgga | 720 |
| agctgagtgg | gaatacagct | gtcgaggagg | cctgcataat agacttttcc | cctggggcaa | 780 |
| caaactgcag | cccaaaggcc | agcattatgc | caacatttgg cagggcgagt | tccggtgac | 840 |
| caacactggt | gaggatggct | tccaaggaac | tgcgccttgtt gatgccttcc | ctcccaatgg | 900 |
| ttatggctta | tacaacatag | tggggaacgc | atgggaatgg acttcagact | ggtggactgt | 960 |
| tcatcattct | gttgaagaaa | cgcttaaccc | aaaaggtccc ccttctggga | agaccgagt | 1020 |
| gaagaaaggt | ggatcctaca | tgtgccatag | gtcttattgt tacaggtatc | gctgtgctgc | 1080 |
| tcggagccag | aacacacctg | atagctctgc | ttcgaatctg ggattccgct | gtgcagccga | 1140 |
| ccgcctgccc | actatggact | gacaaccaag | gaaagtcttc cccagtccaa | ggagcagtcg | 1200 |
| tgtctgacct | acattgggct | tttctcagaa | ctttgaacga tcccatgcaa | agaattccca | 1260 |
| ccctgaggtg | ggttacatac | ctgcccaatg | gccaaaggaa ccgccttgtg | agaccaaatt | 1320 |
| gctgacctgg | gtcagtgcat | gtgctttatg | gtgtggtgca tctttggaga | tcatcaccat | 1380 |

```
attttacttt tgagagtctt taaagaggaa ggggagtgga gggaaccctg agctaggctt    1440
caggaggccc gcgtcctacg caggctctgc cacaggggtt agaccccagg tccgacgctt    1500
gaccttcctg ggcctcaagt gccctcccct atcaaatgaa gggatggaca gcatgacctc    1560
tgggtgtctc tccaactcac cagttctaaa aagggtatca gattctattg tgacttcata    1620
gtgagaattt attatagatt attttttagc tattttttcc atgtgtgaac cttgagtgat    1680
actaatcatg taaagtaaga gttctcttat gtattatttt cggaagaggg gtgtggtgac    1740
tcctttatat tcgtactgca ctttgttttt ccaaggaaat cagtgtcttt tacgttgtta    1800
tgatgaatcc cacatggggc cggtgatggt atgctgaagt tcagccgttg aacacatagg    1860
aatgtctgtg gggtgactct actgtgcttt atcttttaac attaagtgcc tttggttcag    1920
aggggcagtc ataagctctg tttccccctc tccccaaagc cttcagcgaa cgtgaaatgt    1980
gcgctaaacg gggaaacctg tttaattcta gatatagggn aaaaggaacg aggaccttga    2040
atgagctata ttcagggtat ccggtatttt gtaatagggn ataggaaacc ttgttggctg    2100
tggaatatcc gatgctttga atcatgcact gtgttgaata aacgtatctg ctaaatcagg    2160
caaaaaaaaa aaaaaaaaa                                                 2179
```

<210> SEQ ID NO 36
<211> LENGTH: 374
<212> TYPE: PRT
<213> ORGANISM: Homo sapiens

<400> SEQUENCE: 36

```
Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
        115                 120                 125

Tyr Glu Val Ser Asn Thr Glu Phe Glu Lys Phe Val Asn Ser Thr Gly
    130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
```

```
                225                 230                 235                 240
Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
                260                 265                 270

Asp Gly Phe Gln Gly Thr Ala Pro Val Asp Ala Phe Pro Pro Asn Gly
            275                 280                 285

Tyr Gly Leu Tyr Asn Ile Val Gly Asn Ala Trp Glu Trp Thr Ser Asp
        290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Ser Tyr Met Cys
                325                 330                 335

His Arg Ser Tyr Cys Tyr Arg Tyr Arg Cys Ala Ala Arg Ser Gln Asn
                340                 345                 350

Thr Pro Asp Ser Ser Ala Ser Asn Leu Gly Phe Arg Cys Ala Ala Asp
            355                 360                 365

Arg Leu Pro Thr Met Asp
        370

<210> SEQ ID NO 37
<211> LENGTH: 28
<212> TYPE: PRT
<213> ORGANISM: Solanum tuberosum

<400> SEQUENCE: 37

Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp
            20                  25

<210> SEQ ID NO 38
<211> LENGTH: 1524
<212> TYPE: DNA
<213> ORGANISM: Homo sapiens

<400> SEQUENCE: 38
atgagctgcc ccgtgcccgc ctgctgcgcg ctgctgctag tcctggggct ctgccgggcg      60
cgtcccggga cgcactgct  gctcctcgcg gatgacggag gctttgagag tggcgcgtac     120
aacaacagcg ccatcgccac cccgcacctg gacgccttgg cccgccgcag cctcctcttt     180
cgcaatgcct tcacctcggt cagcagctgc tctcccagcc gcgccagcct cctcactggc     240
ctgccccagc atcagaatgg gatgtacggg ctgcaccagg acgtgcacca cttcaactcc     300
ttcgacaagg tgcggagcct gccgctgctg tcagccaag  ctggtgtgcg cacaggcatc     360
atcgggaaga agcacgtggg gccggagacc gtgtacccgt tgactttgc  gtacacggag     420 gagaatggct ccgtcctcca ggtggggcgg aacatcacta gaattaagct gctcgtccgg     480
aaattcctgc agactcagga tgaccggcct ttcttcctct acgtcgcctt ccacgacccc     540
caccgctgtg ggcactccca gcccagtac  ggaaccttct gtgagaagtt tggcaacgga     600
gagagcggca tgggtcgtat cccagactgg accccccagg cctacgaccc actgacgtg     660 ctggtgcctt acttcgtccc caacaccccg gcagcccgag ccgacctggc cgctcagtac     720
accaccgtcg gccgcatgga ccaaggagtt ggactggtgc tccaggagct gcgtgacgcc     780
ggtgtcctga acgacacact ggtgatcttc acgtccgaca acgggatccc cttccccagc     840
```

```
ggcaggacca acctgtactg gccgggcact gctgaaccct tactggtgtc atccccggag    900
cacccaaaac gctggggcca agtcagcgag gcctacgtga gcctcctaga cctcacgccc    960
accatcttgg attggttctc gatcccgtac cccagctacg ccatctttgg ctcgaagacc   1020
atccacctca ctggccggtc cctcctgccg gcgctggagg ccgagcccct ctgggccacc   1080
gtctttggca gccagagcca ccacgaggtc accatgtcct accccatgcg ctccgtgcag   1140
caccggcact tccgcctcgt gcacaacctc aacttcaaga tgcccttttcc catcgaccag   1200
gacttctacg tctcacccac cttccaggac ctcctgaacc gcaccacagc tggtcagccc   1260
acgggctggt acaaggacct ccgtcattac tactaccggg cgcgctggga actctacgac   1320
cggagccggg accccacga gacccagaac ctggccaccg accgcgcttt tgctcagctt   1380
ctggagatgc ttcgggacca gctggccaag tggcagtggg agaccacga ccccctgggtg  1440
tgcgccccccg acggcgtcct ggaggagaag ctctctcccc agtgccagcc cctccacaat  1500
gagctgcatc atcatcatca tcat                                        1524
```

<210> SEQ ID NO 39
<211> LENGTH: 508
<212> TYPE: PRT
<213> ORGANISM: Homo sapiens

<400> SEQUENCE: 39

```
Met Ser Cys Pro Val Pro Ala Cys Cys Ala Leu Leu Val Leu Gly
1               5                   10                  15

Leu Cys Arg Ala Arg Pro Arg Asn Ala Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
        50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255
```

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu His His His His His
            500                 505

<210> SEQ ID NO 40
<211> LENGTH: 1524
<212> TYPE: DNA
<213> ORGANISM: Homo sapiens

<400> SEQUENCE: 40
atgtcttgtc cagttccagc ttgttgcgct ctccttcttg ttcttggatt gtgtagggca     60
aggcctagga acgctctttt gcttcttgct gatgatggcg gattcgagtc cggtgcttac    120
aacaactctg ctatcgctac tccacaccte gatgctcttg ctaggcgttc tcttcttttc    180
cgtaacgctt tcacttccgt gtcctcttgc tcaccttcta gggcttcact tcttactgga    240
cttccacagc accagaacgg aatgtacgga cttcatcagg atgtgcacca cttcaactca    300
ttcgataagg tgagatccct cccactcctc ttgtctcaag ctggtgttag gactggaatc    360
atcggcaaaa agcacgtggg accagagact gtgtacccat tcgatttcgc ttacactgag    420
gaaaacggct ccgttcttca gtgggcagaa atattacta ggatcaagct cctcgtgagg    480
aagttcctcc agactcaaga tgataggcca ttcttcctct acgtggcatt ccatgatcca    540
cataggtgcg acattctca gccacagtac ggaactttct gcgagaagtt cggaaacggt    600
gagtctggta tgggcaggat tccagattgg actccacagg cttacgatcc acttgatgtg    660

```
ctcgttccat acttcgtgcc aaacactcca gctgctagag ctgatcttgc tgctcagtac    720
actactgtgg gaaggatgga tcagggtgtg ggacttgtgc ttcaagagct tagagatgct    780
ggcgtgctca acgatactct cgtgatcttc acttcagata acggcatccc attcccatcc    840
ggaaggacta tctttactg gccaggtact gctgagcctc tccttgtttc ttcaccagag    900
catccaaaga ggtggggaca gtttctgag gcttacgtgt cccttctcga tctcactcca    960
actatcctcg attggttctc catcccttac ccatcctacg ctatcttcgg ctccaagact   1020 atccaccta ctggcagatc tttgctccca gctttggaag ctgaaccact ttgggctact   1080
gtgttcggat ctcagtctca ccacgaggtg acaatgtctt acccaatgag atctgtgcag   1140
cacaggcact tcaggcttgt tcacaacctc aacttcaaga tgccattccc aatcgatcag   1200
gatttctacg tgtcaccaac tttccaggat cttctcaaca ggactactgc aggacaacct   1260
actggctggt acaaggatct taggcactac tactataggg ctaggtggga gctttacgat   1320
aggtccagag atccacacga gactcagaac cttgctactg atccaaggtt cgctcagctc   1380
cttgagatgc ttagggatca gcttgctaag tggcagtggg agactcatga tccatggggtt   1440 tgcgctccag atggtgtgct gaagagaag ttgtctccac agtgccagcc acttcataac   1500
gagcttcatc atcaccatca ccac                                          1524

<210> SEQ ID NO 41
<211> LENGTH: 508
<212> TYPE: PRT
<213> ORGANISM: Homo sapiens

<400> SEQUENCE: 41

Met Ser Cys Pro Val Pro Ala Cys Cys Ala Leu Leu Val Leu Gly
1               5                   10                  15

Leu Cys Arg Ala Arg Pro Arg Asn Ala Leu Leu Leu Ala Asp Asp
                20                  25                  30

Gly Gly Phe Glu Ser Gly Ala Tyr Asn Asn Ser Ala Ile Ala Thr Pro
                35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
                100                 105                 110

Gln Ala Gly Val Arg Thr Gly Ile Ile Gly Lys Lys His Val Gly Pro
            115                 120                 125

Glu Thr Val Tyr Pro Phe Asp Phe Ala Tyr Thr Glu Glu Asn Gly Ser
        130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220
```

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
            245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
            275                 280                 285

Gly Thr Ala Glu Pro Leu Leu Val Ser Ser Pro Glu His Pro Lys Arg
            290                 295                 300

Trp Gly Gln Val Ser Glu Ala Tyr Val Ser Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
            355                 360                 365

Glu Val Thr Met Ser Tyr Pro Met Arg Ser Val Gln His Arg His Phe
370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
            435                 440                 445

Gln Asn Leu Ala Thr Asp Pro Arg Phe Ala Gln Leu Leu Glu Met Leu
450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu His His His His His His
            500                 505

<210> SEQ ID NO 42
<211> LENGTH: 1552
<212> TYPE: DNA
<213> ORGANISM: Homo sapiens

<400> SEQUENCE: 42
aacaatggct tcctccgcta ctactaaatc tttccttatt cttttcttta tgatacttgc    60
aactacttca tcaacatgtg cagtcgaccg tccccggaac gcactgctgc tcctcgcgga   120
tgacggaggc tttgagagtg cgcgtacaa caacagcgcc atcgccaccc gcacctgga    180 cgccttggcc cgccgcagcc tcctctttcg caatgcctcc acctcggtca gcagctgctc   240
tcccagccgc gccagcctcc tcactggcct gccccagcat cagaatggga tgtacgggct   300
gcaccaggac gtgcaccact tcaactcctt cgacaaggtg cggagcctgc cgctgctgct   360
cagccaagct ggtgtgcgca caggcatcat cgggaagaag cacgtggggc cggagaccgt   420
gtacccgttt gactttgcgt acacggagga gaatggctcc gtcctccagg tggggcggaa   480

```
catcactaga attaagctgc tcgtccggaa attcctgcag actcaggatg accggccttt    540
cttcctctac gtcgccttcc acgaccccca ccgctgtggg cactcccagc cccagtacgg    600
aaccttctgt gagaagtttg caacggaga gagcggcatg ggtcgtatcc agactggac     660
cccccaggcc tacgacccac tggacgtgct ggtgccttac ttcgtcccca caccccggc    720
agcccgagcc gacctggccg ctcagtacac caccgtcggc cgcatggacc aaggagttgg    780
actggtgctc caggagctgc gtgacgccgg tgtcctgaac gacacactgg tgatcttcac    840
gtccgacaac gggatcccct tccccagcgg caggaccaac ctgtactggc cgggcactgc    900
tgaaccctta ctggtgtcat ccccggagca cccaaaacgc tggggccaag tcagcgaggc    960
ctacgtgagc ctcctagacc tcacgcccac catcttggat tggttctcga tcccgtaccc   1020
cagctacgcc atctttggct cgaagaccat ccacctcact ggccggtccc tcctgccggc   1080
gctggaggcc gagcccctct gggccaccgt ctttggcagc cagagccacc acgaggtcac   1140
catgtcctac cccatgcgct ccgtgcagca ccggcacttc cgcctcgtgc acaacctcaa   1200
cttcaagatg ccctttccca tcgaccagga cttctacgtc tcacccacct tccaggacct   1260
cctgaaccgc accacagctg gtcagcccac gggctggtac aaggacctcc gtcattacta   1320
ctaccgggcg cgctgggaac tctacgaccg gagccgggac ccccacgaga cccagaacct   1380
ggccaccgac ccgcgctttg ctcagcttct ggagatgctt cgggaccagc tggccaagtg   1440
gcagtgggag acccacgacc cctgggtgtg cgccccgac ggcgtcctgg aggagaagct   1500
ctctccccag tgccagcccc tccacaatga gctgcatcat catcatcatc at           1552
```

<210> SEQ ID NO 43
<211> LENGTH: 516
<212> TYPE: PRT
<213> ORGANISM: Homo sapiens

<400> SEQUENCE: 43

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Arg Pro Arg Asn
                20                  25                  30

Ala Leu Leu Leu Leu Ala Asp Asp Gly Gly Phe Glu Ser Gly Ala Tyr
            35                  40                  45

Asn Asn Ser Ala Ile Ala Thr Pro His Leu Asp Ala Leu Ala Arg Arg
        50                  55                  60

Ser Leu Leu Phe Arg Asn Ala Phe Thr Ser Val Ser Ser Cys Ser Pro
65                  70                  75                  80

Ser Arg Ala Ser Leu Leu Thr Gly Leu Pro Gln His Gln Asn Gly Met
                85                  90                  95

Tyr Gly Leu His Gln Asp Val His His Phe Asn Ser Phe Asp Lys Val
            100                 105                 110

Arg Ser Leu Pro Leu Leu Ser Gln Ala Gly Val Arg Thr Gly Ile
        115                 120                 125

Ile Gly Lys Lys His Val Gly Pro Glu Thr Val Tyr Pro Phe Asp Phe
    130                 135                 140

Ala Tyr Thr Glu Glu Asn Gly Ser Val Leu Gln Val Gly Arg Asn Ile
145                 150                 155                 160

Thr Arg Ile Lys Leu Leu Val Arg Lys Phe Leu Gln Thr Gln Asp Asp
                165                 170                 175

Arg Pro Phe Phe Leu Tyr Val Ala Phe His Asp Pro His Arg Cys Gly
            180                 185                 190
```

His Ser Gln Pro Gln Tyr Gly Thr Phe Cys Glu Lys Phe Gly Asn Gly
         195                 200                 205

Glu Ser Gly Met Gly Arg Ile Pro Asp Trp Thr Pro Gln Ala Tyr Asp
    210                 215                 220

Pro Leu Asp Val Leu Val Pro Tyr Phe Val Pro Asn Thr Pro Ala Ala
225                 230                 235                 240

Arg Ala Asp Leu Ala Ala Gln Tyr Thr Thr Val Gly Arg Met Asp Gln
                245                 250                 255

Gly Val Gly Leu Val Leu Gln Glu Leu Arg Asp Ala Gly Val Leu Asn
            260                 265                 270

Asp Thr Leu Val Ile Phe Thr Ser Asp Asn Gly Ile Pro Phe Pro Ser
        275                 280                 285

Gly Arg Thr Asn Leu Tyr Trp Pro Gly Thr Ala Glu Pro Leu Leu Val
    290                 295                 300

Ser Ser Pro Glu His Pro Lys Arg Trp Gly Gln Val Ser Glu Ala Tyr
305                 310                 315                 320

Val Ser Leu Leu Asp Leu Thr Pro Thr Ile Leu Asp Trp Phe Ser Ile
                325                 330                 335

Pro Tyr Pro Ser Tyr Ala Ile Phe Gly Ser Lys Thr Ile His Leu Thr
            340                 345                 350

Gly Arg Ser Leu Leu Pro Ala Leu Glu Ala Glu Pro Leu Trp Ala Thr
        355                 360                 365

Val Phe Gly Ser Gln Ser His Glu Val Thr Met Ser Tyr Pro Met
    370                 375                 380

Arg Ser Val Gln His Arg His Phe Arg Leu Val His Asn Leu Asn Phe
385                 390                 395                 400

Lys Met Pro Phe Pro Ile Asp Gln Asp Phe Tyr Val Ser Pro Thr Phe
                405                 410                 415

Gln Asp Leu Leu Asn Arg Thr Thr Ala Gly Gln Pro Thr Gly Trp Tyr
            420                 425                 430

Lys Asp Leu Arg His Tyr Tyr Tyr Arg Ala Arg Trp Glu Leu Tyr Asp
        435                 440                 445

Arg Ser Arg Asp Pro His Glu Thr Gln Asn Leu Ala Thr Asp Pro Arg
    450                 455                 460

Phe Ala Gln Leu Leu Glu Met Leu Arg Asp Gln Leu Ala Lys Trp Gln
465                 470                 475                 480

Trp Glu Thr His Asp Pro Trp Val Cys Ala Pro Asp Gly Val Leu Glu
                485                 490                 495

Glu Lys Leu Ser Pro Gln Cys Gln Pro Leu His Asn Glu Leu His His
            500                 505                 510

His His His His
        515

<210> SEQ ID NO 44
<211> LENGTH: 1552
<212> TYPE: DNA
<213> ORGANISM: Homo sapiens

<400> SEQUENCE: 44
aacaatggct tcctccgcta ctactaaatc tttccttatt cttttcttta tgatacttgc     60
aactacttca tcaacatgtg cagtcgacag gcctaggaac gctcttttgc ttcttgctga    120
tgatggcgga ttcgagtccg gtgcttacaa caactctgct atcgctactc cacacctcga    180
tgctcttgct aggcgttctc ttcttttccg taacgctttc acttccgtgt cctcttgctc    240

```
accttctagg gcttcacttc ttactggact tccacagcac cagaacggaa tgtacggact    300
tcatcaggat gtgcaccact tcaactcatt cgataaggtg agatccctcc cactcctctt    360
gtctcaagct ggtgttagga ctggaatcat cggcaaaaag cacgtgggac cagagactgt    420
gtacccattc gatttcgctt acactgagga aaacggctcc gttcttcaag tgggcagaaa    480
tattactagg atcaagctcc tcgtgaggaa gttcctccag actcaagatg ataggccatt    540
cttcctctac gtggcattcc atgatccaca taggtgcgga cattctcagc acagtacgg     600 aactttctgc gagaagttcg gaaacggtga gtctggtatg ggcaggattc cagattggac    660
tccacaggct tacgatccac ttgatgtgct cgttccatac ttcgtgccaa acactccagc    720
tgctagagct gatcttgctg ctcagtacac tactgtggga aggatggatc agggtgtggg    780
acttgtgctt caagagctta gagatgctgg cgtgctcaac gatactctcg tgatcttcac    840
ttcagataac ggcatcccat tcccatccgg aaggactaat ctttactggc caggtactgc    900
tgagcctctc cttgtttctt caccagagca tccaaagagg tggggacaag tttctgaggc    960
ttacgtgtcc cttctcgatc tcactccaac tatcctcgat tggttctcca tcccttaccc   1020
atcctacgct atcttcggct ccaagactat ccaccttact ggcagatctt tgctcccagc   1080
tttggaagct gaaccacttt gggctactgt gttcggatct cagtctcacc acgaggtgac   1140
aatgtcttac ccaatgagat ctgtgcagca caggcacttc aggcttgttc acaacctcaa   1200
cttcaagatg ccattcccaa tcgatcagga tttctacgtg tcaccaactt tccaggatct   1260
tctcaacagg actactgcag acaacctac tggctggtac aaggatctta ggcactacta    1320
ctatagggct aggtgggagc tttacgatag gtccagagat ccacacgaga ctcagaacct   1380
tgctactgat ccaaggttcg ctcagctcct tgagatgctt agggatcagc ttgctaagtg   1440
gcagtgggag actcatgatc catgggtttg cgctccagat ggtgtgcttg aagagaagtt   1500
gtctccacag tgccagccac ttcataacga gcttcatcat caccatcacc ac           1552
```

<210> SEQ ID NO 45  
<211> LENGTH: 516  
<212> TYPE: PRT  
<213> ORGANISM: Homo sapiens

<400> SEQUENCE: 45

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Arg Pro Arg Asn
            20                  25                  30

Ala Leu Leu Leu Leu Ala Asp Asp Gly Gly Phe Glu Ser Gly Ala Tyr
        35                  40                  45

Asn Asn Ser Ala Ile Ala Thr Pro His Leu Asp Ala Leu Ala Arg Arg
    50                  55                  60

Ser Leu Leu Phe Arg Asn Ala Phe Thr Ser Val Ser Ser Cys Ser Pro
65                  70                  75                  80

Ser Arg Ala Ser Leu Leu Thr Gly Leu Pro Gln His Gln Asn Gly Met
                85                  90                  95

Tyr Gly Leu His Gln Asp Val His His Phe Asn Ser Phe Asp Lys Val
            100                 105                 110

Arg Ser Leu Pro Leu Leu Leu Ser Gln Ala Gly Val Arg Thr Gly Ile
        115                 120                 125

Ile Gly Lys Lys His Val Gly Pro Glu Thr Val Tyr Pro Phe Asp Phe
    130                 135                 140
```

```
Ala Tyr Thr Glu Glu Asn Gly Ser Val Leu Gln Val Gly Arg Asn Ile
145                 150                 155                 160

Thr Arg Ile Lys Leu Leu Val Arg Lys Phe Leu Gln Thr Gln Asp Asp
            165                 170                 175

Arg Pro Phe Phe Leu Tyr Val Ala Phe His Asp Pro His Arg Cys Gly
        180                 185                 190

His Ser Gln Pro Gln Tyr Gly Thr Phe Cys Glu Lys Phe Gly Asn Gly
            195                 200                 205

Glu Ser Gly Met Gly Arg Ile Pro Asp Trp Thr Pro Gln Ala Tyr Asp
210                 215                 220

Pro Leu Asp Val Leu Val Pro Tyr Phe Val Pro Asn Thr Pro Ala Ala
225                 230                 235                 240

Arg Ala Asp Leu Ala Ala Gln Tyr Thr Thr Val Gly Arg Met Asp Gln
            245                 250                 255

Gly Val Gly Leu Val Leu Gln Glu Leu Arg Asp Ala Gly Val Leu Asn
        260                 265                 270

Asp Thr Leu Val Ile Phe Thr Ser Asp Asn Gly Ile Pro Phe Pro Ser
            275                 280                 285

Gly Arg Thr Asn Leu Tyr Trp Pro Gly Thr Ala Glu Pro Leu Leu Val
290                 295                 300

Ser Ser Pro Glu His Pro Lys Arg Trp Gly Gln Val Ser Glu Ala Tyr
305                 310                 315                 320

Val Ser Leu Leu Asp Leu Thr Pro Thr Ile Leu Asp Trp Phe Ser Ile
            325                 330                 335

Pro Tyr Pro Ser Tyr Ala Ile Phe Gly Ser Lys Thr Ile His Leu Thr
        340                 345                 350

Gly Arg Ser Leu Leu Pro Ala Leu Glu Ala Glu Pro Leu Trp Ala Thr
            355                 360                 365

Val Phe Gly Ser Gln Ser His His Glu Val Thr Met Ser Tyr Pro Met
370                 375                 380

Arg Ser Val Gln His Arg His Phe Arg Leu Val His Asn Leu Asn Phe
385                 390                 395                 400

Lys Met Pro Phe Pro Ile Asp Gln Asp Phe Tyr Val Ser Pro Thr Phe
            405                 410                 415

Gln Asp Leu Leu Asn Arg Thr Thr Ala Gly Gln Pro Thr Gly Trp Tyr
        420                 425                 430

Lys Asp Leu Arg His Tyr Tyr Tyr Arg Ala Arg Trp Glu Leu Tyr Asp
            435                 440                 445

Arg Ser Arg Asp Pro His Glu Thr Gln Asn Leu Ala Thr Asp Pro Arg
450                 455                 460

Phe Ala Gln Leu Leu Glu Met Leu Arg Asp Gln Leu Ala Lys Trp Gln
465                 470                 475                 480

Trp Glu Thr His Asp Pro Trp Val Cys Ala Pro Asp Gly Val Leu Glu
            485                 490                 495

Glu Lys Leu Ser Pro Gln Cys Gln Pro Leu His Asn Glu Leu His His
        500                 505                 510

His His His His
        515

<210> SEQ ID NO 46
<211> LENGTH: 2326
<212> TYPE: DNA
<213> ORGANISM: Homo sapiens
```

<400> SEQUENCE: 46

```
aacaatggct tcctccgcta ctactaaatc tttccttatt cttttcttta tgatacttgc      60
aactacttca tcaacatgtg cagtcgaccc tgagcccata gtgcgtatcg taggtcgaaa     120
tggtctatgt gttgatgtta gggatggaag attccacaac ggaaacgcaa tacagttgtg     180
gccatgcaag tctaatacag atgcaaatca gctctggact ttgaaaagag acaatactat     240
tcgatctaat ggaaagtgtt taactactta cgggtacagt ccgggagtct atgtgatgat     300
ctatgattgc aatactgctg caactgatgc caccogctgg caaatatggg ataatggaac     360
catcataaat cccagatcta gtctagtttt agcagcgaca tcagggaaca gtggtactac     420
acttacagtg caaaccaaca tttatgccgt tagtcaaggt tggcttccta ctaataatac     480
acaaccttt gtgacaacca ttgttgggct atatggtctg tgcttgcaag caaatagtgg     540
acaagtatgg atagaggact gtagcagtga aaaggctgaa caacagtggg ctctttatgc     600
agatggttca atacgtcctc agcaaaaccg agataattgc cttacaagtg attctaatat     660
acgggaaaca gttgtcaaga tcctctcttg tggccctgca tcctctggcc aacgatggat     720
gttcaagaat gatggaacca ttttaaattt gtatagtggg ttggtgttag atgtgagggc     780
atcggatccg agccttaaac aaatcattct ttaccctctc catggtgacc caaaccaaat     840
atggttacca ttatttctcg agcgtccccg gaacgcactg ctgctcctcg cggatgacgg     900
aggctttgag agtggcgcgt acaacaacag cgccatcgcc accccgcacc tggacgcctt     960
ggcccgccgc agcctcctct ttcgcaatgc cttcacctcg gtcagcagct gctctcccag    1020
ccgcgccagc ctcctcactg gcctgcccca gcatcagaat gggatgtacg ggctgccacca    1080
ggacgtgcac cacttcaact ccttcgacaa ggtgcggagc ctgccgctgc tgctcagcca    1140
agctggtgtg cgcacaggca tcatcgggaa gaagcacgtg gggccggaga ccgtgtaccc    1200
gtttgacttt gcgtacacgg aggagaatgg ctccgtcctc caggtggggc ggaacatcac    1260
tagaattaag ctgctcgtcc ggaaattcct gcagactcag gatgaccggc cttcttcct    1320
ctacgtcgcc ttccacgacc cccaccgctg tgggcactcc cagccccagt acggaacctt    1380
ctgtgagaag tttggcaacg gagagagcgg catgggtcgt atcccagact ggaccccca    1440
ggcctacgac ccactggacg tgctggtgcc ttacttcgtc cccaacaccc cggcagcccg    1500
agccgacctg gccgctcagt acaccaccgt cggccgcatg gaccaaggag ttggactggt    1560
gctccaggag ctgcgtgacg ccggtgtcct gaacgacaca ctggtgatct tcacgtccga    1620
caacgggatc cccttcccca gcggcaggac caacctgtac tggccgggca ctgctgaacc    1680
cttactggtg tcatccccgg agcacccaaa acgctggggc caagtcagcg aggcctacgt    1740
gagcctccta gacctcacgc ccaccatctt ggattggttc tcgatcccgt accccagcta    1800
cgccatcttt ggctcgaaga ccatccacct cactggccgg tccctcctgc cggcgctgga    1860
ggccgagccc ctctgggcca ccgtctttgg cagccagagc caccacgagg tcaccatgtc    1920
ctaccccatg cgctccgtgc agcaccggca cttccgcctc gtgcacaacc tcaacttcaa    1980
gatgcccttt cccatcgacc aggacttcta cgtctcaccc accttccagg acctcctgaa    2040
ccgcaccaca gctggtcagc ccacgggctg gtacaaggac ctccgtcatt actactaccg    2100
ggcgcgctgg gaactctacg accggagccg ggaccccac gagacccaga acctggccac    2160
cgaccccgcg tttgctcagc ttctggagat gcttcgggac cagctggcca agtggcagtg    2220
ggagaccaac gacccctggg tgtgcgcccc cgacggcgtc ctggaggaga agctctctcc    2280
ccagtgccag cccctccaca atgagctgca tcatcatcat catcat                   2326
```

<210> SEQ ID NO 47
<211> LENGTH: 774
<212> TYPE: PRT
<213> ORGANISM: Homo sapiens

<400> SEQUENCE: 47

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Pro Glu Pro Ile
            20                  25                  30

Val Arg Ile Val Gly Arg Asn Gly Leu Cys Val Asp Val Arg Asp Gly
        35                  40                  45

Arg Phe His Asn Gly Asn Ala Ile Gln Leu Trp Pro Cys Lys Ser Asn
    50                  55                  60

Thr Asp Ala Asn Gln Leu Trp Thr Leu Lys Arg Asp Asn Thr Ile Arg
65                  70                  75                  80

Ser Asn Gly Lys Cys Leu Thr Thr Tyr Gly Tyr Ser Pro Gly Val Tyr
                85                  90                  95

Val Met Ile Tyr Asp Cys Asn Thr Ala Ala Thr Asp Ala Thr Arg Trp
            100                 105                 110

Gln Ile Trp Asp Asn Gly Thr Ile Ile Asn Pro Arg Ser Ser Leu Val
        115                 120                 125

Leu Ala Ala Thr Ser Gly Asn Ser Gly Thr Thr Leu Thr Val Gln Thr
    130                 135                 140

Asn Ile Tyr Ala Val Ser Gln Gly Trp Leu Pro Thr Asn Asn Thr Gln
145                 150                 155                 160

Pro Phe Val Thr Thr Ile Val Gly Leu Tyr Gly Leu Cys Leu Gln Ala
                165                 170                 175

Asn Ser Gly Gln Val Trp Ile Glu Asp Cys Ser Ser Glu Lys Ala Glu
            180                 185                 190

Gln Gln Trp Ala Leu Tyr Ala Asp Gly Ser Ile Arg Pro Gln Gln Asn
        195                 200                 205

Arg Asp Asn Cys Leu Thr Ser Asp Ser Asn Ile Arg Glu Thr Val Val
    210                 215                 220

Lys Ile Leu Ser Cys Gly Pro Ala Ser Ser Gly Gln Arg Trp Met Phe
225                 230                 235                 240

Lys Asn Asp Gly Thr Ile Leu Asn Leu Tyr Ser Gly Leu Val Leu Asp
                245                 250                 255

Val Arg Ala Ser Asp Pro Ser Leu Lys Gln Ile Ile Leu Tyr Pro Leu
            260                 265                 270

His Gly Asp Pro Asn Gln Ile Trp Leu Pro Leu Phe Leu Glu Arg Pro
        275                 280                 285

Arg Asn Ala Leu Leu Leu Ala Asp Asp Gly Gly Phe Glu Ser Gly
    290                 295                 300

Ala Tyr Asn Asn Ser Ala Ile Thr Pro His Leu Asp Ala Leu Ala
305                 310                 315                 320

Arg Arg Ser Leu Leu Phe Arg Asn Ala Phe Thr Ser Val Ser Ser Cys
                325                 330                 335

Ser Pro Ser Arg Ala Ser Leu Leu Thr Gly Leu Pro Gln His Gln Asn
            340                 345                 350

Gly Met Tyr Gly Leu His Gln Asp Val His His Phe Asn Ser Phe Asp
        355                 360                 365

Lys Val Arg Ser Leu Pro Leu Leu Leu Ser Gln Ala Gly Val Arg Thr
```

```
              370                 375                 380
Gly Ile Ile Gly Lys Lys His Val Gly Pro Glu Thr Val Tyr Pro Phe
385                 390                 395                 400

Asp Phe Ala Tyr Thr Glu Glu Asn Gly Ser Val Leu Gln Val Gly Arg
                405                 410                 415

Asn Ile Thr Arg Ile Lys Leu Leu Val Arg Lys Phe Leu Gln Thr Gln
                420                 425                 430

Asp Asp Arg Pro Phe Phe Leu Tyr Val Ala Phe His Asp Pro His Arg
                435                 440                 445

Cys Gly His Ser Gln Pro Gln Tyr Gly Thr Phe Cys Glu Lys Phe Gly
                450                 455                 460

Asn Gly Glu Ser Gly Met Gly Arg Ile Pro Asp Trp Thr Pro Gln Ala
465                 470                 475                 480

Tyr Asp Pro Leu Asp Val Leu Val Pro Tyr Phe Val Pro Asn Thr Pro
                485                 490                 495

Ala Ala Arg Ala Asp Leu Ala Ala Gln Tyr Thr Thr Val Gly Arg Met
                500                 505                 510

Asp Gln Gly Val Gly Leu Val Leu Gln Glu Leu Arg Asp Ala Gly Val
                515                 520                 525

Leu Asn Asp Thr Leu Val Ile Phe Thr Ser Asp Asn Gly Ile Pro Phe
530                 535                 540

Pro Ser Gly Arg Thr Asn Leu Tyr Trp Pro Gly Thr Ala Glu Pro Leu
545                 550                 555                 560

Leu Val Ser Ser Pro Glu His Pro Lys Arg Trp Gly Gln Val Ser Glu
                565                 570                 575

Ala Tyr Val Ser Leu Leu Asp Leu Thr Pro Thr Ile Leu Asp Trp Phe
                580                 585                 590

Ser Ile Pro Tyr Pro Ser Tyr Ala Ile Phe Gly Ser Lys Thr Ile His
                595                 600                 605

Leu Thr Gly Arg Ser Leu Leu Pro Ala Leu Glu Ala Glu Pro Leu Trp
                610                 615                 620

Ala Thr Val Phe Gly Ser Gln Ser His His Glu Val Thr Met Ser Tyr
625                 630                 635                 640

Pro Met Arg Ser Val Gln His Arg His Phe Arg Leu Val His Asn Leu
                645                 650                 655

Asn Phe Lys Met Pro Phe Pro Ile Asp Gln Asp Phe Tyr Val Ser Pro
                660                 665                 670

Thr Phe Gln Asp Leu Leu Asn Arg Thr Thr Ala Gly Gln Pro Thr Gly
                675                 680                 685

Trp Tyr Lys Asp Leu Arg His Tyr Tyr Tyr Arg Ala Arg Trp Glu Leu
                690                 695                 700

Tyr Asp Arg Ser Arg Asp Pro His Glu Thr Gln Asn Leu Ala Thr Asp
705                 710                 715                 720

Pro Arg Phe Ala Gln Leu Leu Glu Met Leu Arg Asp Gln Leu Ala Lys
                725                 730                 735

Trp Gln Trp Glu Thr His Asp Pro Trp Val Cys Ala Pro Asp Gly Val
                740                 745                 750

Leu Glu Glu Lys Leu Ser Pro Gln Cys Gln Pro Leu His Asn Glu Leu
                755                 760                 765

His His His His His His
    770

<210> SEQ ID NO 48
```

<211> LENGTH: 2326
<212> TYPE: DNA
<213> ORGANISM: Homo sapiens

<400> SEQUENCE: 48

```
aacaatggct tcctccgcta ctactaaatc tttccttatt cttttcttta tgatacttgc      60
aactacttca tcaacatgtg cagtcgaccc tgagcccata gtgcgtatcg taggtcgaaa     120
tggtctatgt gttgatgtta gggatggaag attccacaac ggaaacgcaa tacagttgtg     180
gccatgcaag tctaatacag atgcaaatca gctctggact ttgaaaagag acaatactat     240
tcgatctaat ggaaagtgtt taactactta cgggtacagt ccgggagtct atgtgatgat     300
ctatgattgc aatactgctg caactgatgc cacccgctgg caaatatggg ataatggaac     360
catcataaat cccagatcta gtctagtttt agcagcgaca tcagggaaca gtggtactac     420
acttacagtg caaaccaaca tttatgccgt tagtcaaggt tggcttccta ctaataatac     480
acaacctttt gtgacaacca ttgttgggct atatggtctg tgcttgcaag caaatagtgg     540
acaagtatgg atagaggact gtagcagtga aaaggctgaa caacagtggg ctctttatgc     600
agatggttca atacgtcctc agcaaaaccg agataattgc cttacaagtg attctaatat     660
acgggaaaca gttgtcaaga tcctctcttg tggccctgca tcctctggcc aacgatggat     720
gttcaagaat gatggaacca ttttaaattt gtatagtggg ttggtgttag atgtgagggc     780
atcggatccg agccttaaac aaatcattct ttaccctctc catggtgacc aaaccaaat     840
atggttacca ttatttctcg agaggcctag gaacgctctt ttgcttcttg ctgatgatgg     900
cggattcgag tccggtgctt acaacaactc tgctatcgct actccacacc tcgatgctct     960
tgctaggcgt tctcttcttt tccgtaacgc tttcacttcc gtgtcctctt gctcaccttc    1020
tagggcttca cttcttactg gacttccaca gcaccagaac ggaatgtacg gacttcatca    1080
ggatgtgcac cacttcaact cattcgataa ggtgagatcc ctcccactcc tcttgtctca    1140
agctggtgtt aggactggaa tcatcggcaa aaagcacgtg ggaccagaga ctgtgtaccc    1200
attcgatttc gcttacactg aggaaaacgg ctccgttctt caagtgggca gaaatattac    1260
taggatcaag ctcctcgtga ggaagttcct ccagactcaa gatgataggc cattcttcct    1320
ctacgtggca ttccatgatc cacataggtg cggacattct cagccacagt acggaacttt    1380
ctgcgagaag ttcggaaacg gtgagtctgg tatgggcagg attccagatt ggactccaca    1440
ggcttacgat ccacttgatg tgctcgttcc atacttcgtg ccaaacactc cagctgctag    1500
agctgatctt gctgctcagt acactactgt gggaaggatg gatcagggtg tgggacttgt    1560
gcttcaagag cttagagatg ctggcgtgct caacgatact ctcgtgatct tcacttcaga    1620
taacggcatc ccattcccat ccggaaggac taatctttac tggccaggta ctgctgagcc    1680
tctccttgtt tcttcaccag agcatccaaa gaggtgggga caagtttctg aggcttacgt    1740
gtcccttctc gatctcactc caactatcct cgattggttc tccatcccct acccatccta    1800
cgctatcttc ggctccaaga ctatccacct tactggcaga tctttgctcc cagctttgga    1860
agctgaacca ctttgggcta ctgtgttcgg atctcagtct caccacgagg tgacaatgtc    1920
ttacccaatg agatctgtgc agcacaggca cttcaggctt gttcacaacc tcaacttcaa    1980
gatgccattc ccaatcgatc aggatttcta cgtgtcacca actttccagg atcttctcaa    2040
caggactact gcaggacaac ctactggctg gtacaaggat cttaggcact actactatag    2100
ggctaggtgg gagctttacg ataggtccag agatccacac gagactcaga accttgctac    2160
tgatccaagg ttcgctcagc tccttgagat gcttagggat cagcttgcta agtggcagtg    2220
```

```
ggagactcat gatccatggg tttgcgctcc agatggtgtg cttgaagaga agttgtctcc   2280
acagtgccag ccacttcata acgagcttca tcatcaccat caccac                 2326
```

<210> SEQ ID NO 49
<211> LENGTH: 774
<212> TYPE: PRT
<213> ORGANISM: Homo sapiens

<400> SEQUENCE: 49

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Pro Glu Pro Ile
            20                  25                  30

Val Arg Ile Val Gly Arg Asn Gly Leu Cys Val Asp Val Arg Asp Gly
        35                  40                  45

Arg Phe His Asn Gly Asn Ala Ile Gln Leu Trp Pro Cys Lys Ser Asn
    50                  55                  60

Thr Asp Ala Asn Gln Leu Trp Thr Leu Lys Arg Asp Asn Thr Ile Arg
65                  70                  75                  80

Ser Asn Gly Lys Cys Leu Thr Thr Tyr Gly Tyr Ser Pro Gly Val Tyr
                85                  90                  95

Val Met Ile Tyr Asp Cys Asn Thr Ala Ala Thr Asp Ala Thr Arg Trp
            100                 105                 110

Gln Ile Trp Asp Asn Gly Thr Ile Ile Asn Pro Arg Ser Ser Leu Val
        115                 120                 125

Leu Ala Ala Thr Ser Gly Asn Ser Gly Thr Thr Leu Thr Val Gln Thr
    130                 135                 140

Asn Ile Tyr Ala Val Ser Gln Gly Trp Leu Pro Thr Asn Asn Thr Gln
145                 150                 155                 160

Pro Phe Val Thr Thr Ile Val Gly Leu Tyr Gly Leu Cys Leu Gln Ala
                165                 170                 175

Asn Ser Gly Gln Val Trp Ile Glu Asp Cys Ser Ser Glu Lys Ala Glu
            180                 185                 190

Gln Gln Trp Ala Leu Tyr Ala Asp Gly Ser Ile Arg Pro Gln Gln Asn
        195                 200                 205

Arg Asp Asn Cys Leu Thr Ser Asp Ser Asn Ile Arg Glu Thr Val Val
    210                 215                 220

Lys Ile Leu Ser Cys Gly Pro Ala Ser Ser Gly Gln Arg Trp Met Phe
225                 230                 235                 240

Lys Asn Asp Gly Thr Ile Leu Asn Leu Tyr Ser Gly Leu Val Leu Asp
                245                 250                 255

Val Arg Ala Ser Asp Pro Ser Leu Lys Gln Ile Ile Leu Tyr Pro Leu
            260                 265                 270

His Gly Asp Pro Asn Gln Ile Trp Leu Pro Leu Phe Leu Glu Arg Pro
        275                 280                 285

Arg Asn Ala Leu Leu Leu Ala Asp Asp Gly Gly Phe Glu Ser Gly
    290                 295                 300

Ala Tyr Asn Asn Ser Ala Ile Ala Thr Pro His Leu Asp Ala Leu Ala
305                 310                 315                 320

Arg Arg Ser Leu Leu Phe Arg Asn Ala Phe Thr Ser Val Ser Ser Cys
                325                 330                 335

Ser Pro Ser Arg Ala Ser Leu Leu Thr Gly Leu Pro Gln His Gln Asn
            340                 345                 350
```

-continued

```
Gly Met Tyr Gly Leu His Gln Asp Val His Phe Asn Ser Phe Asp
            355                 360                 365

Lys Val Arg Ser Leu Pro Leu Leu Ser Gln Ala Gly Val Arg Thr
370                 375                 380

Gly Ile Ile Gly Lys Lys His Val Gly Pro Glu Thr Val Tyr Pro Phe
385                 390                 395                 400

Asp Phe Ala Tyr Thr Glu Glu Asn Gly Ser Val Leu Gln Val Gly Arg
                    405                 410                 415

Asn Ile Thr Arg Ile Lys Leu Leu Val Arg Lys Phe Leu Gln Thr Gln
                420                 425                 430

Asp Asp Arg Pro Phe Phe Leu Tyr Val Ala Phe His Asp Pro His Arg
            435                 440                 445

Cys Gly His Ser Gln Pro Gln Tyr Gly Thr Phe Cys Glu Lys Phe Gly
            450                 455                 460

Asn Gly Glu Ser Gly Met Gly Arg Ile Pro Asp Trp Thr Pro Gln Ala
465                 470                 475                 480

Tyr Asp Pro Leu Asp Val Leu Val Pro Tyr Phe Val Pro Asn Thr Pro
                    485                 490                 495

Ala Ala Arg Ala Asp Leu Ala Ala Gln Tyr Thr Thr Val Gly Arg Met
                500                 505                 510

Asp Gln Gly Val Gly Leu Val Leu Gln Glu Leu Arg Asp Ala Gly Val
            515                 520                 525

Leu Asn Asp Thr Leu Val Ile Phe Thr Ser Asp Asn Gly Ile Pro Phe
            530                 535                 540

Pro Ser Gly Arg Thr Asn Leu Tyr Trp Pro Gly Thr Ala Glu Pro Leu
545                 550                 555                 560

Leu Val Ser Ser Pro Glu His Pro Lys Arg Trp Gly Gln Val Ser Glu
                565                 570                 575

Ala Tyr Val Ser Leu Leu Asp Leu Thr Pro Thr Ile Leu Asp Trp Phe
                580                 585                 590

Ser Ile Pro Tyr Pro Ser Tyr Ala Ile Phe Gly Ser Lys Thr Ile His
            595                 600                 605

Leu Thr Gly Arg Ser Leu Leu Pro Ala Leu Glu Ala Glu Pro Leu Trp
610                 615                 620

Ala Thr Val Phe Gly Ser Gln Ser His His Glu Val Thr Met Ser Tyr
625                 630                 635                 640

Pro Met Arg Ser Val Gln His Arg His Phe Arg Leu Val His Asn Leu
                645                 650                 655

Asn Phe Lys Met Pro Phe Pro Ile Asp Gln Asp Phe Tyr Val Ser Pro
            660                 665                 670

Thr Phe Gln Asp Leu Leu Asn Arg Thr Thr Ala Gly Gln Pro Thr Gly
            675                 680                 685

Trp Tyr Lys Asp Leu Arg His Tyr Tyr Tyr Arg Ala Arg Trp Glu Leu
690                 695                 700

Tyr Asp Arg Ser Arg Asp Pro His Glu Thr Gln Asn Leu Ala Thr Asp
705                 710                 715                 720

Pro Arg Phe Ala Gln Leu Leu Glu Met Leu Arg Asp Gln Leu Ala Lys
                725                 730                 735

Trp Gln Trp Glu Thr His Asp Pro Trp Val Cys Ala Pro Asp Gly Val
                740                 745                 750

Leu Glu Glu Lys Leu Ser Pro Gln Cys Gln Pro Leu His Asn Glu Leu
            755                 760                 765

His His His His His His
```

<210> SEQ ID NO 50
<211> LENGTH: 2353
<212> TYPE: DNA
<213> ORGANISM: Homo sapiens

<400> SEQUENCE: 50

```
aacaatggct tcctccgcta ctactaaatc tttccttatt cttttcttta tgatacttgc      60
aactacttca tcaacatgtg cagtcgacgg agaaacttct actcttagga cttcattcac     120
aagaaacatc gttggtcgtg atggattgtg cgtggatgtg aggaatggat acgacactga     180
tggaactcca cttcagttgt ggccatgtgg aacccagaga accaacgat ggacttttga      240
ctcagacgat acaatcaggt caatgggtaa atgcatgact gcaaacgggt taaacaatgg     300
aagcaatatc gtgatattca actgttctac agctgctgag aacgccatta agtgggaagt     360
acctattgat ggcagcatca tcaatccttc ctccggattg gttatgaccg ctcctcgtgc     420
tgcatcccgt accatcctgt tgcttgagga caatatctac gccgctagcc agggttggac     480
tgtgacaaac aatgtaaagc ccatcgttgc ttccattgtg ggttataaag aaatgtgctt     540
gcagtctaac ggtgaaaaca atggtgtttg gatggaggat tgtgaggcca ccagtttgca     600
gcaacagtgg gcactctatg gtgaccgtac catccgagta aatagtactc gtggcttatg     660
cgtcaccacc aatgggtaca actccaagga tctcatcatc atccttaaat gccaaggatt     720
gcccagccag aggtggtttt tcaactccga cggcgccatc gtaaacccaa agtcaagaca     780
tgttatggat gtgagagcaa gcaatgtctc tcttcgagaa atcattatct ttccagccac     840
tgggaaccct aatcagcaat gggtgacaca gtccttcca agtctcgagc gtccccggaa      900
cgcactgctg ctcctcgcgg atgacggagg ctttgagagt ggcgcgtaca caacagcgc      960
catcgccacc ccgcacctgg acgccttggc ccgccgcagc ctcctctttc gcaatgcctt    1020
cacctcggtc agcagctgct ctcccagccg cgccagcctc ctcactggcc tgccccagca    1080
tcagaatggg atgtacgggc tgcaccagga cgtgcaccac ttcaactcct cgacaaggt     1140
gcggagcctg ccgctgctgc tcagccaagc tggtgtgcgc acaggcatca tcgggaagaa    1200
gcacgtgggg ccggagaccg tgtacccgtt tgactttgcg tacacggagg agaatggctc    1260
cgtcctccag gtggggcgga acatcactag aattaagctg ctcgtccgga aattcctgca    1320
gactcaggat gaccggcctt tcttcctcta cgtcgccttc cacgacccc accgctgtgg     1380
gcactcccag ccccagtacg gaaccttctg tgagaagttt ggcaacgag agagcggcat    1440
gggtcgtatc ccagactgga cccccaggc ctacgaccca ctggacgtgc tggtgcctta    1500
cttcgtcccc aacacccgg cagcccgagc cgacctggcc gctcagtaca ccaccgtcgg    1560
ccgcatggac caaggagttg gactggtgct ccaggagctg cgtgacgccg tgtcctgaa    1620
cgacacactg gtgatcttca cgtccgacaa cgggatcccc ttcccagcg gcaggaccaa    1680
cctgtactgg ccgggcactg ctgaacccct tactggtgtca tccccggagc acccaaaacg    1740
ctggggccaa gtcagcgagg cctacgtgag cctcctagac ctcacgccca ccatcttgga    1800
ttggttctcg atcccgtacc ccagctacgc catctttggc tcgaagacca tccacctcac    1860
tggccggtcc ctcctgccgg cgctggaggc cgagcccctc tgggccaccg tctttggcag    1920
ccagagccac cacgaggtca ccatgtccta ccccatgcgc tccgtgcagc accggcactt    1980
ccgcctcgtg cacaacctca acttcaagat gcccttcccc atcgaccagg acttctacgt    2040
ctcacccacc ttccaggacc tcctgaaccg caccacagct ggtcagccca cgggctggta    2100
```

```
caaggacctc cgtcattact actaccgggc gcgctgggaa ctctacgacc ggagccggga    2160
cccccacgag acccagaacc tggccaccga cccgcgcttt gctcagcttc tggagatgct    2220
tcgggaccag ctggccaagt ggcagtggga gacccacgac ccctgggtgt cgcccccga    2280 cggcgtcctg gaggagaagc tctctcccca gtgccagccc tccacaatg agctgcatca    2340 tcatcatcat cat                                                      2353
```

<210> SEQ ID NO 51
<211> LENGTH: 783
<212> TYPE: PRT
<213> ORGANISM: Homo sapiens

<400> SEQUENCE: 51

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Gly Glu Thr Ser
                20                  25                  30

Thr Leu Arg Thr Ser Phe Thr Arg Asn Ile Val Gly Arg Asp Gly Leu
            35                  40                  45

Cys Val Asp Val Arg Asn Gly Tyr Asp Thr Asp Gly Thr Pro Leu Gln
        50                  55                  60

Leu Trp Pro Cys Gly Thr Gln Arg Asn Gln Arg Trp Thr Phe Asp Ser
65                  70                  75                  80

Asp Asp Thr Ile Arg Ser Met Gly Lys Cys Met Thr Ala Asn Gly Leu
                85                  90                  95

Asn Asn Gly Ser Asn Ile Val Ile Phe Asn Cys Ser Thr Ala Ala Glu
            100                 105                 110

Asn Ala Ile Lys Trp Glu Val Pro Ile Asp Gly Ser Ile Ile Asn Pro
        115                 120                 125

Ser Ser Gly Leu Val Met Thr Ala Pro Arg Ala Ala Ser Arg Thr Ile
    130                 135                 140

Leu Leu Leu Glu Asp Asn Ile Tyr Ala Ala Ser Gln Gly Trp Thr Val
145                 150                 155                 160

Thr Asn Asn Val Lys Pro Ile Val Ala Ser Ile Val Gly Tyr Lys Glu
                165                 170                 175

Met Cys Leu Gln Ser Asn Gly Glu Asn Asn Gly Val Trp Met Glu Asp
            180                 185                 190

Cys Glu Ala Thr Ser Leu Gln Gln Gln Trp Ala Leu Tyr Gly Asp Arg
        195                 200                 205

Thr Ile Arg Val Asn Ser Thr Arg Gly Leu Cys Val Thr Thr Asn Gly
    210                 215                 220

Tyr Asn Ser Lys Asp Leu Ile Ile Ile Leu Lys Cys Gln Gly Leu Pro
225                 230                 235                 240

Ser Gln Arg Trp Phe Phe Asn Ser Asp Gly Ala Ile Val Asn Pro Lys
                245                 250                 255

Ser Arg His Val Met Asp Val Arg Ala Ser Asn Val Ser Leu Arg Glu
            260                 265                 270

Ile Ile Ile Phe Pro Ala Thr Gly Asn Pro Gln Gln Trp Val Thr
        275                 280                 285

Gln Val Leu Pro Ser Leu Glu Arg Pro Arg Asn Ala Leu Leu Leu Leu
    290                 295                 300

Ala Asp Asp Gly Gly Phe Glu Ser Gly Ala Tyr Asn Asn Ser Ala Ile
305                 310                 315                 320
```

-continued

```
Ala Thr Pro His Leu Asp Ala Leu Ala Arg Arg Ser Leu Leu Phe Arg
                325                 330                 335

Asn Ala Phe Thr Ser Val Ser Ser Cys Ser Pro Ser Arg Ala Ser Leu
            340                 345                 350

Leu Thr Gly Leu Pro Gln His Gln Asn Gly Met Tyr Gly Leu His Gln
        355                 360                 365

Asp Val His His Phe Asn Ser Phe Asp Lys Val Arg Ser Leu Pro Leu
    370                 375                 380

Leu Leu Ser Gln Ala Gly Val Arg Thr Gly Ile Ile Gly Lys Lys His
385                 390                 395                 400

Val Gly Pro Glu Thr Val Tyr Pro Phe Asp Phe Ala Tyr Thr Glu Glu
                405                 410                 415

Asn Gly Ser Val Leu Gln Val Gly Arg Asn Ile Thr Arg Ile Lys Leu
            420                 425                 430

Leu Val Arg Lys Phe Leu Gln Thr Gln Asp Asp Arg Pro Phe Phe Leu
        435                 440                 445

Tyr Val Ala Phe His Asp Pro His Arg Cys Gly His Ser Gln Pro Gln
    450                 455                 460

Tyr Gly Thr Phe Cys Glu Lys Phe Gly Asn Gly Glu Ser Gly Met Gly
465                 470                 475                 480

Arg Ile Pro Asp Trp Thr Pro Gln Ala Tyr Asp Pro Leu Asp Val Leu
                485                 490                 495

Val Pro Tyr Phe Val Pro Asn Thr Pro Ala Ala Arg Ala Asp Leu Ala
            500                 505                 510

Ala Gln Tyr Thr Thr Val Gly Arg Met Asp Gln Gly Val Gly Leu Val
        515                 520                 525

Leu Gln Glu Leu Arg Asp Ala Gly Val Leu Asn Asp Thr Leu Val Ile
    530                 535                 540

Phe Thr Ser Asp Asn Gly Ile Pro Phe Pro Ser Gly Arg Thr Asn Leu
545                 550                 555                 560

Tyr Trp Pro Gly Thr Ala Glu Pro Leu Leu Val Ser Ser Pro Glu His
                565                 570                 575

Pro Lys Arg Trp Gly Gln Val Ser Glu Ala Tyr Val Ser Leu Leu Asp
            580                 585                 590

Leu Thr Pro Thr Ile Leu Asp Trp Phe Ser Ile Pro Tyr Pro Ser Tyr
        595                 600                 605

Ala Ile Phe Gly Ser Lys Thr Ile His Leu Thr Gly Arg Ser Leu Leu
    610                 615                 620

Pro Ala Leu Glu Ala Glu Pro Leu Trp Ala Thr Val Phe Gly Ser Gln
625                 630                 635                 640

Ser His His Glu Val Thr Met Ser Tyr Pro Met Arg Ser Val Gln His
                645                 650                 655

Arg His Phe Arg Leu Val His Asn Leu Asn Phe Lys Met Pro Phe Pro
            660                 665                 670

Ile Asp Gln Asp Phe Tyr Val Ser Pro Thr Phe Gln Asp Leu Leu Asn
        675                 680                 685

Arg Thr Thr Ala Gly Gln Pro Thr Gly Trp Tyr Lys Asp Leu Arg His
    690                 695                 700

Tyr Tyr Tyr Arg Ala Arg Trp Glu Leu Tyr Asp Arg Ser Arg Asp Pro
705                 710                 715                 720

His Glu Thr Gln Asn Leu Ala Thr Asp Pro Arg Phe Ala Gln Leu Leu
                725                 730                 735

Glu Met Leu Arg Asp Gln Leu Ala Lys Trp Gln Trp Glu Thr His Asp
```

```
                740                 745                 750
Pro Trp Val Cys Ala Pro Asp Gly Val Leu Glu Glu Lys Leu Ser Pro
        755                 760                 765

Gln Cys Gln Pro Leu His Asn Glu Leu His His His His His His
        770                 775                 780

<210> SEQ ID NO 52
<211> LENGTH: 2353
<212> TYPE: DNA
<213> ORGANISM: Homo sapiens

<400> SEQUENCE: 52
aacaatggct tcctccgcta ctactaaatc tttccttatt cttttcttta tgatacttgc      60
aactacttca tcaacatgtg cagtcgacgg agaaacttct actcttagga cttcattcac     120
aagaaacatc gttggtcgtg atggattgtg cgtggatgtg aggaatggat acgacactga     180
tggaactcca cttcagttgt ggccatgtgg aacccagaga accaacgat ggacttttga      240 ctcagacgat acaatcaggt caatgggtaa atgcatgact gcaaacgggt taacaatgg      300 aagcaatatc gtgatattca actgttctac agctgctgag aacgccatta agtgggaagt     360
acctattgat ggcagcatca tcaatccttc tccggattg gttatgaccg ctcctcgtgc      420
tgcatcccgt accatcctgt tgcttgagga caatatctac gccgctagcc agggttggac     480
tgtgacaaac aatgtaaagc ccatcgttgc ttccattgtg ggttataaag aaatgtgctt     540
gcagtctaac ggtgaaaaca atggtgtttg gatggaggat tgtgaggcca ccagtttgca     600
gcaacagtgg gcactctatg gtgaccgtac catccgagta aatagtactc gtggcttatg     660
cgtcaccacc aatgggtaca actccaagga tctcatcatc atccttaaat gccaaggatt     720
gcccagccaa aggtggtttt tcaactccga cggcgccatc gtaaacccaa agtcaagaca     780
tgttatggat gtgagagcaa gcaatgtctc tcttcgagaa atcattatct ttccagccac     840
tgggaaccct aatcagcaat gggtgacaca agtccttcca agtctcgaga ggcctaggaa     900
cgctcttttg cttcttgctg atgatggcgg attcgagtcc ggtgcttaca caactctgc      960 tatcgctact ccacacctcg atgctcttgc taggcgttct cttcttttcc gtaacgcttt    1020
cacttccgtg tcctcttgct caccttctag ggcttcactt cttactggac ttccacagca    1080
ccagaacgga atgtacggac ttcatcagga tgtgcaccac ttcaactcat cgataaggt     1140 gagatccctc ccactcctct tgtctcaagc tggtgttagg actggaatca tcggcaaaaa    1200
gcacgtggga ccagagactg tgtacccatt cgatttcgct tacactgagg aaaacggctc    1260
cgttcttcaa gtgggcagaa atattactag gatcaagctc ctcgtgagga agttcctcca    1320
gactcaagat gataggccat tcttcctcta cgtggcattc catgatccac ataggtgcgg    1380
acattctcag ccacagtacg gaactttctg cgagaagttc ggaaacggtg agtctggtat    1440
gggcaggatt ccagattgga ctccacaggc ttacgatcca cttgatgtgc tcgttccata    1500
cttcgtgcca aacactccag ctgctagagc tgatcttgct gctcagtaca ctactgtggg    1560
aaggatggat cagggtgtgg acttgtgct tcaagagctt agagatgctg gcgtgctcaa     1620
cgatactctc gtgatcttca cttcagataa cggcatccca ttcccatccg aaggactaa     1680 tctttactgg ccaggtactg ctgagcctct ccttgtttct tcaccagagc atccaaagag    1740
gtggggacaa gtttctgagg cttacgtgtc ccttctcgat ctcactccaa ctatcctcga    1800
ttggttctcc atcccttacc catcctacgc tatcttcggc tccaagacta tccacccttac    1860 tggcagatct ttgctcccag ctttggaagc tgaaccactt tgggctactg tgttcggatc    1920
```

-continued

```
tcagtctcac cacgaggtga caatgtctta cccaatgaga tctgtgcagc acaggcactt    1980
caggcttgtt cacaacctca acttcaagat gccattccca atcgatcagg atttctacgt    2040
gtcaccaact ttccaggatc ttctcaacag gactactgca ggacaaccta ctggctggta    2100
caaggatctt aggcactact actatagggc taggtgggag ctttacgata ggtccagaga    2160
tccacacgag actcagaacc ttgctactga tccaaggttc gctcagctcc ttgagatgct    2220
tagggatcag cttgctaagt ggcagtggga gactcatgat ccatgggttt gcgctccaga    2280
tggtgtgctt gaagagaagt tgtctccaca gtgccagcca cttcataacg agcttcatca    2340
tcaccatcac cac                                                       2353
```

<210> SEQ ID NO 53
<211> LENGTH: 783
<212> TYPE: PRT
<213> ORGANISM: Homo sapiens

<400> SEQUENCE: 53

Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Gly Glu Thr Ser
            20                  25                  30

Thr Leu Arg Thr Ser Phe Thr Arg Asn Ile Val Gly Arg Asp Gly Leu
        35                  40                  45

Cys Val Asp Val Arg Asn Gly Tyr Asp Thr Asp Gly Thr Pro Leu Gln
    50                  55                  60

Leu Trp Pro Cys Gly Thr Gln Arg Asn Gln Arg Trp Thr Phe Asp Ser
65                  70                  75                  80

Asp Asp Thr Ile Arg Ser Met Gly Lys Cys Met Thr Ala Asn Gly Leu
                85                  90                  95

Asn Asn Gly Ser Asn Ile Val Ile Phe Asn Cys Ser Thr Ala Ala Glu
            100                 105                 110

Asn Ala Ile Lys Trp Glu Val Pro Ile Asp Gly Ser Ile Ile Asn Pro
        115                 120                 125

Ser Ser Gly Leu Val Met Thr Ala Pro Arg Ala Ala Ser Arg Thr Ile
    130                 135                 140

Leu Leu Leu Glu Asp Asn Ile Tyr Ala Ala Ser Gln Gly Trp Thr Val
145                 150                 155                 160

Thr Asn Asn Val Lys Pro Ile Val Ala Ser Ile Val Gly Tyr Lys Glu
                165                 170                 175

Met Cys Leu Gln Ser Asn Gly Glu Asn Asn Gly Val Trp Met Glu Asp
            180                 185                 190

Cys Glu Ala Thr Ser Leu Gln Gln Gln Trp Ala Leu Tyr Gly Asp Arg
        195                 200                 205

Thr Ile Arg Val Asn Ser Thr Arg Gly Leu Cys Val Thr Thr Asn Gly
    210                 215                 220

Tyr Asn Ser Lys Asp Leu Ile Ile Ile Leu Lys Cys Gln Gly Leu Pro
225                 230                 235                 240

Ser Gln Arg Trp Phe Phe Asn Ser Asp Gly Ala Ile Val Asn Pro Lys
                245                 250                 255

Ser Arg His Val Met Asp Val Arg Ala Ser Asn Val Ser Leu Arg Glu
            260                 265                 270

Ile Ile Ile Phe Pro Ala Thr Gly Asn Pro Asn Gln Gln Trp Val Thr
        275                 280                 285

```
Gln Val Leu Pro Ser Leu Glu Arg Pro Arg Asn Ala Leu Leu Leu
    290                 295                 300

Ala Asp Asp Gly Gly Phe Glu Ser Gly Ala Tyr Asn Asn Ser Ala Ile
305                 310                 315                 320

Ala Thr Pro His Leu Asp Ala Leu Ala Arg Arg Ser Leu Leu Phe Arg
                325                 330                 335

Asn Ala Phe Thr Ser Val Ser Ser Cys Ser Pro Ser Arg Ala Ser Leu
            340                 345                 350

Leu Thr Gly Leu Pro Gln His Gln Asn Gly Met Tyr Gly Leu His Gln
        355                 360                 365

Asp Val His His Phe Asn Ser Phe Asp Lys Val Arg Ser Leu Pro Leu
    370                 375                 380

Leu Leu Ser Gln Ala Gly Val Arg Thr Gly Ile Ile Gly Lys Lys His
385                 390                 395                 400

Val Gly Pro Glu Thr Val Tyr Pro Phe Asp Phe Ala Tyr Thr Glu Glu
                405                 410                 415

Asn Gly Ser Val Leu Gln Val Gly Arg Asn Ile Thr Arg Ile Lys Leu
            420                 425                 430

Leu Val Arg Lys Phe Leu Gln Thr Gln Asp Asp Arg Pro Phe Phe Leu
        435                 440                 445

Tyr Val Ala Phe His Asp Pro His Arg Cys Gly His Ser Gln Pro Gln
    450                 455                 460

Tyr Gly Thr Phe Cys Glu Lys Phe Gly Asn Gly Glu Ser Gly Met Gly
465                 470                 475                 480

Arg Ile Pro Asp Trp Thr Pro Gln Ala Tyr Asp Pro Leu Asp Val Leu
                485                 490                 495

Val Pro Tyr Phe Val Pro Asn Thr Pro Ala Ala Arg Ala Asp Leu Ala
            500                 505                 510

Ala Gln Tyr Thr Thr Val Gly Arg Met Asp Gln Gly Val Gly Leu Val
        515                 520                 525

Leu Gln Glu Leu Arg Asp Ala Gly Val Leu Asn Asp Thr Leu Val Ile
    530                 535                 540

Phe Thr Ser Asp Asn Gly Ile Pro Phe Pro Ser Gly Arg Thr Asn Leu
545                 550                 555                 560

Tyr Trp Pro Gly Thr Ala Glu Pro Leu Leu Val Ser Ser Pro Glu His
                565                 570                 575

Pro Lys Arg Trp Gly Gln Val Ser Glu Ala Tyr Val Ser Leu Leu Asp
            580                 585                 590

Leu Thr Pro Thr Ile Leu Asp Trp Phe Ser Ile Pro Tyr Pro Ser Tyr
        595                 600                 605

Ala Ile Phe Gly Ser Lys Thr Ile His Leu Thr Gly Arg Ser Leu Leu
    610                 615                 620

Pro Ala Leu Glu Ala Glu Pro Leu Trp Ala Thr Val Phe Gly Ser Gln
625                 630                 635                 640

Ser His His Glu Val Thr Met Ser Tyr Pro Met Arg Ser Val Gln His
                645                 650                 655

Arg His Phe Arg Leu Val His Asn Leu Asn Phe Lys Met Pro Phe Pro
            660                 665                 670

Ile Asp Gln Asp Phe Tyr Val Ser Pro Thr Phe Gln Asp Leu Leu Asn
        675                 680                 685

Arg Thr Thr Ala Gly Gln Pro Thr Gly Trp Tyr Lys Asp Leu Arg His
    690                 695                 700

Tyr Tyr Tyr Arg Ala Arg Trp Glu Leu Tyr Asp Arg Ser Arg Asp Pro
```

His Glu Thr Gln Asn Leu Ala Thr Asp Pro Arg Phe Ala Gln Leu Leu
705                 710                 715                 720

Glu Met Leu Arg Asp Gln Leu Ala Lys Trp Gln Trp Glu Thr His Asp
            725                 730                 735

Pro Trp Val Cys Ala Pro Asp Gly Val Leu Glu Lys Leu Ser Pro
        740                 745                 750

Gln Cys Gln Pro Leu His Asn Glu Leu His His His His His
    755                 760                 765

770                 775                 780

<210> SEQ ID NO 54
<211> LENGTH: 2298
<212> TYPE: DNA
<213> ORGANISM: Homo sapiens

<400> SEQUENCE: 54

| | | | | |
|---|---|---|---|---|
| atgagctgcc | ccgtgcccgc | ctgctgcgcg | ctgctgctag | tcctggggct | ctgccgggcg | 60 |
| cgtccccgga | acgcactgct | gctcctcgcg | gatgacggag | ctttgagag | tggcgcgtac | 120 |
| aacaacagcg | ccatcgccac | ccgcacctg | acgccttgg | cccgccgcag | cctcctcttt | 180 |
| cgcaatgcct | tcacctcggt | cagcagctgc | tctcccagcc | gcgccagcct | cctcactggc | 240 |
| ctgccccagc | atcagaatgg | gatgtacggg | ctgcaccagg | acgtgcacca | cttcaactcc | 300 |
| ttcgacaagg | tgcggagcct | gccgctgctg | tcagccaag | ctggtgtgcg | cacaggcatc | 360 |
| atcgggaaga | agcacgtggg | gccggagacc | gtgtacccgt | ttgactttgc | gtacacggag | 420 |
| gagaatggct | ccgtcctcca | ggtggggcgg | aacatcacta | gaattaagct | gctcgtccgg | 480 |
| aaattcctgc | agactcagga | tgaccggcct | ttcttcctct | acgtcgcctt | ccacgacccc | 540 |
| caccgctgtg | ggcactccca | gccccagtac | ggaaccttct | gtgagaagtt | tggcaacgga | 600 |
| gagagcggca | tgggtcgtat | cccagactgg | accccccagg | cctacgaccc | actggacgtg | 660 |
| ctggtgcctt | acttcgtccc | caacacccgg | cagcccgag | ccgacctggc | cgctcagtac | 720 |
| accaccgtcg | gccgcatgga | ccaaggagtt | ggactggtgc | tccaggagct | gcgtgacgcc | 780 |
| ggtgtcctga | cgacacact | ggtgatcttc | acgtccgaca | acgggatccc | cttccccagc | 840 |
| ggcaggacca | acctgtactg | gccgggcact | gctgaaccct | actggtgtc | atccccggag | 900 |
| cacccaaaac | gctggggcca | agtcagcgag | gcctacgtga | gctcctaga | cctcacgccc | 960 |
| accatcttgg | attggttctc | gatcccgtac | cccagctacg | ccatctttgg | ctcgaagacc | 1020 |
| atccacctca | ctggccggtc | cctcctgccg | gcgctggagg | ccgagcccct | ctgggccacc | 1080 |
| gtctttggca | gccagagcca | ccacgaggtc | accatgtcct | accccatgcg | ctccgtgcag | 1140 |
| caccggcact | tccgcctcgt | gcacaacctc | aacttcaaga | tgcccttcc | catcgaccag | 1200 |
| gacttctacg | tctcacccac | cttccaggac | tcctgaacc | gcaccacagc | tggtcagccc | 1260 |
| acgggctggt | acaaggacct | ccgtcattac | tactaccggg | cgcgctggga | actctacgac | 1320 |
| cggagccggg | accccacga | acccagaac | ctggccaccg | accgcgctt | tgctcagctt | 1380 |
| ctggagatgc | ttcgggacca | gctggccaag | tggcagtggg | agacccacga | ccctgggtg | 1440 |
| tgcgcccccg | acgcgtcct | ggaggagaag | ctctctcccc | agtgccagcc | cctccacaat | 1500 |
| gagctgctcg | agcctgagcc | catagtgcgt | atcgtaggtc | gaaatggtct | atgtgttgat | 1560 |
| gttagggatg | gaagattcca | caacggaaac | gcaatacagt | tgtggccatg | caagtctaat | 1620 |
| acagatgcaa | atcagctctg | gactttgaaa | agagacaata | ctattcgatc | taatggaaag | 1680 |
| tgtttaacta | cttacgggta | cagtccggga | gtctatgtga | tgatctatga | ttgcaatact | 1740 |

```
gctgcaactg atgccacccg ctggcaaata tgggataatg gaaccatcat aaatcccaga   1800
tctagtctag ttttagcagc gacatcaggg aacagtggta ctacacttac agtgcaaacc   1860
aacatttatg ccgttagtca aggttggctt cctactaata atacacaacc ttttgtgaca   1920
accattgttg ggctatatgg tctgtgcttg caagcaaata gtggacaagt atggatagag   1980
gactgtagca gtgaaaaggc tgaacaacag tgggctcttt atgcagatgg ttcaatacgt   2040
cctcagcaaa accgagataa ttgccttaca agtgattcta atatacggga aacagttgtc   2100
aagatcctct cttgtggccc tgcatcctct ggccaacgat ggatgttcaa gaatgatgga   2160
accattttaa atttgtatag tgggttggtg ttagatgtga gggcatcgga tccgagcctt   2220
aaacaaatca ttctttaccc tctccatggt gacccaaacc aaatatggtt accattattt   2280
catcatcatc accaccac                                                 2298
```

<210> SEQ ID NO 55
<211> LENGTH: 766
<212> TYPE: PRT
<213> ORGANISM: Homo sapiens

<400> SEQUENCE: 55

```
Met Ser Cys Pro Val Pro Ala Cys Cys Ala Leu Leu Val Leu Gly
1               5                   10                  15

Leu Cys Arg Ala Arg Pro Arg Asn Ala Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
        50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
                100                 105                 110

Gln Ala Gly Val Arg Thr Gly Ile Ile Gly Lys Lys His Val Gly Pro
            115                 120                 125

Glu Thr Val Tyr Pro Phe Asp Phe Ala Tyr Thr Glu Glu Asn Gly Ser
        130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
                180                 185                 190

Phe Cys Glu Lys Phe Gly Asn Gly Glu Ser Gly Met Gly Arg Ile Pro
            195                 200                 205

Asp Trp Thr Pro Gln Ala Tyr Asp Pro Leu Asp Val Leu Val Pro Tyr
        210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
                260                 265                 270
```

```
Asp Asn Gly Ile Pro Phe Pro Ser Gly Arg Thr Asn Leu Tyr Trp Pro
            275                 280                 285

Gly Thr Ala Glu Pro Leu Leu Val Ser Ser Pro Glu His Pro Lys Arg
        290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu Leu Glu Pro Glu Pro Ile Val Arg Ile Val
            500                 505                 510

Gly Arg Asn Gly Leu Cys Val Asp Val Arg Asp Gly Arg Phe His Asn
        515                 520                 525

Gly Asn Ala Ile Gln Leu Trp Pro Cys Lys Ser Asn Thr Asp Ala Asn
    530                 535                 540

Gln Leu Trp Thr Leu Lys Arg Asp Asn Thr Ile Arg Ser Asn Gly Lys
545                 550                 555                 560

Cys Leu Thr Thr Tyr Gly Tyr Ser Pro Gly Val Tyr Val Met Ile Tyr
                565                 570                 575

Asp Cys Asn Thr Ala Ala Thr Asp Ala Thr Arg Trp Gln Ile Trp Asp
            580                 585                 590

Asn Gly Thr Ile Ile Asn Pro Arg Ser Ser Leu Val Leu Ala Ala Thr
        595                 600                 605

Ser Gly Asn Ser Gly Thr Thr Leu Thr Val Gln Thr Asn Ile Tyr Ala
    610                 615                 620

Val Ser Gln Gly Trp Leu Pro Thr Asn Asn Thr Gln Pro Phe Val Thr
625                 630                 635                 640

Thr Ile Val Gly Leu Tyr Gly Leu Cys Leu Gln Ala Asn Ser Gly Gln
                645                 650                 655

Val Trp Ile Glu Asp Cys Ser Ser Glu Lys Ala Glu Gln Gln Trp Ala
            660                 665                 670

Leu Tyr Ala Asp Gly Ser Ile Arg Pro Gln Gln Asn Arg Asp Asn Cys
        675                 680                 685
```

```
Leu Thr Ser Asp Ser Asn Ile Arg Glu Thr Val Val Lys Ile Leu Ser
        690                 695                 700
Cys Gly Pro Ala Ser Ser Gly Gln Arg Trp Met Phe Lys Asn Asp Gly
705                 710                 715                 720
Thr Ile Leu Asn Leu Tyr Ser Gly Leu Val Leu Asp Val Arg Ala Ser
                725                 730                 735
Asp Pro Ser Leu Lys Gln Ile Ile Leu Tyr Pro Leu His Gly Asp Pro
            740                 745                 750
Asn Gln Ile Trp Leu Pro Leu Phe His His His His His His
                755                 760                 765

<210> SEQ ID NO 56
<211> LENGTH: 2298
<212> TYPE: DNA
<213> ORGANISM: Homo sapiens

<400> SEQUENCE: 56
```

| | | | | | |
|---|---|---|---|---|---|
| atgtcttgtc | cagttccagc | ttgttgcgct | ctccttcttg | ttcttggatt | gtgtagggca | 60 |
| aggcctagga | acgctctttt | gcttcttgct | gatgatggcg | gattcgagtc | cggtgcttac | 120 |
| aacaactctg | ctatcgctac | tccacacctc | gatgctcttg | ctaggcgttc | tcttcttttc | 180 |
| cgtaacgctt | tcacttccgt | gtcctcttgc | tcaccttcta | gggcttcact | tcttactgga | 240 |
| cttccacagc | accagaacgg | aatgtacgga | cttcatcagg | atgtgcacca | cttcaactca | 300 |
| ttcgataagg | tgagatccct | cccactcctc | ttgtctcaag | ctggtgttag | gactggaatc | 360 |
| atcggcaaaa | agcacgtggg | accagagact | gtgtacccat | tcgatttcgc | ttacactgag | 420 |
| gaaaacggct | ccgttcttca | agtgggcaga | aatattacta | ggatcaagct | cctcgtgagg | 480 |
| aagttcctcc | agactcaaga | tgataggcca | ttcttcctct | acgtggcatt | ccatgatcca | 540 |
| cataggtgcg | gacattctca | gccacagtac | ggaactttct | gcgagaagtt | cggaaacggt | 600 |
| gagtctggta | tggcaggat | tccagattgg | actccacagg | cttacgatcc | acttgatgtg | 660 |
| ctcgttccat | acttcgtgcc | aaacactcca | gctgctagag | ctgatcttgc | tgctcagtac | 720 |
| actactgtgg | aaggatgga | tcagggtgtg | ggacttgtgc | ttcaagagct | tagagatgct | 780 |
| ggcgtgctca | acgatactct | cgtgatcttc | acttcagata | acggcatccc | attcccatcc | 840 |
| ggaaggacta | atctttactg | gccaggtact | gctgagcctc | tccttgtttc | ttcaccagag | 900 |
| catccaaaga | ggtggggaca | agtttctgag | gcttacgtgt | cccttctcga | tctcactcca | 960 |
| actatcctcg | attggttctc | catcccttac | ccatcctacg | ctatcttcgg | ctccaagact | 1020 |
| atccacctta | ctggcagatc | tttgctccca | gctttggaag | ctgaaccact | ttgggctact | 1080 |
| gtgttcggat | ctcagtctca | ccacgagtg | acaatgtctt | acccaatgag | atctgtgcag | 1140 |
| cacaggcact | tcaggcttgt | tcacaacctc | aacttcaaga | tgccattccc | aatcgatcag | 1200 |
| gatttctacg | tgtcaccaac | tttccaggat | cttctcaaca | ggactactgc | aggacaacct | 1260 |
| actggctggt | acaaggatct | taggcactac | tactataggg | ctaggtggga | gctttacgat | 1320 |
| aggtccagag | atccacacga | gactcagaac | cttgctactg | atccaaggtt | cgctcagctc | 1380 |
| cttgagatgc | ttagggatca | gcttgctaag | tggcagtggg | agactcatga | tccatgggtt | 1440 |
| tgcgctccag | atggtgtgct | tgaagagaag | ttgtctccac | agtgccagcc | acttcataac | 1500 |
| gagcttctcg | agcctgagcc | catagtgcgt | atcgtaggtc | gaaatggtct | atgtgttgat | 1560 |
| gttagggatg | gaagattcca | caacggaaac | gcaatacagt | tgtggccatg | caagtctaat | 1620 |
| acagatgcaa | atcagctctg | gactttgaaa | agagacaata | ctattcgatc | taatggaaag | 1680 |

-continued

```
tgtttaacta cttacgggta cagtccggga gtctatgtga tgatctatga ttgcaatact    1740
gctgcaactg atgccacccg ctggcaaata tgggataatg aaccatcat aaatcccaga     1800 tctagtctag ttttagcagc gacatcaggg aacagtggta ctacacttac agtgcaaacc   1860 aacattatg ccgttagtca aggttggctt cctactaata atacacaacc ttttgtgaca    1920
accattgttg ggctatatgg tctgtgcttg caagcaaata gtggacaagt atggatagag   1980
gactgtagca gtgaaaaggc tgaacaacag tgggctcttt atgcagatgg ttcaatacgt   2040
cctcagcaaa accgagataa ttgccttaca agtgattcta atatacggga aacagttgtc   2100
aagatcctct cttgtggccc tgcatcctct ggccaacgat ggatgttcaa gaatgatgga   2160
accattttaa atttgtatag tgggttggtg ttagatgtga gggcatcgga tccgagcctt   2220
aaacaaatca ttctttaccc tctccatggt gacccaaacc aaatatggtt accattattt   2280
catcatcatc accaccac                                                 2298
```

<210> SEQ ID NO 57
<211> LENGTH: 766
<212> TYPE: PRT
<213> ORGANISM: Homo sapiens

<400> SEQUENCE: 57

```
Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
        50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
```

```
                260             265             270
Asp Asn Gly Ile Pro Phe Pro Ser Gly Arg Thr Asn Leu Tyr Trp Pro
            275             280             285

Gly Thr Ala Glu Pro Leu Leu Val Ser Ser Pro Glu His Pro Lys Arg
        290             295             300

Trp Gly Gln Val Ser Glu Ala Tyr Val Ser Leu Leu Asp Leu Thr Pro
305             310             315             320

Thr Ile Leu Asp Trp Phe Ser Ile Pro Tyr Pro Ser Tyr Ala Ile Phe
                325             330             335

Gly Ser Lys Thr Ile His Leu Thr Gly Arg Ser Leu Leu Pro Ala Leu
            340             345             350

Glu Ala Glu Pro Leu Trp Ala Thr Val Phe Gly Ser Gln Ser His His
        355             360             365

Glu Val Thr Met Ser Tyr Pro Met Arg Ser Val Gln His Arg His Phe
    370             375             380

Arg Leu Val His Asn Leu Asn Phe Lys Met Pro Phe Pro Ile Asp Gln
385             390             395             400

Asp Phe Tyr Val Ser Pro Thr Phe Gln Asp Leu Leu Asn Arg Thr Thr
                405             410             415

Ala Gly Gln Pro Thr Gly Trp Tyr Lys Asp Leu Arg His Tyr Tyr Tyr
            420             425             430

Arg Ala Arg Trp Glu Leu Tyr Asp Arg Ser Arg Asp Pro His Glu Thr
        435             440             445

Gln Asn Leu Ala Thr Asp Pro Arg Phe Ala Gln Leu Leu Glu Met Leu
    450             455             460

Arg Asp Gln Leu Ala Lys Trp Gln Trp Glu Thr His Asp Pro Trp Val
465             470             475             480

Cys Ala Pro Asp Gly Val Leu Glu Glu Lys Leu Ser Pro Gln Cys Gln
                485             490             495

Pro Leu His Asn Glu Leu Leu Glu Pro Glu Pro Ile Val Arg Ile Val
            500             505             510

Gly Arg Asn Gly Leu Cys Val Asp Val Arg Asp Gly Arg Phe His Asn
        515             520             525

Gly Asn Ala Ile Gln Leu Trp Pro Cys Lys Ser Asn Thr Asp Ala Asn
    530             535             540

Gln Leu Trp Thr Leu Lys Arg Asp Asn Thr Ile Arg Ser Asn Gly Lys
545             550             555             560

Cys Leu Thr Thr Tyr Gly Tyr Ser Pro Gly Val Tyr Val Met Ile Tyr
                565             570             575

Asp Cys Asn Thr Ala Ala Thr Asp Ala Thr Arg Trp Gln Ile Trp Asp
            580             585             590

Asn Gly Thr Ile Ile Asn Pro Arg Ser Ser Leu Val Leu Ala Ala Thr
        595             600             605

Ser Gly Asn Ser Gly Thr Thr Leu Thr Val Gln Thr Asn Ile Tyr Ala
    610             615             620

Val Ser Gln Gly Trp Leu Pro Thr Asn Asn Thr Gln Pro Phe Val Thr
625             630             635             640

Thr Ile Val Gly Leu Tyr Gly Leu Cys Leu Gln Ala Asn Ser Gly Gln
                645             650             655

Val Trp Ile Glu Asp Cys Ser Ser Glu Lys Ala Glu Gln Gln Trp Ala
            660             665             670

Leu Tyr Ala Asp Gly Ser Ile Arg Pro Gln Gln Asn Arg Asp Asn Cys
        675             680             685
```

```
Leu Thr Ser Asp Ser Asn Ile Arg Glu Thr Val Val Lys Ile Leu Ser
        690                 695                 700
Cys Gly Pro Ala Ser Ser Gly Gln Arg Trp Met Phe Lys Asn Asp Gly
705                 710                 715                 720
Thr Ile Leu Asn Leu Tyr Ser Gly Leu Val Leu Asp Val Arg Ala Ser
                725                 730                 735
Asp Pro Ser Leu Lys Gln Ile Ile Leu Tyr Pro Leu His Gly Asp Pro
            740                 745                 750
Asn Gln Ile Trp Leu Pro Leu Phe His His His His His His
        755                 760                 765
```

<210> SEQ ID NO 58
<211> LENGTH: 2326
<212> TYPE: DNA
<213> ORGANISM: Homo sapiens

<400> SEQUENCE: 58

```
aacaatggct tcctccgcta ctactaaatc tttccttatt cttttcttta tgatacttgc      60
aactacttca tcaacatgtg cagtcgaccg tccccggaac gcactgctgc tcctcgcgga     120
tgacggaggc tttgagagtg gcgcgtacaa caacagcgcc atcgccaccc cgcacctgga     180
cgccttggcc cgccgcagcc tcctctttcg caatgccttc acctcggtca gcagctgctc     240
tcccagccgc gccagcctcc tcactggcct gccccagcat cagaatggga tgtacgggct     300
gcaccaggac gtgcaccact tcaactcctt cgacaaggtg cggagcctgc gctgctgct     360
cagccaagct ggtgtgcgca caggcatcat cgggaagaag cacgtggggc cggagaccgt     420
gtaccgtttt gactttgcgt acacggagga gaatggctcc gtcctccagg tggggcggaa     480
catcactaga attaagctgc tcgtccggaa attcctgcag actcaggatg accggccttt     540
cttcctctac gtcgccttcc acgaccccca ccgctgtggg cactcccagc ccagtacgg      600
aaccttctgt gagaagtttg caacggaga gagcggcatg gtcgtatcc agactggac       660
ccccaggcc tacgacccac tggacgtgct ggtgccttac ttcgtcccca caccccggc      720
agcccgagcc gacctggccg ctcagtacac accgtcggc cgcatggacc aaggagttgg     780
actggtgctc caggagctgc gtgacgccgg tgtcctgaac gacacactgg tgatcttcac     840
gtccgacaac gggatcccct tccccagcgg caggaccaac ctgtactggc gggcactgc      900
tgaacccta ctggtgtcat ccccggagca cccaaaacgc tggggccaag tcagcgaggc     960
ctacgtgagc ctcctagacc tcacgcccac catcttggat tggttctcga tcccgtaccc    1020
cagctacgcc atctttggct cgaagaccat ccacctcact ggccggtccc tcctgccggc    1080
gctggaggcc gagcccctct gggccaccgt ctttggcagc cagagccacc acgaggtcac    1140
catgtcctac cccatgcgct ccgtgcagca ccggcacttc cgcctcgtgc acaacctcaa    1200
cttcaagatg ccctttccca tcgaccagga cttctacgtc tcacccacct tccaggacct    1260
cctgaaccgc accacagctg gtcagcccac gggctggtac aaggacctcc gtcattacta    1320
ctaccgggcg cgctgggaac tctacgaccg gagccgggac ccccacgaga cccagaacct    1380
ggccaccgac ccgcgctttg ctcagcttct ggagatgctt cggaccagc tggccaagtg    1440
gcagtgggag acccacgacc cctgggtgtg cgccccgac ggcgtcctgg aggagaagct    1500
ctctccccag tgccagcccc tccacaatga gctgctcgag cctgagccca tagtgcgtat    1560
cgtaggtcga atggtctat gtgttgatgt tagggatgga agattccaca acggaaacgc    1620
aatacagttg tggccatgca agctctaatac agatgcaaat cagctctgga ctttgaaaag    1680
```

```
agacaatact attcgatcta atggaaagtg tttaactact tacgggtaca gtccgggagt    1740
ctatgtgatg atctatgatt gcaatactgc tgcaactgat gccacccgct ggcaaatatg    1800
ggataatgga accatcataa atcccagatc tagtctagtt ttagcagcga catcagggaa    1860
cagtggtact acacttacag tgcaaaccaa catttatgcc gttagtcaag gttggcttcc    1920
tactaataat acacaacctt ttgtgacaac cattgttggg ctatatggtc tgtgcttgca    1980
agcaaatagt ggacaagtat ggatagagga ctgtagcagt gaaaaggctg aacaacagtg    2040
ggctctttat gcagatggtt caatacgtcc tcagcaaaac cgagataatt gccttacaag    2100
tgattctaat atacgggaaa cagttgtcaa gatcctctct tgtggccctg catcctctgg    2160
ccaacgatgg atgttcaaga atgatggaac cattttaaat ttgtatagtg ggttggtgtt    2220
agatgtgagg gcatcggatc cgagcctaa acaaatcatt ctttaccctc tccatggtga    2280
cccaaaccaa atatggttac cattatttca tcatcatcac caccac                  2326
```

<210> SEQ ID NO 59
<211> LENGTH: 774
<212> TYPE: PRT
<213> ORGANISM: Homo sapiens

<400> SEQUENCE: 59

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Arg Pro Arg Asn
            20                  25                  30

Ala Leu Leu Leu Leu Ala Asp Asp Gly Gly Phe Glu Ser Gly Ala Tyr
        35                  40                  45

Asn Asn Ser Ala Ile Ala Thr Pro His Leu Asp Ala Leu Ala Arg Arg
    50                  55                  60

Ser Leu Leu Phe Arg Asn Ala Phe Thr Ser Val Ser Ser Cys Ser Pro
65                  70                  75                  80

Ser Arg Ala Ser Leu Leu Thr Gly Leu Pro Gln His Gln Asn Gly Met
                85                  90                  95

Tyr Gly Leu His Gln Asp Val His His Phe Asn Ser Phe Asp Lys Val
            100                 105                 110

Arg Ser Leu Pro Leu Leu Leu Ser Gln Ala Gly Val Arg Thr Gly Ile
        115                 120                 125

Ile Gly Lys Lys His Val Gly Pro Glu Thr Val Tyr Pro Phe Asp Phe
    130                 135                 140

Ala Tyr Thr Glu Glu Asn Gly Ser Val Leu Gln Val Gly Arg Asn Ile
145                 150                 155                 160

Thr Arg Ile Lys Leu Leu Val Arg Lys Phe Leu Gln Thr Gln Asp Asp
                165                 170                 175

Arg Pro Phe Phe Leu Tyr Val Ala Phe His Asp Pro His Arg Cys Gly
            180                 185                 190

His Ser Gln Pro Gln Tyr Gly Thr Phe Cys Glu Lys Phe Gly Asn Gly
        195                 200                 205

Glu Ser Gly Met Gly Arg Ile Pro Asp Trp Thr Pro Gln Ala Tyr Asp
    210                 215                 220

Pro Leu Asp Val Leu Val Pro Tyr Phe Val Pro Asn Thr Pro Ala Ala
225                 230                 235                 240

Arg Ala Asp Leu Ala Ala Gln Tyr Thr Thr Val Gly Arg Met Asp Gln
                245                 250                 255
```

Gly Val Gly Leu Val Leu Gln Glu Leu Arg Asp Ala Gly Val Leu Asn
            260                 265                 270

Asp Thr Leu Val Ile Phe Thr Ser Asp Asn Gly Ile Pro Phe Pro Ser
        275                 280                 285

Gly Arg Thr Asn Leu Tyr Trp Pro Gly Thr Ala Glu Pro Leu Leu Val
    290                 295                 300

Ser Ser Pro Glu His Pro Lys Arg Trp Gly Gln Val Ser Glu Ala Tyr
305                 310                 315                 320

Val Ser Leu Leu Asp Leu Thr Pro Thr Ile Leu Asp Trp Phe Ser Ile
                325                 330                 335

Pro Tyr Pro Ser Tyr Ala Ile Phe Gly Ser Lys Thr Ile His Leu Thr
            340                 345                 350

Gly Arg Ser Leu Leu Pro Ala Leu Glu Ala Glu Pro Leu Trp Ala Thr
        355                 360                 365

Val Phe Gly Ser Gln Ser His His Glu Val Thr Met Ser Tyr Pro Met
    370                 375                 380

Arg Ser Val Gln His Arg His Phe Arg Leu Val His Asn Leu Asn Phe
385                 390                 395                 400

Lys Met Pro Phe Pro Ile Asp Gln Asp Phe Tyr Val Ser Pro Thr Phe
                405                 410                 415

Gln Asp Leu Leu Asn Arg Thr Thr Ala Gly Gln Pro Thr Gly Trp Tyr
            420                 425                 430

Lys Asp Leu Arg His Tyr Tyr Tyr Arg Ala Arg Trp Glu Leu Tyr Asp
        435                 440                 445

Arg Ser Arg Asp Pro His Glu Thr Gln Asn Leu Ala Thr Asp Pro Arg
    450                 455                 460

Phe Ala Gln Leu Leu Glu Met Leu Arg Asp Gln Leu Ala Lys Trp Gln
465                 470                 475                 480

Trp Glu Thr His Asp Pro Trp Val Cys Ala Pro Asp Gly Val Leu Glu
                485                 490                 495

Glu Lys Leu Ser Pro Gln Cys Gln Pro Leu His Asn Glu Leu Leu Glu
            500                 505                 510

Pro Glu Pro Ile Val Arg Ile Val Gly Arg Asn Gly Leu Cys Val Asp
        515                 520                 525

Val Arg Asp Gly Arg Phe His Asn Gly Asn Ala Ile Gln Leu Trp Pro
    530                 535                 540

Cys Lys Ser Asn Thr Asp Ala Asn Gln Leu Trp Thr Leu Lys Arg Asp
545                 550                 555                 560

Asn Thr Ile Arg Ser Asn Gly Lys Cys Leu Thr Thr Tyr Gly Tyr Ser
                565                 570                 575

Pro Gly Val Tyr Val Met Ile Tyr Asp Cys Asn Thr Ala Ala Thr Asp
            580                 585                 590

Ala Thr Arg Trp Gln Ile Trp Asp Asn Gly Thr Ile Ile Asn Pro Arg
        595                 600                 605

Ser Ser Leu Val Leu Ala Ala Thr Ser Gly Asn Ser Gly Thr Thr Leu
    610                 615                 620

Thr Val Gln Thr Asn Ile Tyr Ala Val Ser Gln Gly Trp Leu Pro Thr
625                 630                 635                 640

Asn Asn Thr Gln Pro Phe Val Thr Thr Ile Val Gly Leu Tyr Gly Leu
                645                 650                 655

Cys Leu Gln Ala Asn Ser Gly Gln Val Trp Ile Glu Asp Cys Ser Ser
            660                 665                 670

Glu Lys Ala Glu Gln Gln Trp Ala Leu Tyr Ala Asp Gly Ser Ile Arg

```
              675                 680                 685
Pro Gln Gln Asn Arg Asp Asn Cys Leu Thr Ser Asp Ser Asn Ile Arg
        690                 695                 700

Glu Thr Val Val Lys Ile Leu Ser Cys Gly Pro Ala Ser Ser Gly Gln
705                 710                 715                 720

Arg Trp Met Phe Lys Asn Asp Gly Thr Ile Leu Asn Leu Tyr Ser Gly
                    725                 730                 735

Leu Val Leu Asp Val Arg Ala Ser Asp Pro Ser Leu Lys Gln Ile Ile
                740                 745                 750

Leu Tyr Pro Leu His Gly Asp Pro Asn Gln Ile Trp Leu Pro Leu Phe
            755                 760                 765

His His His His His His
        770
```

<210> SEQ ID NO 60
<211> LENGTH: 2326
<212> TYPE: DNA
<213> ORGANISM: Homo sapiens

<400> SEQUENCE: 60

```
aacaatggct tcctccgcta ctactaaatc tttccttatt cttttcttta tgatacttgc    60
aactacttca tcaacatgtg cagtcgacag gcctaggaac gctcttttgc ttcttgctga   120
tgatggcgga ttcgagtccg gtgcttacaa caactctgct atcgctactc cacacctcga   180
tgctcttgct aggcgttctc ttcttttccg taacgctttc acttccgtgt cctcttgctc   240
accttctagg gcttcacttc ttactggact tccacagcac cagaacggaa tgtacggact   300
tcatcaggat gtgcaccact tcaactcatt cgataaggtg agatccctcc cactcctctt   360
gtctcaagct ggtgttagga ctggaatcat cggcaaaaag cacgtgggac cagagactgt   420
gtacccattc gatttcgctt acactgagga aaacggctcc gttcttcaag tgggcagaaa   480
tattactagg atcaagctcc tcgtgaggaa gttcctccag actcaagatg ataggccatt   540
cttcctctac gtggcattcc atgatccaca taggtgcgga cattctcagc cacagtacgg   600
aactttctgc gagaagttcg gaaacggtga gtctggtatg gcaggattcc agattggac    660
tccacaggct tacgatccac ttgatgtgct cgttccatac ttcgtgccaa acactccagc   720
tgctagagct gatcttgctg ctcagtacac tactgtggga aggatggatc agggtgtggg   780
acttgtgctt caagagctta gagatgctgg cgtgctcaac gatactctcg tgatcttcac   840
ttcgataaac ggcatcccat ccccatccgg aaggactaat ctttactggc aggtactgc    900
tgagcctctc cttgtttctt caccagagca tccaaagagg tggggacaag tttctgaggc   960
ttacgtgtcc cttctcgatc tcactccaac tatcctcgat tggttctcca tcccttaccc  1020
atcctacgct atcttcggct ccaagactat ccaccttact ggcagatctt tgctcccagc  1080
tttggaagct gaaccacttt gggctactgt gttcggatct cagtctcacc acgaggtgac  1140
aatgtcttac ccaatgagat ctgtgcagca caggcacttc aggcttgttc acaacctcaa  1200
cttcaagatg ccattcccaa tcgatcagga tttctacgtg tcaccaactt tccaggatct  1260
tctcaacagg actactgcag acaacctac tggctggtac aaggatctta ggcactacta  1320
ctatagggct aggtgggagc tttacgatag gtccagagat ccacacgaga ctcagaacct  1380
tgctactgat ccaaggttcg ctcagctcct tgagatgctt agggatcagc ttgctaagtg  1440
gcagtgggag actcatgatc catgggtttg cgctccagat ggtgtgcttg aagagaagtt  1500
gtctccacag tgccagccac ttcataacga gcttctcgag cctgagccca tagtgcgtat  1560
```

-continued

```
cgtaggtcga aatggtctat gtgttgatgt tagggatgga agattccaca acggaaacgc   1620
aatacagttg tggccatgca agtctaatac agatgcaaat cagctctgga cttttgaaaag  1680 agacaatact attcgatcta atggaaagtg tttaactact tacgggtaca gtccgggagt   1740
ctatgtgatg atctatgatt gcaatactgc tgcaactgat gccacccgct ggcaaatatg   1800
ggataatgga accatcataa atcccagatc tagtctagtt ttagcagcga catcagggaa   1860
cagtggtact acacttacag tgcaaaccaa cattttatgcc gttagtcaag gttggcttcc   1920
tactaataat acacaacctt tgtgacaac cattgttggg ctatatggtc tgtgcttgca    1980
agcaaatagt ggacaagtat ggatagagga ctgtagcagt gaaaaggctg aacaacagtg   2040
ggctctttat gcagatggtt caatacgtcc tcagcaaaac cgagataatt gccttacaag   2100
tgattctaat atacgggaaa cagttgtcaa gatcctctct tgtggccctg catcctctgg   2160
ccaacgatgg atgttcaaga atgatggaac cattttaaat ttgtatagtg ggttggtgtt   2220
agatgtgagg gcatcggatc cgagccttaa acaaatcatt ctttaccctc tccatggtga   2280
cccaaaccaa atatggttac cattatttca tcatcatcac caccac                  2326
```

<210> SEQ ID NO 61
<211> LENGTH: 774
<212> TYPE: PRT
<213> ORGANISM: Homo sapiens

<400> SEQUENCE: 61

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Arg Pro Arg Asn
                20                  25                  30

Ala Leu Leu Leu Leu Ala Asp Asp Gly Gly Phe Glu Ser Gly Ala Tyr
            35                  40                  45

Asn Asn Ser Ala Ile Ala Thr Pro His Leu Asp Ala Leu Ala Arg Arg
        50                  55                  60

Ser Leu Leu Phe Arg Asn Ala Phe Thr Ser Val Ser Ser Cys Ser Pro
65                  70                  75                  80

Ser Arg Ala Ser Leu Leu Thr Gly Leu Pro Gln His Gln Asn Gly Met
                85                  90                  95

Tyr Gly Leu His Gln Asp Val His His Phe Asn Ser Phe Asp Lys Val
                100                 105                 110

Arg Ser Leu Pro Leu Leu Leu Ser Gln Ala Gly Val Arg Thr Gly Ile
            115                 120                 125

Ile Gly Lys Lys His Val Gly Pro Glu Thr Val Tyr Pro Phe Asp Phe
        130                 135                 140

Ala Tyr Thr Glu Glu Asn Gly Ser Val Leu Gln Val Gly Arg Asn Ile
145                 150                 155                 160

Thr Arg Ile Lys Leu Leu Val Arg Lys Phe Leu Gln Thr Gln Asp Asp
                165                 170                 175

Arg Pro Phe Phe Leu Tyr Val Ala Phe His Asp Pro His Arg Cys Gly
            180                 185                 190

His Ser Gln Pro Gln Tyr Gly Thr Phe Cys Glu Lys Phe Gly Asn Gly
        195                 200                 205

Glu Ser Gly Met Gly Arg Ile Pro Asp Trp Thr Pro Gln Ala Tyr Asp
    210                 215                 220

Pro Leu Asp Val Leu Val Pro Tyr Phe Val Pro Asn Thr Pro Ala Ala
225                 230                 235                 240
```

```
Arg Ala Asp Leu Ala Ala Gln Tyr Thr Thr Val Gly Arg Met Asp Gln
            245                 250                 255

Gly Val Gly Leu Val Leu Gln Glu Leu Arg Asp Ala Gly Val Leu Asn
            260                 265                 270

Asp Thr Leu Val Ile Phe Thr Ser Asp Asn Gly Ile Pro Phe Pro Ser
            275                 280                 285

Gly Arg Thr Asn Leu Tyr Trp Pro Gly Thr Ala Glu Pro Leu Leu Val
            290                 295                 300

Ser Ser Pro Glu His Pro Lys Arg Trp Gly Gln Val Ser Glu Ala Tyr
305                 310                 315                 320

Val Ser Leu Leu Asp Leu Thr Pro Thr Ile Leu Asp Trp Phe Ser Ile
            325                 330                 335

Pro Tyr Pro Ser Tyr Ala Ile Phe Gly Ser Lys Thr Ile His Leu Thr
            340                 345                 350

Gly Arg Ser Leu Leu Pro Ala Leu Glu Ala Glu Pro Leu Trp Ala Thr
            355                 360                 365

Val Phe Gly Ser Gln Ser His His Glu Val Thr Met Ser Tyr Pro Met
    370                 375                 380

Arg Ser Val Gln His Arg His Phe Arg Leu Val His Asn Leu Asn Phe
385                 390                 395                 400

Lys Met Pro Phe Pro Ile Asp Gln Asp Phe Tyr Val Ser Pro Thr Phe
            405                 410                 415

Gln Asp Leu Leu Asn Arg Thr Thr Ala Gly Gln Pro Thr Gly Trp Tyr
            420                 425                 430

Lys Asp Leu Arg His Tyr Tyr Arg Ala Arg Trp Glu Leu Tyr Asp
            435                 440                 445

Arg Ser Arg Asp Pro His Glu Thr Gln Asn Leu Ala Thr Asp Pro Arg
450                 455                 460

Phe Ala Gln Leu Leu Glu Met Leu Arg Asp Gln Leu Ala Lys Trp Gln
465                 470                 475                 480

Trp Glu Thr His Asp Pro Trp Val Cys Ala Pro Asp Gly Val Leu Glu
            485                 490                 495

Glu Lys Leu Ser Pro Gln Cys Gln Pro Leu His Asn Glu Leu Leu Glu
            500                 505                 510

Pro Glu Pro Ile Val Arg Ile Val Gly Arg Asn Gly Leu Cys Val Asp
            515                 520                 525

Val Arg Asp Gly Arg Phe His Asn Gly Asn Ala Ile Gln Leu Trp Pro
530                 535                 540

Cys Lys Ser Asn Thr Asp Ala Asn Gln Leu Trp Thr Leu Lys Arg Asp
545                 550                 555                 560

Asn Thr Ile Arg Ser Asn Gly Lys Cys Leu Thr Thr Tyr Gly Tyr Ser
            565                 570                 575

Pro Gly Val Tyr Val Met Ile Tyr Asp Cys Asn Thr Ala Ala Thr Asp
            580                 585                 590

Ala Thr Arg Trp Gln Ile Trp Asp Asn Gly Thr Ile Ile Asn Pro Arg
            595                 600                 605

Ser Ser Leu Val Leu Ala Ala Thr Ser Gly Asn Ser Gly Thr Thr Leu
            610                 615                 620

Thr Val Gln Thr Asn Ile Tyr Ala Val Ser Gln Gly Trp Leu Pro Thr
625                 630                 635                 640

Asn Asn Thr Gln Pro Phe Val Thr Thr Ile Val Gly Leu Tyr Gly Leu
            645                 650                 655
```

```
Cys Leu Gln Ala Asn Ser Gly Gln Val Trp Ile Glu Asp Cys Ser Ser
              660                 665                 670

Glu Lys Ala Glu Gln Gln Trp Ala Leu Tyr Ala Asp Gly Ser Ile Arg
          675                 680                 685

Pro Gln Gln Asn Arg Asp Asn Cys Leu Thr Ser Asp Ser Asn Ile Arg
      690                 695                 700

Glu Thr Val Val Lys Ile Leu Ser Cys Gly Pro Ala Ser Ser Gly Gln
705                 710                 715                 720

Arg Trp Met Phe Lys Asn Asp Gly Thr Ile Leu Asn Leu Tyr Ser Gly
              725                 730                 735

Leu Val Leu Asp Val Arg Ala Ser Asp Pro Ser Leu Lys Gln Ile Ile
          740                 745                 750

Leu Tyr Pro Leu His Gly Asp Pro Asn Gln Ile Trp Leu Pro Leu Phe
      755                 760                 765

His His His His His His
    770
```

<210> SEQ ID NO 62
<211> LENGTH: 2331
<212> TYPE: DNA
<213> ORGANISM: Homo sapiens

<400> SEQUENCE: 62

```
atgagctgcc ccgtgcccgc ctgctgcgcg ctgctgctag tcctgggggct ctgccgggcg    60
cgtccccgga acgcactgct gctcctcgcg gatgacggag ctttgagag tggcgcgtac   120
aacaacagcg ccatcgccac cccgcacctg acgccttgg cccgccgcag cctcctcttt   180
cgcaatgcct tcacctcggt cagcagctgc tctcccagcc gcgccagcct cctcactggc   240
ctgccccagc atcagaatgg gatgtacggg ctgcaccagg acgtgcacca cttcaactcc   300
ttcgacaagg tgcggagcct gccgctgctg ctcagccaag ctggtgtgcg cacaggcatc   360
atcgggaaga agcacgtggg gccggagacc gtgtacccgt ttgactttgc gtacacggag   420
gagaatggct ccgtcctcca ggtggggcgg aacatcacta gaattaagct gctcgtccgg   480
aaattcctgc agactcagga tgaccggcct ttcttcctct acgtcgcctt ccacgacccc   540
caccgctgtg ggcactccca gccccagtac ggaaccttct gtgagaagtt tggcaacgga   600
gagagcggca tgggtcgtat cccagactgg accccccagg cctacgaccc actgacgtg   660
ctggtgcctt acttcgtccc caacaccccg gcagcccgag ccgacctggc cgctcagtac   720
accaccgtcg ccgcatgga ccaaggagtt ggactggtgc tccaggagct gcgtgacgcc   780
ggtgtcctga cgacacact ggtgatcttc acgtccgaca acgggatccc cttccccagc   840
ggcaggacca acctgtactg gccgggcact gctgaaccct actggtgtc atccccggag   900
cacccaaaac gctgggggcca agtcagcgag gcctacgtga gcctcctaga cctcacgccc   960
accatcttgg attggttctc gatcccgtac cccagctacg ccatctttgg ctcgaagacc  1020
atccacctca ctggccggtc cctcctgccg gcgctggagg ccgagcccct ctgggccacc  1080
gtctttggca gccagagcca ccacgaggtc accatgtcct accccatgcg ctccgtgcag  1140
caccggcact tccgcctcgt gcacaacctc aacttcaaga tgccctttcc catcgaccag  1200
gacttctacg tctcacccac cttccaggac tcctgaacc gcaccacagc tggtcagccc  1260
acgggctggt acaaggacct ccgtcattac tactaccggg cgcgctggga actctacgac  1320
cggagccggg accccacga cccagaaac ctggccaccg accgcgcttt gctcagcttt  1380
ctggagatgc ttcgggacca gctggccaag tggcagtggg agacccacga cccctggggtg  1440
```

```
tgcgccccg acggcgtcct ggaggagaag ctctctcccc agtgccagcc cctccacaat   1500
gagctgctcg agggagaaac ttctactctt aggacttcat tcacaagaaa catcgttggt   1560
cgtgatggat tgtgcgtgga tgtgaggaat ggatacgaca ctgatggaac tccacttcag   1620
ttgtggccat gtggaaccca gagaaaccaa cgatggactt ttgactcaga cgatacaatc   1680
aggtcaatgg gtaaatgcat gactgcaaac gggttaaaca atggaagcaa tatcgtgata   1740
ttcaactgtt ctacagctgc tgagaacgcc attaagtggg aagtacctat tgatggcagc   1800
atcatcaatc cttcctccgg attggttatg accgctcctc gtgctgcatc ccgtaccatc   1860
ctgttgcttg aggacaatat ctacgccgct agccagggtt ggactgtgac aaacaatgta   1920
aagcccatcg ttgcttccat tgtgggttat aaagaaatgt gcttgcagtc taacggtgaa   1980
aacaatggtg tttggatgga ggattgtgag gccaccagtt tgcagcaaca gtgggcactc   2040
tatggtgacc gtaccatccg agtaaatagt actcgtggct tatgcgtcac caccaatggg   2100
tacaactcca aggatctcat catcatcctt aaatgccaag gattgcccag ccagaggtgg   2160
tttttcaact ccgacggcgc catcgtaaac ccaaagtcaa gacatgttat ggatgtgaga   2220
gcaagcaatg tctctcttcg agaaatcatt atctttccag ccactgggaa ccctaatcag   2280
caatgggtga cacaagtcct tccaagtccc gggcatcatc atcatcatca t           2331
```

<210> SEQ ID NO 63
<211> LENGTH: 777
<212> TYPE: PRT
<213> ORGANISM: Homo sapiens

<400> SEQUENCE: 63

```
Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
```

```
            210                 215                 220
Phe Val Pro Asn Thr Pro Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
                260                 265                 270

Asp Asn Gly Ile Pro Phe Pro Ser Gly Arg Thr Asn Leu Tyr Trp Pro
            275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
                340                 345                 350

Glu Ala Glu Pro Leu Trp Ala Thr Val Phe Gly Ser Gln Ser His His
                355                 360                 365

Glu Val Thr Met Ser Tyr Pro Met Arg Ser Val Gln His Arg His Phe
            370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
                420                 425                 430

Arg Ala Arg Trp Glu Leu Tyr Asp Arg Ser Arg Asp Pro His Glu Thr
            435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu Leu Glu Gly Glu Thr Ser Thr Leu Arg Thr
                500                 505                 510

Ser Phe Thr Arg Asn Ile Val Gly Arg Asp Gly Leu Cys Val Asp Val
            515                 520                 525

Arg Asn Gly Tyr Asp Thr Asp Gly Thr Pro Leu Gln Leu Trp Pro Cys
    530                 535                 540

Gly Thr Gln Arg Asn Gln Arg Trp Thr Phe Asp Ser Asp Asp Thr Ile
545                 550                 555                 560

Arg Ser Met Gly Lys Cys Met Thr Ala Asn Gly Leu Asn Asn Gly Ser
                565                 570                 575

Asn Ile Val Ile Phe Asn Cys Ser Thr Ala Ala Glu Asn Ala Ile Lys
                580                 585                 590

Trp Glu Val Pro Ile Asp Gly Ser Ile Ile Asn Pro Ser Ser Gly Leu
            595                 600                 605

Val Met Thr Ala Pro Arg Ala Ala Ser Arg Thr Ile Leu Leu Leu Glu
    610                 615                 620

Asp Asn Ile Tyr Ala Ala Ser Gln Gly Trp Thr Val Thr Asn Asn Val
625                 630                 635                 640
```

```
Lys Pro Ile Val Ala Ser Ile Val Gly Tyr Lys Glu Met Cys Leu Gln
                645                 650                 655

Ser Asn Gly Glu Asn Asn Gly Val Trp Met Glu Asp Cys Glu Ala Thr
            660                 665                 670

Ser Leu Gln Gln Gln Trp Ala Leu Tyr Gly Asp Arg Thr Ile Arg Val
        675                 680                 685

Asn Ser Thr Arg Gly Leu Cys Val Thr Thr Asn Gly Tyr Asn Ser Lys
    690                 695                 700

Asp Leu Ile Ile Ile Leu Lys Cys Gln Gly Leu Pro Ser Gln Arg Trp
705                 710                 715                 720

Phe Phe Asn Ser Asp Gly Ala Ile Val Asn Pro Lys Ser Arg His Val
                725                 730                 735

Met Asp Val Arg Ala Ser Asn Val Ser Leu Arg Glu Ile Ile Ile Phe
            740                 745                 750

Pro Ala Thr Gly Asn Pro Asn Gln Gln Trp Val Thr Gln Val Leu Pro
        755                 760                 765

Ser Pro Gly His His His His His His
    770                 775
```

<210> SEQ ID NO 64
<211> LENGTH: 2331
<212> TYPE: DNA
<213> ORGANISM: Homo sapiens

<400> SEQUENCE: 64

```
atgtcttgtc cagttccagc ttgttgcgct ctccttcttg ttcttggatt gtgtagggca      60
aggcctagga acgctctttt gcttcttgct gatgatggcg gattcgagtc cggtgcttac     120
aacaactctg ctatcgctac tccacaccct gatgctcttg ctaggcgttc tcttcttttc     180
cgtaacgctt tcacttccgt gtcctcttgc tcaccttcta gggcttcact tcttactgga     240
cttccacagc accagaacgg aatgtacgga cttcatcagg atgtgcacca cttcaactca     300
ttcgataagg tgagatccct cccactcctc ttgtctcaag ctggtgttag gactggaatc     360
atcggcaaaa agcacgtggg accagagact gtgtacccat tcgatttcgc ttacactgag     420
gaaaacggct ccgttcttca agtgggcaga atattacta ggatcaagct cctcgtgagg      480
aagttcctcc agactcaaga tgataggcca ttcttcctct acgtggcatt ccatgatcca     540
cataggtgcg acattctca gccacagtac ggaactttct gcgagaagtt cggaaacggt      600
gagtctggta tgggcaggat tccagattgg actccacagg cttacgatcc acttgatgtg     660
ctcgttccat acttcgtgcc aaacactcca gctgctagag ctgatcttgc tgctcagtac     720
actactgtgg gaaggatgga tcagggtgtg ggacttgtgc ttcaagagct tagagatgct     780
ggcgtgctca cgatactct cgtgatcttc acttcagata cggcatccc attcccatcc       840
ggaaggacta tctttactg gccaggtact gctgagcctc tccttgtttc ttcaccagag      900
catccaaaga ggtggggaca gtttctgag gcttacgtgt cccttctcga tctcactcca      960
actatcctcg attggttctc catcccttac ccatcctacg ctatcttcgg ctccaagact    1020
atccacctta ctggcagatc tttgctccca gctttggaag ctgaaccact ttgggctact    1080
gtgttcggat ctcagtctca ccacgaggtg acaatgtctt acccaatgag atctgtgcag    1140
cacaggcact tcaggcttgt tcacaacctc aacttcaaga tgccattccc aatcgatcag    1200
gatttctacg tgtcaccaac tttccaggat cttctcaaca ggactactgc aggacaacct    1260
actggctggt acaaggatct taggcactac tactataggg ctaggtggga gctttacgat    1320
```

-continued

```
aggtccagag atccacacga gactcagaac cttgctactg atccaaggtt cgctcagctc   1380
cttgagatgc ttagggatca gcttgctaag tggcagtggg agactcatga tccatgggtt   1440
tgcgctccag atggtgtgct tgaagagaag ttgtctccac agtgccagcc acttcataac   1500
gagcttctcg agggagaaac ttctactctt aggacttcat tcacaagaaa catcgttggt   1560
cgtgatggat tgtgcgtgga tgtgaggaat ggatacgaca ctgatggaac tccacttcag   1620
ttgtggccat gtgaaccca gagaaaccaa cgatggactt ttgactcaga cgatacaatc    1680
aggtcaatgg gtaaatgcat gactgcaaac gggttaaaca atggaagcaa tatcgtgata   1740
ttcaactgtt ctacagctgc tgagaacgcc attaagtggg aagtacctat tgatggcagc   1800
atcatcaatc cttcctccgg attggttatg accgctcctc gtgctgcatc ccgtaccatc   1860
ctgttgcttg aggacaatat ctacgccgct agccagggtt ggactgtgac aaacaatgta   1920
aagcccatcg ttgcttccat tgtgggttat aaagaaatgt gcttgcagtc taacggtgaa   1980
aacaatggtg tttggatgga ggattgtgag gccaccagtt tgcagcaaca gtgggcactc   2040
tatggtgacc gtaccatccg agtaaatagt actcgtggct tatgcgtcac caccaatggg   2100
tacaactcca aggatctcat catcatcctt aaatgccaag gattgcccag ccagaggtgg   2160
tttttcaact ccgacggcgc catcgtaaac ccaaagtcaa gacatgttat ggatgtgaga   2220
gcaagcaatg tctctcttcg agaaatcatt atctttccag ccactgggaa ccctaatcag   2280
caatgggtga cacaagtcct tccaagtccc gggcatcatc atcatcatca t            2331
```

<210> SEQ ID NO 65
<211> LENGTH: 777
<212> TYPE: PRT
<213> ORGANISM: Homo sapiens

<400> SEQUENCE: 65

```
Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
        50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
                100                 105                 110

Gln Ala Gly Val Arg Thr Gly Ile Ile Gly Lys Lys His Val Gly Pro
            115                 120                 125

Glu Thr Val Tyr Pro Phe Asp Phe Ala Tyr Thr Glu Glu Asn Gly Ser
        130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190
```

```
Phe Cys Glu Lys Phe Gly Asn Gly Glu Ser Gly Met Gly Arg Ile Pro
            195                 200                 205

Asp Trp Thr Pro Gln Ala Tyr Asp Pro Leu Asp Val Leu Val Pro Tyr
210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
            245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
            275                 280                 285

Gly Thr Ala Glu Pro Leu Leu Val Ser Ser Pro Glu His Pro Lys Arg
290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
            355                 360                 365

Glu Val Thr Met Ser Tyr Pro Met Arg Ser Val Gln His Arg His Phe
            370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
            435                 440                 445

Gln Asn Leu Ala Thr Asp Pro Arg Phe Ala Gln Leu Leu Glu Met Leu
450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu Leu Glu Gly Glu Thr Ser Thr Leu Arg Thr
            500                 505                 510

Ser Phe Thr Arg Asn Ile Val Gly Arg Asp Gly Leu Cys Val Asp Val
            515                 520                 525

Arg Asn Gly Tyr Asp Thr Asp Gly Thr Pro Leu Gln Leu Trp Pro Cys
530                 535                 540

Gly Thr Gln Arg Asn Gln Arg Trp Thr Phe Asp Ser Asp Thr Ile
545                 550                 555                 560

Arg Ser Met Gly Lys Cys Met Thr Ala Asn Gly Leu Asn Asn Gly Ser
            565                 570                 575

Asn Ile Val Ile Phe Asn Cys Ser Thr Ala Ala Glu Asn Ala Ile Lys
            580                 585                 590

Trp Glu Val Pro Ile Asp Gly Ser Ile Ile Asn Pro Ser Ser Gly Leu
            595                 600                 605

Val Met Thr Ala Pro Arg Ala Ala Ser Arg Thr Ile Leu Leu Leu Glu
```

```
                610              615              620
Asp Asn Ile Tyr Ala Ala Ser Gln Gly Trp Thr Val Thr Asn Asn Val
625                  630                  635                  640

Lys Pro Ile Val Ala Ser Ile Val Gly Tyr Lys Glu Met Cys Leu Gln
                645                  650                  655

Ser Asn Gly Glu Asn Asn Gly Val Trp Met Glu Asp Cys Glu Ala Thr
                660                  665                  670

Ser Leu Gln Gln Gln Trp Ala Leu Tyr Gly Asp Arg Thr Ile Arg Val
                675                  680                  685

Asn Ser Thr Arg Gly Leu Cys Val Thr Thr Asn Gly Tyr Asn Ser Lys
690                  695                  700

Asp Leu Ile Ile Ile Leu Lys Cys Gln Gly Leu Pro Ser Gln Arg Trp
705                  710                  715                  720

Phe Phe Asn Ser Asp Gly Ala Ile Val Asn Pro Lys Ser Arg His Val
                725                  730                  735

Met Asp Val Arg Ala Ser Asn Val Ser Leu Arg Glu Ile Ile Ile Phe
                740                  745                  750

Pro Ala Thr Gly Asn Pro Asn Gln Gln Trp Val Thr Gln Val Leu Pro
                755                  760                  765

Ser Pro Gly His His His His His His
                770                  775
```

```
<210> SEQ ID NO 66
<211> LENGTH: 2359
<212> TYPE: DNA
<213> ORGANISM: Homo sapiens

<400> SEQUENCE: 66
aacaatggct tcctccgcta ctactaaatc tttccttatt cttttcttta tgatacttgc    60
aactacttca tcaacatgtg cagtcgaccg tccccggaac gcactgctgc cctcgcgga   120
tgacggaggc tttgagagtg gcgcgtacaa caacagcgcc atcgccaccc cgcacctgga   180
cgccttggcc cgccgcagcc tcctctttcg caatgccttc acctcggtca gcagctgctc   240
tcccagccgc gccagcctcc tcactggcct gccccagcat cagaatggga tgtacgggct   300
gcaccaggac gtgcaccact tcaactcctt cgacaaggtg cggagcctgc cgctgctgct   360
cagccaagct ggtgtgcgca caggcatcat cgggaagaag cacgtggggc cggagaccgt   420
gtaccgtttt gactttgcgt acacggagga gaatggctcc gtcctccagg tggggcggaa   480
catcactaga attaagctgc tcgtccggaa attcctgcag actcaggatg accggccttt   540
cttcctctac gtcgccttcc acgaccccca ccgctgtggg cactcccagc ccagtacgg   600
aaccttctgt gagaagtttg caacggaga gagcggcatg gtcgtatcc agactggac   660
cccccaggcc tacgacccac tggacgtgct ggtgccttac ttcgtcccca cacccggc   720
agcccgagcc gacctggccg ctcagtacac caccgtcggc cgcatggacc aaggagttgg   780
actggtgctc caggagctgc gtgacgccgg tgtcctgaac acacactgg tgatcttcac   840
gtccgacaac gggatcccct tccccagcgg caggaccaac ctgtactggc cgggcactgc   900
tgaacccta ctggtgtcat cccggagca cccaaaacgc tggggccaag tcagcgaggc   960
ctacgtgagc ctcctagacc tcacgcccac catcttggat tggttctcga tcccgtaccc  1020
cagctacgcc atctttggct cgaagaccat ccacctcact ggccggtccc tcctgccggc  1080
gctggaggcc gagcccctct gggccaccgt ctttggcagc cagagccacc acgaggtcac  1140
catgtcctac cccatgcgct ccgtgcagca ccggcacttc cgcctcgtgc acaacctcaa  1200
```

```
cttcaagatg ccctttccca tcgaccagga cttctacgtc tcacccacct tccaggacct    1260
cctgaaccgc accacagctg gtcagcccac gggctggtac aaggacctcc gtcattacta    1320
ctaccgggcg cgctgggaac tctacgaccg gagccgggac ccccacgaga cccagaacct    1380
ggccaccgac ccgcgctttg ctcagcttct ggagatgctt cgggaccagc tggccaagtg    1440
gcagtgggag acccacgacc cctgggtgtg cgccccgac ggcgtcctgg aggagaagct    1500
ctctccccag tgccagcccc tccacaatga gctgctcgag ggagaaactt ctactcttag    1560
gacttcattc acaagaaaca tcgttggtcg tgatggattg tgcgtggatg tgaggaatgg    1620
atacgacact gatggaactc cacttcagtt gtggccatgt ggaacccaga aaaccaacg    1680 atggactttt gactcagacg atacaatcag gtcaatgggt aaatgcatga ctgcaaacgg    1740
gttaaacaat ggaagcaata tcgtgatatt caactgttct acagctgctg agaacgccat    1800
taagtgggaa gtaccatttg atggcagcat catcaatcct tcctccggat tggttatgac    1860
cgctcctcgt gctgcatccc gtaccatcct gttgcttgag acaatatct acgccgctag    1920 ccagggttgg actgtgacaa caatgtaaa gcccatcgtt gcttccattg tgggttataa    1980
agaaatgtgc ttgcagtcta acggtgaaaa caatggtgtt tggatggagg attgtgaggc    2040
caccagtttg cagcaacagt gggcactcta tggtgaccgt accatccgag taaatagtac    2100
tcgtggctta tgcgtcacca ccaatgggta caactccaag gatctcatca tcatccttaa    2160
atgccaagga ttgcccagcc agaggtggtt tttcaactcc gacggcgcca tcgtaaaccc    2220
aaagtcaaga catgttatgg atgtgagagc aagcaatgtc tctcttcgag aaatcattat    2280 cttttccagcc actgggaacc ctaatcagca atgggtgaca caagtccttc caagtcccgg    2340
gcatcatcat catcatcat                                                  2359
```

<210> SEQ ID NO 67
<211> LENGTH: 785
<212> TYPE: PRT
<213> ORGANISM: Homo sapiens

<400> SEQUENCE: 67

Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Arg Pro Arg Asn
            20                  25                  30

Ala Leu Leu Leu Leu Ala Asp Asp Gly Gly Phe Glu Ser Gly Ala Tyr
        35                  40                  45

Asn Asn Ser Ala Ile Ala Thr Pro His Leu Asp Ala Leu Ala Arg Arg
    50                  55                  60

Ser Leu Leu Phe Arg Asn Ala Phe Thr Ser Val Ser Ser Cys Ser Pro
65                  70                  75                  80

Ser Arg Ala Ser Leu Leu Thr Gly Leu Pro Gln His Gln Asn Gly Met
                85                  90                  95

Tyr Gly Leu His Gln Asp Val His His Phe Asn Ser Phe Asp Lys Val
            100                 105                 110

Arg Ser Leu Pro Leu Leu Leu Ser Gln Ala Gly Val Arg Thr Gly Ile
        115                 120                 125

Ile Gly Lys Lys His Val Gly Pro Glu Thr Val Tyr Pro Phe Asp Phe
    130                 135                 140

Ala Tyr Thr Glu Glu Asn Gly Ser Val Leu Gln Val Gly Arg Asn Ile
145                 150                 155                 160

-continued

```
Thr Arg Ile Lys Leu Leu Val Arg Lys Phe Leu Gln Thr Gln Asp Asp
            165                 170                 175
Arg Pro Phe Phe Leu Tyr Val Ala Phe His Asp Pro His Arg Cys Gly
        180                 185                 190
His Ser Gln Pro Gln Tyr Gly Thr Phe Cys Glu Lys Phe Gly Asn Gly
    195                 200                 205
Glu Ser Gly Met Gly Arg Ile Pro Asp Trp Thr Pro Gln Ala Tyr Asp
210                 215                 220
Pro Leu Asp Val Leu Val Pro Tyr Phe Val Pro Asn Thr Pro Ala Ala
225                 230                 235                 240
Arg Ala Asp Leu Ala Ala Gln Tyr Thr Thr Val Gly Arg Met Asp Gln
            245                 250                 255
Gly Val Gly Leu Val Leu Gln Glu Leu Arg Asp Ala Gly Val Leu Asn
        260                 265                 270
Asp Thr Leu Val Ile Phe Thr Ser Asp Asn Gly Ile Pro Phe Pro Ser
    275                 280                 285
Gly Arg Thr Asn Leu Tyr Trp Pro Gly Thr Ala Glu Pro Leu Leu Val
290                 295                 300
Ser Ser Pro Glu His Pro Lys Arg Trp Gly Gln Val Ser Glu Ala Tyr
305                 310                 315                 320
Val Ser Leu Leu Asp Leu Thr Pro Thr Ile Leu Asp Trp Phe Ser Ile
            325                 330                 335
Pro Tyr Pro Ser Tyr Ala Ile Phe Gly Ser Lys Thr Ile His Leu Thr
        340                 345                 350
Gly Arg Ser Leu Leu Pro Ala Leu Glu Ala Glu Pro Leu Trp Ala Thr
    355                 360                 365
Val Phe Gly Ser Gln Ser His His Glu Val Thr Met Ser Tyr Pro Met
370                 375                 380
Arg Ser Val Gln His Arg His Phe Arg Leu Val His Asn Leu Asn Phe
385                 390                 395                 400
Lys Met Pro Phe Pro Ile Asp Gln Asp Phe Tyr Val Ser Pro Thr Phe
            405                 410                 415
Gln Asp Leu Leu Asn Arg Thr Thr Ala Gly Gln Pro Thr Gly Trp Tyr
        420                 425                 430
Lys Asp Leu Arg His Tyr Tyr Tyr Arg Ala Arg Trp Glu Leu Tyr Asp
    435                 440                 445
Arg Ser Arg Asp Pro His Glu Thr Gln Asn Leu Ala Thr Asp Pro Arg
450                 455                 460
Phe Ala Gln Leu Leu Glu Met Leu Arg Asp Gln Leu Ala Lys Trp Gln
465                 470                 475                 480
Trp Glu Thr His Asp Pro Trp Val Cys Ala Pro Asp Gly Val Leu Glu
            485                 490                 495
Glu Lys Leu Ser Pro Gln Cys Gln Pro Leu His Asn Glu Leu Leu Glu
        500                 505                 510
Gly Glu Thr Ser Thr Leu Arg Thr Ser Phe Thr Arg Asn Ile Val Gly
    515                 520                 525
Arg Asp Gly Leu Cys Val Asp Val Arg Asn Gly Tyr Asp Thr Asp Gly
530                 535                 540
Thr Pro Leu Gln Leu Trp Pro Cys Gly Thr Gln Arg Asn Gln Arg Trp
545                 550                 555                 560
Thr Phe Asp Ser Asp Asp Thr Ile Arg Ser Met Gly Lys Cys Met Thr
            565                 570                 575
Ala Asn Gly Leu Asn Asn Gly Ser Asn Ile Val Ile Phe Asn Cys Ser
```

```
                    580             585             590
Thr Ala Ala Glu Asn Ala Ile Lys Trp Glu Val Pro Ile Asp Gly Ser
            595                 600                 605

Ile Ile Asn Pro Ser Ser Gly Leu Val Met Thr Ala Pro Arg Ala Ala
    610                 615                 620

Ser Arg Thr Ile Leu Leu Glu Asp Asn Ile Tyr Ala Ala Ser Gln
625                 630                 635                 640

Gly Trp Thr Val Thr Asn Asn Val Lys Pro Ile Val Ala Ser Ile Val
                645                 650                 655

Gly Tyr Lys Glu Met Cys Leu Gln Ser Asn Gly Glu Asn Asn Gly Val
            660                 665                 670

Trp Met Glu Asp Cys Glu Ala Thr Ser Leu Gln Gln Gln Trp Ala Leu
            675                 680                 685

Tyr Gly Asp Arg Thr Ile Arg Val Asn Ser Thr Arg Gly Leu Cys Val
            690                 695                 700

Thr Thr Asn Gly Tyr Asn Ser Lys Asp Leu Ile Ile Ile Leu Lys Cys
705                 710                 715                 720

Gln Gly Leu Pro Ser Gln Arg Trp Phe Phe Asn Ser Asp Gly Ala Ile
                725                 730                 735

Val Asn Pro Lys Ser Arg His Val Met Asp Val Arg Ala Ser Asn Val
            740                 745                 750

Ser Leu Arg Glu Ile Ile Ile Phe Pro Ala Thr Gly Asn Pro Asn Gln
            755                 760                 765

Gln Trp Val Thr Gln Val Leu Pro Ser Pro Gly His His His His
            770                 775                 780

His
785

<210> SEQ ID NO 68
<211> LENGTH: 2359
<212> TYPE: DNA
<213> ORGANISM: Homo sapiens

<400> SEQUENCE: 68
aacaatggct tcctccgcta ctactaaatc tttccttatt cttttcttta tgatacttgc       60
aactacttca tcaacatgtg cagtcgacag gcctaggaac gctcttttgc ttcttgctga      120
tgatggcgga ttcgagtccg gtgcttacaa caactctgct atcgctactc cacacctcga      180
tgctcttgct aggcgttctc ttcttttccg taacgctttc acttccgtgt cctcttgctc      240
accttctagg gcttcacttc ttactggact tccacagcac cagaacggaa tgtacggact      300
tcatcaggat gtgcaccact tcaactcatt cgataaggtg agatccctcc cactcctctt      360
gtctcaagct ggtgttagga ctggaatcat cggcaaaaag cacgtgggac cagagactgt      420
gtacccattc gatttcgctt acactgagga aaacggctcc gttcttcaag tgggcagaaa      480
tattactagg atcaagctcc tcgtgaggaa gttcctccag actcaagatg ataggccatt      540
cttcctctac gtggcattcc atgatccaca taggtgcgga cattctcagc acagtacgg       600 aactttctgc gagaagttcg gaaacggtga gtctggtatg ggcaggattc cagattggac      660
tccacaggct tacgatccac ttgatgtgct cgttccatac ttcgtgccaa acactccagc      720
tgctagagct gatcttgctg ctcagtacac tactgtggga aggatggatc agggtgtggg      780
acttgtgctt caagagctta gagatgctgg cgtgctcaac gatactctcg tgatcttcac      840
ttcagataac ggcatcccat tcccatccgg aaggactaat ctttactggc caggtactgc      900
```

```
tgagcctctc cttgtttctt caccagagca tccaaagagg tggggacaag tttctgaggc      960
ttacgtgtcc cttctcgatc tcactccaac tatcctcgat tggttctcca tcccttaccc     1020
atcctacgct atcttcggct ccaagactat ccaccttact ggcagatctt tgctcccagc     1080
tttggaagct gaaccacttt gggctactgt gttcggatct cagtctcacc acgaggtgac     1140
aatgtcttac ccaatgagat ctgtgcagca caggcacttc aggcttgttc acaacctcaa     1200
cttcaagatg ccattcccaa tcgatcagga tttctacgtg tcaccaactt tccaggatct     1260
tctcaacagg actactgcag acaacctac tggctggtac aaggatctta ggcactacta      1320
ctatagggct aggtgggagc tttacgatag gtccagagat ccacgcgaga ctcgaaccct     1380
tgctactgat ccaaggttcg ctcagctcct tgagatgctt agggatcagc ttgctaagtg     1440
gcagtgggag actcatgatc catgggtttg cgctccagat ggtgtgcttg aagagaagtt     1500
gtctccacag tgccagccac ttcataacga gcttctcgag ggagaaactt ctactcttag     1560
gacttcattc acaagaaaca tcgttggtcg tgatggattg tgcgtggatg tgaggaatgg     1620
atacgacact gatggaactc cacttcagtt gtggccatgt ggaacccaga gaaaccaacg     1680
atggactttt gactcagacg atacaatcag gtcaatgggt aaatgcatga ctgcaaacgg     1740
gttaaacaat ggaagcaata tcgtgatatt caactgttct acagctgctg agaacgccat     1800
taagtgggaa gtaccattg atggcagcat catcaatcct tcctccggat tggttatgac      1860
cgctcctcgt gctgcatccc gtaccatcct gttgcttgag acaatatct acgccgctag       1920
ccagggttgg actgtgacaa acaatgtaaa gcccatcgtt gcttccattg tgggttataa     1980
agaaatgtgc ttgcagtcta acggtgaaaa caatggtgtt tggatggagg attgtgaggc     2040
caccagtttg cagcaacagt gggcactcta tggtgaccgt accatccgag taaatagtac     2100
tcgtggctta tgcgtcacca ccaatgggta caactccaag gatctcatca tcatccttaa     2160
atgccaagga ttgcccagcc agaggtggtt tttcaactcc gacggcgcca tcgtaaaccc     2220
aaagtcaaga catgttatgg atgtgagagc aagcaatgtc tctcttcgag aaatcattat     2280
ctttccagcc actgggaacc ctaatcagca atgggtgaca caagtccttc caagtcccgg     2340
gcatcatcat catcatcat                                                  2359
```

<210> SEQ ID NO 69
<211> LENGTH: 785
<212> TYPE: PRT
<213> ORGANISM: Homo sapiens

<400> SEQUENCE: 69

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Arg Pro Arg Asn
            20                  25                  30

Ala Leu Leu Leu Leu Ala Asp Asp Gly Gly Phe Glu Ser Gly Ala Tyr
        35                  40                  45

Asn Asn Ser Ala Ile Ala Thr Pro His Leu Asp Ala Leu Ala Arg Arg
    50                  55                  60

Ser Leu Leu Phe Arg Asn Ala Phe Thr Ser Val Ser Ser Cys Ser Pro
65                  70                  75                  80

Ser Arg Ala Ser Leu Leu Thr Gly Leu Pro Gln His Gln Asn Gly Met
                85                  90                  95

Tyr Gly Leu His Gln Asp Val His Phe Asn Ser Phe Asp Lys Val
            100                 105                 110
```

-continued

Arg Ser Leu Pro Leu Leu Ser Gln Ala Gly Val Arg Thr Gly Ile
            115                 120                 125

Ile Gly Lys Lys His Val Gly Pro Glu Thr Val Tyr Pro Phe Asp Phe
    130                 135                 140

Ala Tyr Thr Glu Glu Asn Gly Ser Val Leu Gln Val Gly Arg Asn Ile
145                 150                 155                 160

Thr Arg Ile Lys Leu Leu Val Arg Lys Phe Leu Gln Thr Gln Asp Asp
                165                 170                 175

Arg Pro Phe Phe Leu Tyr Val Ala Phe His Asp Pro His Arg Cys Gly
            180                 185                 190

His Ser Gln Pro Gln Tyr Gly Thr Phe Cys Glu Lys Phe Gly Asn Gly
            195                 200                 205

Glu Ser Gly Met Gly Arg Ile Pro Asp Trp Thr Pro Gln Ala Tyr Asp
    210                 215                 220

Pro Leu Asp Val Leu Val Pro Tyr Phe Val Pro Asn Thr Pro Ala Ala
225                 230                 235                 240

Arg Ala Asp Leu Ala Ala Gln Tyr Thr Thr Val Gly Arg Met Asp Gln
                245                 250                 255

Gly Val Gly Leu Val Leu Gln Glu Leu Arg Asp Ala Gly Val Leu Asn
            260                 265                 270

Asp Thr Leu Val Ile Phe Thr Ser Asp Asn Gly Ile Pro Phe Pro Ser
    275                 280                 285

Gly Arg Thr Asn Leu Tyr Trp Pro Gly Thr Ala Glu Pro Leu Leu Val
    290                 295                 300

Ser Ser Pro Glu His Pro Lys Arg Trp Gly Gln Val Ser Glu Ala Tyr
305                 310                 315                 320

Val Ser Leu Leu Asp Leu Thr Pro Thr Ile Leu Asp Trp Phe Ser Ile
                325                 330                 335

Pro Tyr Pro Ser Tyr Ala Ile Phe Gly Ser Lys Thr Ile His Leu Thr
            340                 345                 350

Gly Arg Ser Leu Leu Pro Ala Leu Glu Ala Glu Pro Leu Trp Ala Thr
            355                 360                 365

Val Phe Gly Ser Gln Ser His His Glu Val Thr Met Ser Tyr Pro Met
    370                 375                 380

Arg Ser Val Gln His Arg His Phe Arg Leu Val His Asn Leu Asn Phe
385                 390                 395                 400

Lys Met Pro Phe Pro Ile Asp Gln Asp Phe Tyr Val Ser Pro Thr Phe
                405                 410                 415

Gln Asp Leu Leu Asn Arg Thr Thr Ala Gly Gln Pro Thr Gly Trp Tyr
            420                 425                 430

Lys Asp Leu Arg His Tyr Tyr Tyr Arg Ala Arg Trp Glu Leu Tyr Asp
            435                 440                 445

Arg Ser Arg Asp Pro His Glu Thr Gln Asn Leu Ala Thr Asp Pro Arg
    450                 455                 460

Phe Ala Gln Leu Leu Glu Met Leu Arg Asp Gln Leu Ala Lys Trp Gln
465                 470                 475                 480

Trp Glu Thr His Asp Pro Trp Val Cys Ala Pro Asp Gly Val Leu Glu
                485                 490                 495

Glu Lys Leu Ser Pro Gln Cys Gln Pro Leu His Asn Glu Leu Leu Glu
            500                 505                 510

Gly Glu Thr Ser Thr Leu Arg Thr Ser Phe Thr Arg Asn Ile Val Gly
            515                 520                 525

Arg Asp Gly Leu Cys Val Asp Val Arg Asn Gly Tyr Asp Thr Asp Gly

```
                530             535             540
    Thr Pro Leu Gln Leu Trp Pro Cys Gly Thr Gln Arg Asn Gln Arg Trp
    545                 550                 555                 560

Thr Phe Asp Ser Asp Asp Thr Ile Arg Ser Met Gly Lys Cys Met Thr
                    565                 570                 575

Ala Asn Gly Leu Asn Asn Gly Ser Asn Ile Val Ile Phe Asn Cys Ser
                580                 585                 590

Thr Ala Ala Glu Asn Ala Ile Lys Trp Glu Val Pro Ile Asp Gly Ser
                595                 600                 605

Ile Ile Asn Pro Ser Ser Gly Leu Val Met Thr Ala Pro Arg Ala Ala
    610                 615                 620

Ser Arg Thr Ile Leu Leu Leu Glu Asp Asn Ile Tyr Ala Ala Ser Gln
    625                 630                 635                 640

Gly Trp Thr Val Thr Asn Asn Val Lys Pro Ile Val Ala Ser Ile Val
                    645                 650                 655

Gly Tyr Lys Glu Met Cys Leu Gln Ser Asn Gly Glu Asn Asn Gly Val
                    660                 665                 670

Trp Met Glu Asp Cys Glu Ala Thr Ser Leu Gln Gln Gln Trp Ala Leu
                    675                 680                 685

Tyr Gly Asp Arg Thr Ile Arg Val Asn Ser Thr Arg Gly Leu Cys Val
    690                 695                 700

Thr Thr Asn Gly Tyr Asn Ser Lys Asp Leu Ile Ile Ile Leu Lys Cys
    705                 710                 715                 720

Gln Gly Leu Pro Ser Gln Arg Trp Phe Phe Asn Ser Asp Gly Ala Ile
                    725                 730                 735

Val Asn Pro Lys Ser Arg His Val Met Asp Val Arg Ala Ser Asn Val
                    740                 745                 750

Ser Leu Arg Glu Ile Ile Ile Phe Pro Ala Thr Gly Asn Pro Asn Gln
                    755                 760                 765

Gln Trp Val Thr Gln Val Leu Pro Ser Pro Gly His His His His His
                    770                 775                 780
    His
    785

<210> SEQ ID NO 70
<211> LENGTH: 1140
<212> TYPE: DNA
<213> ORGANISM: Homo sapiens

<400> SEQUENCE: 70
atggctgcgc cgcactagg  gctggtgtgt ggacgttgcc ctgagctggg tctcgtcctc      60
ttgctgctgc tgctctcgct gctgtgtgga gcggcaggga gccaggaggc cgggaccggt     120
gcgggcgcgg ggtccttgc  gggttcttgc ggctgcggca cgcccagcg  gcctggcgcc     180 catggcagtt cggcagccgc tcaccgatac tcgcggagg  ctaacgctcc gggcccgta      240 cccggagagc ggcaactcgc gcactcaaag atggtcccca tccctgctgg agtatttaca     300
atgggcacag atgatcctca gataaagcag gatggggaag cacctgcgag gagagttact     360
attgatgcct ttacatgga  tgcctatgaa gtcagtaata ctgaatttga aagtttgtg      420 aactcaactg gctatttgac agaggctgag aagtttggcg actccttgt  ctttgaaggc     480 atgttgagtg agcaagtgaa gaccaatatt caacaggcag ttgcagctgc tccctggtgg     540
ttacctgtga aaggcgctaa ctggagacac ccagaagggc ctgactctac tattctgcac     600
aggccggatc atccagttct ccatgtgtcc tggaatgatg cggttgccta ctgcacttgg     660
```

```
gcaggaaagc ggctgcccac ggaagctgag tgggaataca gctgtcgagg aggcctgcat      720
aatagacttt tccctgggg caacaaactg cagcccaaag gccagcatta tgccaacatt       780
tggcagggcg agtttccggt gaccaacact ggtgaggatg gcttccaagg aactgcgcct      840
gttgatgcct tccctcccaa tggttatggc ttatacaaca tagtggggaa cgcatgggaa      900
tggacttcag actggtggac tgttcatcat tctgttgaag aaacgcttaa cccaaaaggt      960
cccccttctg ggaagaccg agtgaagaaa ggtggatcct acatgtgcca taggtcttat      1020
tgttacaggt atcgctgtgc tgctcggagc cagaacacac ctgatagctc tgcttcgaat     1080
ctgggattcc gctgtgcagc cgaccgcctg cccactatgg accatcatca tcatcatcat     1140
```

<210> SEQ ID NO 71
<211> LENGTH: 380
<212> TYPE: PRT
<213> ORGANISM: Homo sapiens

<400> SEQUENCE: 71

```
Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
        115                 120                 125

Tyr Glu Val Ser Asn Thr Glu Phe Glu Lys Phe Val Asn Ser Thr Gly
    130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
        275                 280                 285
```

-continued

Tyr Gly Leu Tyr Asn Ile Val Gly Asn Ala Trp Glu Trp Thr Ser Asp
    290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
                340                 345                 350

Thr Pro Asp Ser Ser Ala Ser Asn Leu Gly Phe Arg Cys Ala Ala Asp
            355                 360                 365

Arg Leu Pro Thr Met Asp His His His His His His
    370                 375                 380

<210> SEQ ID NO 72
<211> LENGTH: 1140
<212> TYPE: DNA
<213> ORGANISM: Homo sapiens

<400> SEQUENCE: 72
atggctgctc agctcttgg acttgtttgt ggaagatgtc cagagcttgg actcgtgctc      60
cttttgcttc ttttgtcact tctctgcgga gctgctggat ctcaagaggc tggaactggt    120
gctggtgctg atctcttgc tggatcttgt ggatgtggaa ctccacaaag accaggtgct    180
catggatctt cagctgctgc tcataggtac tctaggaag ctaatgctcc aggtccagtt     240
ccaggtgaga gacagcttgc tcactctaag atggtgccaa ttccagctgg cgtgttcact    300
atgggaactg atgatccaca gatcaagcag gatggtgagg ctccagctag aagggtgaca    360
atcgatgctt tctacatgga tgcttacgag gtgtccaaca ctgagttcga agttcgtg      420
aactccactg ctaccttac tgaggctgag aagttcggcg attccttcgt tttcgaggga    480
atgctctctg agcaggttaa gactaacatc agcaggctg ttgctgctgc tccatggtgg    540
cttccagtta agggtgctaa ttggagacat ccagagggcc cagattccac tattcttcat    600
aggccagatc acccagtgct ccacgtttca tggaatgatg ctgtggctta ctgcacttgg    660
gctggaaaga gacttccaac tgaagctgag tgggagtact cttgtagggg aggacttcac    720
aacaggcttt tcccatgggg aaacaagttg cagccaaagg acagcactac gctaatatt    780
tggcaaggcg agttcccagt gactaacact ggtgaggatg gattccaagg tactgctcca    840
gttgatgctt tcccaccaaa tggatacggc ctctacaaca tcgttggaaa cgcttgggag    900
tggacttccg attggtggac tgttcatcac tccgtggaag agactctcaa cccaaaggga    960
ccaccatctg gaaaggatag ggttaagaaa ggcggctcct acatgtgcca taggtcttac   1020
tgttacaggt acaggtgcgc tgctaggtcc cagaatactc cagattcctc tgcttccaac   1080
ctcggattca gatgtgctgc tgataggctc ccaactatga tcatcatca ccatcaccac    1140

<210> SEQ ID NO 73
<211> LENGTH: 380
<212> TYPE: PRT
<213> ORGANISM: Homo sapiens

<400> SEQUENCE: 73

Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly

| | | | | | | | | | | | |
|---|---|---|---|---|---|---|---|---|---|---|---|
| | | 35 | | | | 40 | | | | 45 | |

Ser Cys Gly Cys Gly Thr Pro Gln Arg Pro Gly Ala His Gly Ser Ser
 50                  55                  60

Ala Ala Ala His Arg Tyr Ser Arg Glu Ala Asn Ala Pro Gly Pro Val
 65                  70                  75                  80

Pro Gly Glu Arg Gln Leu Ala His Ser Lys Met Val Pro Ile Pro Ala
                 85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
        115                 120                 125

Tyr Glu Val Ser Asn Thr Glu Phe Glu Lys Phe Val Asn Ser Thr Gly
130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
        275                 280                 285

Tyr Gly Leu Tyr Asn Ile Val Gly Asn Ala Trp Glu Trp Thr Ser Asp
290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp His His His His His
370                 375                 380

<210> SEQ ID NO 74
<211> LENGTH: 1129
<212> TYPE: DNA
<213> ORGANISM: Homo sapiens

<400> SEQUENCE: 74
aacaatggct tcctccgcta ctactaaatc tttccttatt cttttcttta tgatacttgc    60
aactacttca tcaacatgtg cagtcgacag ccaggaggcc gggaccggtg cgggcgcggg   120
gtcccttgcg ggttcttgcg gctgcggcac gccccagcgg cctggcgccc atggcagttc   180

```
ggcagccgct caccgatact cgcgggaggc taacgctccg ggccccgtac ccggagagcg      240
gcaactcgcg cactcaaaga tggtccccat ccctgctgga gtatttacaa tgggcacaga      300
tgatcctcag ataaagcagg atggggaagc acctgcgagg agagttacta ttgatgcctt      360
ttacatggat gcctatgaag tcagtaatac tgaatttgag aagtttgtga actcaactgg      420
ctatttgaca gaggctgaga gtttggcga ctcctttgtc tttgaaggca tgttgagtga       480
gcaagtgaag accaatattc aacaggcagt tgcagctgct ccctggtggt tacctgtgaa      540
aggcgctaac tggagacacc cagaagggcc tgactctact attctgcaca ggccggatca     600
tccagttctc catgtgtcct ggaatgatgc ggttgcctac tgcacttggg cagggaagcg     660
gctgcccacg gaagctgagt gggaatacag ctgtcgagga ggcctgcata atagacttt      720 cccctggggc aacaaactgc agcccaaagg ccagcattat gccaacattt ggcagggcga     780
gtttccggtg accaacactg gtgaggatgg cttccaagga actgcgcctg ttgatgcctt     840
ccctcccaat ggttatggct tatacaacat agtggggaac gcatgggaat ggacttcaga     900
ctggtggact gttcatcatt ctgttgaaga aacgcttaac ccaaaaggtc ccccttctgg      960
gaaagaccga gtgaagaaag gtggatccta catgtgccat aggtcttatt gttacaggta    1020
tcgctgtgct gctcggagcc agaacacacc tgatagctct gcttcgaatc tgggattccg    1080
ctgtgcagcc gaccgcctgc ccactatgga ccatcatcat catcatcat                 1129
```

<210> SEQ ID NO 75
<211> LENGTH: 375
<212> TYPE: PRT
<213> ORGANISM: Homo sapiens

<400> SEQUENCE: 75

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Ser Gln Glu Ala
                20                  25                  30

Gly Thr Gly Ala Gly Ala Gly Ser Leu Ala Gly Ser Cys Gly Cys Gly
                35                  40                  45

Thr Pro Gln Arg Pro Gly Ala His Gly Ser Ala Ala Ala His Arg
    50                  55                  60

Tyr Ser Arg Glu Ala Asn Ala Pro Gly Pro Val Pro Gly Arg Gln
65                  70                  75                  80

Leu Ala His Ser Lys Met Val Pro Ile Pro Ala Gly Val Phe Thr Met
                85                  90                  95

Gly Thr Asp Asp Pro Gln Ile Lys Gln Asp Gly Glu Ala Pro Ala Arg
                100                 105                 110

Arg Val Thr Ile Asp Ala Phe Tyr Met Asp Ala Tyr Glu Val Ser Asn
                115                 120                 125

Thr Glu Phe Glu Lys Phe Val Asn Ser Thr Gly Tyr Leu Thr Glu Ala
                130                 135                 140

Glu Lys Phe Gly Asp Ser Phe Val Phe Glu Gly Met Leu Ser Glu Gln
145                 150                 155                 160

Val Lys Thr Asn Ile Gln Gln Ala Val Ala Ala Pro Trp Trp Leu
                165                 170                 175

Pro Val Lys Gly Ala Asn Trp Arg His Pro Glu Gly Pro Asp Ser Thr
                180                 185                 190

Ile Leu His Arg Pro Asp His Pro Val Leu His Val Ser Trp Asn Asp
                195                 200                 205
```

```
Ala Val Ala Tyr Cys Thr Trp Ala Gly Lys Arg Leu Pro Thr Glu Ala
    210                 215                 220
Glu Trp Glu Tyr Ser Cys Arg Gly Gly Leu His Asn Arg Leu Phe Pro
225                 230                 235                 240
Trp Gly Asn Lys Leu Gln Pro Lys Gly Gln His Tyr Ala Asn Ile Trp
                245                 250                 255
Gln Gly Glu Phe Pro Val Thr Asn Thr Gly Glu Asp Gly Phe Gln Gly
            260                 265                 270
Thr Ala Pro Val Asp Ala Phe Pro Asn Gly Tyr Gly Leu Tyr Asn
        275                 280                 285
Ile Val Gly Asn Ala Trp Glu Trp Thr Ser Asp Trp Trp Thr Val His
    290                 295                 300
His Ser Val Glu Glu Thr Leu Asn Pro Lys Gly Pro Pro Ser Gly Lys
305                 310                 315                 320
Asp Arg Val Lys Lys Gly Gly Ser Tyr Met Cys His Arg Ser Tyr Cys
                325                 330                 335
Tyr Arg Tyr Arg Cys Ala Ala Arg Ser Gln Asn Thr Pro Asp Ser Ser
            340                 345                 350
Ala Ser Asn Leu Gly Phe Arg Cys Ala Ala Asp Arg Leu Pro Thr Met
        355                 360                 365
Asp His His His His His His
    370                 375

<210> SEQ ID NO 76
<211> LENGTH: 1129
<212> TYPE: DNA
<213> ORGANISM: Homo sapiens

<400> SEQUENCE: 76
aacaatggct tcctccgcta ctactaaatc tttccttatt cttttcttta tgatacttgc      60
aactacttca tcaacatgtg cagtcgactc tcaagaggct ggaactggtg ctggtgctgg     120
atctcttgct ggatcttgtg gatgtggaac tccacaaaga ccaggtgctc atggatcttc     180
agctgctgct cataggtact ctagggaagc taatgctcca ggtccagttc caggtgagag     240
acagcttgct cactctaaga tggtgccaat tccagctggc gtgttcacta tgggaactga     300
tgatccacag atcaagcagg atggtgaggc tccagctaga agggtgacaa tcgatgcttt     360
ctacatggat gcttacgagg tgtccaacac tgagttcgag aagttcgtga actccactgg     420
ctaccttact gaggctgaga agttcggcga ttccttcgtt ttcgagggaa tgctctctga     480
gcaggttaag actaacatcc agcaggctgt tgctgctgct ccatggtggc ttccagttaa     540
gggtgctaat tggagacatc agagggccc agattccact attcttcata ggccagatca     600
cccagtgctc cacgtttcat ggaatgatgc tgtggcttac tgcacttggg ctggaaagag     660
acttccaact gaagctgagt gggagtactc ttgtagggga ggacttcaca acaggctttt     720
cccatgggga aacaagttgc agccaaaggg acagcactac gctaatattt ggcaaggcga     780
gttcccagtg actaacactg gtgaggatgg attccaaggt actgctccag ttgatgcttt     840
cccaccaaat ggatacggcc tctacaacat cgttggaaac gcttgggagt ggacttccga     900
ttggtggact gttcatcact ccgtggaaga gactctcaac ccaaagggac accatctgg     960 aaaggatagg gttaagaaag cgggctccta catgtgccat aggtcttact gttacaggta    1020
caggtgcgct gctaggtccc agaatactcc agattcctct gcttccaacc tcggattcag    1080
atgtgctgct gataggctcc caactatgga tcatcatcac catcaccac                1129
```

```
<210> SEQ ID NO 77
<211> LENGTH: 375
<212> TYPE: PRT
<213> ORGANISM: Homo sapiens

<400> SEQUENCE: 77

Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Ser Gln Glu Ala
            20                  25                  30

Gly Thr Gly Ala Gly Ala Gly Ser Leu Ala Gly Ser Cys Gly Cys Gly
        35                  40                  45

Thr Pro Gln Arg Pro Gly Ala His Gly Ser Ser Ala Ala Ala His Arg
    50                  55                  60

Tyr Ser Arg Glu Ala Asn Ala Pro Gly Pro Val Pro Gly Glu Arg Gln
65                  70                  75                  80

Leu Ala His Ser Lys Met Val Pro Ile Pro Ala Gly Val Phe Thr Met
                85                  90                  95

Gly Thr Asp Asp Pro Gln Ile Lys Gln Asp Gly Glu Ala Pro Ala Arg
            100                 105                 110

Arg Val Thr Ile Asp Ala Phe Tyr Met Asp Ala Tyr Glu Val Ser Asn
        115                 120                 125

Thr Glu Phe Glu Lys Phe Val Asn Ser Thr Gly Tyr Leu Thr Glu Ala
    130                 135                 140

Glu Lys Phe Gly Asp Ser Phe Val Phe Glu Gly Met Leu Ser Glu Gln
145                 150                 155                 160

Val Lys Thr Asn Ile Gln Gln Ala Val Ala Ala Pro Trp Trp Leu
                165                 170                 175

Pro Val Lys Gly Ala Asn Trp Arg His Pro Glu Gly Pro Asp Ser Thr
            180                 185                 190

Ile Leu His Arg Pro Asp His Pro Val Leu His Val Ser Trp Asn Asp
        195                 200                 205

Ala Val Ala Tyr Cys Thr Trp Ala Gly Lys Arg Leu Pro Thr Glu Ala
    210                 215                 220

Glu Trp Glu Tyr Ser Cys Arg Gly Gly Leu His Asn Arg Leu Phe Pro
225                 230                 235                 240

Trp Gly Asn Lys Leu Gln Pro Lys Gly Gln His Tyr Ala Asn Ile Trp
                245                 250                 255

Gln Gly Glu Phe Pro Val Thr Asn Thr Gly Glu Asp Gly Phe Gln Gly
            260                 265                 270

Thr Ala Pro Val Asp Ala Phe Pro Asn Gly Tyr Gly Leu Tyr Asn
    275                 280                 285

Ile Val Gly Asn Ala Trp Glu Trp Thr Ser Asp Trp Trp Thr Val His
290                 295                 300

His Ser Val Glu Glu Thr Leu Asn Pro Lys Gly Pro Pro Ser Gly Lys
305                 310                 315                 320

Asp Arg Val Lys Lys Gly Gly Ser Tyr Met Cys His Arg Ser Tyr Cys
                325                 330                 335

Tyr Arg Tyr Arg Cys Ala Ala Arg Ser Gln Asn Thr Pro Asp Ser Ser
            340                 345                 350

Ala Ser Asn Leu Gly Phe Arg Cys Ala Ala Asp Arg Leu Pro Thr Met
        355                 360                 365

Asp His His His His His His
    370                 375
```

<210> SEQ ID NO 78
<211> LENGTH: 1141
<212> TYPE: DNA
<213> ORGANISM: Homo sapiens

<400> SEQUENCE: 78

```
aacaatggct tcctccgcta ctactaaatc tttccttatt cttttcttta tgatacttgc      60
aactacttca tcaacatgtg cagtcgacag ccaggaggcc gggaccggtg cgggcgcggg     120
gtcccttgcg ggttcttgcg gctgcggcac gccccagcgg cctggcgccc atggcagttc     180
ggcagccgct caccgatact cgcgggaggc taacgctccg gccccgtac ccggagagcg      240
gcaactcgcg cactcaaaga tggtccccat ccctgctgga gtatttacaa tgggcacaga     300
tgatcctcag ataaagcagg atggggaagc acctgcgagg agagttacta ttgatgcctt     360
ttacatggat gcctatgaag tcagtaatac tgaatttgag aagtttgtga actcaactgg     420
ctatttgaca gaggctgaga gtttggcga ctcctttgtc tttgaaggca tgttgagtga      480
gcaagtgaag accaatattc aacaggcagt tgcagctgct ccctggtggt tacctgtgaa     540
aggcgctaac tggagacacc cagaagggcc tgactctact attctgcaca ggccggatca     600
tccagttctc catgtgtcct ggaatgatgc ggttgcctac tgcacttggg cagggaagcg     660
gctgcccacg gaagctgagt gggaatacag ctgtcgagga ggcctgcata atagactttt     720
cccctggggc aacaaactgc agcccaaagg ccagcattat gccaacattt ggcagggcga     780
gtttccggtg accaacactg tgaggatgg cttccaagga actgcgcctg ttgatgcctt      840
ccctcccaat ggttatggct tatacaacat agtggggaac gcatgggaat ggacttcaga     900
ctggtggact gttcatcatt ctgttgaaga aacgcttaac ccaaaaggtc cccttctgg      960
gaaagaccga gtgaagaaag gtggatccta catgtgccat aggtcttatt gttacaggta    1020
tcgctgtgct gctcggagcc agaacacacc tgatagctct gcttcgaatc tgggattccg    1080
ctgtgcagcc gaccgcctgc ccactatgga ccatcatcat catcatcata aggatgaact    1140
t                                                                    1141
```

<210> SEQ ID NO 79
<211> LENGTH: 379
<212> TYPE: PRT
<213> ORGANISM: Homo sapiens

<400> SEQUENCE: 79

```
Met Ala Ser Ser Ala Thr Thr Lys Ser Phe Leu Ile Leu Phe Met
1               5                   10                  15

Ile Leu Ala Thr Thr Ser Ser Thr Cys Ala Val Asp Ser Gln Glu Ala
            20                  25                  30

Gly Thr Gly Ala Gly Ala Gly Ser Leu Ala Gly Ser Cys Gly Cys Gly
        35                  40                  45

Thr Pro Gln Arg Pro Gly Ala His Gly Ser Ala Ala Ala His Arg
    50                  55                  60

Tyr Ser Arg Glu Ala Asn Ala Pro Gly Pro Val Pro Gly Glu Arg Gln
65                  70                  75                  80

Leu Ala His Ser Lys Met Val Pro Ile Pro Ala Gly Val Phe Thr Met
                85                  90                  95

Gly Thr Asp Asp Pro Gln Ile Lys Gln Asp Gly Glu Ala Pro Ala Arg
            100                 105                 110

Arg Val Thr Ile Asp Ala Phe Tyr Met Asp Ala Tyr Glu Val Ser Asn
```

|  |  |  | 115 |  |  |  | 120 |  |  |  | 125 |  |  |
|---|---|---|---|---|---|---|---|---|---|---|---|---|---|
| Thr | Glu | Phe | Glu | Lys | Phe | Val | Asn | Ser | Thr | Gly | Tyr | Leu | Thr | Glu | Ala |
|  |  |  | 130 |  |  |  | 135 |  |  |  | 140 |  |  |
| Glu | Lys | Phe | Gly | Asp | Ser | Phe | Val | Phe | Glu | Gly | Met | Leu | Ser | Glu | Gln |
| 145 |  |  |  |  | 150 |  |  |  |  | 155 |  |  |  |  | 160 |
| Val | Lys | Thr | Asn | Ile | Gln | Gln | Ala | Val | Ala | Ala | Pro | Trp | Trp | Leu |
|  |  |  |  | 165 |  |  |  |  | 170 |  |  |  |  | 175 |
| Pro | Val | Lys | Gly | Ala | Asn | Trp | Arg | His | Pro | Glu | Gly | Pro | Asp | Ser | Thr |
|  |  |  | 180 |  |  |  | 185 |  |  |  | 190 |  |  |
| Ile | Leu | His | Arg | Pro | Asp | His | Pro | Val | Leu | His | Val | Ser | Trp | Asn | Asp |
|  |  |  | 195 |  |  |  | 200 |  |  |  | 205 |  |  |
| Ala | Val | Ala | Tyr | Cys | Thr | Trp | Ala | Gly | Lys | Arg | Leu | Pro | Thr | Glu | Ala |
|  |  |  | 210 |  |  |  | 215 |  |  |  | 220 |  |  |
| Glu | Trp | Glu | Tyr | Ser | Cys | Arg | Gly | Gly | Leu | His | Asn | Arg | Leu | Phe | Pro |
| 225 |  |  |  |  | 230 |  |  |  |  | 235 |  |  |  |  | 240 |
| Trp | Gly | Asn | Lys | Leu | Gln | Pro | Lys | Gly | Gln | His | Tyr | Ala | Asn | Ile | Trp |
|  |  |  |  | 245 |  |  |  |  | 250 |  |  |  |  | 255 |
| Gln | Gly | Glu | Phe | Pro | Val | Thr | Asn | Thr | Gly | Glu | Asp | Gly | Phe | Gln | Gly |
|  |  |  | 260 |  |  |  | 265 |  |  |  | 270 |  |  |
| Thr | Ala | Pro | Val | Asp | Ala | Phe | Pro | Pro | Asn | Gly | Tyr | Gly | Leu | Tyr | Asn |
|  |  |  | 275 |  |  |  | 280 |  |  |  | 285 |  |  |
| Ile | Val | Gly | Asn | Ala | Trp | Glu | Trp | Thr | Ser | Asp | Trp | Trp | Thr | Val | His |
|  |  |  | 290 |  |  |  | 295 |  |  |  | 300 |  |  |
| His | Ser | Val | Glu | Glu | Thr | Leu | Asn | Pro | Lys | Gly | Pro | Pro | Ser | Gly | Lys |
| 305 |  |  |  |  | 310 |  |  |  |  | 315 |  |  |  |  | 320 |
| Asp | Arg | Val | Lys | Lys | Gly | Gly | Ser | Tyr | Met | Cys | His | Arg | Ser | Tyr | Cys |
|  |  |  |  | 325 |  |  |  |  | 330 |  |  |  |  | 335 |
| Tyr | Arg | Tyr | Arg | Cys | Ala | Ala | Arg | Ser | Gln | Asn | Thr | Pro | Asp | Ser | Ser |
|  |  |  | 340 |  |  |  | 345 |  |  |  | 350 |  |  |
| Ala | Ser | Asn | Leu | Gly | Phe | Arg | Cys | Ala | Ala | Asp | Arg | Leu | Pro | Thr | Met |
|  |  |  | 355 |  |  |  | 360 |  |  |  | 365 |  |  |
| Asp | His | His | His | His | His | Lys | Asp | Glu | Leu |
|  |  |  | 370 |  |  |  | 375 |  |  |

<210> SEQ ID NO 80
<211> LENGTH: 1141
<212> TYPE: DNA
<213> ORGANISM: Homo sapiens

<400> SEQUENCE: 80

```
aacaatggct tcctccgcta ctactaaatc tttccttatt cttttcttta tgatacttgc     60
aactacttca tcaacatgtg cagtcgactc tcaagaggct ggaactggtg ctggtgctgg    120
atctcttgct ggatcttgtg gatgtggaac tccacaaaga ccaggtgctc atggatcttc    180
agctgctgct cataggtact ctagggaagc taatgctcca ggtccagttc aggtgagag    240
acagcttgct cactctaaga tggtgccaat tccagctggc gtgttcacta tgggaactga    300
tgatccacag atcaagcagg atggtgaggc tccagctaga agggtgacaa tcgatgcttt    360
ctacatggat gcttacgagg tgtccaacac tgagttcgag aagttcgtga actccactgg    420
ctaccttact gaggctgaga agttcggcga ttccttcgtt ttcgagggaa tgctctctga    480
gcaggttaag actaacatcc agcaggctgt tgctgctgct ccatggtggc ttccagttaa    540
gggtgctaat tggagacatc cagagggccc agattccact attcttcata ggccagatca    600
cccagtgctc cacgtttcat ggaatgatgc tgtggcttac tgcacttggg ctggaaagag    660
```

```
acttccaact gaagctgagt gggagtactc ttgtagggga ggacttcaca acaggctttt      720
cccatgggga aacaagttgc agccaaaggg acagcactac gctaatattt ggcaaggcga      780
gttcccagtg actaacactg gtgaggatgg attccaaggt actgctccag ttgatgcttt      840
cccaccaaat ggatacggcc tctacaacat cgttggaaac gcttgggagt ggacttccga      900
ttggtggact gttcatcact ccgtggaaga gactctcaac ccaaagggac accatctgg       960 aaaggatagg gttaagaaag gcggctccta catgtgccat aggtcttact gttacaggta      1020
caggtgcgct gctaggtccc agaatactcc agattcctct gcttccaacc tcggattcag      1080
atgtgctgct gataggctcc caactatgga tcatcatcac catcaccaca aggatgaact      1140
t                                                                    1141
```

<210> SEQ ID NO 81
<211> LENGTH: 379
<212> TYPE: PRT
<213> ORGANISM: Homo sapiens

<400> SEQUENCE: 81

```
Met Ala Ser Ser Ala Thr Thr Lys Ser Phe Leu Ile Leu Phe Phe Met
1               5                   10                  15

Ile Leu Ala Thr Thr Ser Ser Thr Cys Ala Val Asp Ser Gln Glu Ala
            20                  25                  30

Gly Thr Gly Ala Gly Ala Gly Ser Leu Ala Gly Ser Cys Gly Cys Gly
        35                  40                  45

Thr Pro Gln Arg Pro Gly Ala His Gly Ser Ser Ala Ala Ala His Arg
    50                  55                  60

Tyr Ser Arg Glu Ala Asn Ala Pro Gly Pro Val Pro Gly Glu Arg Gln
65                  70                  75                  80

Leu Ala His Ser Lys Met Val Pro Ile Pro Ala Gly Val Phe Thr Met
                85                  90                  95

Gly Thr Asp Asp Pro Gln Ile Lys Gln Asp Gly Glu Ala Pro Ala Arg
            100                 105                 110

Arg Val Thr Ile Asp Ala Phe Tyr Met Asp Ala Tyr Glu Val Ser Asn
        115                 120                 125

Thr Glu Phe Glu Lys Phe Val Asn Ser Thr Gly Tyr Leu Thr Glu Ala
    130                 135                 140

Glu Lys Phe Gly Asp Ser Phe Val Phe Glu Gly Met Leu Ser Glu Gln
145                 150                 155                 160

Val Lys Thr Asn Ile Gln Gln Ala Val Ala Ala Pro Trp Trp Leu
                165                 170                 175

Pro Val Lys Gly Ala Asn Trp Arg His Pro Glu Gly Pro Asp Ser Thr
            180                 185                 190

Ile Leu His Arg Pro Asp His Pro Val Leu His Val Ser Trp Asn Asp
        195                 200                 205

Ala Val Ala Tyr Cys Thr Trp Ala Gly Lys Arg Leu Pro Thr Glu Ala
    210                 215                 220

Glu Trp Glu Tyr Ser Cys Arg Gly Gly Leu His Asn Arg Leu Phe Pro
225                 230                 235                 240

Trp Gly Asn Lys Leu Gln Pro Lys Gly Gln His Tyr Ala Asn Ile Trp
                245                 250                 255

Gln Gly Glu Phe Pro Val Thr Asn Thr Gly Glu Asp Gly Phe Gln Gly
            260                 265                 270

Thr Ala Pro Val Asp Ala Phe Pro Pro Asn Gly Tyr Gly Leu Tyr Asn
```

-continued

```
               275                 280                 285
Ile Val Gly Asn Ala Trp Glu Trp Thr Ser Asp Trp Trp Thr Val His
    290                 295                 300

His Ser Val Glu Glu Thr Leu Asn Pro Lys Gly Pro Pro Ser Gly Lys
305                 310                 315                 320

Asp Arg Val Lys Lys Gly Gly Ser Tyr Met Cys His Arg Ser Tyr Cys
                325                 330                 335

Tyr Arg Tyr Arg Cys Ala Ala Arg Ser Gln Asn Thr Pro Asp Ser Ser
                340                 345                 350

Ala Ser Asn Leu Gly Phe Arg Cys Ala Ala Asp Arg Leu Pro Thr Met
                355                 360                 365

Asp His His His His His His Lys Asp Glu Leu
    370                 375

<210> SEQ ID NO 82
<211> LENGTH: 4
<212> TYPE: PRT
<213> ORGANISM: Homo sapiens

<400> SEQUENCE: 82

Lys Asp Glu Leu
1
```

METHOD OF CO-EXPRESSING A SULFATASE AND A SULFATASE MODIFYING FACTOR IN A PLANT OR PLANT CELL

CROSS-REFERENCE TO RELATED APPLICATIONS

The present application is a continuation of U.S. application Ser. No. 15/325,661, filed Jan. 11, 2017, which is the National Stage of International Application Number PCT/US2015/040030, filed Jul. 10, 2015, which claims the benefit of U.S. Provisional Application Ser. No. 62/023,571, filed Jul. 11, 2014, which is hereby incorporated by reference herein in its entirety, including any figures, tables, nucleic acid sequences, amino acid sequences, or drawings.

SEQUENCE LISTING

The Sequence Listing for this application is labeled "2SX7611.TXT" which was created on Feb. 11, 2022 and is 348 KB. The entire contents of the sequence listing is incorporated herein by reference in its entirety.

BACKGROUND OF THE INVENTION

There is a need in the art for an effective enzyme replacement therapy (ERT) for patients having disorders associated with sulfatase enzymes. For example, Sanfilippo A (mucopolysaccharidosis MPS-IIIA) is a rare genetic lysosomal storage disorder (LSD) affecting about 1 in 150,000 births, with prevalence as high as $1/24,000$ in some regions. MPS-IIIA is caused by a genetic defect in the gene for the lysosomal enzyme heparan N-sulfatase (N-sulfoglucosamine sulfohydrolase; SGSH) and is characterized by relatively mild somatic features but severe neurological manifestations (decline of learning abilities, hyperactivity, behavior problems, sleep difficulties, seizures) leading to dementia and death during puberty or early adulthood. Currently treatment options are limited to symptom management and development of an effective ERT drug has been hindered by the challenges of severe central nervous system (CNS) involvement in this disease. Humans have multiple sulfatases wherein deficiencies are linked to complex pathologies.

In lysosomal ERT development, the targeting of drug delivery to disease susceptible organs, tissues, cells, and intracellular lysosomes remains challenging. Of the ERTs commercially available for lysosomal disorders, none address neurological pathologies of these diseases. For these ERTs, delivery is based on ERT glycan structure to exploit uptake by high-mannose or mannose-6P receptors. The inventors use genetic engineering to test the potential of fusions of ERT's with non-toxic plant lectin subunits of ricin (RTB) and nigrin (NBB) to facilitate cell uptake and lysosomal delivery. In preliminary studies, it has been demonstrated that RTB a) efficiently carries proteins (>70 kDa) into a broad array of human cells, including brain microvessel endothelial cell layers using mannose/M6P-independent routes, b) transports associated proteins across oral or nasal mucosal surfaces, and c) that RTB:ERT fusions reduce disease substrate levels to normal in lysosomal disease cells including Hurler (MPS I), GM1 gangliosidosis, and Sanfilippo (MPS IIIA) patient fibroblasts. These lectin carriers will provide a fundamental advance in ERTs by improving efficacy through enzyme delivery to a broader array of diseased cells and pathologies and by introducing transmucosal administration strategies to reduce the burden of current patient treatment options.

The promise of plant-made bioproduction systems to effectively meet the stringent manufacture and regulatory criteria for ERT biologics has now been recognized with recent FDA approval of ELELYSO, Protalix/Pfizer's plant-made glucocerebrosidase ERT for Gaucher disease. This plant-based product is less expensive and less susceptible to viral contamination issues that have recently plagued traditional CHO-based manufacture of LSD ERTs. BioStrategies LC founders, Radin and Cramer, pioneered development of plant-based expression of human lysosomal enzymes (U.S. Pat. No. 5,929,304) and continue to develop new technologies to improve production and efficacy of these ERTs. Nevertheless, since plants do not possess the class of mammalian sulfatase related enzymes described in this patent specification, it was not obvious that active forms of these proteins could be successfully expressed in plants.

BRIEF SUMMARY OF THE INVENTION

The subject invention concerns materials and methods for treating or preventing disease and conditions associated with various sulfatase enzymes that are defective or that are not properly expressed in a person or animal. In one embodiment, the disease is Sanfilippo A (MPS-IIIA) disease. The subject invention also concerns materials and methods for treating or preventing multiple sulfatase deficiency (MSD) in a person or animal. The present invention utilizes the ability of plants to produce bioactive sulfatases and employ a new transient expression system to bring additional advantages of speed and flexible scaled up manufacture that could be particularly well suited for lysosomal stage disorders and other rare disease targets.

Compounds within the scope of the invention include, but are not limited to, a mammalian sulfatase, sulfatase modifying factor (SUMF1), or a fusion protein comprising i) a mammalian sulfatase or SUMF1, or an enzymatically active fragment or variant thereof, and ii) a plant lectin or a binding subunit thereof. In a specific embodiment, the mammalian sulfatase is a human sulfatase, or an enzymatically active fragment or variant thereof. In another embodiment, the enzyme is a sulfatase modifying factor. In still another embodiment the mammalian sulfatase and sulfatase modifying factor (SUMF1) are co-expressed in a plant cell so as to produce an enzymatically active sulfatase product. In one embodiment, the plant lectin is the non-toxic subunit of the lectin ricin (RTB) or nigrin (NBB). Polynucleotides encoding the fusion proteins are also contemplated for the subject invention. In one embodiment, the polynucleotide is optimized for expression in a plant, e.g., using codons preferred for plant expression.

BRIEF DESCRIPTION OF THE DRAWINGS

FIG. 1. Western blots of crude leaf extracts (72 h post-infiltration) probed with anti-SGSH antibodies showing comparative yields of SGSH constructs (Table 6). Std, rhSGSH [100 ng]; pBK, leaves infiltrated with "empty vector" control.

FIG. 2. Western blots of crude leaf extracts (72 h post-infiltration) probed with anti-SUMF1 antibodies showing comparative yields of SUMF1 constructs (Table 7). Std, rhSUMF1 [100 ng]; pBK, leaves infiltrated with "empty vector" control.

FIG. 3. Enzyme units of plant-made SGSH. rhSGSH and rhSUMF1, mammalian cell-derived SGSH and SUMF1, respectively. 1 U: sulfamidase catalyzing hydrolysis of 1 nmol of 4 MU per min.

Figure 4:
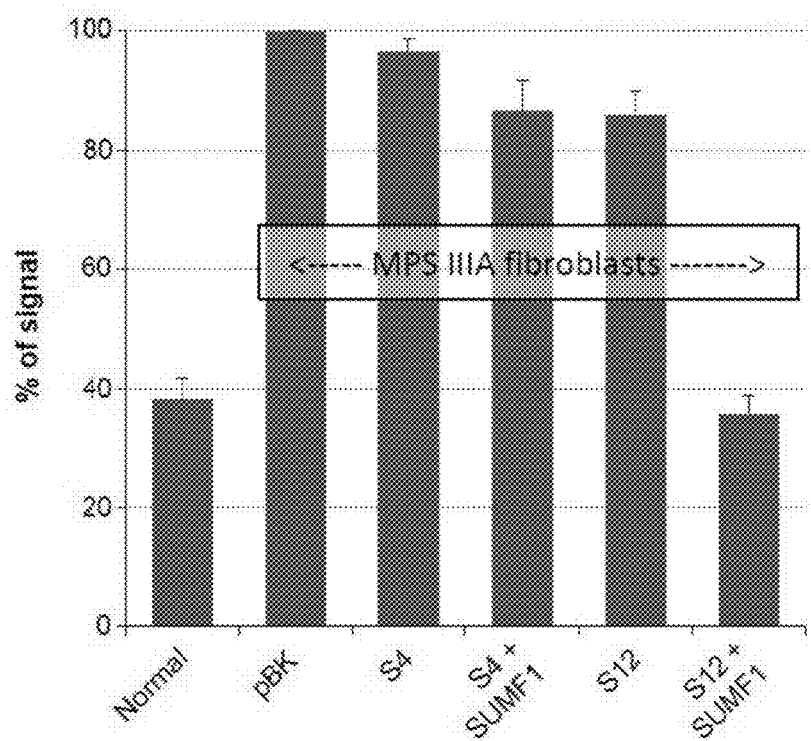

FIG. 4. Correction of MPS IIIA fibroblast cell by SGSH: RTB. Normal (Corriel #GM00010) and MPS IIIA (#GM01881) cells were incubated with SGSH constructs for 72 h. Cells were stained with Lysotracker-red and DAPI and analyzed for lysosomal volume/cell by high-through put imaging (BD Pathway 855 Bioimager). MPS IIIA cells treated with "empty vector control" fractions (pBK) was used as reference unit to estimate the impact of each treatment.

Figure 5:
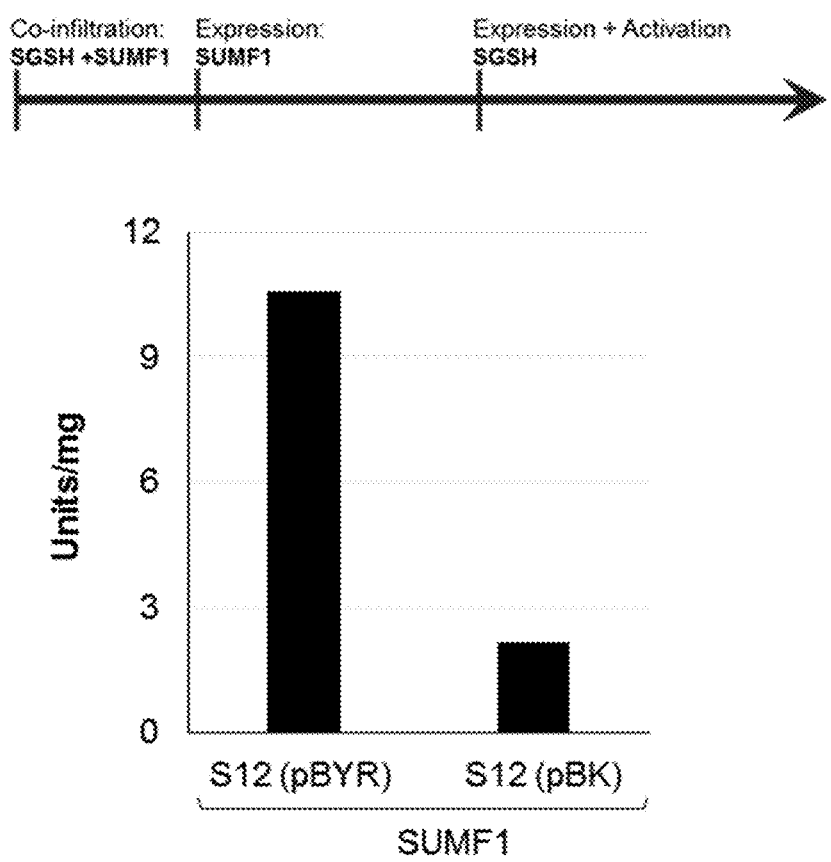

FIG. 5. Enzyme units of plant-made SGSH using viral and bacterial vectors. Timing expression of SUMF1 and SGSH using viral vector. 1U: sulfamidase catalyzing hydrolysis of 1 nmol of 4 MU per min.

BRIEF DESCRIPTION OF THE SEQUENCES

SEQ ID NO:1 is a nucleotide sequence encoding a sulfatase enzyme of the present invention.
SEQ ID NO:2 is an amino acid sequence of a sulfatase enzyme of the present invention.
SEQ ID NO:3 is a nucleotide sequence encoding a sulfatase enzyme of the present invention.
SEQ ID NO:4 is an amino acid sequence of a sulfatase enzyme of the present invention.
SEQ ID NO:5 is a nucleotide sequence encoding a sulfatase enzyme of the present invention.
SEQ ID NO:6 is an amino acid sequence of a sulfatase enzyme of the present invention.
SEQ ID NO:7 is a nucleotide sequence encoding a sulfatase enzyme of the present invention.
SEQ ID NO:8 is an amino acid sequence of a sulfatase enzyme of the present invention.
SEQ ID NO:9 is a nucleotide sequence encoding a sulfatase enzyme of the present invention.
SEQ ID NO:10 is an amino acid sequence of a sulfatase enzyme of the present invention.
SEQ ID NO:11 is a nucleotide sequence encoding a sulfatase enzyme of the present invention.
SEQ ID NO:12 is an amino acid sequence of a sulfatase enzyme of the present invention.
SEQ ID NO:13 is a nucleotide sequence encoding a sulfatase enzyme of the present invention.
SEQ ID NO:14 is an amino acid sequence of a sulfatase enzyme of the present invention.
SEQ ID NO:15 is a nucleotide sequence encoding a sulfatase enzyme of the present invention.
SEQ ID NO:16 is an amino acid sequence of a sulfatase enzyme of the present invention.
SEQ ID NO:17 is a nucleotide sequence encoding a sulfatase enzyme of the present invention.
SEQ ID NO:18 is an amino acid sequence of a sulfatase enzyme of the present invention.
SEQ ID NO:19 is a nucleotide sequence encoding a sulfatase enzyme of the present invention.
SEQ ID NO:20 is an amino acid sequence of a sulfatase enzyme of the present invention.
SEQ ID NO:21 is a nucleotide sequence encoding a sulfatase enzyme of the present invention.
SEQ ID NO:22 is an amino acid sequence of a sulfatase enzyme of the present invention.
SEQ ID NO:23 is a nucleotide sequence encoding a sulfatase enzyme of the present invention.
SEQ ID NO:24 is an amino acid sequence of a sulfatase enzyme of the present invention.
SEQ ID NO:25 is a nucleotide sequence encoding a sulfatase enzyme of the present invention.
SEQ ID NO:26 is an amino acid sequence of a sulfatase enzyme of the present invention.
SEQ ID NO:27 is a nucleotide sequence encoding a sulfatase enzyme of the present invention.
SEQ ID NO:28 is an amino acid sequence of a sulfatase enzyme of the present invention.
SEQ ID NO:29 is a nucleotide sequence encoding a sulfatase enzyme of the present invention.
SEQ ID NO:30 is an amino acid sequence of a sulfatase enzyme of the present invention.
SEQ ID NO:31 is a nucleotide sequence encoding a sulfatase enzyme of the present invention.
SEQ ID NO:32 is an amino acid sequence of a sulfatase enzyme of the present invention.
SEQ ID NO:33 is a nucleotide sequence encoding a sulfatase enzyme of the present invention.
SEQ ID NO:34 is an amino acid sequence of a sulfatase enzyme of the present invention.
SEQ ID NO:35 is a nucleotide sequence encoding a SUMF1 enzyme of the present invention.
SEQ ID NO:36 is an amino acid sequence of a SUMF1 enzyme of the present invention.
SEQ ID NO:37 is the amino acid sequence of a modified patatin sequence that can be used in the present invention.
SEQ ID NOs:38, 40, 42, 44, 46, 48, 50, 52, 54, 56, 58, 60, 62, 64, 66, 68, 70, 72, 74, 76, 78, and 80 are nucleotide sequences of a construct of the invention as denoted in Tables 6 and 7.
SEQ ID NOs:39, 41, 43, 45, 47, 49, 51, 53, 55, 57, 59, 61, 63, 65, 67, 69, 71, 73, 75, 77, 79, and 81 are amino acid sequences of a polypeptide encoded by a construct of the invention as denoted in Tables 6 and 7.
SEQ ID NO:82 is an ER retention sequence.

DETAILED DESCRIPTION OF THE INVENTION

The subject invention concerns materials and methods for treating or preventing disease and conditions associated with various sulfatase enzymes that are defective or that are not properly expressed in a person or animal. In one embodiment, the disease is Sanfilippo A (MPS-IIIA) disease. The subject invention also concerns materials and methods for treating or preventing multiple sulfatase deficiency (MSD) in a person or animal. Examples of diseases and their associated enzymes are shown in Table 1.

TABLE 1

| Gene (symbol) | Accession No | Disease | Enzyme | Reference |
| --- | --- | --- | --- | --- |
| Galactosamine (N-acetyl)-6 sulfate sulfatase (GALNS) (SEQ ID NO: 1) | NM_000512 | Mucoposysaccharidosis IVA (MPS-IVA), Morquio A syndrome | N-acetylgalactosamine-6-sulfatase (SEQ ID NO: 2) | [1] |
| Glucosamine (N-acetyl)-6 sulfatase (GNS) (SEQ ID NO: 3) | NM_002076 | Mucoposysaccharidosis IIID (MPS-IIID), Sanfilippo D syndrome | N-acetylglucosamine-6-sulfatase (SEQ ID NO: 4) | [2] |

TABLE 1-continued

| Gene (symbol) | Accession No | Disease | Enzyme | Reference |
|---|---|---|---|---|
| N-sulfoglucosamine sulfohydrolase (SGSH) (SEQ ID NO: 5) | NM_000199 | Mucopolysaccharidosis IIIA (MPS-IIIA), Sanfilippo A syndrome | N-sulphoglucosamine sulphohydrolase, sulfamidase (SEQ ID NO: 6) | [3] |
| Sulfatase 1 (SULF1) (SEQ ID NO: 7) | NM_015170 | NI | Extracellular sulfatase Sulf-1 (hSulf1) (SEQ ID NO: 8) | [4] |
| Sulfatase 2 (SULF2) (SEQ ID NO: 9) | NM_018837 | NI | Extracellular sulfatase Sulf-2 (hSulf2) (SEQ ID NO: 10) | [4] |
| Iduronate 2-sulfatase (IDS) (SEQ ID NO: 11) | NM_000202 | Mucopolysaccharidosis II (MPS-II), Hunter syndrome | Iduronate 2-sulfatase (SEQ ID NO: 12) | [5] |
| Arylsulfatase A (ARSA) (SEQ ID NO: 13) | NM_000487 | Metachromatic leukodystrophy (MLD) | Arylsulfatase A (ASA) (SEQ ID NO: 14) | [6] |
| Arylsulfatase B (ARSB) (SEQ ID NO: 15) | NM_000046 | Mucopolysaccharidosis VI (MPS-VI), Maroteaux-Lamy syndrome | Arylsulfatase B (ASB) (SEQ ID NO: 16) | [7] |
| Steroid sulfatase (STS) Arylsulfatase C (ARSC) (SEQ ID NO: 17) | NM_000351 | X-linked ichthyosis (XLI) | Steryl-sulfatase (SEQ ID NO: 18) | [8] |
| Arylsulfatase D (ARSD) (SEQ ID NO: 19) | NM_001669 | NI | Arylsulfatase D (ASD) (SEQ ID NO: 20) | [9] |
| Arylsulfatase E (ARSE) (SEQ ID NO: 21) | NM_000047 | Chondrodysplasia punctata 1 (CDPX1) | Arylsulfatase E (ASE) (SEQ ID NO: 22) | [9] |
| Arylsulfatase F (ARSF) (SEQ ID NO: 23) | NM_004042 | NI | Arylsulfatase F (ASF) (SEQ ID NO: 24) | [9] |
| Arylsulfatase G (ARSG) (SEQ ID NO: 25) | NM_014960 | NI | Arylsulfatase G (ASG) (SEQ ID NO: 26) | [10] |
| Arylsulfatase H (ARSH) (SEQ ID NO: 27) | NM_001011719 | NI | Arylsulfatase H (ASH) (SEQ ID NO: 28) | [11] |
| Arylsulfatase I (ARSI) (SEQ ID NO: 29) | NM_001012301 | NI | Arylsulfatase I (ASI) (SEQ ID NO: 30) | [11] |
| Arylsulfatase J (ARSJ) (SEQ ID NO: 31) | NM_024590 | NI | Arylsulfatase J (ASJ) (SEQ ID NO: 32) | [11] |
| Arylsulfatase K (ARSK) (SEQ ID NO: 33) | NM_198150 | NI | Arylsulfatase K (ASK) (SEQ ID NO: 34) | [11] |
| Sulfatase modifying factor 1 (SUMF1) (SEQ ID NO: 35) | NM_182760 | Multiple sulfatase deficiency (MSD) | Sulfatase-modifying factor 1 C-α-formylglycine-generating enzyme (FGE) (SEQ ID NO: 36) | [12, 13] |

NI, not identified

Compounds within the scope of the invention include, but are not limited to a mammalian sulfatase and/or sulfatase modifying factor 1 (SUMF1) or an enzymatically active fragment or variant thereof, or a fusion protein comprising i) a mammalian sulfatase protein, or an enzymatically active fragment or variant thereof, and ii) a plant lectin or a binding subunit thereof. In one embodiment, the sulfatase, or fusion protein containing the sulfatase, are co-expressed with the SUMF1 so as to activate the sulfatase during synthesis. In another embodiment, a fusion protein comprises i) a mammalian sulfatase modifying factor 1 (SUMF1) protein, or an enzymatically active fragment or variant thereof, and ii) a plant lectin or a binding subunit thereof. The mammalian sulfatase can be one that normalizes the cellular phenotype of a lysosomal disease when expressed in a cell or that reduces the symptoms of a lysosomal disease in an animal or human (examples of diseases are shown in Table 1). In one embodiment, the sulfatase is activated by a co-expressed SUMF1 enzyme by converting a cysteine at the active site to a formyl glycine amino acid. Examples of sulfatases contemplated by the present invention are shown in Table 1. Optionally, the sulfatase or the SUMF1 protein can be linked to the plant lectin by a linker sequence of amino acids. In a specific embodiment, the mammalian protein is a human protein, or an enzymatically active fragment or variant thereof. In one embodiment, the mammalian SUMF1 protein or the SUMF1 fusion protein comprises an ER retention sequence, such as KDEL (SEQ ID NO:82). In a specific embodiment, the ER retention sequence is located at the C-terminus of the SUMF1 or SUMF1 fusion protein. In some embodiments, the mammalian sulfatase comprises the amino acid sequence shown in any of SEQ ID NOs: 2, 4, 6, 8, 10, 12, 14, 16, 18, 20, 22, 24, 26, 28, 30, 32, or 34, or an enzymatically active fragment or variant thereof. In some embodiments, the SUMF1 protein comprises the amino acid sequence shown in SEQ ID NO:36, or an enzymatically active fragment or variant thereof. The plant lectin portion of the fusion protein can be any plant lectin such as those described herein. In one embodiment, the plant lectin is the non-toxic B subunit of the lectin ricin (RTB) or nigrin (NBB). Amino acid sequences of numerous plant lectins, and nucleotide sequences encoding them, are known in the art. In specific embodiments, the fusion protein comprises the amino acid sequence shown in any of SEQ ID NOs:39, 41, 43, 45, 47, 49, 51, 53, 55, 57, 59, 61, 63, 65, 67, 69, 71, 73, 75, 77, 79, or 81, or an enzymatically active fragment or variant thereof. Polynucleotides encoding the fusion proteins are also contemplated for the subject invention. In some embodiments, the polynucleotides comprise the protein encoding nucleotide sequence of any of SEQ ID NOs: 1, 3, 5, 7, 9, 11, 13, 15, 17, 19, 21, 23, 25, 27, 29, 31, 33, or 35. In one embodiment, the polynucleotide is optimized for expression in a plant, e.g., using codons preferred for plant expression. In a specific embodiment, the polynucleotide is optimized for expression in Nicotiana Sp. In a more specific embodiment, the polynucleotide is optimized for expression in Nicotiana benthamiana. In one embodiment, a polynucleotide of the invention comprises the nucleotide sequence of any of SEQ ID NOs:38, 40, 42, 44, 46, 48, 50, 52, 54, 56, 58, 60, 62, 64, 66, 68, 70, 72, 74, 76, 78, or 80. In one embodiment, the fusion protein is produced in plants using a plant-based expression system such as described in U.S. Pat. No. 5,929,304.

In one embodiment, a compound of the invention comprises a sulfatase or a fusion protein wherein the sulfatase is heparan N-sulfatase, or the fusion protein comprises i) the enzyme heparan N-sulfatase (SGSH), or an enzymatically active fragment or variant thereof, and ii) a plant lectin or a binding subunit thereof. In a more specific embodiment, the heparan N-sulfatase comprises the amino acid sequence shown in SEQ ID NO:6, or an enzymatically active fragment or variant thereof. In a specific embodiment, the heparan N-sulfatase is a human heparan N-sulfatase, or an enzymatically active fragment or variant thereof. In one embodiment, the plant lectin is the non-toxic B subunit lectin of ricin (RTB) or nigrin (NBB). In one embodiment, the SGSH portion and the plant lectin portion of the fusion protein can be linked by a linker sequence of amino acids. In one embodiment of the invention, a fusion protein with SUMF1 comprises an ER retention sequence, such as KDEL (SEQ ID NO:82). In a specific embodiment, the ER retention sequence is located at the C-terminus of the fusion protein.

The subject invention also concerns a mammalian sulfatase modifying factor 1 (SUMF1), or an enzymatically active fragment or variant thereof. In one embodiment, the mammalian SUMF1 protein is a human SUMF1 protein. In a specific embodiment, a SUMF1 protein comprises the amino acid sequence shown in SEQ ID NO:36. The subject invention also concerns polynucleotides encoding a SUMF1 protein. In one embodiment, a polynucleotide of the invention comprises the nucleotide sequence shown in SEQ ID NO:35. In one embodiment, the polynucleotide is optimized for expression in a plant, e.g., using codons preferred for plant expression. In one embodiment, the polynucleotide is optimized for expression in Nicotiana sp. In a specific embodiment, the polynucleotide is optimized for expression in N. benthamiana (SEQ ID NO:40). In one embodiment, a SUMF1 protein of the invention comprises an ER retention sequence, such as KDEL (SEQ ID NO:82). In a specific embodiment, the ER retention sequence is located at the C-terminus of the SUMF1 protein (SEQ ID NOs:79 and 81).

The subject invention also concerns methods for treating or preventing diseases or conditions associated with sulfatase enzymes, such as MPS-IIIA disease, in a person or animal (e.g., a disease where the sulfatase enzyme is defective or non-functional or partially functional). Examples of diseases and the associated enzymes are shown in Table 1. In one embodiment, the method comprises administering a therapeutically effective amount of a sulfatase or a fusion protein of the present invention, or an enzymatically active fragment or variant thereof, to the person or animal. In one embodiment, the sulfatase or fusion protein comprises a human sulfatase. Human sulfatases that can be used in the subject method include, but are not limited to, those shown in Table 1. Human sulfatases contemplated for use in the fusion protein include, but are not limited to, those shown in Table 1. In specific embodiments, the sulfatase or fusion protein comprises a sulfatase sequence shown in any of SEQ ID NOs: 2, 4, 6, 8, 10, 12, 14, 16, 18, 20, 22, 24, 26, 28, 30, 32, or 34, or an enzymatically active fragment or variant thereof. In one embodiment, the sulfatase or fusion protein is administered intravenously, by injection or infusion, or by inhalation via nasal cavity or lung, or orally, ocularly, vaginally, anally, rectally, or transmembraneously or transdermally, subcutaneously, intradermally, intravenously, intramuscularly, intraperitoneally, or intrasternally, such as by injection. In one embodiment, the person is a fetus, a newborn, or an infant. Optionally, the methods include screening the person or animal to determine if it has a disease or condition associated with sulfatase enzymes. In one embodiment, the method reduces disease phenotype in cells and tissue of the body. In a further embodiment, the method reduces disease symptoms in the central nervous system and/or brain.

The subject invention also concerns methods for treating multiple sulfatase deficiency (MSD) in a person or animal. In one embodiment, the method comprises administering a therapeutically effective amount of a mammalian SUMF1 protein, or an enzymatically active fragment or variant thereof, to the person or animal. In another embodiment, the method comprises administering a therapeutically effective amount of a fusion protein to the person or animal, wherein the fusion protein comprises i) a mammalian SUMF1 protein, or an enzymatically active fragment or variant thereof, and ii) a plant lectin or a binding subunit thereof. In one embodiment, the mammalian SUMF1 is a human SUMF1. Optionally, the SUMF1 protein or SUMF1 fusion protein can comprise an ER retention sequence, such as KDEL (SEQ ID NO:82). In one embodiment, the ER retention sequence is located at the C-terminus of the protein. In one embodiment, the SUMF1 protein or SUMF1 fusion protein is expressed in a plant cell. In another embodiment, a SUMF1 protein or SUMF1 fusion protein is expressed in an animal cell. In a specific embodiment, the human SUMF1 protein or SUMF1 fusion protein comprises the amino acid sequence in SEQ ID NO:36, or an enzymatically active fragment or variant thereof. In one embodiment, the SUMF1 protein or the fusion protein is administered to the person or animal via intravenous injection or infusion. In one embodiment, the person is a fetus, a newborn, or an infant. Optionally, the methods include screening the person or animal to determine if it has MSD disease or a condition associated with MSD.

The subject invention also concerns methods for preparing sulfatase enzymes and sulfatase fusion proteins of the present invention. In one embodiment, a method comprises transforming a plant or plant cell with i) polynucleotide encoding a sulfatase enzyme or a sulfatase fusion protein of the invention, and ii) a polynucleotide encoding a mammalian sulfatase modifying factor 1 (SUMF1) or a SUMF1 fusion protein of the invention; and expressing the sulfatase or sulfatase fusion protein and the SUMF1 protein or SUMF1 fusion protein in the plant. Methods for transforming a plant or plant cell with a polynucleotide are known in the art and include, for example, *Agrobacterium* infection, biolistic methods, and electroporation. The plant or plant cell can be transiently or stably transformed with the polynucleotide(s). In another embodiment, a method comprises using a plant or plant cell that has a polynucleotide encoding a mammalian SUMF1 protein or a SUMF1 fusion protein stably incorporated into its genome and that expresses SUMF1, and transforming the plant or plant cell with a polynucleotide encoding a sulfatase enzyme or a sulfatase fusion protein of the invention, and expressing the sulfatase or sulfatase fusion protein in the plant or plant cell, wherein the sulfatase or sulfatase fusion protein is activated by the expressed SUMF1 or SUMF1 fusion protein. In a further embodiment, a method comprises using a plant or plant cell that has a polynucleotide encoding a mammalian sulfatase enzyme or a sulfatase fusion protein of the invention stably incorporated into its genome and that expresses the sulfatase enzyme or the sulfatase fusion protein, and transforming the plant or plant cell with a polynucleotide encoding a mammalian SUMF1 protein or a SUMF1 fusion protein of the invention, and expressing the SUMF1 or SUMF1 fusion protein in the plant or plant cell, wherein the sulfatase or sulfatase fusion protein is activated by the expressed SUMF1 or SUMF1 fusion protein. In a further embodiment, a method comprises using a plant or plant cell that has i) a polynucleotide encoding a mammalian SUMF1 protein or a SUMF1 fusion protein stably incorporated into its genome and that expresses SUMF1 and that has ii) a polynucleotide encoding a mammalian sulfatase enzyme or a sulfatase fusion protein of the invention stably incorporated into its genome and that expresses the sulfatase enzyme or the sulfatase fusion protein, wherein the expressed sulfatase or sulfatase fusion protein is activated by the expressed SUMF1 or SUMF1 fusion protein. Methods for stably incorporating a polynucleotide into the genome of a plant or plant cell are known in the art. The polynucleotides utilized in the methods can be provided in an expression construct. In one embodiment, the cells are grown in tissue culture. In another embodiment, the cells are grown in a bioreactor.

Following transient or stable expression in the plant or plant cell, the sulfatase enzyme or sulfatase fusion protein and/or the SUMF1 protein or the SUMF1 fusion protein can be isolated from the plant. In one embodiment, transient expression of the enzyme or fusion protein in the plant or plant cell occurs for 1 to 5 days (typically, 2 to 5 days) prior to isolation of the enzyme or fusion protein from the plant or plant cell. Methods for protein isolation and purification are known in the art and include, for example, affinity chromatography. Co-expression of the sulfatase or sulfatase fusion protein and SUMF1 or SUMF1 fusion protein results in activation of the sulfatase or sulfatase fusion protein by the SUMF1 or SUMF1 fusion protein. The activated sulfatase or sulfatase fusion protein can be used to treat or prevent diseases or conditions in a person or animal that are associated with defective sulfatases and/or improper expression of sulfatases. Plants and plant cells that can be used in the synthesis methods include, but are not limited to, rice, wheat, barley, oats, rye, sorghum, maize, sugarcane, pineapple, onion, bananas, coconut, lilies, turfgrasses, millet, tomato, cucumber, squash, peas, alfalfa, melon, chickpea, chicory, clover, kale, lentil, soybean, beans, tobacco, potato, sweet potato, yams, cassava, radish, broccoli, spinach, cabbage, rape, apple trees, citrus (including oranges, mandarins, grapefruit, lemons, limes and the like), grape, cotton, sunflower, strawberry, lettuce, and hop. In one embodiment, the plant is a *Nicotiana* sp. In a specific embodiment, the plant is *N. benthamiana*.

The subject invention also concerns methods for producing a SUMF1 protein or a SUMF1 fusion protein of the present invention. In one embodiment, a method comprises transforming a cell with a polynucleotide encoding a SUMF1 protein or a SUMF1 fusion protein, or an enzymatically active fragment or variant thereof, and expressing the SUMF1 protein or the SUMF1 fusion protein in the cell. Following expression, the SUMF1 or SUMF1 fusion protein can be isolated from the cell. Optionally, the SUMF1 or SUMF1 fusion protein can be co-expressed in the cell along with a sulfatase enzyme or sulfatase fusion protein of the present invention. In one embodiment, the cell is a plant cell. The cell can be transiently or stably transformed with the polynucleotide. In one embodiment, the cell is an animal cell. In a specific embodiment, the animal cell is a cell line, such as a mammalian cell line (e.g., Chinese hamster ovary (CHO) cell line). In one embodiment, the cells are grown in tissue culture. In another embodiment, the cells are grown in a bioreactor. In one embodiment, the mammalian SUMF1 is a human SUMF1. Optionally, the SUMF1 protein can comprise an ER retention sequence, such as KDEL (SEQ ID NO:82) located at the C-terminus of the protein. Plants and plant cells that can be used in the synthesis methods include, but are not limited to, rice, wheat, barley, oats, rye, sorghum, maize, sugarcane, pineapple, onion, bananas, coconut, lilies, turfgrasses, millet, tomato, cucumber, squash, peas, alfalfa, melon, chickpea, chicory, clover, kale, lentil, soybean, beans, tobacco, potato, sweet potato, yams, cassava, radish, broccoli, spinach, cabbage, rape, apple trees, citrus (including oranges, mandarins, grapefruit, lemons, limes and the like), grape, cotton, sunflower, strawberry, lettuce, and hop. In one embodiment, the plant is a *Nicotiana* sp. In a specific embodiment, the plant is *N. benthamiana*.

Plant lectins for use in the fusion proteins that are contemplated within the scope of the invention include, but are not limited to, those B subunits from AB toxins such as ricins, abrins, nigrins, and mistletoe toxins, viscumin toxins, ebulins, pharatoxin, hurin, phasin, and pulchellin. They may also include lectins such as wheat germ agglutinin, peanut agglutinin, and tomato lectin that, while not part of the AB toxin class, are still capable of binding to animal cell surfaces and mediating endocytosis and transcytosis. Specific examples of plant lectins including their binding affinities and trafficking behavior are discussed further below. Therapeutic compounds and agents contemplated within the scope of the invention include, but are not limited to large molecular weight molecules including therapeutic proteins and peptides. Examples of therapeutic compounds and agents are discussed further below.

Within the scope of the present invention, selection of a specific plant lectin candidate to use in delivery of a particular therapeutic compound or agent is based on the specific sugar affinity of the lectin, its uptake efficiency into specific target cells, its pattern of intracellular trafficking, its in vivo biodistribution and pharmacodynamics, or other features of the lectin or therapeutic compound. Alternatively, multiple lectins can be tested to identify the lectin—therapeutic compound combination that provides greatest efficacy. For example, two lectins, RTB and NNB, were selected for proof-of-concept of the invention based on trafficking of their respective AB toxins, ricin from *Ricinus* communis and nigrin-b from *Sambucus nigra* (e.g., see Sandvig, K. and van Deurs, B. (1999); Simmons et al. (1986); Citores et al. (1999); Citores et al. (2003)). The uptake and trafficking of ricin and/or RTB, a galactose/galactosamine-specific lectin, has been extensively studied. This lectin has high affinity for surface glycolipids and glycoproteins providing access to a broad array of cells and enters cells by multiple endocytotic routes. These include absorptive-mediated endocytosis involving clathrin-dependent and clathrin-independent routes; caveolin-dependent and independent routes; dynamin-dependent and independent routes, and macropinocytosis based on the lectin binding to cell surface glycoproteins and glycolipids. RTB also accesses cells by receptor-mediated endocytosis based on interaction with its N-linked glycans with the high-mannose receptor (MMR) of animal cells. Upon endocytosis, RTB traverses preferentially to lysosomes (lysosomal pathway) or cycles back to the cell membrane (transcytosis pathway), with a small amount (generally less than 5%) moving "retrograde" to the endoplasmic reticulum. The NBB lectin, Nigrin B B-subunit from *Sambucus nigra*, exploits different uptake and intracellular trafficking routes compared to RTB, and thus provides unique in vivo pharmacodynamics. In contrast to RTB, NBB has strong affinity for N-acetyl-galactosamine, low affinity for lactose, very limited retrograde trafficking but strong accumulation in lysosomes. Plant-made DsReD:NNB (red fluorescent protein NBB fusion) is rapidly taken up into multiple mammalian cells and efficiently delivered to lysosomes. Recombinantly produced RTB and NBB have been operatively associated with both small molecules (by chemical conjugation technologies) and protein macromolecule by genetic fusion that retain selective lectin binding as well as functionality of the associated protein or agent. These operatively associated products are rapidly endocytosed into multiple cell types and tissues and deliver fully functional 'payload' into internal structures including lysosomes, endosomes, endoplasmic reticulum, and sarcoplasmic reticulum. Of particular significance, these lectins mobilize delivery of enzymes and other large proteins into "hard-to-treat" cells of the central nervous system (including, but not limited to, brain capillary endothelial cells, neurons, glial cells, and astrocytes), skeletal systems (including, but not limited to, cartilage, osteoblasts, chondrocytes, fibroblasts, and monocytes), and the respiratory system (including, but not limited to, lung airway epithelium, lung smooth muscle cells, and macrophages) (Radin et al., unpublished). These cells and tissues represent some of the most challenging targets for delivery of therapeutic agents highlighting the utility and novelty of the invention to address currently unmet needs in therapeutic compound delivery in human and animal medicine.

Additional plant lectins that are contemplated within the scope of the invention are those having particular carbohydrate binding affinities including, but not limited to, lectins that bind glucose, glucosamine, galactose, galactosamine, N-acetyl-glucosamine, N-acetyl-galactosamine, mannose, fucose, sialic acid, neuraminic acid, and/or N-acetyl-neuraminic acid, or have high affinity for certain target tissue or cells of interest. There are hundreds of plant lectins that have been identified and experimental strategies to identify plant lectins, their respective genes, and their sugar binding affinities are widely known by those skilled in the art. The diversity of plant sources for lectins and their sugar binding affinities is exemplified in Table 2 (adapted from Table 3 of Van Damme et al., (1998)).

TABLE 2

Type 2 Ribosome-Inactivating Proteins and Related Lectins: Occurrence, Molecular Structure, and Specificity

| Species | Tissue | Structure[a] | Specificity | Sequence Available[b] |
|---|---|---|---|---|
| Marolectins | | | | |
| *Sambucus nigra* | Bark | [P22] | NANA | Nu |
| | Fruit | [P22] | NANA | Nu |
| Holoectins | | | | |
| *Sambucus nigra* | Bark | II $[P30]_2$ | GalNAc > Gal | Nu |
| | Seed | III $[P30]_2$ | GalNAc > Gal | |
| | Fruit | IVf $[P32]_2$ | Gal/GalNAc | Nu (SNA-IV) |
| | Leaf | IVI $[P32]_2$ | Gal/GalNAc | Nu |
| | Leaf | IV4I $[P32]_4$ | Gal/GalNAc | |
| Chimerolectins | | | | |
| *Abrus precatorius* | Seed | [P(34 + 32)] | Gal > GalNAc | Pr, Nu (Abrin) |
| | Seed | $[P(33 + 29)]_2$ | Gal | Pr (APA) |
| *Adenia digitata* | Root | [P(28 + 38)] | Gal > GalNAc | |
| *Adenia volkensii* | Root | [P(29 + 36)] | Gal | |
| *Cinnamonum camphora* | Seed | $[P(30 + 33)]_2$ | Unknown | |
| *Eranthis hyemalis* | Tuber | [P(30 + 32)] | GalNAc | |
| *Iris hybrid* | Bulb | [P(27 + 34)] | GalNAc | |
| *Momordica charantia* | Seed | $[P(28 + 30)]_2$ | Gal > GalNAc | |
| *Phoradendron californicum* | Plant | [P(31 + 38)] | Gal | |
| *Ricinus communis* | Seed | [P(32 + 34)] | Gal > GalNAc | Pr, Nu (Ricin) |
| | Seed | $[P(32 + 36)]_2$ | Gal >> GalNAc | Pr, Nu (RCA) |
| *Sambucus canadensis* | Bark | I $[P(32 + 35)]_4$ | NANA | |
| *Sambucus ebulus* | Bark | I $[P(32 + 37)]_4$ | NANA | |
| | Leaf | $[P(26 + 30)]_2$ | GalNAc | |
| *Sambucus nigra* | Seed | Vs $[P(26 + 32)]_2$ | GalNAc > Gal | |
| | Bark | I $[P(32 + 35)]_4$ | NANA | Nu (SNA-I) |
| | Bark | I' $[P(32 + 35)_2$ | NANA | Nu (SNA-I') |

TABLE 2-continued Type 2 Ribosome-Inactivating Proteins and
Related Lectins: Occurrence, Molecular Structure, and Specificity

| Species | Tissue | Structure[a] | Specificity | Sequence Available[b] |
|---|---|---|---|---|
| | Bark | V [P(26 + 32)]$_2$ | GalNAc > Gal | Nu (SNA-V) |
| | Fruit | If [P(32 + 35)]$_2$ | NANA | Nu |
| | Fruit | Vf [P(26 +$_2$ 32)] | GalNAc > Gal | Nu |
| Sambucus racemosa | Bark | I [P(30 + 36)]$_4$ | NANA | |
| Sambucus sieboldiana | Bark | I [P(31 + 37)]$_4$ | NANA | Nu (SSA-I) |
| | Bark | [P(27 + 32)] | GalNAc > Gal | Nu (Sieboldin) |
| Viscum album | Plant | I [P(29 + 34)]$_{1-2}$ | Gal | |
| | Plant | II[P(29 + 34)] | Gal/GalNAc | |
| | Plant | III [P(25 + 30)] | GalNAc > Gal | |
| Type 2 RIP with inactive B chain | | | | |
| Sambucus nigra | Bark | [P(32 + 32)] | — | Nu (LRPSN) |

[a][PX] stands for protomer with a molecular mass of X kDa. [P(Y + Z)] Indicates that the protomer is cleaved in two polypeptides of Y and Z kDa.
[b]Pr, protein sequence; Nu, nucleotide sequence. The abbreviation in brackets refers to the sequence name used in the dendrogram (FIG. 20).

As a further example of plant lectins contemplated herein, Table 3 exemplifies the large number of different lectins identified from the *Sambucus* species alone. This group includes nigrin B, the source on NBB.

TABLE 3

Ribosome-inactivating proteins
(RIPs) and lectins from *Sambucus* species.
Adapted from Table 1 of Ferreras et al. (2011)

| Proteins | Species | Tissues |
|---|---|---|
| Type 1 RIPs | | |
| Ebulitins α, β and γ | S. ebulus | Leaves |
| Nigritins f1 and f2 | S. nigra | Fruits |
| Heterodimeric type 2 RIPs | | |
| Ebulin l | S. ebulus | Leaves |
| Ebulin f | S. ebulus | Fruits |
| Ebulins r1 and r2 | S. ebulus | Rhizome |
| Nigrin b, basic nigrin b, SNA I', SNLRPs | S. nigra | Bark |
| Nigrins l1 and l2 | S. nigra | Leaves |
| Nigrin f | S. nigra | Fruits |
| Nigrin s | S. nigra | Seeds |
| Sieboldin b | S. sieboldiana | Bark |
| Basic racemosin b | S. racemosa | Bark |
| Tetrameric type 2 RIPs | | |
| SEA | S. ebulus | Rhizome |
| SNA I | S. nigra | Bark |
| SNAIf | S. nigra | Fruits |
| SNAflu-I | S. nigra | Flowers |
| SSA | S. sieboldiana | Bark |
| SRA | S. racemosa | Bark |
| Monomeric lectins | | |
| SEL1m | S. ebulus | Leaves |
| SEA II | S. ebulus | Rhizome |
| SNA II | S. nigra | Bark |
| SNA1m and SNAIV1 | S. nigra | Leaves |
| SNA IV | S. nigra | Fruits |
| SNA III | S. nigra | Seeds |
| SSA-b-3 and SSA-b-4 | S. sieboldiana | Bark |
| SRAbm | S. racemosa | Bark |
| Homodimeric lectins | | |
| SEL1d | S. ebulus | Leaves |
| SELfd | S. ebulus | Fruits |
| SNA1d | S. nigra | Leaves |

The subject invention also concerns polynucleotides that comprise nucleotide sequences encoding a sulfatase and/or a SUMF1 protein and/or fusion protein (or compound) of the invention. In one embodiment, the polynucleotides comprise nucleotide sequences that are optimized for expression in a particular expression system, e.g., a plant expression system, such as a tobacco plant. In one embodiment, the polynucleotide is optimized for expression in *Nicotiana* sp. In a specific embodiment, the polynucleotide is optimized for expression in *N. benthamiana*. The subject invention also concerns the sulfatases, SUMF1 proteins, and fusion polypeptides encoded by polynucleotides of the invention.

The present invention contemplates products in which the plant lectin is operatively associated with the therapeutic component by one of many methods known in the art. For example, genetic fusions between a plant lectin protein and a therapeutic protein can orient the lectin partner on either the C- or N-terminus of the therapeutic component. The coding regions can be linked precisely such that the last C-terminal residue of one protein is adjacent to the first N-terminal residue of the mature (i.e., without signal peptide sequences) second protein. Alternatively, additional amino acid residues can be inserted between the two proteins as a consequence of restriction enzyme sites used to facilitate cloning at the DNA level. Additionally, the fusions can be constructed to have amino acid linkers between the proteins to alter the physical spacing. These linkers can be short or long, flexible (e.g., the commonly used $(Gly_4Ser)_3$ 'flexi' linker) or rigid (e.g., containing spaced prolines), provide a cleavage domain (e.g., see Chen et al. (2010)), or provide cysteines to support disulfide bond formation. The plant lectins are glycoproteins and in nature are directed through the plant endomembrane system during protein synthesis and post-translational processing. For this reason, production of recombinant fusion proteins comprising a plant lectin and a therapeutic protein partner may require that a signal peptide be present on the N-terminus of the fusion product (either on the lectin or on the therapeutic protein depending on the orientation of the fusion construct) in order to direct the protein into the endoplasmic reticulum during synthesis. This signal peptide can be of plant or animal origin and is typically cleaved from the mature plant lectin or fusion protein product during synthesis and processing in the plant or other eukaryotic cell. In one embodiment, a modified patatin signal sequence (PoSP) is utilized: MASSAT-TKSFLILFFMILATTSSTCAVD (SEQ ID NO:37) (see GenBank accession number CAA27588.1, version GI:21514 by Bevan et al. and referenced at "The structure and transcription start site of a major potato tuber protein gene" *Nucleic Acid Res.* 14 (11), 4625-4638 (1986)).

Compounds of the subject invention can also be prepared by producing the plant lectin and the therapeutic drug or protein separately and operatively linking them by a variety of chemical methods. Examples of such in vitro operative associations include conjugation, covalent binding, protein-protein interactions or the like (see, e.g., Lungwitz et al. (2005); Lovrinovic and Niemeyer (2005)). For example, N-hydroxysuccinimde (NHS)-derivatized small molecules and proteins can be attached to recombinant plant lectins by covalent interactions with primary amines (N-terminus and lysine residues). This chemistry can also be used with NHS-biotin to attach biotin molecules to the plant lectin supporting subsequent association with streptavidin (which binds strongly to biotin) and which itself can be modified to carry additional payload(s). In another example, hydrazine-derivatized small molecules or proteins can be covalently bound to oxidized glycans present on the N-linked glycans of the plant lectin. Proteins can also be operatively linked by bonding through intermolecular disulfide bond formation between a cysteine residue on the plant lectins and a cysteine residue on the selected therapeutic protein. It should be noted that the plant AB toxins typically have a single disulfide bond that forms between the A and B subunits. Recombinant production of plant B subunit lectins such as RTB and NBB yield a product with an 'unpaired' cysteine residue that is available for disulfide bonding with a "payload" protein. Alternatively, this cysteine (e.g., $Cys_4$ in RTB) can be eliminated in the recombinant plant lectin product by replacement with a different amino acid or elimination of the first 4-6 amino acids of the N-terminus to eliminate the potential for disulfide bonding with itself or other proteins.

- NBB: See GenBank accession number P33183.2, version GI:17433713 (containing subunits A and B) by Van Damme et al. and referenced at "Characterization and molecular cloning of *Sambucus nigra* agglutinin V (nigrin b), a GalNAc-specific type-2 ribosome-inactivating protein from the bark of elderberry (*Sambucus nigra*)" *Eur. J. Biochem.* 237 (2), 505-513 (1996). PDB ID: 3CA3 (for B subunit) by Maveyraud et al. and referenced at "Structural basis for sugar recognition, including the to carcinoma antigen, by the lectin sna-ii from *Sambucus nigra" Proteins* 75 p. 89 (2009).
- SGSH: See GenBank accession number NP 000190.1, version GI:4506919 by Van de Kamp et al. and referenced at "Genetic heterogeneity and clinical variability in the Sanfilippo syndrome (type A, B, and C)" *Clin. Genet.* 20 (2), 152-160 (1981).
- RTB: See GenBank accession number pbd/2AAI/B, version GI:494727 (containing subunits A and B) by Montfort et al. and referenced at "The three-dimensional structure of ricin at 2.8 A" *J. Biol Chem.* 262 (11), 5398-5403 (1987).

In vivo administration of the subject compounds, polynucleotides and compositions containing them, can be accomplished by any suitable method and technique presently or prospectively known to those skilled in the art. The subject compounds can be formulated in a physiologically- or pharmaceutically-acceptable form and administered by any suitable route known in the art including, for example, oral, nasal, rectal, transdermal, vaginal, and parenteral routes of administration. As used herein, the term parenteral includes subcutaneous, intradermal, intravenous, intramuscular, intraperitoneal, and intrasternal administration, such as by injection. Administration of the subject compounds of the invention can be a single administration, or at continuous or distinct intervals as can be readily determined by a person skilled in the art. In one embodiment, a polynucleotide encoding a therapeutic fusion product of the invention is stably incorporated into the genome of a person of animal in need of treatment. Methods for providing gene therapy are well known in the art. In one embodiment, a polynucleotide is provided in an expression construct and encodes an amino acid sequence of any of SEQ ID NOs: 2, 4, 6, 8, 10, 12, 14, 16, 18, 20, 22, 24, 26, 28, 30, 32, 34, or 36, or an enzymatically active fragment or variant thereof.

The compounds of the subject invention, and compositions comprising them, can also be administered utilizing liposome and nano-technology, slow release capsules, implantable pumps, and biodegradable containers, and orally or intestinally administered intact plant cells expressing the therapeutic product. These delivery methods can, advantageously, provide a uniform dosage over an extended period of time.

Compounds of the subject invention can be formulated according to known methods for preparing physiologically acceptable compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

Compounds and agents of the invention, and compositions thereof, may be locally administered at one or more anatomical sites, optionally in combination with a pharmaceutically acceptable carrier such as an inert diluent. Compounds and agents of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and agents, and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and agents and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising a compound and/or agent of the invention in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns kits comprising a compound and/or composition and/or agent and/or polynucleotide of the invention in one or more containers. Kits of the invention can optionally include pharmaceutically acceptable carriers and/or diluents. In one embodiment, a kit of the invention includes one or more other components, adjuncts, or adjuvants as described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent and/or polynucleotide of the invention is provided in the kit as a solid, such as a tablet, pill, or powder form. In another embodiment, a compound and/or agent and/or polynucleotide of the invention is provided in the kit as a liquid or solution. In one embodiment, the kit comprises an ampoule or syringe containing a compound and/or agent of the invention in liquid or solution form.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cultured cells or tissues of such human and non-human species.

The subject invention also concerns bacterial cells, and animals, animal tissue, and animal cells, and plants, plant tissue, and plant cells of the invention that comprise or express a polynucleotide or the protein encoded by the polynucleotide of the invention, or a fragment or variant thereof. Plant tissue includes, but is not limited to, leaf, stem, seed, scion, roots, and rootstock. Plants within the scope of the present invention include monocotyledonous plants, such as, for example, rice, wheat, barley, oats, rye, sorghum, maize, sugarcane, pineapple, onion, bananas, coconut, lilies, turfgrasses, and millet. Plants within the scope of the present invention also include dicotyledonous plants, such as, for example, tomato, cucumber, squash, peas, alfalfa, melon, chickpea, chicory, clover, kale, lentil, soybean, beans, tobacco, potato, sweet potato, yams, cassava, radish, broccoli, spinach, cabbage, rape, apple trees, citrus (including oranges, mandarins, grapefruit, lemons, limes and the like), grape, cotton, sunflower, strawberry, lettuce, and hop. In one embodiment, the plant is a *Nicotiana* sp. In a specific embodiment, the plant is *N. benthamiana*. Herb plants containing a polynucleotide of the invention are also contemplated within the scope of the invention. Herb plants include parsley, sage, rosemary, thyme, and the like. Trees are also contemplated within the scope of the subject invention. In one embodiment, a plant, plant tissue, or plant cell is a transgenic plant, plant tissue, or plant cell. In another embodiment, a plant, plant tissue, or plant cell is one that has been obtained through a breeding program.

Polynucleotides encoding a sulfatase, a SUMF1 protein, and/or a fusion product of the present invention, or an enzymatically active fragment or variant thereof, can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation. In one embodiment, an expression construct comprises a polynucleotide encoding an amino acid sequence of any of SEQ ID NOs: 2, 4, 6, 8, 10, 12, 14, 16, 18, 20, 22, 24, 26, 28, 30, 32, 34, or 36, or an enzymatically active fragment or variant thereof.

An expression construct of the invention can comprise a promoter sequence operably linked to a polynucleotide sequence of the invention, for example a sequence encoding a fusion polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

Constitutive promoters (such as the CaMV, ubiquitin, actin, or NOS promoter), developmentally-regulated promoters, and inducible promoters (such as those promoters that can be induced by heat, light, hormones, or chemicals) are also contemplated for use with polynucleotide expression constructs of the invention. If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, prolifera promoter, Ap3 promoter, heat shock promoters, T-DNA 1'- or 2'-promoter of *A. tumefaciens*, polygalacturonase promoter, chalcone synthase A (CHS-A) promoter from *petunia*, tobacco PR-la promoter, ubiquitin promoter, actin promoter, alcA gene promoter, pin2 promoter (Xu et al., 1993), maize WipI promoter, maize trpA gene promoter (U.S. Pat. No. 5,625, 136), maize CDPK gene promoter, and RUBISCO SSU promoter (U.S. Pat. No. 5,034,322) can also be used. Tissue-specific promoters, for example fruit-specific promoters, such as the E8 promoter of tomato (accession number: AF515784; Good et al. (1994)) can be used. Fruit-specific promoters such as flower organ-specific promoters can be used with an expression construct of the present invention for expressing a polynucleotide of the invention in the flower organ of a plant. Examples of flower organ-specific promoters include any of the promoter sequences described in U.S. Pat. Nos. 6,462,185; 5,639,948; and 5,589,610. Seed-specific promoters such as the promoter from a β-phaseolin gene (for example, of kidney bean) or a glycinin gene (for example, of soybean), and others, can also be used. Endosperm-specific promoters include, but are not limited to, MEG1 (EPO application No. EP1528104) and those described by Wu et al. (1998), Furtado et al. (2002), and Hwang et al. (2002). Root-specific promoters, such as any of the promoter sequences described in U.S. Pat. No. 6,455,760 or 6,696,623, or in published U.S. patent application Nos. 20040078841; 20040067506; 20040019934; 20030177536; 20030084486; or 20040123349, can be used with an expression construct of the invention.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

Polynucleotides of the present invention can be composed of either RNA or DNA. Preferably, the polynucleotides are composed of DNA. In one embodiment, the DNA is complementary DNA (cDNA) prepared from or based on a messenger RNA (mRNA) template sequence. The subject invention also encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode polypeptides and enzymes of the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, polypeptides and enzymes of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding a wild type polypeptide of the invention are also encompassed within the scope of the invention.

Substitution of amino acids other than those specifically exemplified or naturally present in a wild type polypeptide or enzyme of the invention are also contemplated within the scope of the present invention. For example, non-natural amino acids can be substituted for the amino acids of a polypeptide, so long as the polypeptide having the substituted amino acids retains substantially the same biological or functional activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexyl-alanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a wild type polypeptide or enzyme of the present invention are also encompassed within the scope of the invention.

Amino acids can be generally categorized in the following classes: non-polar, uncharged polar, basic, and acidic. Conservative substitutions whereby a polypeptide or enzyme of the present invention having an amino acid of one class is replaced with another amino acid of the same class fall within the scope of the subject invention so long as the polypeptide having the substitution still retains substantially the same biological or functional activity (e.g., enzymatic) as the polypeptide that does not have the substitution. Polynucleotides encoding a polypeptide or enzyme having one or more amino acid substitutions in the sequence are contemplated within the scope of the present invention. Table 4 provides a listing of examples of amino acids belonging to each class.

TABLE 4

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode functional polypeptides of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a polypeptide or enzyme of the present invention can be generated as described herein and tested for the presence of biological or enzymatic function using standard techniques known in the art. Thus, an ordinarily skilled artisan can readily prepare and test fragments and variants of a polypeptide or enzyme of the invention and determine whether the fragment or variant retains functional or biological activity (e.g., enzymatic activity) relative to full-length or a non-variant polypeptide.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and)(BLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and)(BLAST) can be used. See NCBI/NIH website.

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

Techniques for transforming plant cells with a polynucleotide or gene are known in the art and include, for example, *Agrobacterium* infection, transient uptake and gene expression in plant seedlings, biolistic methods, electroporation, calcium chloride treatment, PEG-mediated transformation, etc. U.S. Pat. No. 5,661,017 teaches methods and materials for transforming an algal cell with a heterologous polynucleotide. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention. In one embodiment, the cell is transformed with a polynucleotide sequence comprising a sequence encoding the amino acid sequence shown in any of SEQ ID NOs: 2, 4, 6, 8, 10, 12, 14, 16, 18, 20, 22, 24, 26, 28, 30, 32, 34, or 36, or an enzymatically active fragment or variant thereof.

The subject invention also concerns cells transformed with a polynucleotide of the present invention encoding a polypeptide or enzyme of the invention. In one embodiment, the cell is transformed with a polynucleotide sequence comprising a sequence encoding the amino acid sequence shown in any of SEQ ID NOs: 2, 4, 6, 8, 10, 12, 14, 16, 18, 20, 22, 24, 26, 28, 30, 32, 34, or 36, or an enzymatically active fragment or variant thereof. In one embodiment, the polynucleotide is stably incorporated into the genome of the cell. In another embodiment, the polynucleotide is not incorporated into the cell genome and is transiently expressed. In one embodiment, the polynucleotide sequence of the invention is provided in an expression construct of the invention. The transformed cell can be a prokaryotic cell, for example, a bacterial cell such as *E. coli* or *B. subtilis*, or the transformed cell can be a eukaryotic cell, for example, a plant cell, including protoplasts, or an animal cell. Plant cells include, but are not limited to, dicotyledonous, monocotyledonous, and conifer cells. Animal cells include human cells, mammalian cells, avian cells, and insect cells. Mammalian cells include, but are not limited to, COS, 3T3, and CHO cells. Cells of the invention can be grown in vitro, e.g., in a bioreactor or in tissue culture. Cells of the invention can also be grown in vivo, e.g., as ascites in a mammal, in a seed of a plant (such as corn or soybean seeds), etc.

Single letter amino acid abbreviations are defined in Table 5.

TABLE 5

| Letter Symbol | Amino Acid |
|---|---|
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

All patents, patent applications, provisional applications, and publications referred to or cited herein are incorporated by reference in their entirety, including all figures and tables, to the extent they are not inconsistent with the explicit teachings of this specification. Following are examples that illustrate procedures for practicing the invention.

These examples should not be construed as limiting. All percentages are by weight and all solvent mixture proportions are by volume unless otherwise noted.

Example 1—Produce SGSH and SGSH-Lectin Fusion Proteins

Construct design and plant-based expression. Sixteen gene constructs encoding SGSH and SGSH fusions with RTB and NBB (Table 6) were developed and expressed transiently in *N. benthamiana* leaves. Variants assessing signal peptides (human SGSH vs. plant-derived signal peptide), codon usage (SGSH sequence vs tobacco codon optimized), and fusion orientation were compared for product yield and quality (FIG. 1). Constructs were introduced into *Agrobacterium tumefaciens*, and induced cultures were vacuum infiltrated into leaves of intact plants and incubated for 2 to 5 days prior to harvest (Medrano et al., 2009). All constructs produced recombinant products of the expected sizes (56 kDa for SGSH; 91 kDa for lectin-SGSH fusions) that cross-reacted with anti-RTB, anti-His-tag, and anti-SGSH antibodies as appropriate (e.g., see FIG. 1). All constructs that used the native human signal peptide showed significantly lower product than those using the BioStrategies' plant signal peptide (PoSP). Expression kinetics in planta indicated abundant product at 48 and 72 h post-infiltration indicating product stability. FIG. 1 compares protein yields of selected constructs. For lectin-SGSH fusions (S5-S16), PoSP and lectin fused at the C-terminus (S12 for RTB and S16 for NBB) gave better protein yields (although some cleavage between the domains was observed with this orientation, the amount of full length protein is higher than lectin fused at the N-terminus). Based on these results, we selected a construct harboring SGSH (S4), SGSH-RTB fusion (S12) and SGSH-NBB fusion (S16) for further studies in Examples 2 and 3.

TABLE 6

Sulfamidase and lectin fusion constructs

| Construct | Abbr. | Signal peptide SGSH | Signal peptide PoSP | SGSH N-term Nat | SGSH N-term Opt | SGSH C-term Nat | SGSH C-term Opt | RTBtr N-term | RTBtr C-term | NBB N-term | NBB C-term | His tag |
|---|---|---|---|---|---|---|---|---|---|---|---|---|
| hSP:SGSH$^{NAT}$:His (nucleotide: SEQ ID NO: 38) (amino acid: SEQ ID NO: 39) | S1 | X | | X | | | | | | | | X |
| hSP:SGSH$^{OPT}$:His (nucleotide: SEQ ID NO: 40) (amino acid: SEQ ID NO: 41) | S2 | X | | | X | | | | | | | X |
| PoSP:SGSH$^{NAT}$:His (nucleotide: SEQ ID NO: 42) (amino acid: SEQ ID NO: 43) | S3 | | X | X | | | | | | | | X |
| PoSP:SGSH$^{OPT}$:His (nucleotide: SEQ ID NO: 44) (amino acid: SEQ ID NO: 45) | S4 | | X | | X | | | | | | | X |
| PoSP:RTBtr:SGSH$^{NAT}$:His (nucleotide: SEQ ID NO: 46) (amino acid: SEQ ID NO: 47) | S5 | | X | | | X | | X | | | | X |
| PoSP:RTBtr:SGSH$^{OPT}$:His (nucleotide: SEQ ID NO: 48) (amino acid: SEQ ID NO: 49) | S6 | | X | | | | X | X | | | | X |
| PoSP:NBB:SGSH$^{NAT}$:His (nucleotide: SEQ ID NO: 50) (amino acid: SEQ ID NO: 51) | S7 | | X | | | X | | | | X | | X |
| PoSP:NBB:SGSH$^{OPT}$:His (nucleotide: SEQ ID NO: 52) (amino acid: SEQ ID NO: 53) | S8 | | X | | | | X | | | X | | X |
| hSP:SGSH$^{NAT}$:RTBtr:His (nucleotide: SEQ ID NO: 54) (amino acid: SEQ ID NO: 55) | S9 | X | | X | | | | | X | | | X |
| hSP:SGSH$^{OPT}$:RTBtr:His (nucleotide: SEQ ID NO: 56) (amino acid: SEQ ID NO: 57) | S10 | X | | | X | | | | X | | | X |
| PoSP:SGSH$^{NAT}$:RTBtr:His (nucleotide: SEQ ID NO: 58) (amino acid: SEQ ID NO: 59) | S11 | | X | X | | | | | X | | | X |
| PoSP:SGSH$^{OPT}$:RTBtr:His (nucleotide: SEQ ID NO: 60) (amino acid: SEQ ID NO: 61) | S12 | | X | | X | | | | X | | | X |
| hSP:SGSH$^{NAT}$:NBB:His (nucleotide: SEQ ID NO: 62) (amino acid: SEQ ID NO: 63) | S13 | X | | X | | | | | | | X | X |
| hSP:SGSH$^{OPT}$:NBB:His (nucleotide: SEQ ID NO: 64) (amino acid: SEQ ID NO: 65) | S14 | X | | | X | | | | | | X | X |
| PoSP:SGSH$^{NAT}$:NBB:His (nucleotide: SEQ ID NO: 66) (amino acid: SEQ ID NO: 67) | S15 | | X | X | | | | | | | X | X |
| PoSP:SGSH$^{OPT}$:NBB:His (nucleotide: SEQ ID NO: 68) (amino acid: SEQ ID NO: 69) | S16 | | X | | X | | | | | | X | X |

Constructs harboring only SGSH were considered as located at the N-term in this table.
PoSP, Patatin Optimized Signal Peptide/
Nat, native sequence/
Opt, codon optimized sequence based on *Nicotiana tabacum*/
N-term, N terminus/
C-term, C terminus/
His tag, 6x histidine tag

TABLE 7

Sulfatase modifying factor 1 (FGE)

| Construct | Abbr. | Signal peptide | | SUMF1 | | His tag | KDEL |
| --- | --- | --- | --- | --- | --- | --- | --- |
| | | SUMF1 | PoSP | Nat | Opt | | |
| hSP:SUMF1$^{NAT}$:His (nucleotide: SEQ ID NO: 70) (amino acid: SEQ ID NO: 71) | F1 | X | | X | | X | |
| hSP:SUMF1$^{OPT}$:His (nucleotide: SEQ ID NO: 72) (amino acid: SEQ ID NO: 73) | F2 | X | | | X | X | |
| PoSP:SUMF1$^{NAT}$:His (nucleotide: SEQ ID NO: 74) (amino acid: SEQ ID NO: 75) | F3 | | X | X | | X | |
| PoSP:SUMF1$^{OPT}$:His (nucleotide: SEQ ID NO: 76) (amino acid: SEQ ID NO: 77) | F4 | | X | | X | X | |
| PoSP:SUMF1$^{NAT}$:His:KDEL (nucleotide: SEQ ID NO: 78) (amino acid: SEQ ID NO: 79) | F5 | | X | X | | X | X |
| PoSP:SUMF1$^{OPT}$:His:KDEL (nucleotide: SEQ ID NO: 80) (amino acid: SEQ ID NO: 81) | F6 | | X | | X | X | X |

PoSP, Patatin Optimized Signal Peptide
Nat, native sequence
Opt, codon optimized sequence based on *Nicotiana tabacum*
His tag, 6x histidine tag
KDEL, KDEL retrieval sequence (SEQ ID NO: 82)

Example 2—Assess SGSH Enzyme and Carbohydrate-Binding Activity of Plant-Made SGSH and SGSH-Lectin Fusions Assessment of SGSH activity. Plant tissues expressing S4, S12 and S16 constructs were used for extraction and initial purification of the SGSH and SGSH-fusion proteins. Several extraction buffers and clarification strategies were tested with the goal to obtain initial test material to assess activity. Leaf extracts were subjected to an initial affinity chromatography enrichment step (Nickel IMAC was used for the His-tagged S4; lactose resin for the S12 RTB fusion, and N-acetyl-galactosamine resin for the S16 NBB fusion). Recovery of the S12 and S16 products on selective sugar affinity columns confirmed lectin activity of the products. These proteins were quantified and used to assess SGSH activity based on the standard 2-step fluorometric assay as described (Karpova et. al., 1996) and using recombinant human SGSH (Novoprotein; made in HEK293 cells) as control proteins. No sulfamidase activity was detected in the plant-derived products.

Figure 2:
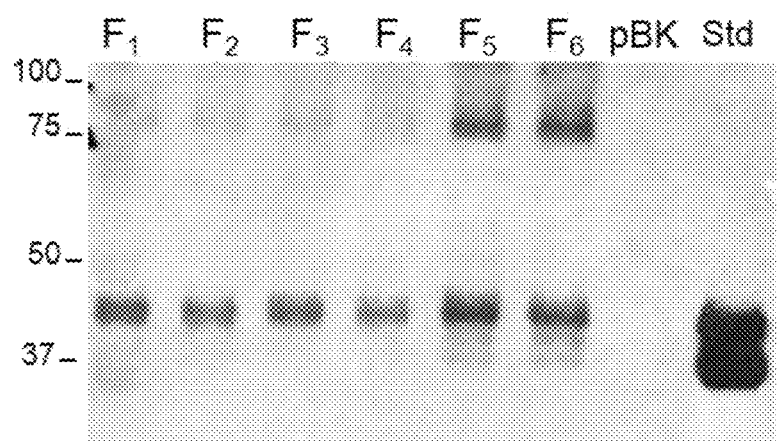

SUMF1. Sulfatases carry a unique amino acid in their active site, Cα-formylglycine (FGly), which is required for their catalytic activity. In this reaction, a specific cysteine is oxidized to FGly by the formylglycine-generating enzyme (FGE), as a post/co-translational modification that happens in nascent sulfatase polypeptides within the endoplasmic reticulum in mammalian cells. FGE is encoded by the sulfatase modifying factor 1 (SUMF1) gene. Phylogenetic studies have not identified SUMF1 homologs in plants and plants do not contain sulfatases that contain this modification. To support co-expression studies, we developed six new constructs for expression of human SUMF1 (Table 7). Native cDNA sequence encoding human SUMF1 (NCBI NM 182760) and tobacco-codon optimized SUMF1 cDNA were synthesized (GENEART) to include a C-term hexa-histidine tag. Two signal peptides were tested (SUMF1 SP vs our plant PoSP). In addition, constructs adding a C-terminal KDEL ER retrieval sequence (SEQ ID NO:82) were developed. SUMF1 acts on SGSH in the ER; its ER-localization is mediated by a region within the N-terminus (residues 34-68; Malalyalam et al., 2008). This retention mechanism does not appear highly effective in animal cells (significant amounts of SUMF1 are secreted) and the ability of plants to "read" this ER signal was unknown. We therefore produced a KDEL-modified version to ensure ER retention of SUMF1 in plants. SUMF1 constructs (Table 7) were expressed transiently in *N. benthamiana* leaves and yields were assessed at 48, 72, and 96 hr post-infiltration. All constructs produced recombinant products of the expected sizes (42 kDa) that cross-reacted with anti-SUMF1 (FIG. 2) and anti-His antibodies. The highest expression of SUMF1 was at 72 h post-infiltration; codon optimization and signal peptide did not have significant impact on protein yield. However, the KDEL signal (SEQ ID NO:82) appears to enhance protein stability; SUMF1-KDEL remained at high levels at both 72 and 96 hr. F6 was selected for initial co-expression studies.

Figure 3:
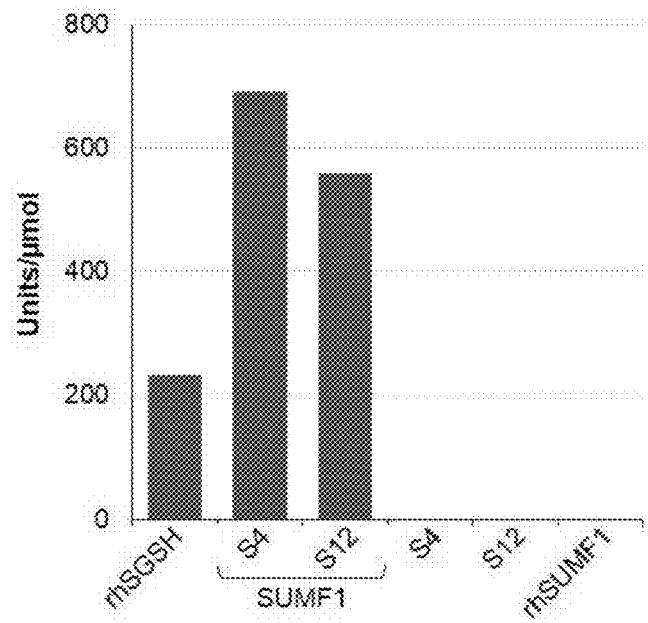

SUMF1/SGSH co-expression yields active sulfamidase. In order to determine if SUMF1 mediated formylglycine modification of SGSH in plants leading to production of an enzymatically active sulfatase, leaves were infiltrated with a 1:1 mixed culture of *Agrobacterium tumefaciens* ("Agro") harboring SUMF1 (F6) and SGSH (S4 or S12). Leaves were harvested at 72 h post-infiltration and purified by affinity chromatography, as described above for S4 and S12 constructs. Mammalian cell-derived SGSH and plant-derived SGSH (S4) and SGSH-RTB (S12) that were expressed in the presence or absence of SUMF1 (F6) were tested for sulfamidase enzymatic activity (FIG. 3) and shown as units/µmol to encompass differences in molecular size of each protein. As shown in FIG. 3, plant-made SGSH (S4 and S12) were enzymatically active only when SUMF1 was co-expressed, and were more active than SGSH made in HEK293 human cells. SGSH:NBB (S16) showed analogous SGSH activity when expressed with SUMF1 (not shown). For the S12 product, protein identity (both SGSH and RTB) and FGly modification were confirmed through peptide sequencing by mass spectrometry (MS/MS; UAMS Biomedical Research Center). FGly modification was only found when SGSH was co-expressed with SUMF1. Our results demonstrate plants can produce fully active SGSH when co-expressed with SUMF1 and that the lectin fusion partner does not inhibit enzyme activity. Interestingly, co-expression with SUMF1-KDEL provided greater SGSH product yields than un-modified forms (not shown) suggesting broader applications using other production platforms or for gene therapy approaches for the entire sulfatase family.

Example 3—Demonstrate Uptake, Lysosomal Delivery, and Reduction of "Disease Substrate" in MPS IIIA Cultured Cells Treated with SGSH and SGSH-Lectin Fusions MPS IIIA patients are deficient in SGSH activity leading to pathological accumulation of sulfated glucosaminoglycans (GAGs) with cellular phenotypes including elevated GAGs and increased lysosomal volume per cell. As a further demonstration that the plant-produced SGSH was fully functional following modification by SUMF1, MPS IIIA patient fibroblasts (GM01881) were treated with plant-produced SGSH (S4) or SGSH-RTB (S12) that were expressed in the presence and absence of co-expressed SUMF1 (FIG. 4). S12 (SGSH:RTB) produced in the presence of SUMF1 effectively reduced GAG content and lysosomal volume to "normal" levels. SGSH alone (S4+/−SUMF1) was not corrective indicating that lectin-based delivery as well as FGly activation are critical in phenotype correction. These results indicate that RTB effectively delivers active SGSH to the site of GAG disease substrate accumulation resulting in disease phenotype correction at the cellular level. Analogous results have been demonstrated with S16 (SGSH:NBB; co-expressed with SUMF1; data not shown) indicating that multiple plant lectins can facilitate cellular uptake and lysosomal delivery of plant-made sulfatases.

Example 4—Increase Sulfatase Activity by Modifying Co-Expression Parameters of SGSH and SUMF1

SUMF1 is localized to the ER and acts on mammalian sulfatases as they are co-translationally inserted into rough ER. The strategy for plant based SGSH and SUMF1 production in Example 2 and Example 3 involved co-expression where the kinetics of expression were the same and demonstrated that the SGSH enzymatic activity directly reflects the FGly modification mediated by SUMF1. Strategies that differentially change the kinetics of either SGSH or SUMF1 production such that SUMF1 is present in the plant ER prior and during the production phase for SGSH may result in a greater efficiency of SGSH modification and provide a higher specific activity product. Two strategies were selected for testing this (among many that could be used including expressing SGSH and SUMF1 under control of differentially expressed promoters, transiently expressing SGSH in a stable transgenic plant engineered to constitutively express the SUMF1 transgene, and other strategies providing SUMF1 activity prior and during production of the sulfatase). First, the S12 (SGSH:RTB) gene was introduced into a plant Agro/viral vectoring system (pBYR) (Huang et al., 2009) which is typically infiltrated at lower levels with a delayed initiation of high-level expression. Agro cultures bearing SUMF1 in the pBK (NCBI GU982971) vector were co-infiltrated with Agro strains bearing either S12 (SGSH:

RTB) in pBK or in the Agro/viral vector pBYR. SGSH activity was then assessed in protein purified from leaf extracts and compared to the recombinant human SGSH produced in human HEK293 cells. The specific activity of plant-derived S12 product produced using the mixed Agro (SUMF1) and Agro/viral (S12 SGSH:RTB) co-expression parameters was 3-5 fold higher than S12 produced using a 1:1 ratio of the same genes both expressed using the pBK Agro vectoring system (shown in FIG. 5). The specific activity of the product was also 6-9 fold more active than human cell-derived rhSGSH indicating higher levels of FGly modification.

A second demonstration that directed expression such that onset of SUMF1 production occurs earlier than SGSH increases the yield of active SGSH was also shown. In this example, a culture of Agro bearing the SUMF1 gene construct (F6) were induced by treatment with acetosyringone for 24 hours. Acetosyringone speeds activation of bacterial virulence leading to faster expression of transfected recombinant proteins. The induced culture was then mixed with Agro cultures bearing the S12 (SGSH:RTB) construct that was not induced. The mixed culture was then vacuum infiltrated into leaves of intact *N. benthamiana* plants and the plants were incubated for 3 to 5 days and harvested. The S12 sulfatase enzyme activity was 2-fold higher under conditions where the SUMF1-bearing Agro was selectively pre-induced by acetosyringone compared to previous infiltrations where both the SUMF1 and S12 strains were simultaneously activated by acetosyrongone. These results indicate that having plant cells "pre-loaded" with the SUMF1 modifying protein yields S12 wherein a significantly greater proportion of the SGSH product is modified to its fully functional form. By modifying the temporal parameters for expression (through either induction or viral vectoring systems), we demonstrated that the plant-based system yields sulfatase product with significantly greater specific activity (higher FGly modification) than the commercially available products produced in human cells (as much as 9-fold greater).

Example 5—Demonstrate In Vivo Efficacy of SUMF1-Activated Sulfatase Enzyme Replacement Therapeutics by Treating Sulfatase-Deficient Mice The biochemical and behavioral aspects of disease development have been well-characterized in the SGSH-deficient MPS-IIIA mouse model. These mice show elevated heparan sulfate levels detected at birth, lysosomal vacuolarization evident by 3-6 weeks of age and progressively worsening of behavioral/cognitive problems (altered activity, aggression, gait dysfunction, learning deficits, leading to lethargy and death) (Crawley et al., 2006). To assess in vivo efficacy of the S12 (SGSH:RTB) and S16 (SGSH:NBB) these fusion products are synthesized in plants that are co-expressing SUMF1 or SUMF1 modified with KDEL (SEQ ID NO:82) and purified to at least 95% purity of sulfatase enzyme activity with endotoxin levels below that recommended for mouse trials. MPS IIIA mice (e.g., 6-8 week old mice) are treated with the plant-derived S12 or S16 fusion product by i.v.-administration in doses ranging from 1 to 5 mg/kg in MPS-IIIA mice and analysis is done by methods similar to those described previously for this disease model (Rozaklis et al., 2011) and compared with wild type and untreated MPS IIIA control mice. For short-term biodistribution analyses, genotype-confirmed MPS-IIIA mice and unaffected −/+ or +/+ are treated (i.v., tail vein) with 100-150 μl 'vehicle' (PBS), S12, or S16. At 1, 2, and 3 hr, serum is collected by orbital bleed from 3 mice/group to determine serum clearance of the product. At 4, 12, and 24 hr after injection, 3 mice/time point (MPS-IIIA and WT mice) are euthanized, serum collected (heart puncture) and liver, spleen, and brain tissues are either formalin fixed or snap-frozen in liquid nitrogen for subsequent analyses. SGSH levels and enzyme activity is measured in tissues and serum as described (Rozaklis et al., 2011). Presence of the S12 and S16 products in specific tissues is confirmed by immuno-histochemistry of fixed tissue.

To demonstrate efficacy in reducing GAG levels (the MPS IIIA disease substrate) and correcting the tissue pathology (e.g., cellular vacuolization; accumulation of associated gangliosides), MPS IIIA mice are treated 1-2 times per week with doses ranging from 0.5 to 5 mg/kg body weight for 4-6 weeks and the mice are harvested to assess SGSH levels, GAG levels and cellular morphology in selected tissues (e.g., liver, kidney, and multiple tissues of the brain). To demonstrate impacts on behavior of this neurodegenerative disease, weekly treatment can be extended to a total of 12-16 weeks and assessment of behavioral aspects are performed by open-field tests measuring activity and rearing behaviors (MPS-IIIA mice display reduced activity/gait) and memory/learning tests (e.g., using a Morris water maze). At study endpoint (72 hr after final injection), mice are euthanized and blood collected by heart puncture. Some animals from each group are fixation-perfused and processed for histo-logical analyses. For biochemical analyses, livers, spleens and brains of non-perfused animals are sliced and frozen for heparan sulfate analyses. Immunohistological analyses include assessment of neuronal pathology in the cerebral cortex and hippocampus (e.g., using LIMP-II and GM3 as markers which are significantly elevated in untreated MPS IIIA mice). Extended administration of the S12 and S16 fusions is expected to lead to increased sulfatase activity, decreased GAG levels, and improvement in cellular pheno-type and behavior in the MPS IIIA mice.

Example 6—Demonstrate In Vivo Efficacy of SUMF1 Enzyme Replacement Therapeutics in Treating the SUMF1$^{-/-}$ Mouse Model for Multiple Sulfatase Deficiency Similar to Example 5, plant-made SUMF1 fusions are used as an enzyme replacement therapy for treating SUMF1$^{-/-}$ mice. This mouse model shows similar disease development as multiple sulfatase deficiency patients (Settembre et al., 2007). Specifically, SUMF1$^{-/-}$ mice show growth retardation and skeletal abnormalities, neurological defects, and early mortality. At the cellular level, there is significant vacuolization, lysosomal storage of glycosami-noglycans, and inflammatory responses characterized by abundant highly vacuolated macrophages. For these studies, SUMF1 fusions are produced in plants and purified to greater than 95% enzyme purity with acceptable endotoxin levels. These products may include: RTB:SUMF1, NBB:SUMF1, RTB: SUMF1-KDEL, NBB: SUMF1-KDEL, SUMF1: RTB-KDEL or SUMF1:NBB-KDEL with the lec-tin providing uptake and the KDEL (SEQ ID NO:82) or SUMF1 domains directing subcellular trafficking to the ER. SUMF1 fusions are administered to mice and serum and tissues processed as previously described in Example 5. In addition, tissues are assayed for sulfatase activity (which is totally lacking in this mutant mouse strain due to absence of SUMF1). Extended administration of the SUMF1-lectin fusions results in increased sulfatase activity, decreased GAG levels, and improvement in macrophage morphology and disease phenotype.

It should be understood that the examples and embodi-ments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof dis-closed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,938,949
U.S. Pat. No. 5,034,322
U.S. Pat. No. 5,106,739
U.S. Pat. No. 5,589,610
U.S. Pat. No. 5,625,136
U.S. Pat. No. 5,639,948
U.S. Pat. No. 5,661,017
U.S. Pat. No. 5,929,304
U.S. Pat. No. 6,455,760
U.S. Pat. No. 6,462,185
U.S. Pat. No. 6,696,623
U.S. Published Application No. 20030084486
U.S. Published Application No. 20030177536
U.S. Published Application No. 20040019934
U.S. Published Application No. 20040067506
U.S. Published Application No. 20040078841
U.S. Published Application No. 20040123349
European Application No. EP1528104
Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
Chen et al. (2010) BioTechniques 49:513-518.
Clancy, M. and Hannah, L. C. (2002) "Splicing of the maize Sh1 first intron is essential for enhancement of gene expression, and a T-rich motif increases expression with-out affecting splicing" *Plant Physiol.* 130(2):918-29.
Furtado, A. et al. (2002) "Tools for Use in the Genetic Engineering of Barley" *Proceedings of the* 10*th Austra-lian Barley Technical Symposium*, Canberra, ACT, Aus-tralia.
Good, X. et al. (1994) "Reduced ethylene synthesis by transgenic tomatoes expressing S-adenosylmethionine hydrolase" *Plant Molec. Biol.* 26:781-790.
Hwang, Y-S. et al. (2002) "Analysis of the Rice Endosperm-Specific Globulin Promoter in Transformed Rice Cells" *Plant Cell Rep.* 20:842-847.
Karlin S. and Altschul, S. F. (1990) "Methods for Assessing the Statistical Significance of Molecular Sequence Fea-tures by Using General Scoring Schemes" *Proc. Natl. Acad. Sci. USA* 87:2264-2268.
Karlin S. and Altschul, S. F. (1993) "Applications and Statistics for Multiple High-Scoring Segments in Molecu-lar Sequences" *Proc. Natl. Acad. Sci. USA* 90:5873-5877.
Lewin, B. (1985) *Genes II*, John Wiley & Sons, Inc., p. 96.
Lovrinovic and Niemeyer (2005) BBRC 335:943-948.
Lungwitz et al. (2005) *Eur. J. Pharmacet. Bioparmacet.* 60:247-266.

Wu, C-L. et al. (1998) "Promoters of Rice Seed Storage Protein Genes Direct Endosperm-Specific Gene Expression in Transgenic Rice" *Plant and Cell Physiology*, 39(8):885-889.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

Van Damme et al. "Characterization and molecular cloning of *Sambucus nigra* agglutinin V (nigrin b), a GalNAc-specific type-2 ribosome-inactivating protein from the bark of elderberry (*Sambucus nigra*)" *Eur. J Biochem.* 237 (2), 505-513 (1996).

Maveyraud et al. "Structural basis for sugar recognition, including the to carcinoma antigen, by the lectin sna-ii from *Sambucus nigra*" *Proteins* 75 p. 89 (2009).

Van de Kamp et al. "Genetic heterogeneity and clinical variability in the Sanfilippo syndrome (type A, B, and C)" *Clin. Genet.* 20 (2), 152-160 (1981).

Montfort et al. "The three-dimensional structure of ricin at 2.8 A" *J. Biol Chem.* 262 (11), 5398-5403 (1987).

Citores L, Munoz R, Rojo M A, Jimenez P, Ferreras J M, Girbes T (2003) Cell. Molec. Biol. 49:461-465.

Citores L, Munoz R, De Benito F M, Iglesias R, Ferreras J M, Girbes T (1996) Cell. Molec. Biol. 42(4):473-476.

Ferreras et al., (2011) *Toxins* 3: 420-441.

Sandvig K, van Deurs B (1999) FEBS Lett 452(1-2):67-70.

Simmons B M, Stahl P D, Russell J H (1986) J Biol Chem 261(17):7912-7920.

Van Damme et al., (1998) Crit. Rev. Plant Sci. 17: 575-692.

Bevan et al. "The structure and transcription start site of a major potato tuber protein gene" *Nucleic Acid Res.* 14 (11), 4625-4638 (1986).

Malalyalam et al., 2008

Huang Z, Chen Q, Hjelm B, Arntzen C, Mason H. A DNA replicon system for rapid high-level production of virus-like particle in plants. Biotechnol Bioeng, 2009, 103(4): 706-714.

Crawley A C, Gliddon B L, Auclair D, Brodie S L, Hirte C, King B M, Fuller M, Hemsley K M, Hopwood J J. Characterization of a C57B L/6 congenic mouse strain of mucopolysaccharidosis type IIIA. *Brain Res,* 2006, 1104 (1):1-17.

Settembre C, Annunziata I, Spampanato C, Zarcone, D, Cobellis G, Nusco E, Zito E, Tacchetti C, Cosma M P, Ballabio A. 2007. Sytemic inflammation and neurodegeneration of a mouse model of multiple sulfatase deficiency. Proc. Natl. Acad. Sci USA, 2007, 104:4506-11.

1. Meikle P J, Hopwood J J, Clague A E, Carey W F: Prevalence of lysosomal storage disorders. *JAMA* 1999, 281(3):249-254.

2. Hollak C E, Aerts J M, Ayme S, Manuel J: Limitations of drug registries to evaluate orphan medicinal products for the treatment of lysosomal storage disorders. *Orphanet J Rare Dis* 2011, 6:16.

3. Grabowski G A: Treatment perspectives for the lysosomal storage diseases. *Expert Opin Emerg Drugs* 2008, 13(1): 197-211.

4. Du H, Cameron T L, Garger S J, Pogue G P, Hamm L A, White E, Hanley K M, Grabowski G A: Wolman disease/cholesteryl ester storage disease: efficacy of plant-produced human lysosomal acid lipase in mice. *J Lipid Res* 2008, 49(8):1646-1657.

5. Aviezer D, Brill-Almon E, Shaaltiel Y, Hashmueli S, Bartfeld D, Mizrachi S, Liberman Y, Freeman A, Zimran A, Galun E: A plant-derived recombinant human glucocerebrosidase enzyme—a preclinical and phase I investigation. *PLoS One* 2009, 4(3):e4792.

6. Zimran A, Brill-Almon E, Chertkoff R, Petakov M, Blanco-Favela F, Munoz E T, Solorio-Meza S E, Amato D, Duran G, Giona F et al: Pivotal trial with plant cell-expressed recombinant glucocerebrosidase, taliglucerase alfa, a novel enzyme replacement therapy for Gaucher disease. *Blood* 2011, 118(22):5767-5773.

7. Pastores G, Shankar S P, Szer J, Petakov M, Cox T M, Giraldo P, Rosenbaum H, Amato D J, Mengel E, Chertkoff R et al: Plant cell-expressed recombinant glucocerebrosidase: Taliglucerase alfa as therapy for Gaucher disease in adults patients previously treated with imiglucerase: 24-month results. *Mol Genet Metab* 2013, 108(2):573-574.

8. Medrano G, Reidy M, Liu J, Ayala J, Dolan M, Cramer C: Rapid system for evaluating bioproduction capacity of complex pharmaceutical proteins in plants. *Methods Mol Biol* 2009, 483:51-67.

9. Huang Z, Phoolcharoen W, Lai H, Piensook K, Cardineau G, Zeitlin L, Whaley K J, Arntzen C J, Mason H S, Chen Q: High-level rapid production of full-size monoclonal antibodies in plants by a single-vector DNA replicon system. *Biotechnol Bioeng* 2010, 106(1):9-17.

10. D'Aoust M A, Couture M M, Charland N, Trepanier S, Landry N, Ors F, Vezina L P: The production of hemagglutinin-based virus-like particles in plants: a rapid, efficient and safe response to pandemic influenza. *Plant Biotechnol J* 2010, 8(5):607-619.

11. Whaley K J, Hiatt A, Zeitlin L: Emerging antibody products and *Nicotiana* manufacturing. *Hum Vaccines* 2011, 7(3):349-356.

12. Komarova T V, Baschieri S, Donini M, Marusic C, Benvenuto E, Dorokhov Y L: Transient expression systems for plant-derived biopharmaceuticals. *Expert Rev Vaccines* 2010, 9(8):859-876.

13. Lai H, Chen Q: Bioprocessing of plant-derived virus-like particles of Norwalk virus capsid protein under current Good Manufacture Practice regulations. *Plant Cell Rep* 2012, 31(3):573-584.

14. Landry N, Ward B J, Trepanier S, Montomoli E, Dargis M, Lapini G, Vezina L P: Preclinical and clinical development of plant-made virus-like particle vaccine against avian H5N1 influenza. *PLoS One* 2010, 5(12):e15559.

15. Landis S C, Amara S G, Asadullah K, Austin C P, Blumenstein R, Bradley E W, Crystal R G, Darnell R B, Ferrante R J, Fillit H et al: A call for transparent reporting to optimize the predictive value of preclinical research. *Nature* 2012, 490(7419):187-191.

16. Sandvig K, van Deurs B: Endocytosis and intracellular transport of ricin: recent discoveries. *FEBS Lett* 1999, 452(1-2):67-70.

17. Jackman M R, Shurety W, Ellis J A, Luzio J P: Inhibition of apical but not basolateral endocytosis of ricin and folate in Caco-2 cells by cytochalasin D. *J Cell Sci* 1994, 107 (Pt 9):2547-2556.

18. Frankel A, Fu T, Burbage C, Tagge E, Harris B, Vesely J, Willingham M: Lectin-deficient ricin toxin intoxicates cells bearing the D-mannose receptor. *Carbohyd Res* 1997, 300(3):251-258.

19. Simmons B M, Stahl P D, Russell J H: Mannose receptor-mediated uptake of ricin toxin and ricin A chain by macrophages. Multiple intracellular pathways for a chain translocation. *J Biol Chem* 1986, 261(17):7912-7920.

20. Morlon-Guyot J, Helmy M, Lombard-Frasca S, Pignol D, Pieroni G, Beaumelle B: Identification of the ricin lipase site and implication in cytotoxicity. *J Biol Chem* 2003, 278(19):17006-17011.
21. Stechmann B, Bai S, Gobbo E, Lopez R, Merer G, Pinchard S, Panigai L, Tenza D, Raposo G, Beaumelle B et al: Inhibition of retrograde transport protects mice from lethal ricin challenge. *Cell* 2010, 141(2):231-242.
22. Choi N, Estes M, Langridge W: Mucosal immunization with a ricin toxin B subunit-rotavirus NSP4 fusion protein stimulates a Th1 lymphocyte response. *J Biotechnol* 2006, 121(2):272-283.
23. Donayre-Torres A, Esquivel-Soto E, Gutiérrez-Xicoténcatl M L, Esquivel-Guadarrama F, Gomez-Lim M: Production and purification of immunologically active core protein p24 from HIV-1 fused to ricin toxin B subunit in *E. coli. Virol J* 2009, 6:17.
24. Medina-Bolivar F, Wright R, Funk V, Sentz D, Barroso L, Wilkins T, Petri W J, Cramer C: A non-toxic lectin for antigen delivery of plant-based mucosal vaccines. *Vaccine* 2003, 21(9-10):997-1005.
25. Cramer C L, Reidy M, Dolan M C: Methods of delivery of molecules to cells using ricin subunit and compositions relating to same. U S Published Application No. 2010/0240597.
26. Reidy M J: Engineering of the RTB lectin as a carrier platform for proteins and antigens. Blacksburg, VA: PhD Dissertation, Virginia Polytechnic Institute and Arkansas State University; 2007.
27. Liu J: Plant-derived murine IL-12 and ricin b-murine IL-12 fusions. Blacksburg, VA: PhD Dissertation, Virginia Polytechnic Institute and Arkansas State University; 2006.
28. Citores L, Munoz R, Rojo M A, Jimenez P, Ferreras J M, Girbes T: Evidence for distinct cellular internalization pathways of ricin and nigrin b. *Cell Mol Biol* 2003, 49 Online Pub:OL461-465.
29. Battelli M G, Citores L, Buonamici L, Ferreras J M, de Benito F M, Stirpe F, Girbes T: Toxicity and cytotoxicity of nigrin b, a two-chain ribosome-inactivating protein from *Sambucus nigra*: comparison with ricin. *Arch Toxicol* 1997, 71(6):360-364.
30. Citores L, Munoz R, De Benito F M, Iglesias R, Ferreras J M, Girbes T: Differential sensitivity of HELA cells to the type 2 ribosome-inactivating proteins ebulin 1, nigrin b and nigrin f as compared with ricin. *Cell Mol Biol* 1996, 42(4):473-476.
31. Zhang Y, Pardridge W M: Delivery of beta-galactosidase to mouse brain via the blood-brain barrier transferrin receptor. *J Pharmacol Exp Ther* 2005, 313(3):1075-1081.
32. Begley D J, Pontikis C C, Scarpa M: Lysosomal storage diseases and the blood-brain barrier. *Curr Pharm Design* 2008, 14(16):1566-1580.
33. Audi J, Belson M, Patel M, Schier J, Osterloh J: Ricin poisoning: a comprehensive review. *JAMA* 2005, 294(18): 2342-2351.
34. Broadwell R D, Balin B J, Salcman M: Transcytotic pathway for blood-borne protein through the blood-brain barrier. *Proc Natl Acad Sci USA* 1988, 85(2):632-636.
35. Thorne R G, Emory C R, Ala T A, Frey W H, 2nd: Quantitative analysis of the olfactory pathway for drug delivery to the brain. *Brain Res* 1995, 692(1-2):278-282.
36. Bell C L, Gurda B L, Van Vliet K, Agbandje-McKenna M, Wilson J M: Identification of the galactose binding domain of the adeno-associated virus serotype 9 capsid. *J Virol* 2012, 86(13):7326-7333.
37. Shen S, Bryant K D, Brown S M, Randell S H, Asokan A: Terminal N-linked galactose is the primary receptor for adeno-associated virus 9. *J Biol Chem* 2011, 286(15): 13532-13540.
38. Trickier W J, Lantz S M, Murdock R C, Schrand A M, Robinson B L, Newport G D, Schlager J J, Oldenburg S J, Paule M G, Slikker W, Jr. et al: Silver nanoparticle induced blood-brain barrier inflammation and increased permeability in primary rat brain microvessel endothelial cells. *Toxicol Sci* 2010, 118(1):160-170.
39. Bachmeier C J, Trickier W J, Miller D W: Comparison of drug efflux transport kinetics in various blood-brain barrier models. *Drug Metab Dispos* 2006, 34(6):998-1003.
40. Tessitore A, del PMM, Sano R, Ma Y, Mann L, Ingrassia A, Laywell E D, Steindler D A, Hendershot L M, d'Azzo A: GM1-ganglioside-mediated activation of the unfolded protein response causes neuronal death in a neurodegenerative gangliosidosis. *Mol Cell* 2004, 15(5):753-766.
41. Crawley A C, Gliddon B L, Auclair D, Brodie S L, Hirte C, King B M, Fuller M, Hemsley K M, Hopwood J J: Characterization of a C57B L/6 congenic mouse strain of mucopolysaccharidosis type IIIA. *Brain Res* 2006, 1104 (1):1-17.
42. Gliddon B L, Hopwood J J: Enzyme-replacement therapy from birth delays the development of behavior and learning problems in mucopolysaccharidosis type IIIA mice. *Pediatr Res* 2004, 56(1):65-72.
43. Polito V A, Abbondante S, Polishchuk R S, Nusco E, Salvia R, Cosma M P: Correction of CNS defects in the MPSII mouse model via systemic enzyme replacement therapy. *Hum Mol Genet* 2010, 19(24):4871-4885.
44. Grubb J H, Vogler C, Tan Y, Shah G N, MacRae A F, Sly W S: Infused Fc-tagged beta-glucuronidase crosses the placenta and produces clearance of storage in utero in mucopolysaccharidosis VII mice. *Proc Natl Acad Sci USA* 2008, 105(24):8375-8380.
45. Vogler C, Levy B, Grubb J H, Galvin N, Tan Y, Kakkis E, Pavloff N, Sly W S: Overcoming the blood-brain barrier with high-dose enzyme replacement therapy in murine mucopolysaccharidosis VII. *Proc Natl Acad Sci USA* 2005, 102(41):14777-14782.
46. Blanz J, Stroobants S, Lullmann-Rauch R, Morelle W, Ludemann M, D'Hooge R, Reuterwall H, Michalski J C, Fogh J, Andersson C et al: Reversal of peripheral and central neural storage and ataxia after recombinant enzyme replacement therapy in alpha-mannosidosis mice. *Hum Mol Genet* 2008, 17(22):3437-3445.
47. Matzner U, Lullmann-Rauch R, Stroobants S, Andersson C, Weigelt C, Eistrup C, Fogh J, D'Hooge R, Gieselmann V: Enzyme replacement improves ataxic gait and central nervous system histopathology in a mouse model of metachromatic leukodystrophy. *Mol Ther* 2009, 17(4): 600-606.
48. Rozaklis T, Beard H, Hassiotis S, Garcia A R, Tonini M, Luck A, Pan J, Lamsa J C, Hopwood J J, Hemsley K M: Impact of high-dose, chemically modified sulfamidase on pathology in a murine model of MPS IIIA. *Exp Neurol* 2011, 230(1):123-130.
49. Hemsley K M, Beard H, King B M, Hopwood J J: Effect of high dose, repeated intra-cerebrospinal fluid injection of sulphamidase on neuropathology in MPS IIIA mice. *Genes Brain Behav* 2008, 7:740-753.
50. Hemsley K M, Luck A J, Crawley A C, Hassiotis S, Beard H, King B, Rozek T, Rozaklis T, Fuller M, Hopwood J J: Examination of intravenous and intra-CSF 50. protein delivery for treatment of neurological disease. *Eur J Neurosci* 2009, 29(6):1197-1214.
51. Fraldi A, Hemsley K, Crawley A, Lombardi A, Lau A, Sutherland L, Auricchio A, Ballabio A, Hopwood J J: Functional correction of CNS lesions in an MPS-IIIA mouse model by intracerebral AAV-mediated delivery of sulfamidase and SUMF1 genes. *Hum Mol Genet* 2007, 16(22):2693-2702.
52. Sorrentino N C, D'Orsi L, Sambri I, Nusco E, Monaco C, Spampanato C, Polishchuk E, Saccone P, De Leonibus E, Ballabio A et al: A highly secreted sulphamidase engineered to cross the blood-brain barrier corrects brain lesions of mice with mucopolysaccharidoses type IIIA. *EMBO Mol Med* 2013, 5(5):675-690.
53. Karpova E A, Voznyi Ya V, Keulemans J L, Hoogeveen A T, Winchester B, Tsvetkova I V, van Diggelen O P: A fluorimetric enzyme assay for the diagnosis of Sanfilippo disease type A (MPS IIIA). *J Inherit Metab Dis* 1996, 19(3):278-285.
54. Landgrebe J, Dierks T, Schmidt B, von Figura K: The human SUMF1 gene, required for posttranslational sulfatase modification, defines a new gene family which is conserved from pro- to eukaryotes. *Gene* 2003, 316:47-56.
55. Mariappan M, Gande S L, Radhakrishnan K, Schmidt B, Dierks T, von Figura K: The non-catalytic N-terminal extension of formylglycine-generating enzyme is required for its biological activity and retention in the endoplasmic reticulum. *J Biol Chem* 2008, 283(17):11556-11564.
56. Diez-Roux G, Ballabio A: Sulfatases and human disease. *Annu Rev Genom Hum Genet* 2005, 6:355-379.
57. Cosma M P, Pepe S, Annunziata I, Newbold R F, Grompe M, Parenti G, Ballabio A: The multiple sulfatase deficiency gene encodes an essential and limiting factor for the activity of sulfatases. *Cell* 2003, 113(4):445-456.
58. Zito E, Buono M, Pepe S, Settembre C, Annunziata I, Surace E M, Dierks T, Monti M, Cozzolino M, Pucci P et al: Sulfatase modifying factor 1 trafficking through the cells: from endoplasmic reticulum to the endoplasmic reticulum. *EMBO J* 2007, 26(10):2443-2453.
59. Sardiello M, Annunziata I, Roma G, Ballabio A: Sulfatases and sulfatase modifying factors: an exclusive and promiscuous relationship. *Hum Mol Genet* 2005, 14(21): 3203-3217.
60. Annunziata I, Bouche V, Lombardi A, Settembre C, Ballabio A: Multiple sulfatase deficiency is due to hypomorphic mutations of the SUMF1 gene. *Hum Mutat* 2007, 28(9):928.
61. Cosma M P, Pepe S, Parenti G, Settembre C, Annunziata I, Wade-Martins R, Di Domenico C, Di Natale P, Mankad A, Cox B et al: Molecular and functional analysis of SUMF1 mutations in multiple sulfatase deficiency. *Hum Mutat* 2004, 23(6):576-581.
62. McCullen C A, Binns A N: *Agrobacterium tumefaciens* and plant cell interactions and activities required for interkingdom macromolecular transfer. *Annu Rev Cell Dev Biol* 2006, 22:101-127.
63. Acosta-Gamboa W: Development of plant lectin RTB for delivery of therapeutic proteins. Jonesboro, A R: PhD dissertation. Arkansas State University; 2012.
64. Huynh H T, Grubb J H, Vogler C, Sly W S: Biochemical evidence for superior correction of neuronal storage by chemically modified enzyme in murine mucopolysaccharidosis VII. *Proc Natl Acad Sci USA* 2012, 109(42): 17022-17027.
65. Hemsley K M, King B, Hopwood J J: Injection of recombinant human sulfamidase into the C S F via the cerebellomedullary cistern in MPS IIIA mice. *Mol Genet Metab* 2007, 90(3):313-328.
66. Trim P J, Lau A A, Hopwood J J, Snel M F: A simple method for early age phenotype confirmation using toe tissue from a mouse model of MPS IIIA. *Rapid Commun Mass Spectrom* 2014, 28(8):933-938.
67. Whitfield P D, Nelson P, Sharp P C, Bindloss C A, Dean C, Ravenscroft E M, Fong B A, Fietz M J, Hopwood J J, Meikle P J: Correlation among genotype, phenotype, and biochemical markers in Gaucher disease: implications for the prediction of disease severity. *Mol Genet Metab* 2002, 75(1):46-55.
68. Boado R J, Hui E K, Lu J Z, Zhou Q H, Pardridge W M: Reversal of lysosomal storage in brain of adult MPS-I mice with intravenous Trojan horse-iduronidase fusion protein. *Mol Pharm* 2011, 8(4): 1342-1350.
69. Grabowski G A: Perspectives on gene therapy for lysosomal storage diseases that affect hematopoiesis. *Curr Hematol Rep* 2003, 2(4):356-362.
70. Beck M: Therapy for lysosomal storage disorders. *IUBMB Life* 2010, 62(1):33-40.
71. Hemsley K M, Norman E J, Crawley A C, Auclair D, King B, Fuller M, Lang D L, Dean C J, Jolly R D, Hopwood J J: Effect of cisternal sulfamidase delivery in MPS IIIA Huntaway dogs—a proof of principle study. *Mol Genet Metab* 2009, 98(4):383-392.
72. Smallshaw J E, Vitetta E S: Ricin vaccine development. *Curr Top Microbiol Immunol* 2012, 357:259-272.
73. Yermakova A, Mantis N J: Protective immunity to ricin toxin conferred by antibodies against the toxin's binding subunit (RTB). *Vaccine* 2011, 29(45):7925-7935.
74. Rayon C, Lerouge P, Faye L: The protein N-glycosylation in plants. *J Exp Bot* 1998, 49(326):1463-1472.
75. Chargelegue D, Vine N D, van Dolleweerd C J, Drake P M, Ma J K: A murine monoclonal antibody produced in transgenic plants with plant-specific glycans is not immunogenic in mice. *Transgenic Res* 2000, 9(3):187-194.

I claim:

1. A method for producing an enzymatically active sulfatase fusion protein having sulfatase activity, and/or an enzymatically active mammalian sulfatase protein having sulfatase activity, comprising co-expressing in a plant or plant cell: (1) a polynucleotide encoding a mammalian sulfatase fusion protein, and/or a polynucleotide encoding a mammalian sulfatase protein; and (2) a polynucleotide encoding a mammalian sulfatase modifying factor 1 (SUMF1) protein or a SUMF1 fusion protein, wherein the expressed sulfatase fusion protein and/or the expressed mammalian sulfatase protein produced by the method is enzymatically activated in the plant or plant cell by the expressed SUMF1 protein or the expressed SUMF1 fusion protein, wherein the expressed mammalian sulfatase fusion protein and/or the expressed mammalian sulfatase protein comprises a signal peptide operably linked thereto, and wherein the signal peptide comprises the amino acid sequence of SEQ ID NO: 37.

2. The method according to claim 1, wherein the mammalian sulfatase protein is N-acetylgalactosamine-6-sulfatase, N-acetylglucosamin-6-sulfatase, N-sulphoglucosamine sulphohydrolase, sulfamidase, human extracellular sulfatase Sulf-1 (hSulf1), human extracellular sulfatase Sulf-2 (hSulf2), iduronate 2-sulfatase, arylsulfatase A (ASA), arylsulfatase B (ASB), steryl-sulfatase, arylsulfatase D (ASD), arylsulfatase E (ASE), arylsulfatase F (ASF), arylsulfatase G (ASG), arylsulfatase H (ASH), arylsulfatase I (ASI), arylsulfatase J (ASJ), or arylsulfatase K (ASK).

3. The method according to claim 2, wherein the mammalian sulfatase protein comprises the amino acid sequence of SEQ ID NOs: 2, 4, 6, 8, 10, 12, 14, 16, 18, 20, 22, 24, 26, 28, 30, 32, or 34, or an enzymatically active fragment or an enzymatically active variant thereof.

4. The method according to claim 1, wherein the SUMF1 protein comprises the amino acid sequence of SEQ ID NO: 36.

5. The method according to claim 1, wherein the SUMF1 fusion protein comprises the amino acid sequence of any of SEQ ID NOs: 71, 73, 75, 77, 79, or 81.

6. The method according to claim 1, comprising co-expressing in a plant or plant cell: (1) a polynucleotide encoding a mammalian sulfatase fusion protein; and (2) a polynucleotide encoding a mammalian sulfatase modifying factor 1 (SUMF1) fusion protein.

7. The method according to claim 6, the SUMF1 fusion protein comprising a mammalian SUMF1 protein and a plant lectin or a binding subunit thereof.

* * * * *

UNITED STATES PATENT AND TRADEMARK OFFICE
CERTIFICATE OF CORRECTION

| | | |
|---|---|---|
| PATENT NO. | : 12,168,784 B2 | Page 1 of 1 |
| APPLICATION NO. | : 17/651106 | |
| DATED | : December 17, 2024 | |
| INVENTOR(S) | : David N. Radin | |

It is certified that error appears in the above-identified patent and that said Letters Patent is hereby corrected as shown below:

In the Specification

Column 1:
Line 30, "A (mucopolysaccharidosis MPS-III A" should read -- A (mucopolysaccharidosis IIIA; MPS-IIIA) --.

Column 12:
Table 2, Line 18, "[P(30+33)]$_2$ Unknown" should read -- [P(30+33)]$_?$ Unknown --.

Column 15:
Line 44, "the to carcinoma antigen," should read -- the tn carcinoma antigen, --.

Column 23:
Line 2, "NBLAST and)(BLAST programs" should read -- NBLAST and XBLAST programs --.
Line 9, "(N BLAST and)(BLAST)" should read -- (NBLAST and XBLAST) --.

Signed and Sealed this
Tenth Day of June, 2025

Coke Morgan Stewart
*Acting Director of the United States Patent and Trademark Office*